United States Patent
Binch et al.

(10) Patent No.: US 7,041,687 B2
(45) Date of Patent: May 9, 2006

(54) INDAZOLE COMPOUNDS USEFUL AS PROTEIN KINASE INHIBITORS

(75) Inventors: Hayley Binch, Harwell (GB); Guy Brenchley, Grove Wantage (GB); Julian M. C. Golec, Swindon (GB); Ronald Knegtel, Abingdon (GB); Michael Mortimore, Burford (GB); Sanjay Patel, Abingdon (GB); Alistair Rutherford, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 405 days.

(21) Appl. No.: 10/350,806

(22) Filed: Jan. 23, 2003

(65) Prior Publication Data

US 2004/0009968 A1    Jan. 15, 2004

Related U.S. Application Data

(60) Provisional application No. 60/351,597, filed on Jan. 25, 2002.

(51) Int. Cl.
*A61K 31/41* (2006.01)

(52) U.S. Cl. ............... 514/359; 548/364.1; 548/300.1; 548/358.1

(58) Field of Classification Search ............... 514/359; 548/364.2, 300.1, 358.1
See application file for complete search history.

(56) References Cited

U.S. PATENT DOCUMENTS

2002/0103229 A1    8/2002    Bhagwat et al.

FOREIGN PATENT DOCUMENTS

| WO | WO 00/71508 | 11/2000 |
|----|-------------|---------|
| WO | WO 00/76971 | 12/2000 |
| WO | WO 01/56988 | 8/2001 |
| WO | WO 01/85719 | 11/2001 |
| WO | WO 02/10137 | 2/2002 |
| WO | WO 02/083648 | 10/2002 |
| WO | WO 02/100833 | 12/2002 |

OTHER PUBLICATIONS

Nicolaides, E.D., et al., "Potential antiviral agents," J. Med. Chem., 11(1):74-79 (1968).

*Primary Examiner*—James O. Wilson
*Assistant Examiner*—Jason H. Johnsen
(74) *Attorney, Agent, or Firm*—Lisa A. Dixon; Vertex Pharmaceuticals Incorporated

(57) ABSTRACT

The present invention provides compounds of formula I:

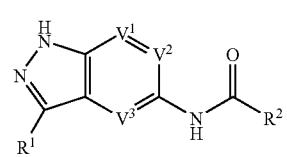

or a pharmaceutically acceptable derivative thereof, wherein $R^1$, $R^2$, $V^1$, $V^2$, and $V^3$ are as described in the specification. These compounds are inhibitors of protein kinase, particularly inhibitors of AKT, PKA, PDK1, p70S6K, or ROCK kinase, mammalian protein kinases involved in proliferative and neurodegenerative disorders. The invention also provides pharmaceutical compositions comprising the compounds of the invention and methods of utilizing those compositions in the treatment of various disorders.

16 Claims, No Drawings

INDAZOLE COMPOUNDS USEFUL AS PROTEIN KINASE INHIBITORS

CROSS REFERENCE TO RELATED APPLICATIONS

This application claims priority to U.S. Provisional Patent Application No. 60/351,597 filed Jan. 25, 2002, the contents of which are incorporated herein by reference.

FIELD OF THE INVENTION

The present invention is in the field of medicinal chemistry and relates to compounds that are protein kinase inhibitors, compositions containing such compounds and methods of use. More particularly, the compounds are inhibitors of AKT, PKA, PDK1, p70S6K, and ROCK kinases and are useful for treating diseases, such as cancer.

BACKGROUND OF THE INVENTION

The search for new therapeutic agents has been greatly aided in recent years by better understanding of the structure of enzymes and other biomolecules associated with target diseases. One important class of enzymes that has been the subject of extensive study is the protein kinases.

Protein kinases mediate intracellular signal transduction. They do this by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell. Examples of such stimuli include environmental and chemical stress signals (e.g. osmotic shock, heat shock, ultraviolet radiation, bacterial endotoxin, $H_2O_2$), cytokines (e.g. interleukin-1 (IL-1) and tumor necrosis factor α (TNF-α)), and growth factors (e.g. granulocyte macrophage-colony-stimulating factor (GM-CSF), and fibroblast growth factor (FGF). An extracellular stimulus may effect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents. A challenge has been to find protein kinase inhibitors that act in a selective manner. Since there are numerable protein kinases that are involved in a variety of cellular responses, non-selective inhibitors may lead to unwanted side effects.

AKT (also known as PKB or Rac-PK beta), a serine/threonine protein kinase, has been shown to be overexpressed in several types of cancer and is a mediator of normal cell functions [(Khwaja, A., Nature, 401, pp. 33–34, 1999); (Yuan, Z. Q., et al., Oncogene, 19, pp. 2324–2330, 2000); (Namikawa, K., et al., J. Neurosci., 20, pp. 2875–2886, 2000)]. AKT comprises an N-terminal pleckstrin homology (PH) domain, a kinase domain and a C-terminal "tail" region. Three isoforms of human AKT kinase (AKT-1, -2 and -3) have been reported so far [(Cheng, J. Q., Proc. Natl. Acad. Sci. USA, 89, pp. 9267–9271, 1992); (Brodbeck, D. et al., J. Biol. Chem. 274, pp. 9133–9136, 1999)]. The PH domain binds 3-phosphoinositides, which are synthesized by phosphatidyl inositol 3-kinase (PI3K) upon stimulation by growth factors such as platelet derived growth factor (PDGF), nerve growth factor (NGF) and insulin-like growth factor (IGF-1) [(Kulik et al., Mol. Cell. Biol., 17, pp. 1595–1606, 1997); (Hemmings, B. A., Science, 275, pp. 628–630, 1997)]. Lipid binding to the PH domain promotes translocation of AKT to the plasma membrane and facilitates phosphorylation by another PH-domain-containing protein kinases, PDK1 at Thr308, Thr309, and Thr305 for the AKT isoforms 1, 2 and 3, respectively. A second, as of yet unknown, kinase is required for the phosphorylation of Ser473, Ser474 or Ser472 in the C-terminal tails of AKT-1, -2 and -3 respectively, in order to yield a fully activated AKT enzyme.

Once localized to the membrane, AKT mediates several functions within the cell including the metabolic effects of insulin (Calera, M. R. et al., J. Biol. Chem., 273, pp. 7201–7204, 1998), induction of differentiation and/or proliferation, protein synthesisans stress responses (Alessi, D. R. et al., Curr. Opin. Genet. Dev., 8, pp. 55–62, 1998).

Manifestations of altered AKT regulation appear in both injury and disease, the most important role being in cancer. The first account of AKT was in association with human ovarian carcinomas where expression of AKT was found to be amplified in 15% of cases (Cheng, J. Q. et al., Prod. Natl. Acad. Sci. U.S.A., 89, pp. 9267–9271, 1992). It has also been found to be overexpressed in 12% of pancreatic cancers (Cheng, J. Q. et al., Proc. Natl. Acad. Sci. U.S.A., 93, pp. 3636–3641, 1996). It was demonstrated that AKT-2 was over-expressed in 12% of ovarian carcinomas and that amplification of AKT was especially frequent in 50% of undifferentiated tumours, suggesting that AKT may also be associated with tumour aggressiveness (Bellacosa, et al., Int. J. Cancer, 64, pp. 280–285, 1995).

PKA (also known as cAMP-dependent protein kinase) has been shown to regulate many vital functions including energy metabolism, gene transcription, proliferation, differentiation, reproductive function, secretion, neuronal activity, memory, contractility and motility (Beebe, S. J., Semin. Cancer Biol., 5, pp. 285–294, 1994). PKA is a tetrameric holoenzyme, which contains two catalytic subunits bound to a homo-dimeric regulatory subunit (which acts to inhibit the catalytic sub-units). On binding of cAMP (enzyme activation), the catalytic subunits dissociate from the regulatory subunits to yield the active serine/threonine kinase (McKnight, G. S. et al., Recent Prog. Horm. Res., 44, pp. 307, 1988). Three isoforms of the catalytic subunit (C-α, C-β and C-γ have been reported to date (Beebe, S. J. et al., J. Biol. Chem., 267, pp. 25505–25512, 1992) with the C-α subunit being the most extensively studied, primarily because of its elevated expression in primary and metastatic melanomas (Becker, D. et al., Oncogene, 5, pp. 1133, 1990). To date, strategies to modulate the activity of the C-α subunit involve the use of antibodies, molecules that block PKA activity by targeting regulatory dimers and antisense oligonucleotides expression.

Rho-associated coiled-coil forming kinase (ROCK) (Ishizaki, T. et al., EMBO J., 15, pp. 1885–1893, 1996) is a 160 kDa serine/threonine kinase that activates the small G-protein RhoA. ROCK has been implicated in numerous diseases including hypertension [(Chitaley, et al., Curr. Hypertens. Rep. 2001 Apr., 3(2), pp.139–144); (Uehata, M. et al., Nature, 389, pp. 990–994, 1997)], erectile dysfunction (Chitaley, K. et al., Nature Medicine, 7, pp. 119–122, 2001), angiogenesis (Uchida, S. et al., Biochem. Biophys. Res.

Commun., 269 (2), pp. 633–40, 2000), neuroregeneration (Bito, H. et al., *Neuron,* 26, pp. 431–441, 2000), metastasis [(Takamura, M. et al., *Hepatology,* 33, pp. 577–581, 2001); (Genda, T. et al., *Hepatology,* 30, pp. 1027–1036, 1999)], glaucoma (Rao, et al., *Invest. Ophthalmol. Vis. Sci.,* 42, pp. 1029–37, 2001), inflammation (Ishizuka, T. et al., *J. Immunol.,* 167, pp. 2298–2304, 2001), arteriosclerosis (Smimokawa, et al., *Arterioscler. Thromb. Vasc. Biol.,* 11, pp. 2351–2358, 2000), immunosuppresion (Lou, Z. et al., *J. Immunol.,* 167, pp. 5749–5757, 2001), restenosis (Seaholtz, et al., *Circ. Res.,* 84, pp. 1186–1193, 1999), asthma (Yoshii, et al., *Am. J. Respir. Cell Mol. Biol.,* 20, pp. 1190–1200, 1999), cardiac hypertrophy (Kuwahara, K. et al., *FEBS Lett.,* 452, pp. 314–318, 1999).

The ribosomal protein kinases p70S6K-1 and -2 are members of the AGC sub-family of protein kinases that consists of, amongst others, PKB and MSK. The p70S6 kinases catalyze the phosphorylation and subsequent activation of the ribosomal protein S6, which has been implicated in the translational up-regulation of mRNAs coding for the components of protein synthetic apparatus.

These mRNAs contain an oligopyrimidine tract at their 5' transcriptional start site, termed a 5TOP, which has been shown to be essential for their regulation at the translational level (Volarevic, S. et al., *Prog. Nucleic Acid Res. Mol. Biol.* 65, pp 101–186, 2001). p70 S6K dependent S6 phosphorylation is stimulated in response to a variety of hormones and growth factors primarily via the P13K pathway (Coffer, P. J. et al., *Biochem. Biophys. Res. Commun,* 198, 7 pp 780–786, 1994), which maybe under the regulation of mTOR, since rapamycin acts to inhibit p70S6K activity and blocks protein synthesis, specifically as a result of a down-regulation of translation of these mRNA's encoding ribosomal proteins (Kuo, C. J. et al., *Nature,* 358, pp 70–73, 1992).

In vitro PDK1 catalyses the phosphorylation of Thr252 in the activation loop of the p70 catalytic domain, which is indispensable for p70 activity (Alessi, D. R., *Curr. Biol.,* 8, pp 69–81, 1998). The use of rapamycin and gene deletion studies of dp70S6K from *Drosophila* and p70S6K1 from mouse have established the central role p70 plays in both cell growth and proliferation signaling.

The 3-phosphoinositide-dependent protein kinase-1 (PDK1) plays a key role in regulating the activity of a number of kinases belonging to the AGC subfamily of protein kinases (Alessi, D. et al., *Biochem. Soc. Trans,* 29, pp. 1, 2001). These include isoforms of protein kinase B (PKB, also known as AKT), p70 ribosomal S6 kinase (S6K) (Avruch, J. et al., *prog. Mol. Subcell. Biol.,* 2001, 26, pp. 115, 2001), and p90 ribosomal S6 kinase (Frödin, M. et al., *EMBO J.,* 19, pp. 2924–2934, 2000). PDK1 mediated signaling is activated in response to insulin and growth factors and as a consequence of attachment of the cell to the extracellular matrix (integrin signaling). Once activated these enzymes mediate many diverse cellular events by phosphorylating key regulatory proteins that play important roles controlling processes such as cell survival, growth, proliferation and glucose regulation [(Lawlor, M. A. et al., *J. Cell Sci.,* 114, pp. 2903–2910, 2001), (Lawlor, M. A. et al., *EMBO J.,* 21, pp. 3728–3738, 2002)]. PDK1 is a 556 amino acid protein, with an N-terminal catalytic domain and a C-terminal pleckstrin homology (PH) domain, which activates its substrates by phosphorylating these kinases at their activation loop (Belham, C. et al., *Curr. Biol.,* 9, pp. R93–R96, 1999). Many human cancers including prostate and NSCL have elevated PDK1 signaling pathway function resulting from a number of distinct genetic events such as PTEN mutations or over-expression of certain key regulatory proteins [(Graff, J. R., *Expert Opin. Ther. Targets,* 6, pp. 103–113, 2002), (Brognard, J., et al., *Cancer Res.,* 61, pp. 3986–3997, 2001)]. Inhibition of PDK1 as a potential mechanism to treat cancer was demonstrated by transfection of a PTEN negative human cancer cell line (U87MG) with antisense oligonucleotides directed against PDK1. The resulting decrease in PDK1 protein levels led to a reduction in cellular proliferation and survival (Flynn, P., et al., *Curr. Biol.,* 10, pp. 1439–1442, 2000). Consequently the design of ATP binding site inhibitors of PDK1 offers, amongst other treatments, an attractive target for cancer chemotherapy.

The diverse range of cancer cell genotypes has been attributed to the manifestation of the following six essential alterations in cell physiology: self-sufficiency in growth signaling, evasion of apoptosis, insensitivity to growth-inhibitory signaling, limitless replicative potential, sustained angiogenesis, and tissue invasion leading to metastasis (Hanahan, D. et al., *Cell,* 100, pp. 57–70, 2000). PDK1 is a critical mediator of the P13K signalling pathway, which regulates a multitude of cellular function including growth, proliferation and survival. Consequently inhibition of this pathway could affect four or more of the six defining requirements for cancer progression, as such it is anticipated that a PDK1 inhibitor will have an effect on the growth of a very wide range of human cancers.

Specifically, increased levels of PI3K pathway activity has been directly associated with the development of a number of human caners, progression to an aggressive refractory state (acquired resistance to chemotherapies) and poor prognosis. This increased activity has been attributed to a series of key events including decreased activity of negative pathway regulators such as the phosphatase PTEN, activating mutations of positive pathway regulators such as Ras, and overexpression of components of the pathway itself such as PKB, examples include: brain (gliomas), breast, colon, head and neck, kidney, lung, liver, melanoma, ovarian, pancreatic, prostate, sarcoma, thyroid [(Teng, D. H. et al., *Cancer Res.,* 57, pp. 5221–5225, 1997), (Brognard, J. et al., *Cancer Res.,* 61, pp. 3986–3997, 2001), (Cheng, J. Q. et al., *Proc. Natl. Acad. Sci.,* 93, pp. 3636–3641, 1996), *Int. J. Cancer,* 64, pp. 280, 1995), (Graff, J. R., *Expert Opin. Ther. Targets,* 6, pp. 103–113, 2002), *Am. J. Pathol.,* 159, pp. 431, 2001)].

Additionally, decreased pathway function through gene knockout, gene knockdown, dominant negative studies and small molecule inhibitors of the pathway have been demonstrated to reverse many of the cancer phenotypes in vitro (some studies have also demonstrated a similar effect in vivo) such as block proliferation, reduce viability and sensitize cancer cells to known chemotherapies in a series of cell lines, representing the following cancers: pancreatic [(Cheng, J. Q. et al., *Proc. Natl. Acad. Sci.,* 93, pp. 3636–3641, 1996), *Neoplasia,* 3, pp. 278, 2001)], lung [(Brognard, J. et al., *Cancer Res.,* 61, pp. 3986–3997, 2001), *Neoplasia,* 3, pp. 278, 2001)], ovarian [(Hayakawa, J. et al., *Cancer Res.,* 60, pp. 5988–5994, 2000), *Neoplasia,* 3, pp. 278, 2001)], breast (*Mol. Cancer Ther.,* 1, pp. 707, 2002), colon [(*Neoplasia,* 3, pp. 278, 2001), (Arico, S. et al., *J. Biol. Chem.,* 277, pp. 27613–27621, 2002)], cervical (*Neoplasia,* 3, pp. 278, 2001), prostate [(*Endocrinology,* 142, pp. 4795, 2001), (Thakkar, H. et al. *J. Biol. Chem.,* 276, pp. 38361–38369, 2001), (Chen, X. et al., *Oncogene,* 20, pp. 6073–6083, 2001)] and brain (glioblastomas) [(Flynn, P. et al., *Curr. Biol.,* 10, pp. 1439–1442, 2000)].

Accordingly, there is a great need to develop inhibitors of AKT, PKA, PDK1, p70S6K, and ROCK protein kinases that are useful in treating various diseases or conditions associated with AKT, PKA, PDK1, p70S6K, and ROCK activation, particularly given the inadequate treatments currently available for the majority of these disorders.

SUMMARY OF THE INVENTION

It has now been found that compounds of this invention, and pharmaceutically acceptable compositions thereof, are effective as inhibitors of AKT, PKA, PDK1, p70S6K, and ROCK protein kinases. These compounds have the formula I:

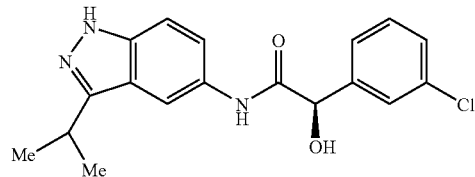

or a pharmaceutically acceptable salt thereof, wherein $V^1$, $V^2$, $V^3$, $R^1$, and $R^2$ are as defined below.

These compounds, and pharmaceutically acceptable compositions thereof, are useful for treating or lessening the severity of a variety of disorders, including allergic disorders such as asthma, inflammatory disease, proliferative disorders, and neurological disorders.

DESCRIPTION OF THE INVENTION

The present invention relates to a compound of formula I:

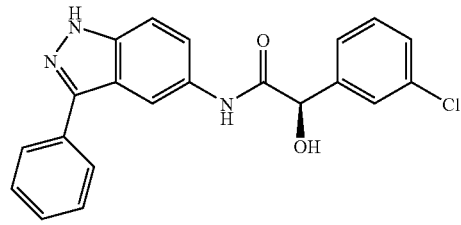

or a pharmaceutically acceptable salt thereof, wherein:
$R^1$ is selected from halogen, CN, $N(R^4)_2$, T-R, or T-Ar;
each T is independently selected from a valence bond or a $C_{1-6}$ alkylidene chain, wherein up to two methylene units of T are optionally, and independently, replaced by —O—, —N(R)—, —S—, —N(R)C(O)—, —C(O)N(R)—, —C(O)—, or —SO$_2$—;
each R is independently selected from hydrogen or an optionally substituted $C_{1-6}$ aliphatic group, or:
  two R groups on the same nitrogen, taken together with the nitrogen atom attached thereto, form a 5–7 membered saturated, partially unsaturated, or aromatic ring having 1–3 heteroatoms independently selected from nitrogen, oxygen, or sulfur;
$R^2$ is selected from Q-Ar, Q-N($R^5$)$_2$, or Q-C(R)(Q-Ar)$R^3$, wherein:
  R and $R^3$ optionally form a 5–7 membered saturated or partially unsaturated ring having 0–4 heteroatoms independently selected from nitrogen, oxygen, or sulfur;
each Q is independently selected from a valence bond or a $C_{1-4}$ alkylidene chain;

each Ar is independently an optionally substituted ring selected from a 5–7 membered saturated, partially unsaturated, or fully unsaturated monocyclic ring having 0–4 heteroatoms independently selected from nitrogen, oxygen, or sulfur, or an 8–10 membered saturated, partially unsaturated, or fully unsaturated bicyclic ring having 0–4 heteroatoms independently selected from nitrogen, oxygen, or sulfur;
$R^3$ is selected from R', $Ar^1$, Q-OR$^5$, Q-OC(O)R$^5$, Q-CONHR$^5$, Q-OC(O)NHR$^5$, Q-SR$^5$, Q-N(R$^4$)$_2$, N(R)(Q-Ar), N(R)C(O)Q-N(R$^4$)$_2$, or N(R)Q-N(R$^4$)$_2$;
R' is an optionally substituted $C_{1-6}$ aliphatic group;
each $R^4$ is independently selected from R, COR$^5$, CO$_2$R$^5$, CON(R$^5$)$_2$, SO$_2$R$^5$, SO$_2$N(R$^5$)$_2$, or $Ar^1$;
each $R^5$ is independently selected from R or Ar;
$V^1$, $V^2$ and $V^3$ are each independently selected from nitrogen or C(R$^6$);
each $R^6$ is independently selected from R, $Ar^1$, halogen, CN, NO$_2$, OR, SR, N(R$^4$)$_2$, N(R)COR, N(R)CON(R$^4$)$_2$, N(R)C(O)OR, CON(R$^4$)$_2$, OC(O)N(R$^4$)$_2$, CO$_2$R, OC(O)R, N(R)SO$_2$R, N(R)SO$_2$N(R$^4$)$_2$, SO$_2$R, or SO$_2$N(R$^4$)$_2$; and
each $Ar^1$ is independently selected from an optionally substituted 5–7 membered saturated, partially unsaturated, or fully unsaturated monocyclic ring having 0–4 heteroatoms independently selected from nitrogen, oxygen, or sulfur;
provided that:
when $V^1$, $V^2$, and $V^3$ are each CH, T is a valence bond, and $R^2$ is Q-C(R)(Q-Ar)R$^3$, wherein Ar is an optionally substituted phenyl ring, then $R^3$ is other than Q-OR$^5$ or C(O)NH$_2$; and
when $V^1$, $V^2$, and $V^3$ are each CH and $R^1$ is hydrogen then $R^2$ is Q-C(R)(Q-Ar)R$^3$, wherein $R^3$ is other than R', Q-OC(O)R$^5$, or OCH$_2$phenyl.

As used herein, the following definitions shall apply unless otherwise indicated. The phrase "optionally substituted" is used interchangeably with the phrase "substituted or unsubstituted." Unless otherwise indicated, an optionally substituted group may have a substituent at each substitutable position of the group, and each substitution is independent of the other.

The term "aliphatic" or "aliphatic group" as used herein means a straight-chain or branched $C_1$–$C_{12}$ hydrocarbon chain that is completely saturated or that contains one or more units of unsaturation, or a monocyclic $C_3$–$C_8$ hydrocarbon or bicyclic $C_8$–$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3–7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0–4 heteroatoms selected from oxygen, sulfur or nitrogen, the nitrogen may be N (as in 3,4-dihydro-2H-pyrrolyl), NH (as in pyrrolidinyl) or NR$^+$ (as in N-substituted pyrrolidinyl).

The term "aryl" used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heterocycle", "heterocyclyl", or "heterocyclic" as used herein means non-aromatic, monocyclic, bicyclic or tricyclic ring systems having five to fourteen ring members in which one or more ring members is a heteroatom, wherein each ring in the system contains 3 to 7 ring members.

The term "heteroaryl", used alone or as part of a larger moiety as in "heteroaralkyl" or "heteroarylalkoxy", refers to monocyclic, bicyclic and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl, heteroaryl, aralkyl, or heteroaralkyl group are selected from halogen, oxo, N$_3$, —R°, —OR°, —SR°, 1,2-methylene-dioxy, 1,2-ethylenedioxy, protected OH (such as acyloxy), phenyl (Ph), Ph substituted with R°, —O(Ph), O—(Ph) substituted with R°, —CH$_2$(Ph), —CH$_2$(Ph) substituted with R°, —CH$_2$CH$_2$(Ph), —CH$_2$CH$_2$(Ph) substituted with R°, —NO$_2$, —CN, —N(R°)$_2$, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, or —(CH$_2$)$_y$NHC(O)R°, wherein y is 0–4, each R° is independently selected from hydrogen, optionally substituted C$_{1-6}$ aliphatic, an unsubstituted 5–6 membered heteroaryl or heterocyclic ring having 0–4 heteroatoms independently selected from nitrogen, oxygen, or sulfur, phenyl (Ph), —O(Ph), or —CH$_2$(Ph)—CH$_2$(Ph). Substituents on the aliphatic group of R° are selected from NH$_2$, NH(C$_{1-4}$ aliphatic), N(C$_{1-4}$ aliphatic)$_2$, halogen, C$_{1-4}$ aliphatic, OH, O—(C$_{1-4}$ aliphatic), NO$_2$, CN, CO$_2$H, CO$_2$(C$_{1-4}$ aliphatic), —O(halo C$_{1-4}$ aliphatic), or halo C$_{1-4}$ aliphatic.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O—(C$_{1-4}$ aliphatic), NO$_2$, CN, CO$_2$H, CO$_2$(C$_{1-4}$ aliphatic), —O(halo C$_{1-4}$ aliphatic), or halo C$_{1-4}$ aliphatic.

Substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl (Ph), optionally substituted —O(Ph), optionally substituted —CH$_2$(Ph), optionally substituted —CH$_2$CH$_2$(Ph), or an unsubstituted 5–6 membered heteroaryl or heterocyclic ring. Substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O—(C$_{1-4}$ aliphatic), NO$_2$, CN, CO$_2$H, CO$_2$(C$_{1-4}$ aliphatic), —O(halo C$_{1-4}$ aliphatic), or halo C$_{1-4}$ aliphatic.

The term "alkylidene chain" refers to a straight or branched carbon chain that may be fully saturated or have one or more units of unsaturation and has two points of connection to the rest of the molecule.

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

Compounds of this invention may exist in alternative tautomeric forms. Unless otherwise indicated, the representation of either tautomer is meant to include the other.

One embodiment of the present invention relates to a compound of formula Ia:

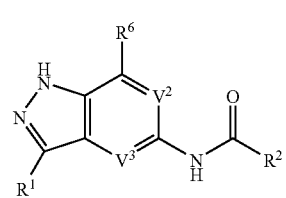

Ia or a pharmaceutically acceptable salt thereof, wherein R$^1$ and R$^2$ are as defined above for compounds of formula I.

According to one preferred embodiment, the present invention relates to a compound of formula I wherein V$^1$ is N, V$^2$ is CH, and V$^3$ is CH.

Preferred compounds of formula I include those wherein $V^1$ is C—$R^6$, $V^2$ is CH, and $V^3$ is CH or N.

Another preferred embodiment of the present invention relates to a compound of formula I wherein $V^1$ is C—$R^6$, $V^2$ is CH, and $V^3$ is N.

Another preferred embodiment of the present invention relates to a compound of formula I wherein $V^1$ is C—$R^6$, $V^2$ is CH, and $V^3$ is CH.

According to another preferred embodiment, the present invention relates to a compound of formula Ia wherein $V^2$ is CH and $V^3$ is N.

According to another preferred embodiment, the present invention relates to a compound of formula Ia wherein $V^2$ and $V^3$ are each N.

Preferred $R^1$ groups of formula I or Ia include hydrogen, halogen, CN, $N(R^4)_2$, and optionally substituted $C_{1-6}$ aliphatic. Examples of such $R^1$ groups include chloro, bromo, fluoro, $NH_2$, NHME, NHEt, NH—(optionally substituted phenyl), NH-cyclohexyl, $NHCH_2$(optionally substituted phenyl), NHC(O)(optionally substituted phenyl), NHC(O)NH(optionally substituted phenyl), $NHC(O)CH_2$(optionally substituted phenyl), $NHC(O)CH_2CH_2$(optionally substituted phenyl), N(R)C(O)(optionally substituted phenyl), NHC(O)naphthyl, NHC(O)thienyl, NRC(O)thienyl, SC(O)thienyl, $CH_2C(O)$thienyl, NHC(O)pyridyl, NHC(O)furanyl, methyl, ethyl, propyl, isopropyl, cyclopropyl, acetylenyl, and t-butyl.

The optional substituents of the phenyl rings of $R^1$ of formula I or Ia, when present, are optionally substituted $R^\circ$, halogen, nitro, CN, $OR^\circ$, $SR^\circ$, $N(R^\circ)_2$, $SO_2R^\circ$, $C(O)R^\circ$, C(O)OR, and $C(O)N(R^\circ)_2$, wherein each $R^\circ$ is as defined supra. Examples of such groups include chloro, bromo, fluoro, CN, nitro, OMe, OPh, $OCF_3$, $OCH_2Ph$, OEt, $SCHF_2$, methyl, ethyl, isopropyl, propyl, vinyl, $CF_3$, acetylenyl, $CH_2Ph$, $CH_2NH_2$, $CH_2N(Et)_2$, $CH_2$morpholin-4-yl, $CH_2$piperidin-1-yl, $CH_2$imidazol-1-yl, $CH_2$piperazin-1-yl, $C(O)NH_2$, C(O)Me, $SO_2Me$, NHEt, and NHMe.

When $R^1$ of formula I or Ia is T-Ar, preferred Ar groups are selected from an optionally substituted 5–6 membered saturated, partially unsaturated, or fully unsaturated monocyclic ring having 0–4 heteroatoms independently selected from nitrogen, oxygen, or sulfur. Examples of such Ar rings include optionally substituted phenyl, thienyl, furan, and pyridyl rings. Preferred T moieties of the T-Ar group of $R^1$ are selected from a valence bond, —N(R)C(O)—, —NH—, —$NHCH_2$—, —$NHSO_2$—, —$CH_2NH$—, —SC(O)—, —$CH_2C(O)$—, —C≡C—, —$CH_2$— or —$CH_2CH_2$—. More preferred T moieties of the T-Ar group of $R^1$ are selected from —NHC(O)—, —NH—, —$NHCH_2$—, —$CH_2$—, —C≡C—, or —$CH_2CH_2$—. Most preferred T moieties of the T-Ar group of $R^1$ are selected from —N(R)C(O)—, —NH—, or —$NHCH_2$—. Preferred substituents on the Ar group, when present, include fluoro and $CF_3$, Me, Et, iPr, vinyl, acetylene, Ar, Cl, $CF_3$, nitro, CN, OMe, OPh, $OCF_3$, $SO_2NH2$, C(O)OEt, C(O)OH, $CH_2CO_2H$, $CH_2CH_2CO_2H$, $CH_2NH_2$ and $C(O)NH_2$, thienyl, oxazolyl, isoxazolyl, and tetrazolyl.

Preferred Q groups of formula I or Ia are selected from a valence bond, —$CH_2$—, or —$CH_2CH_2$—.

When $R^2$ of formula I or Ia is Q-Ar, preferred Ar groups are an optionally substituted ring selected from a 5–6 membered saturated, partially unsaturated, or fully unsaturated monocyclic ring having 0–4 heteroatoms independently selected from nitrogen, oxygen, or sulfur, or a 9–10 membered saturated, partially unsaturated, or fully unsaturated bicyclic ring having 0–4 heteroatoms independently selected from nitrogen, oxygen, or sulfur. Examples of such monocyclic rings include phenyl, pyridyl, pyrimidinyl, pyridonyl, furanyl, tetrazolyl, thienyl, cyclopentyl, cyclohexyl, and cycloheptyl. Examples of such bicyclic rings include benzo[1,3]dioxolyl, indan-1-onyl, naphthyl, benzothiophenyl, 2,3-dihydro-1H-isoindolyl, indanyl, benzofuranyl, and indolyl.

When present, preferred substituents on the Ar ring of $R^2$ include $R^\circ$, halogen, oxo, $OR^\circ$, phenyl, optionally substituted dialkylamino, haloalkyl, $C(O)R^\circ$, NHC(O)R, or $SR^\circ$. Examples of such preferred substituents include chloro, bromo, fluoro, OH, OMe, $NHC(O)CH_3$, OEt, C(O)phenyl, Ophenyl, $N(CH_2CH_2Cl)_2$, $N(Me)_2$, $CF_3$, and $SCF_3$. Other examples of preferred Ar groups of formula I or Ia also include those shown in Table 1 below.

When the $R^2$ group of formula I or Ia is Q-C(R)(Q-Ar)$R^3$, preferred $R^3$ groups include R', Q-$OR^5$, Q-$N(R^4)_2$, $Ar^1$, $N(R)C(O)Q-N(R^4)_2$, and $N(R)Q-N(R^4)_2$. Examples of such $R^3$ groups include $CH_2OH$, OH, $NH_2$, $CH_2NH_2$, $CH_2NHMe$, $CH_2N(Me)_2$, $CH_2CH_2NH_2$, $CH_2CH_2NHMe$, $CH_2CH_2N(Me)_2$, $CH_2C(Me)_2NH_2$, $CH_2C(Me)_2CHMe$, $NHCO_2$t-butyl, phenyl, cyclopentyl, methyl, ethyl, isopropyl, cyclopropyl, $NH(CH_2)_3NH_2$, $NH(CH_2)_2NH_2$, $NH(CH_2)_2NHEt$, $NHCH_2$pyridyl, $NHSO_2$phenyl, $NHC(O)CH_2C(O)$Ot-butyl, $NHC(O)CH_2NH_3$, and $NHCH_2$-imidazol-4-yl.

More preferably, the $R^3$ group of formula I or Ia is selected from OH, $NH_2$, $CH_2NH_2$, $CH_2NHMe$, $CH_2N(Me)_2$, $CH_2CH_2NH_2$, $CH_2CH_2NHMe$, $CH_2CH_2N(Me)_2$, $CH_2C(Me)_2NH_2$, $CH_2C(Me)_2CHMe$, $NHCO_2$t-butyl, phenyl, $NH(CH_2)_3NH_2$, $NH(CH_2)_2NH_2$, $NH(CH_2)_2NHEt$, $NHCH_2$pyridyl, $NHSO_2$phenyl, $NHC(O)CH_2C(O)$Ot-butyl, $NHC(O)CH_2NH_3$, and $NHCH_2$-imidazol-4-yl.

Most preferably, the $R^3$ group of formula I or Ia is selected from $CH_2CH_2NH_2$.

Preferred rings formed by the R and $R^3$ moieties of the Q-C(R)(Q-Ar)$R^3$ group of $R^2$ are selected from a 5–6 membered saturated ring having 0–2 heteroatoms independently selected from nitrogen, oxygen, or sulfur. Examples of such rings formed by R and $R^3$ include piperidinyl, pyrrolidinyl, piperazinyl, morpholinyl, and thiomorpholinyl.

When the $R^2$ group of formula I or Ia is Q-C(R)(Q-Ar)$R^3$, preferred Ar groups of the Q-C(R)(Q-Ar)$R^3$ moiety are selected from an optionally substituted 5–6 membered saturated, partially unsaturated, or fully unsaturated monocyclic ring having 0–4 heteroatoms independently selected from nitrogen, oxygen, or sulfur, or an optionally substituted 9–10 membered saturated, partially unsaturated, or fully unsaturated bicyclic ring having 0–4 heteroatoms independently selected from nitrogen, oxygen, or sulfur. Examples of such monocyclic rings include phenyl, pyridyl, furanyl, pyridone, and thienyl. Examples of such bicyclic rings include benzo[1,3]dioxolyl, naphthyl, indanyl, and indolyl. When present, preferred substituents on the Ar ring of the Q-C(R)(Q-Ar)$R^3$ group of $R^2$ include $R^\circ$, halogen, $OR^\circ$, phenyl, $N(R^\circ)_2$, $NHC(O)R^\circ$, or $SR^\circ$. Examples of such groups include fluoro, chloro, bromo, $CF_3$, OH, OMe, OPh, $OCH_2Ph$, SMe, $NH_2$, NHC(O)Me, methyl, ethyl, isopropyl, isobutyl, and cyclopropyl.

Preferred $R^6$ groups of formula I or Ia, when present, are selected from halogen, R, and $Ar^1$. More preferred $R^6$ groups of formula I or Ia, when present, are selected from halogen, optionally substituted $C_{1-4}$ aliphatic, or an optionally substituted 5–6 membered saturated, partially unsaturated, or fully unsaturated monocyclic ring having 0–4 heteroatoms independently selected from nitrogen, oxygen, or sulfur. Examples of such groups include chloro, bromo, methyl, ethyl, t-butyl, cyclopropyl, isopropyl, phenyl, and pyridyl.

According to another embodiment, the present invention relates to a compound of formula I':

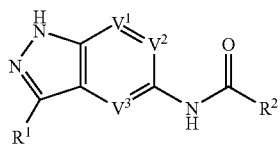

or a pharmaceutically acceptable salt thereof, wherein:
$R^1$ is selected from halogen, CN, $N(R^4)_2$, T-R, or T'-Ar;
T is selected from a valence bond or a $C_{1-6}$ alkylidene chain, wherein up to two methylene units of T are optionally, and independently, replaced by —O—, —N(R)—, —S—, —N(R)C(O)—, —C(O)N(R)—, —C(O)—, or —SO$_2$—;
T' is a $C_{1-6}$ alkylidene chain, wherein up to two methylene units of T' are optionally, and independently, replaced by —O—, —N(R)—, —S—, —N(R)C(O)—, —C(O)N(R)—, —C(O)—, or —SO$_2$—;
each R is independently selected from hydrogen or an optionally substituted $C_{1-6}$ aliphatic group, or:
two R groups on the same nitrogen, taken together with the nitrogen atom attached thereto, form a 5–7 membered saturated, partially unsaturated, or aromatic ring having 1–3 heteroatoms independently selected from nitrogen, oxygen, or sulfur;
$R^2$ is selected from Q-Ar, Q-N(R$^5$)$_2$, or Q-C(R)(Q-Ar)R$^3$, wherein:
R and $R^3$ optionally form a 5–7 membered saturated or partially unsaturated ring having 0–4 heteroatoms independently selected from nitrogen, oxygen, or sulfur;
each Q is independently selected from a valence bond or a $C_{1-4}$ alkylidene chain;
each Ar is independently an optionally substituted ring selected from a 5–7 membered saturated, partially unsaturated, or fully unsaturated monocyclic ring having 0–4 heteroatoms independently selected from nitrogen, oxygen, or sulfur, or an 8–10 membered saturated, partially unsaturated, or fully unsaturated bicyclic ring having 0–4 heteroatoms independently selected from nitrogen, oxygen, or sulfur;
$R^3$ is selected from R', Ar$^1$, Q-OR$^5$, Q-CONHR$^5$, Q-OC(O)NHR$^5$, Q-SR$^5$, Q-N(R$^4$)$_2$, N(R)(Q-Ar), N(R)C(O)Q-N(R$^4$)$_2$, or N(R)Q-N(R$^4$)$_2$;
R' is an optionally substituted $C_{1-6}$ aliphatic group;
each $R^4$ is independently selected from R, COR$^5$ CO$_2$R$^5$ CON(R$^5$)$_2$, SO$_2$R$^5$, SO$_2$N(R$^5$)$_2$, or Ar$^1$;
each $R^5$ is independently selected from R or Ar;
$V^1$, $V^2$ and $V^3$ are each independently selected from nitrogen or C(R$^6$);
each $R^6$ is independently selected from R, Ar$^1$, halogen, CN, NO$_2$, OR, SR, N(R$^4$)$_2$, N(R)COR, N(R)CON(R$^4$)$_2$, N(R)C(O)OR, CON(R$^4$)$_2$, OC(O)N(R$^4$)$_2$, CO$_2$R, OC(O)R, N(R)SO$_2$R, N(R)SO$_2$N(R$^4$)$_2$, SO$_2$R, or SO$_2$N(R$^4$)$_2$; and
each Ar$^1$ is independently selected from an optionally substituted 5–7 membered saturated, partially unsaturated, or fully unsaturated monocyclic ring having 0–4 heteroatoms independently selected from nitrogen, oxygen, or sulfur;
provided that:
when $V^1$, $V^2$, and $V^3$ are each CH and $R^1$ is hydrogen, then $R^2$ is Q-C(R)(Q-Ar)R$^3$, wherein $R^3$ is other than R', Q-OC(O)R$^5$, or OCH$_2$phenyl.
Preferred $R^1$ and $R^2$ groups of formula I' are those described above for compounds of formulae I and Ia. When $R^1$ is T'-Ar, preferred T' groups of formula I' are selected from —NHC(O)—, —NH—, —NHCH$_2$—, —NHSO$_2$—, —CH$_2$NH—, —CH$_2$—, —C≡C—, or —CH$_2$CH$_2$—. More preferred T' groups of formula I' are selected from —NHC(O)—, —NH—, —NHCH$_2$—, —NHSO$_2$—, or —CH$_2$NH—.

According to another embodiment, the present invention relates to a compound of formula Ib:

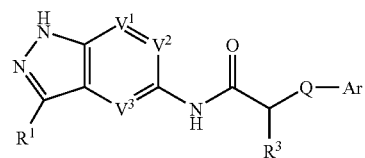

or a pharmaceutically acceptable salt thereof, wherein $R^1$, $R^3$, Q, and Ar are as defined above for compounds of formula I.

Preferred $R^1$ groups of formula Ib include those described above for compounds of formula I and Ia.

Preferred $V^1$, $V^2$, and $V^3$ groups of formula Ib are the preferred $V^1$, $V^2$, and $V^3$ groups set forth for compounds of formula I, supra.

Preferred Q groups of formula Ib include those described above for compounds of formula I and Ia.

Preferred Ar groups of formula Ib include an optionally substituted ring selected from a 5–6 membered saturated, partially unsaturated, or fully unsaturated monocyclic ring having 0–4 heteroatoms independently selected from nitrogen, oxygen, or sulfur, or a 9–10 membered saturated, partially unsaturated, or fully unsaturated bicyclic ring having 0–4 heteroatoms independently selected from nitrogen, oxygen, or sulfur. Examples of such monocyclic rings include phenyl, pyridyl, thienyl, furanyl, cyclopentyl, cyclohexyl, and cycloheptyl. Examples of such bicyclic rings include benzo[1,3]dioxolyl, indan-1-onyl, naphthyl, benzothiophenyl, 2,3-dihydro-1H-isoindolyl, indanyl, benzofuranyl, and indolyl. When present, preferred substituents on the Ar group of formula Ib include R°, halogen, OR°, phenyl, optionally substituted dialkylamino, haloalkyl, C(O)R°, or SR°. Examples of such preferred substituents include tetrazolyl, oxazolyl, isoxazolyl, chloro, bromo, fluoro, OH, OMe, OEt, C(O)phenyl, Ophenyl, N(CH$_2$CH$_2$Cl)$_2$, N(Me)$_2$, CF$_3$, and SCF$_3$.

Preferred $R^3$ groups of formula Ib include R', Q-OR$^5$, Q-N(R$^4$)$_2$, Ar$^1$, N(R)C(O)Q-N(R$^4$)$_2$, and N(R)Q-N(R$^4$)$_2$. Examples of such $R^3$ groups include CH$_2$OH, OH, NH$_2$, CH$_2$NH$_2$, CH$_2$NHMe, CH$_2$N(Me)$_2$, CH$_2$CH$_2$NH$_2$, CH$_2$CH$_2$NHMe, CH$_2$C(Me)$_2$NH$_2$, CH$_2$C(Me)$_2$CHMe, CH$_2$CH$_2$N(Me)$_2$, CH$_2$CH$_2$NH$_2$, NHCO$_2$t-butyl, phenyl, cyclopentyl, methyl, ethyl, isopropyl, cyclopropyl, NH(CH$_2$)$_3$NH$_2$, NH(CH$_2$)$_2$NH$_2$, NH(CH$_2$)$_2$NHEt, NHCH$_2$pyridyl, NHSO$_2$phenyl, NHC(O)CH$_2$C(O)Ot-butyl, NHC(O)CH$_2$NH$_3$, and NHCH$_2$-imidazol-4-yl.

More preferably, the $R^3$ group of formula Ib is selected from OH, NH$_2$, CH$_2$NH$_2$, CH$_2$NHMe, CH$_2$N(Me)$_2$, CH$_2$CH$_2$NH$_2$, CH$_2$CH$_2$NHMe, CH$_2$CH$_2$N(Me)$_2$, CH$_2$C(Me)$_2$NH$_2$, CH$_2$C(Me)$_2$CHMe, NHCO$_2$t-butyl, phenyl, NH(CH$_2$)$_3$NH$_2$, NH(CH$_2$)$_2$NH$_2$, NH(CH$_2$)$_2$NHEt, NHCH$_2$pyridyl, NHSO$_2$phenyl, NHC(O)CH$_2$C(O)Ot-butyl, NHC(O)CH$_2$NH$_3$, and NHCH$_2$-imidazol-4-yl.

Most preferably, the $R^3$ group of formula Ib is selected from CH$_2$CH$_2$NH$_2$.

Preferred rings formed by the R and $R^3$ moieties of the Q-C(R)(Q-Ar)$R^3$ group of formula Ib are selected from a 5–6 membered saturated ring having 0–2 heteroatoms independently selected from nitrogen, oxygen, or sulfur. Examples of such rings formed by R and $R^3$ include piperidinyl, pyrrolidinyl, piperazinyl, morpholinyl, and thiomorpholinyl.

Another embodiment of the present invention relates to a compound of formula IIa:

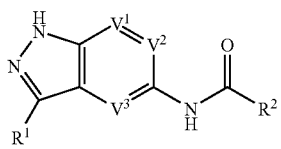

IIa or a pharmaceutically acceptable salt thereof, wherein:

$R^1$ is selected from halogen, CN, N($R^4$)$_2$, or T-R;

T is selected from a valence bond or a $C_{1-6}$ alkylidene chain, wherein up to two methylene units of T are optionally, and independently, replaced by —O—, —N(R)—, —S—, —N(R)C(O)—, —C(O)N(R)—, —C(O)—, or —SO$_2$—;

each R is independently selected from hydrogen or an optionally substituted $C_{1-6}$ aliphatic group, or:

two R groups on the same nitrogen, taken together with the nitrogen atom attached thereto, form a 5–7 membered saturated, partially unsaturated, or aromatic ring having 1–3 heteroatoms independently selected from nitrogen, oxygen, or sulfur;

$R^2$ is Q-C(R)(Q-Ar)$R^3$, wherein:

R and $R^3$ optionally form a 5–7 membered saturated or partially unsaturated ring having 0–4 heteroatoms independently selected from nitrogen, oxygen, or sulfur;

each Q is independently selected from a valence bond or a $C_{1-4}$ alkylidene chain;

each Ar is independently an optionally substituted ring selected from a 5–7 membered saturated, partially unsaturated, or fully unsaturated monocyclic ring having 0–4 heteroatoms independently selected from nitrogen, oxygen, or sulfur, or an 8–10 membered saturated, partially unsaturated, or fully unsaturated bicyclic ring having 0–4 heteroatoms independently selected from nitrogen, oxygen, or sulfur;

$R^3$ is selected from R', Ar$^1$, Q-OR$^5$, Q-OC(O)R$^5$, Q-CONHR$^5$, Q-OC(O)NHR$^5$, Q-SR$^5$, Q-N($R^4$)$_2$, N(R)(Q-Ar), N(R)C(O)Q-N($R^4$)$_2$, or N(R)Q-N($R^4$)$_2$;

R' is an optionally substituted $C_{1-6}$ aliphatic group;

each $R^4$ is independently selected from R, COR, CO$_2$R, CON(R)$_2$, SO$_2$R, SO$_2$N(R)$_2$, or Ar$^1$;

each $R^5$ is independently selected from R or Ar;

$V^1$, $V^2$ and $V^2$ are each independently selected from nitrogen or C($R^6$);

each $R^6$ is independently selected from R, Ar$^1$, halogen CN, NO$_2$, OR, SR, N($R^4$)$_2$, N(R)COR, N(R)CON($R^4$)$_2$, N(R)C(O)OR, CON($R^4$)$_2$, OC(O)N($R^4$)$_2$, CO$_2$R, OC(O)R, N(R)SO$_2$R, N(R)SO$_2$N($R^4$)$_2$, SO$_2$R, or SO$_2$N($R^4$)$_2$; and each Ar$^1$ is independently selected from an optionally substituted 5–7 membered saturated, partially unsaturated, or fully unsaturated monocyclic ring having 0–4 heteroatoms independently selected from nitrogen, oxygen, or sulfur;

provided that when $R^1$ is hydrogen then $R^3$ is other than R', Q-OC(O)R$^5$, or OCH$_2$phenyl.

Preferred $R^1$ groups of formula IIa include halogen, N($R^4$)$_2$, and optionally substituted $C_{1-6}$ aliphatic. Examples of such groups include chloro, bromo, fluoro, NH$_2$, NHMe, NHEt, NH-cyclohexyl, methyl, ethyl, propyl, isopropyl, cyclopropyl, acetylenyl, and t-butyl.

Preferred $V^1$, $V^2$, and $V^3$ groups of formula IIa are the preferred $V^1$, $V^2$, and $V^3$ groups set forth for compounds of formula I, supra.

Preferred Q groups of formula IIa are selected from a valence bond, —CH$_2$—, or —CH$_2$CH$_2$—.

Preferred $R^3$ groups of formula IIa include R', Q-OR$^5$, Q-N($R^4$)$_2$, Ar$^1$, N(R)C(O)Q-N($R^4$)$_2$, and N(R)Q-N($R^4$)$_2$. Examples of such $R^3$ groups include CH$_2$OH, OH, NH$_2$, CH$_2$NH$_2$, CH$_2$NHMe, CH$_2$N(Me)$_2$, CH$_2$CH$_2$NH$_2$, CH$_2$CH$_2$NHMe, CH$_2$C(Me)$_2$NH$_2$, CH$_2$C(Me)$_2$CHMe, CH$_2$CH$_2$N(Me)$_2$, CH$_2$CH$_2$NH$_2$, NHCO$_2$t-butyl, phenyl, cyclopentyl, methyl, ethyl, isopropyl, cyclopropyl, NH(CH$_2$)$_3$NH$_2$, NH(CH$_2$)$_2$NH$_2$, NH(CH$_2$)$_2$NHEt, NHCH$_2$pyridyl, NHSO$_2$phenyl, NHC(O)CH$_2$C(O)Ot-butyl, NHC(O)CH$_2$NH$_3$, and NHCH$_2$-imidazol-4-yl.

More preferably, the $R^3$ group of formula IIa is selected from OH, NH$_2$, CH$_2$NH$_2$, CH$_2$NHMe, CH$_2$N(Me)$_2$, CH$_2$CH$_2$NH$_2$, CH$_2$CH$_2$NHMe, CH$_2$CH$_2$N(Me)$_2$, CH$_2$C(Me)$_2$NH$_2$, CH$_2$C(Me)$_2$CHMe, NHCO$_2$t-butyl, phenyl, NH(CH$_2$)$_3$NH$_2$, NH(CH$_2$)$_2$NH$_2$, NH(CH$_2$)$_2$NHEt, NHCH$_2$pyridyl, NHSO$_2$phenyl, NHC(O)CH$_2$C(O)Ot-butyl, NHC(O)CH$_2$NH$_3$, and NHCH$_2$-imidazol-4-yl.

Most preferably, the $R^3$ group of formula IIa is selected from CH$_2$CH$_2$NH$_2$.

Preferred rings formed by the R and $R^3$ moieties of $R^2$ of formula IIa are selected from a 5–6 membered saturated ring having 0–2 heteroatoms independently selected from nitrogen, oxygen, or sulfur. Examples of such rings formed by R and $R^3$ include piperidinyl, pyrrolidinyl, piperazinyl, morpholinyl, and thiomorpholinyl.

Preferred Ar groups of $R^2$ of formula IIa are selected from an optionally substituted 5–6 membered saturated, partially unsaturated, or fully unsaturated monocyclic ring having 0–4 heteroatoms independently selected from nitrogen, oxygen, or sulfur, or an optionally substituted 9–10 membered saturated, partially unsaturated, or fully unsaturated bicyclic ring having 0–4 heteroatoms independently selected from nitrogen, oxygen, or sulfur. Examples of such monocyclic rings include phenyl, pyridyl, furanyl, and thienyl. Examples of such bicyclic rings include benzo[1,3]dioxolyl, naphthyl, indanyl, and indolyl. When present, preferred substituents on the Ar ring of the Q-C(R)(Q-Ar)$R^3$ group of $R^2$ of formula IIa include R°, halogen, OR°, phenyl, N(R°)$_2$, NHC(O)R°, or SR°. Examples of such groups include fluoro, chloro, bromo, CF$_3$, OH, OMe, OPh, OCH$_2$PH, SMe, NH$_2$, NHC(O)Me, methyl, ethyl, isopropyl, isobutyl, and cyclopropyl.

Another embodiment relates to a compound of formula IIb:

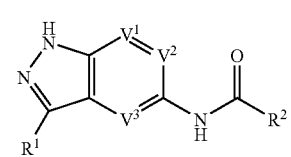

IIb or a pharmaceutically acceptable salt thereof, wherein:

$R^1$ is T-Ar;

each T is independently selected from a valence bond or a $C_{1-6}$ alkylidene chain, wherein up to two methylene units of T are optionally, and independently, replaced by —O—, —N(R)—, —S—, —N(R)C(O)—, —C(O)N(R)—, —C(O)—, or —SO$_2$—;

each R is independently selected from hydrogen or an optionally substituted $C_{1-6}$ aliphatic group, or:
two R groups on the same nitrogen, taken together with the nitrogen atom attached thereto, form a 5–7 membered saturated, partially unsaturated, or aromatic ring having 1–3 heteroatoms independently selected from nitrogen, oxygen, or sulfur;

$R^2$ is Q-C(R)(Q-Ar)$R^3$, wherein:
R and $R^3$ optionally form a 5–7 membered saturated or partially unsaturated ring having 0–4 heteroatoms independently selected from nitrogen, oxygen, or sulfur;

each Q is independently selected from a valence bond or a $C_{1-4}$ alkylidene chain;

each Ar is independently an optionally substituted ring selected front a 5–7 membered saturated, partially unsaturated, or fully unsaturated monocyclic ring having 0–4 heteroatoms independently selected from nitrogen, oxygen, or sulfur, or an 8–10 membered saturated, partially unsaturated, or fully unsaturated bicyclic ring having 0–4 heteroatoms independently selected from nitrogen, oxygen, or sulfur;

$R^3$ is selected from R', $Ar^1$, Q-OR$^5$, Q-OC(O)R$^5$, Q-CONHR$^5$, Q-OC(O)NHR$^5$, Q-SR$^5$, Q-N(R$^4$)$_2$, N(R)(Q-Ar), N(R)C(O)Q-N(R$^4$)$_2$, or N(R)Q-N(R$^4$)$_2$;

R' is an optionally substituted $C_{1-6}$ aliphatic group;

each $R^4$ is independently selected from R, COR$^5$, CO$_2$R$^5$, CON(R$^5$)$_2$, SO$_2$R$^5$, SO$_2$N(R$^5$)$_2$, or $Ar^1$;

each $R^5$ is independently selected from R or Ar;

$V^1$, $V^2$ and $V^3$ are each independently selected from nitrogen or C(R$^6$);

each $R^6$ is independently selected from R, $Ar^1$, halogen, CN, NO$_2$, OR, SR, N(R$^4$)$_2$, N(R)COR, N(R)CON(R$^4$)$_2$, N(R)C(O)OR, CON(R$^4$)$_2$, OC(O)N(R$^4$)$_2$, CO$_2$R, OC(O)R, N(R)SO$_2$R, N(R)SO$_2$N(R$^4$)$_2$, SO$_2$R, or SO$_2$N(R$^4$)$_2$; and each $Ar^1$ is independently selected from an optionally substituted 5–7 membered saturated, partially unsaturated, or fully unsaturated monocyclic ring having 0–4 heteroatoms independently selected from nitrogen, oxygen, or sulfur;

provided that when $V^1$, $V^2$, and $V^3$ are each CH, T is a valence bond, and $R^2$ is Q-C(R)(Q-Ar)$R^3$, wherein Ar is an optionally substituted phenyl ring, then $R^3$ is other than Q-OR$^5$ or C(O)NH$_2$.

Preferred $V^1$, $V^2$, and $V^3$ groups of formula IIb are those set forth for compounds of formula I, supra.

Preferred Ar groups of $R^1$ of formula IIb are selected from an optionally substituted 5–6 membered aryl ring having 0–4 heteroatoms independently selected from nitrogen, oxygen, or sulfur. Preferred T moieties of the T-Ar group of $R^1$ of formula IIb are selected from a valence bond, —NHC(O)—, —NH—, —NHCH$_2$—, —NHSO$_2$—, —CH$_2$NH—, —C≡C—, —CH$_2$— or —CH$_2$CH$_2$—. Most preferred T moieties of the T-Ar group of $R^1$ are selected from —NHC(O)—, —NH—, —NHCH$_2$—, —CH$_2$— or —CH$_2$CH$_2$—. Examples of $R^1$ groups of formula IIb include NHCH$_2$(optionally substituted phenyl), NHC(O)(optionally substituted phenyl), NHC(O)NH(optionally substituted phenyl), NHC(O)CH$_2$(optionally substituted phenyl), NHC(O)CH$_2$CH$_2$(optionally substituted phenyl), NHC(O)(optionally substituted phenyl), NHC(O)naphthyl, NHC(O)thienyl, NHC(O)pyridyl, NHC(O)furanyl, methyl, ethyl, propyl, isopropyl, cyclopropyl, acetylenyl, and t-butyl.

Preferred substituents on the Ar group of $R^1$ of formula IIb, when present, include R°, halogen, nitro, CN, OR°, SR°, N(R°)$_2$, SO$_2$R°, C(O)R°, C(O)OR, and C(O)N(R°)$_2$, wherein each R° is as defined supra. Examples of such groups include chloro, bromo, fluoro, CN, nitro, OMe, OPh, OCF$_3$, OCH$_2$Ph, OEt, SCHF$_2$, methyl, ethyl, isopropyl, propyl, vinyl, CF$_3$, acetylenyl, CH$_2$Ph, CH$_2$NH$_2$, CH$_2$N(Et)$_2$, CH$_2$morpholin-4-yl, CH$_2$piperdin-1-yl, CH$_2$imidazol-1-yl, CH$_2$piperazin-1-yl, C(O)NH$_2$, C(O)Me, SO$_2$Me, NHEt, and NHMe.

Preferred Q groups of formula IIb are those set forth above for compounds of formula I and Ib.

Preferred $R^3$ groups of formula IIb include R', Q-OR$^5$, Q-N(R$^4$)$_2$, $Ar^1$, N(R)C(O)Q-N(R$^4$)$_2$, and N(R)Q-N(R$^4$)$_2$. Examples of such $R^3$ groups include CH$_2$OH, OH, NH$_2$, CH$_2$NH$_2$, CH$_2$NHMe, CH$_2$N(Me)$_2$, CH$_2$CH$_2$NH$_2$, CH$_2$CH$_2$NHMe, CH$_2$C(Me)$_2$NH$_2$, CH$_2$C(Me)$_2$CHMe, CH$_2$CH$_2$N(Me)$_2$, CH$_2$CH$_2$NH$_2$, NHCO$_2$t-butyl, phenyl, cyclopentyl, methyl, ethyl, isopropyl, cyclopropyl, NH(CH$_2$)$_3$NH$_2$, NH(CH$_2$)$_2$NH$_2$, NH(CH$_2$)$_2$NHEt, NHCH$_2$pyridyl, NHSO$_2$phenyl, NHC(O)CH$_2$C(O)Ot-butyl, NHC(O)CH$_2$NH$_3$, and NHCH$_2$-imidazol-4-yl.

More preferably, the $R^3$ group of formula IIb is selected from CH$_2$NHMe, CH$_2$N(Me)$_2$, CH$_2$CH$_2$NH$_2$, CH$_2$CH$_2$NHMe, CH$_2$CH$_2$N(Me)$_2$, CH$_2$C(Me)$_2$NH$_2$, CH$_2$C(Me)$_2$CHMe, NHCO$_2$t-butyl, phenyl, NH(CH$_2$)$_3$NH$_2$, NH(CH$_2$)$_2$NH$_2$, NH(CH$_2$)$_2$NHEt, NHCH$_2$pyridyl, NHSO$_2$phenyl, NHC(O)CH$_2$C(O)Ot-butyl, NHC(O)CH$_2$NH$_3$, and NHCH$_2$-imidazol-4-yl.

Most preferably, the $R^3$ group of formula IIb is selected from CH$_2$CH$_2$NH$_2$.

Preferred rings formed by the R and $R^3$ moieties of $R^2$ of formula IIb are selected from a 5–6 membered saturated ring having 0–2 heteroatoms independently selected from nitrogen, oxygen, or sulfur. Examples of such rings formed by R and $R^3$ include piperidinyl, pyrrolidinyl, piperazinyl, morpholinyl, and thiomorpholinyl.

Preferred Ar groups of $R^2$ of formula IIb are selected from an optionally substituted 5–6 membered saturated, partially unsaturated, or fully unsaturated monocyclic ring having 0–4 heteroatoms independently selected from nitrogen, oxygen, or sulfur, or an optionally substituted 9–10 membered saturated, partially unsaturated, or fully unsaturated bicyclic ring having 0–4 heteroatoms independently selected from nitrogen, oxygen, or sulfur. Examples of such monocyclic rings include phenyl, pyridyl, pyrimidinyl, pyridonyl, furanyl, tetrazolyl, thienyl, cyclopentyl, cyclohexyl, and cycloheptyl. Examples of such bicyclic rings include benzo[1,3]dioxolyl, indan-1-onyl, naphthyl, benzothiophenyl, 2,3-dihydro-1H-isoindolyl, indanyl, benzofuranyl, and indolyl. When present, preferred substituents on the Ar ring of the Q-C(R)(Q-Ar)R$^3$ group of $R^2$ of formula IIb include R°, halogen, OR°, phenyl, N(R°)$_2$, NHC(O)R°, or SR°. Examples of such groups include fluoro, chloro, bromo, CF$_3$, OH, OMe, OPh, OCH$_2$PH, SMe, NH$_2$, NHC(O)Me, methyl, ethyl, isopropyl, isobutyl, and cyclopropyl.

According to another embodiment, the present invention relates to a compound of formula III:

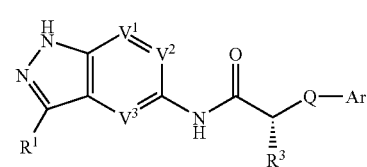

or a pharmaceutically acceptable salt thereof, wherein $R^1$, $R^3$, Q, and Ar are as defined above for compounds of formula I. Preferred $V^1$, $V^2$, $V^3$, $R^1$, $R^3$, Q, and Ar groups of formula III are those set forth above for compounds of formula I or Ib.

According to another embodiment, the present invention relates to a compound of formula IV:

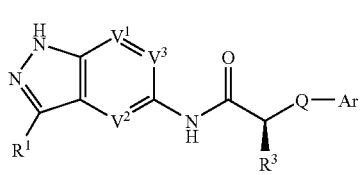

IV or a pharmaceutically acceptable salt thereof, wherein $R^1$, $R^3$, Q, and Ar are as defined above for compounds of formula I. Preferred $V^1$, $V^2$, $V^3$, $R^1$, $R^3$, Q, and Ar groups of formula IV are those set forth above for compounds of formula I or Ib.

According to another embodiment, the present invention relates to a compound of formula V:

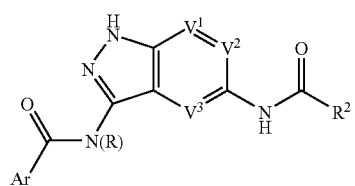

V or a pharmaceutically acceptable salt thereof, wherein:
each R is independently selected from hydrogen or an optionally substituted $C_{1-6}$ aliphatic group, or:
  two R groups on the same nitrogen, taken together with the nitrogen atom attached thereto, form a 5–7 membered saturated, partially unsaturated, or aromatic ring having 1–3 heteroatoms independently selected from nitrogen, oxygen, or sulfur;
$R^2$ is Q-C(R)(Q-Ar)$R^3$, wherein:
  R and $R^3$ optionally form a 5–7 membered saturated or partially unsaturated ring having 0–4 heteroatoms independently selected from nitrogen, oxygen, or sulfur;
each Q is independently selected from a valence bond or a $C_{1-4}$ alkylidene chain;
each Ar is independently an optionally substituted ring selected from a 5–7 membered saturated, partially unsaturated, or fully unsaturated monocyclic ring having 0–4 heteroatoms independently selected from nitrogen, oxygen, or sulfur, or an 8–10 membered saturated, partially unsaturated, or fully unsaturated bicyclic ring having 0–4 heteroatoms independently selected from nitrogen, oxygen, or sulfur;
$R^3$ is selected from R', $Ar^1$, Q-OR$^5$, Q-OC(O)R$^5$, Q-CONHR$^5$, Q-OC(O)NHR$^5$, Q-SR$^5$, Q-N(R$^4$)$_2$, N(R)(Q-Ar), N(R)C(O)Q-N(R$^4$)$_2$, or N(R)Q-N(R$^4$)$_2$;
R' is an optionally substituted $C_{1-6}$ aliphatic group;
each $R^4$ is independently selected from R, COR$^5$, CO$_2$R$^5$, CON(R$^5$)$_2$, SO$_2$R$^5$, SO$_2$N(R$^5$)$_2$, or $Ar^1$;
each $R^5$ is independently selected from R or Ar;
$V^1$, $V^2$ and $V^3$ are each independently selected from nitrogen or C(R$^6$);
each $R^6$ is independently selected from R, $Ar^1$, halogen, CN, NO$_2$, OR, SR, N(R$^4$)$_2$, N(R)COR, N(R)CON(R$^4$)$_2$, N(R) C(O)OR, CON(R$^4$)$_2$, OC(O)N(R$^4$)$_2$, CO$_2$R, OC(O)R, N(R)SO$_2$R, N(R)SO$_2$N(R$^4$)$_2$, SO$_2$R, or SO$_2$N(R$^4$)$_2$; and each $Ar^1$ is independently selected from an optionally substituted 5–7 membered saturated, partially unsaturated, or fully unsaturated monocyclic ring having 0–4 heteroatoms independently selected from nitrogen, oxygen, or sulfur.

Preferred Ar groups of formula V are those set forth for compounds of formula I or Ib, supra.

Preferred $V^1$, $V^2$, and $V^3$ groups of formula V are those set forth for compounds of formula I or Ib, supra.

Preferred $R^2$ groups of formula V are those set forth for compounds of formula I or Ib, supra.

Representative compounds of formula I are set forth in Table 1 below.

TABLE 1

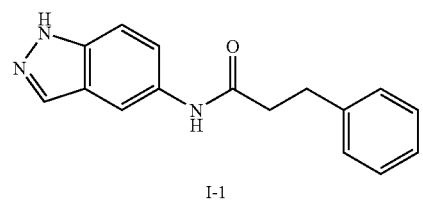

I-1

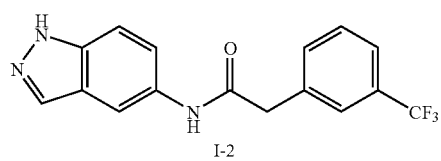

I-2

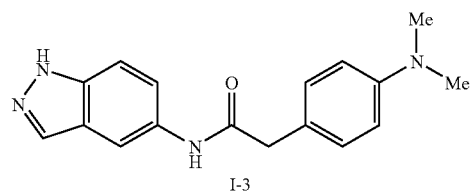

I-3

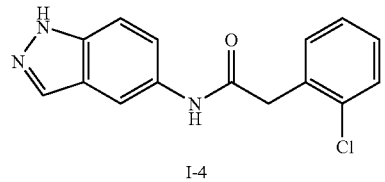

I-4

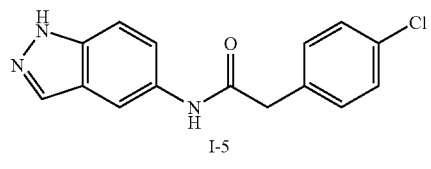

I-5

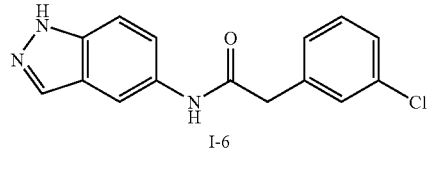

I-6

TABLE 1-continued
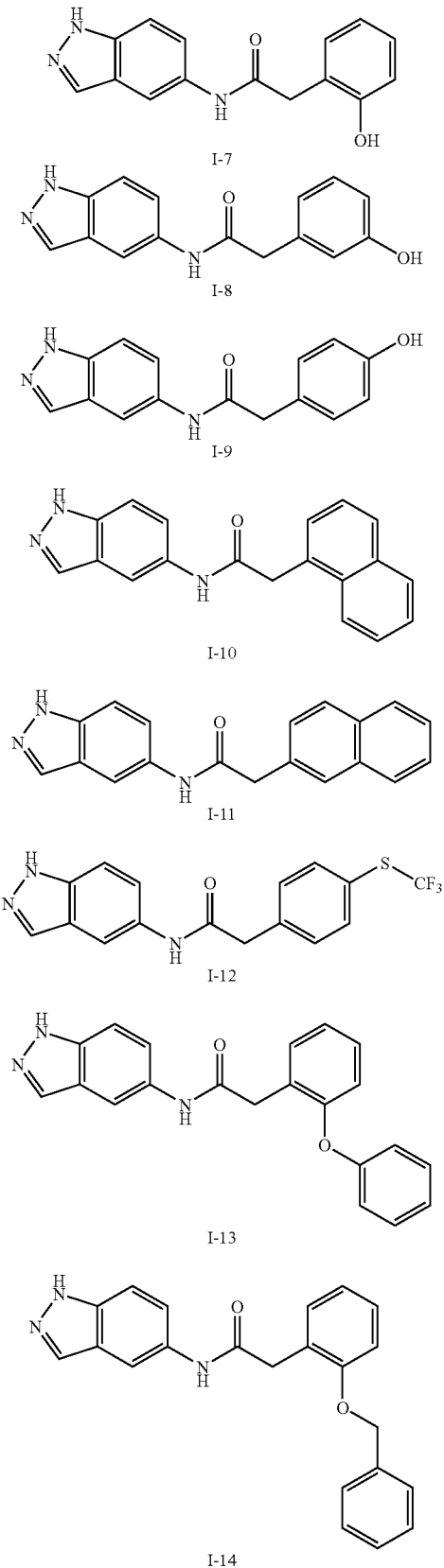
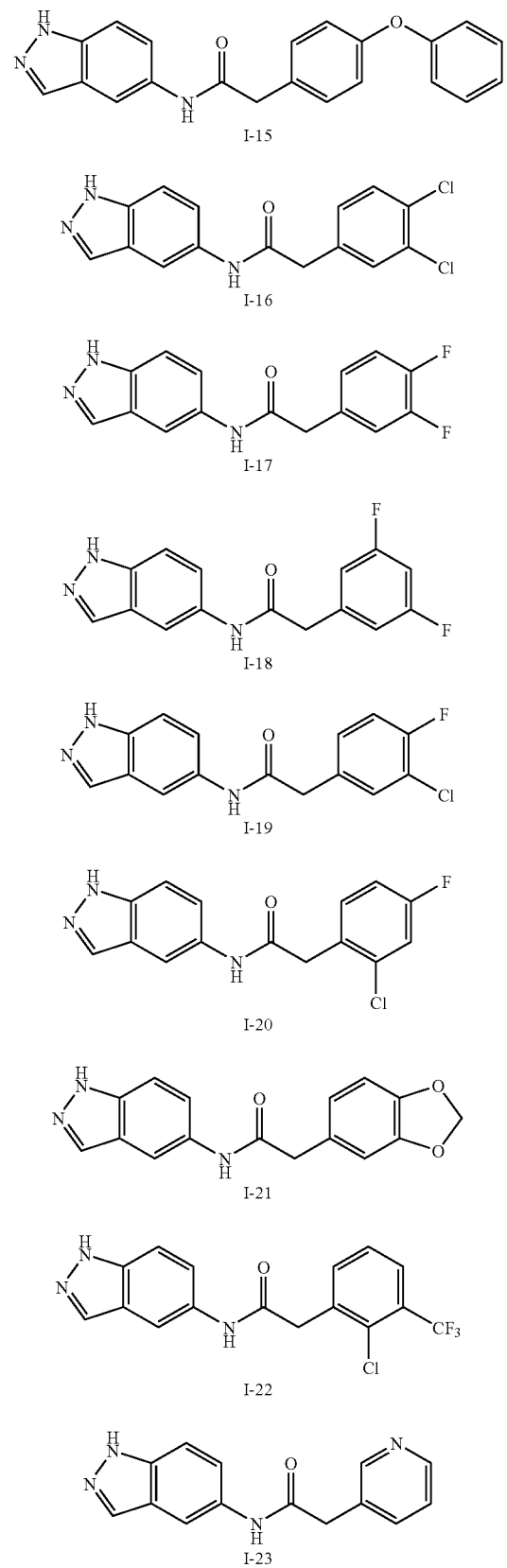

TABLE 1-continued
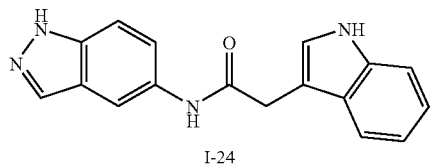
I-24
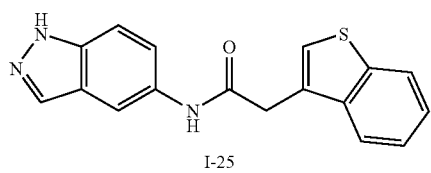
I-25
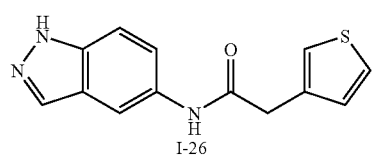
I-26
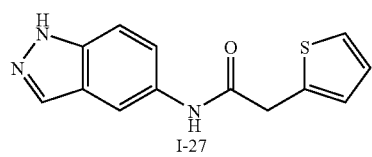
I-27
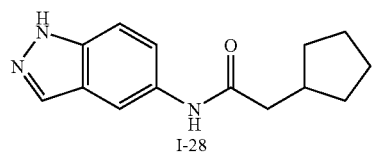
I-28
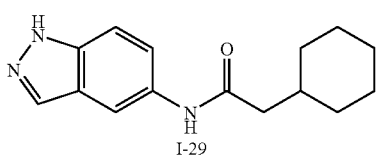
I-29
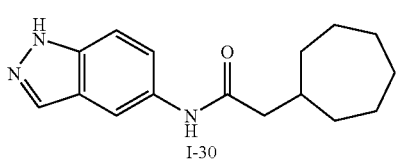
I-30
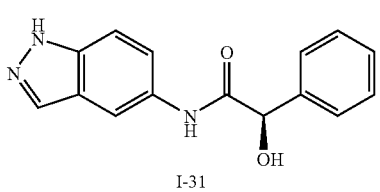
I-31
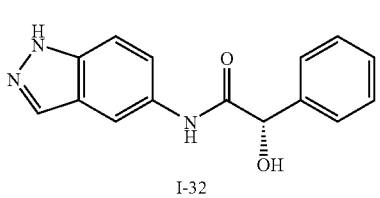
I-32
TABLE 1-continued
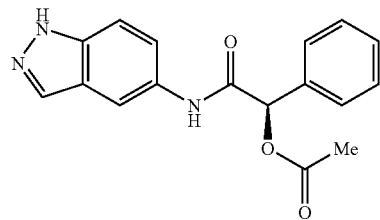
I-33
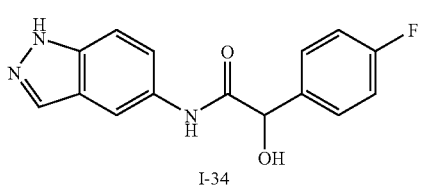
I-34
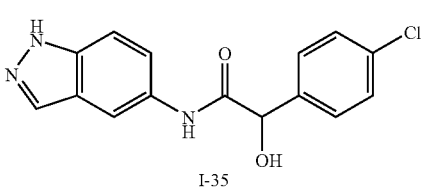
I-35
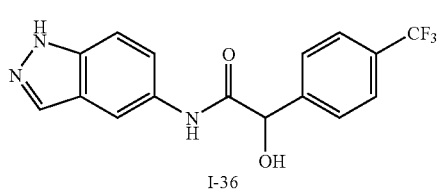
I-36
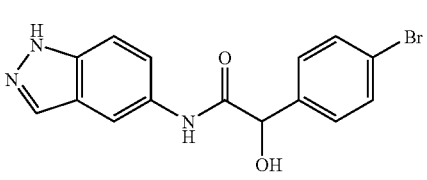
I-37
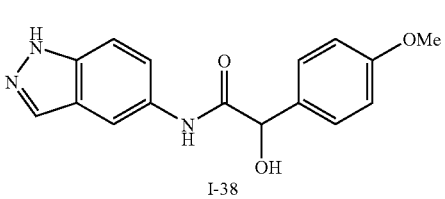
I-38
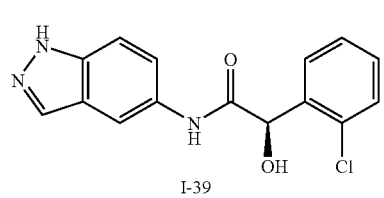
I-39
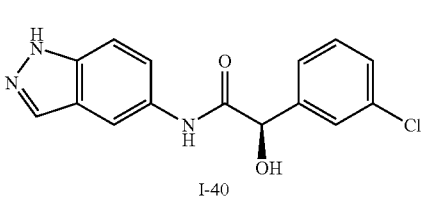
I-40

TABLE 1-continued
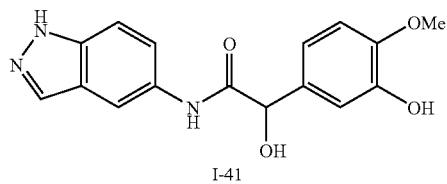
I-41
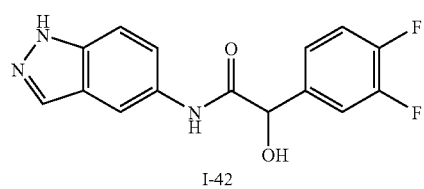
I-42
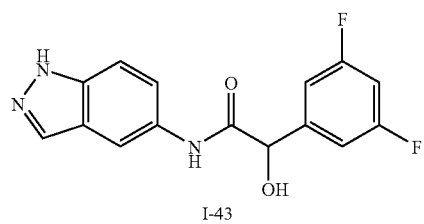
I-43
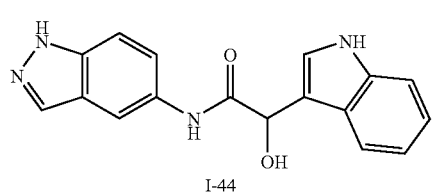
I-44
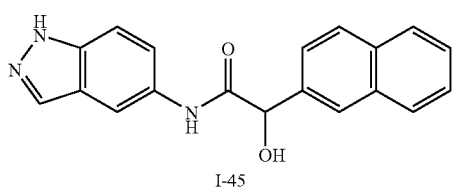
I-45
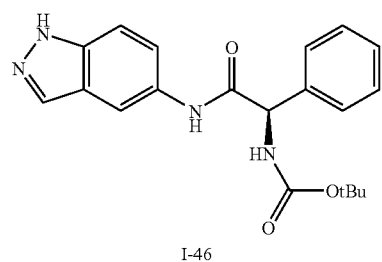
I-46
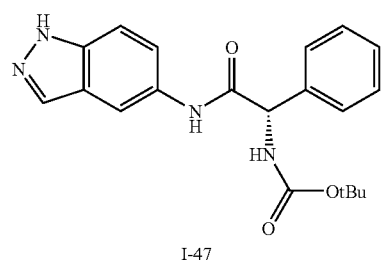
I-47
TABLE 1-continued
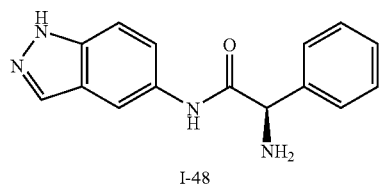
I-48
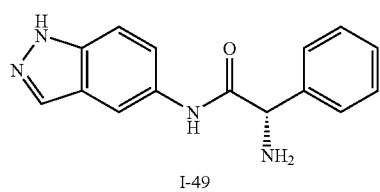
I-49
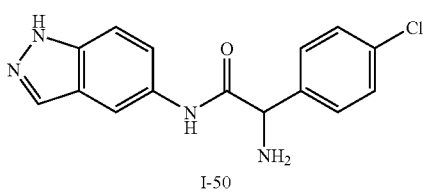
I-50
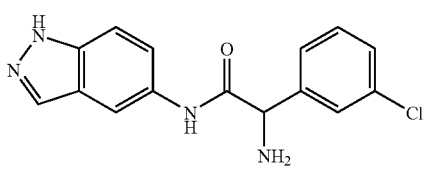
I-51
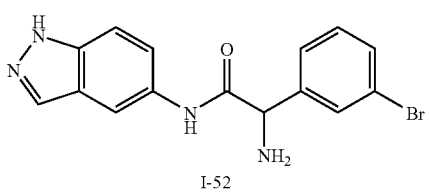
I-52
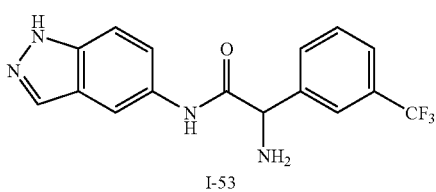
I-53
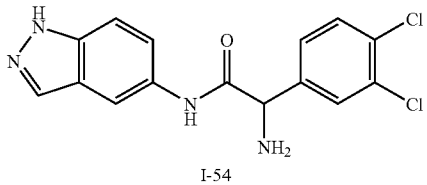
I-54
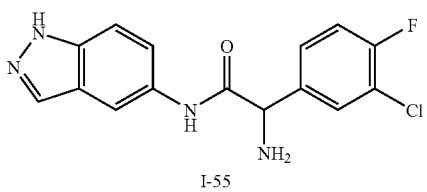
I-55

TABLE 1-continued
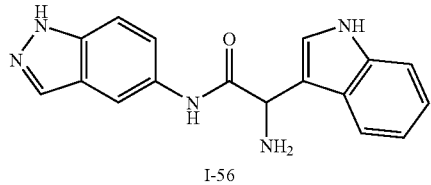
I-56
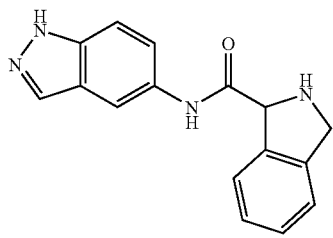
I-57
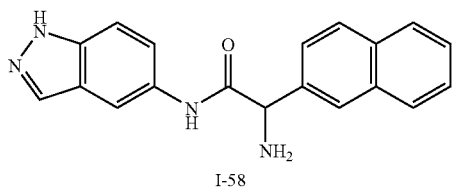
I-58
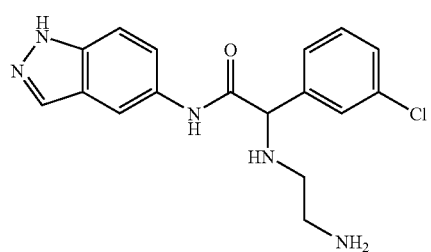
I-59
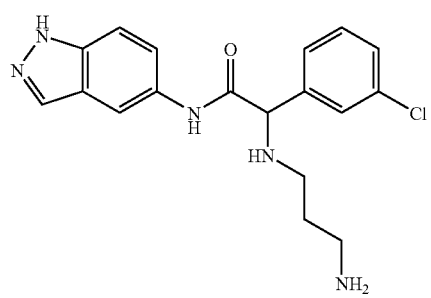
I-60
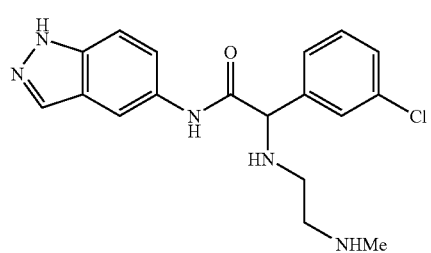
I-61
TABLE 1-continued
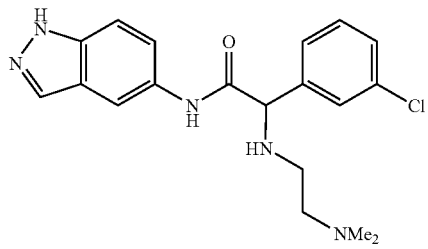
I-62
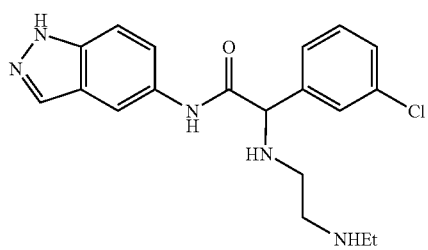
I-63
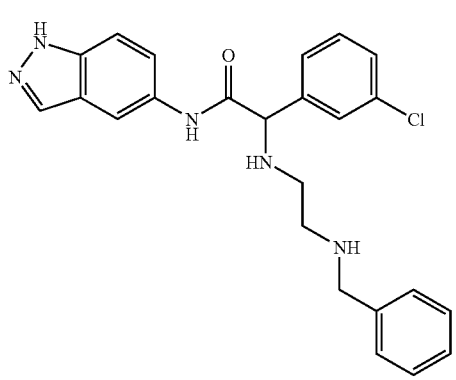
I-64
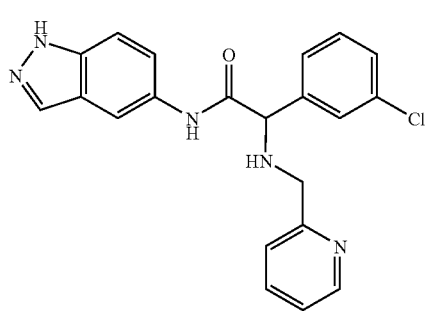
I-65
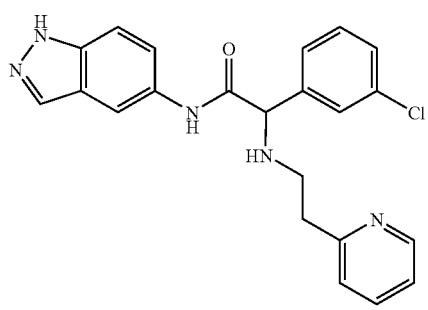
I-66

TABLE 1-continued
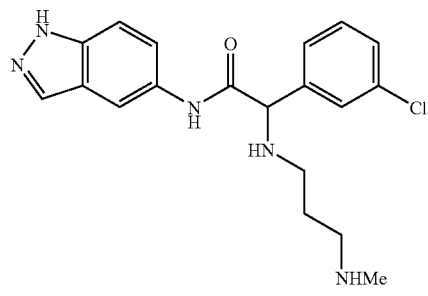
I-67
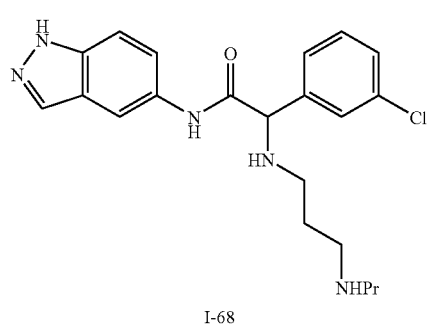
I-68
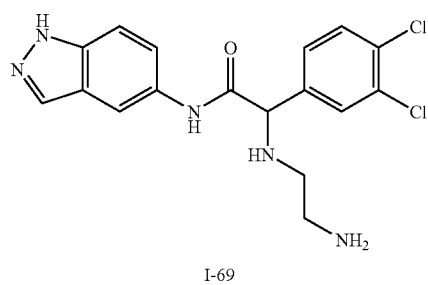
I-69
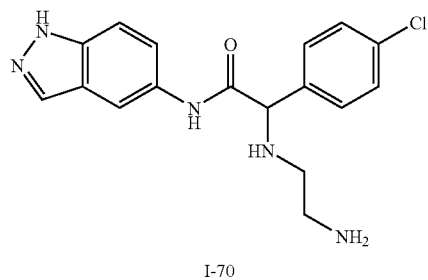
I-70
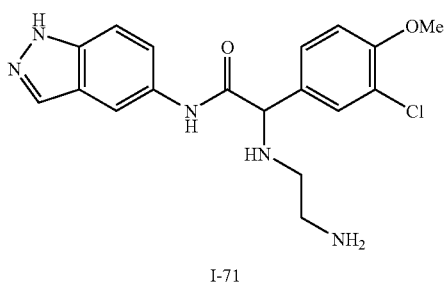
I-71
TABLE 1-continued
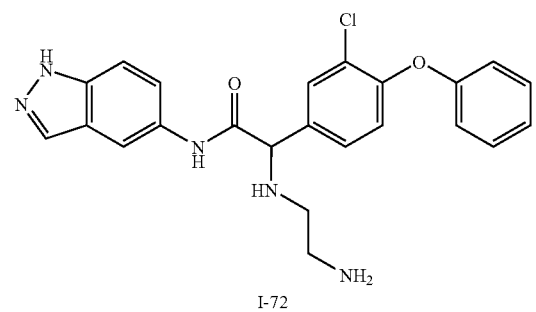
I-72
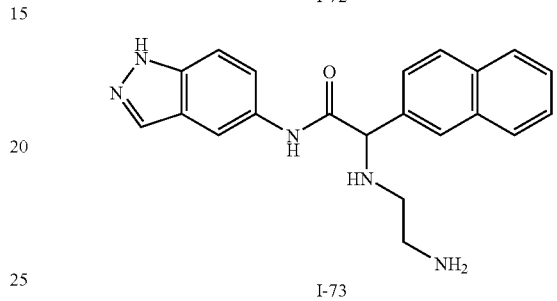
I-73
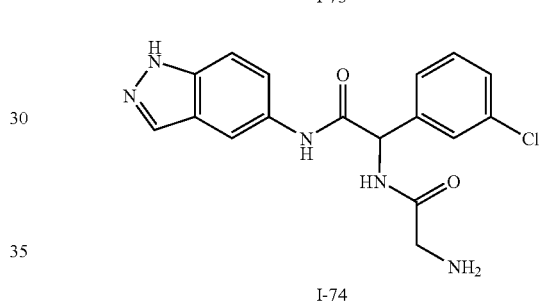
I-74
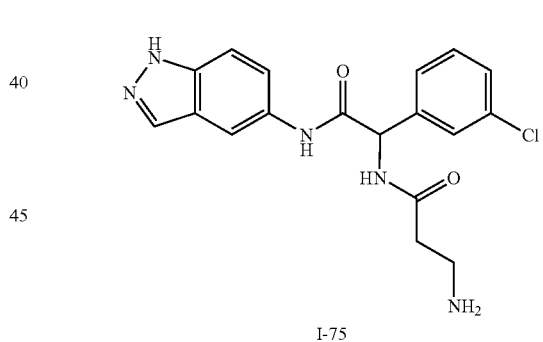
I-75
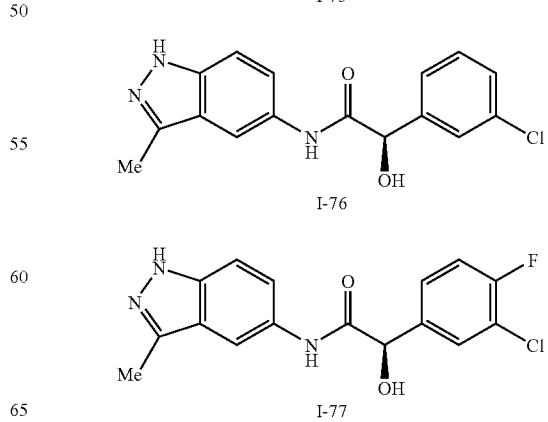
I-76
I-77

TABLE 1-continued
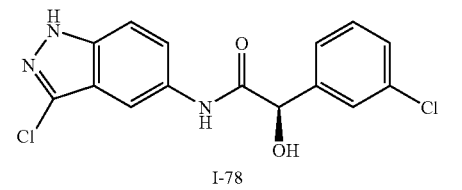
I-78
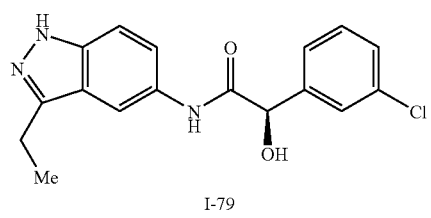
I-79
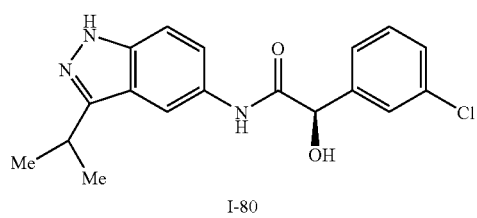
I-80
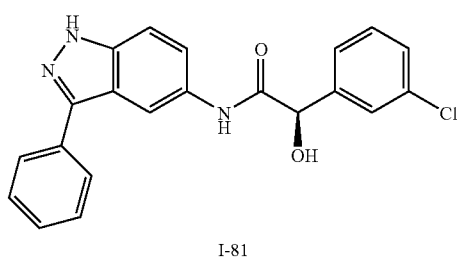
I-81
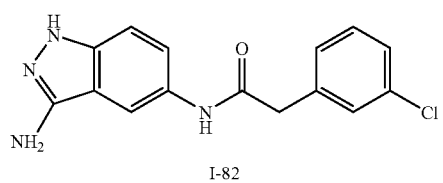
I-82
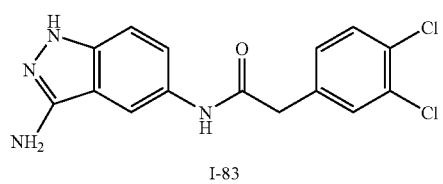
I-83
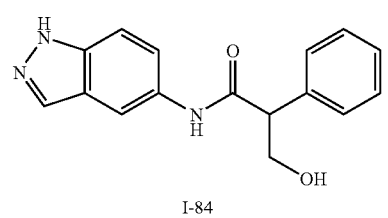
I-84
TABLE 1-continued
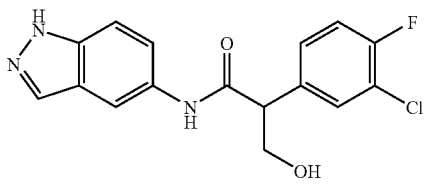
I-85
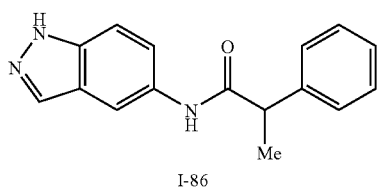
I-86
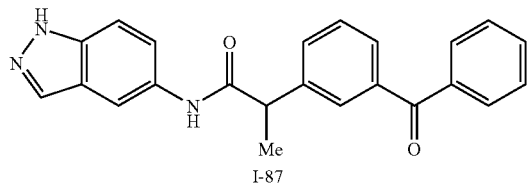
I-87
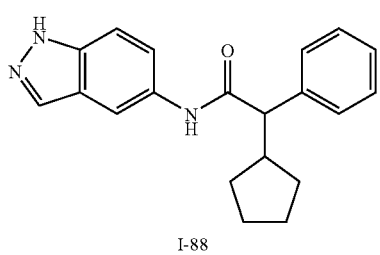
I-88
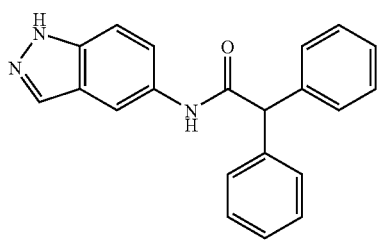
I-89
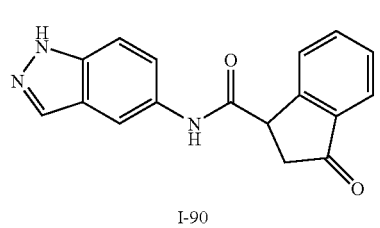
I-90
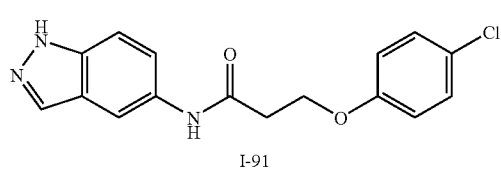
I-91

TABLE 1-continued
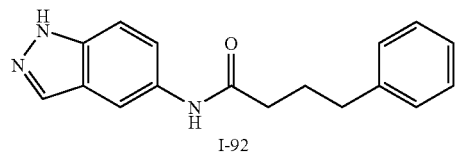
I-92
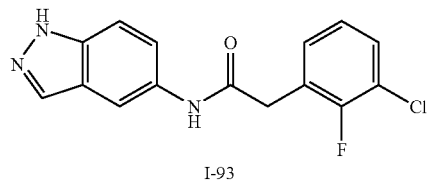
I-93
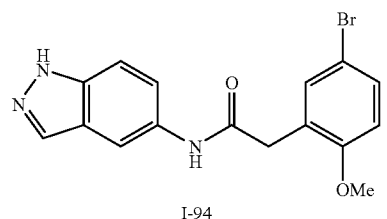
I-94
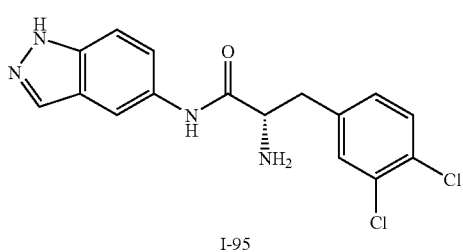
I-95
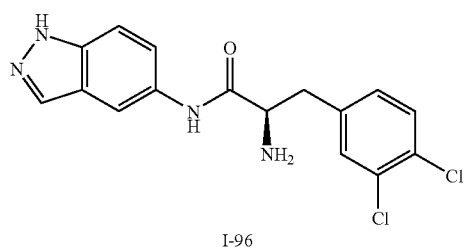
I-96
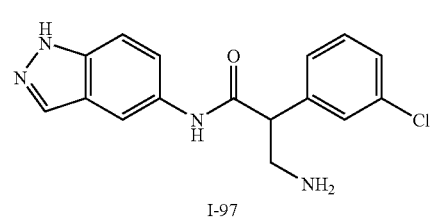
I-97
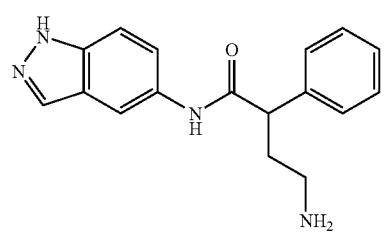
I-98
TABLE 1-continued
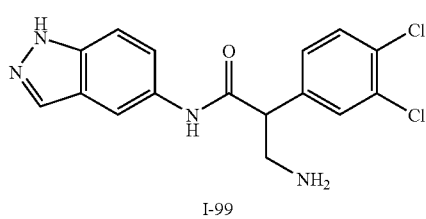
I-99
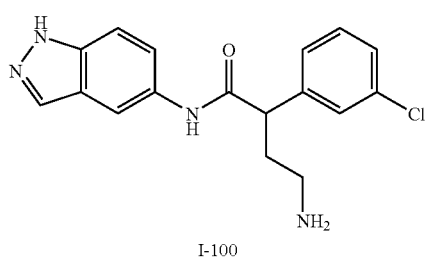
I-100
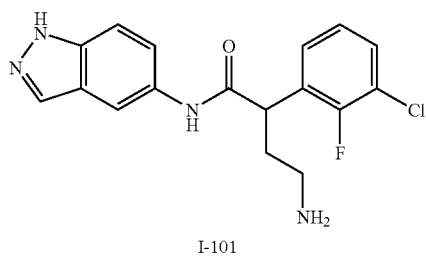
I-101
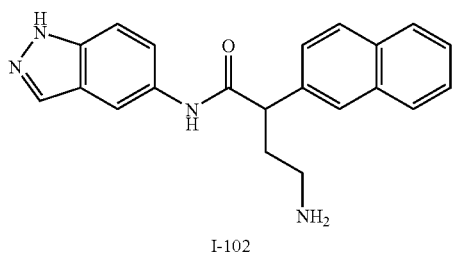
I-102
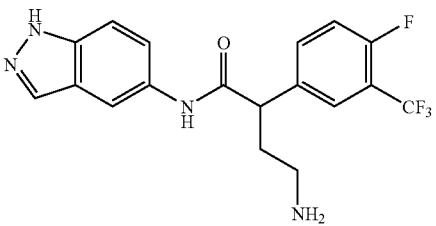
I-103
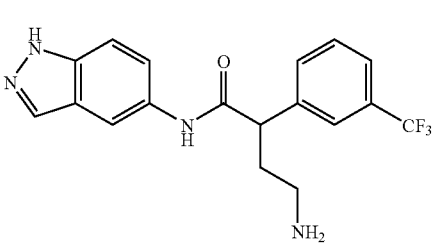
I-104

TABLE 1-continued
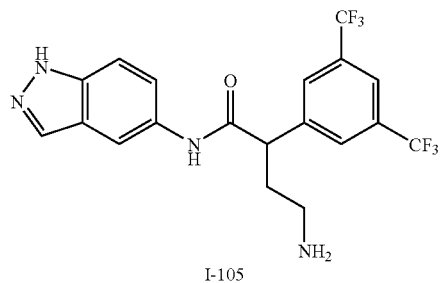
I-105
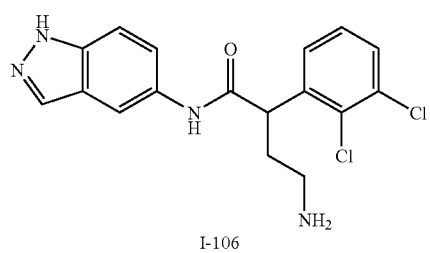
I-106
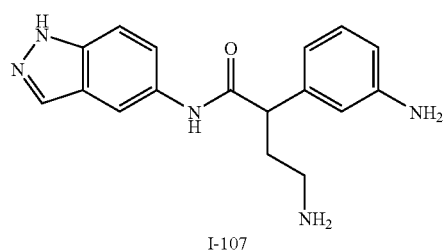
I-107
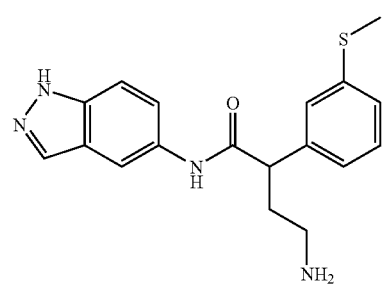
I-108
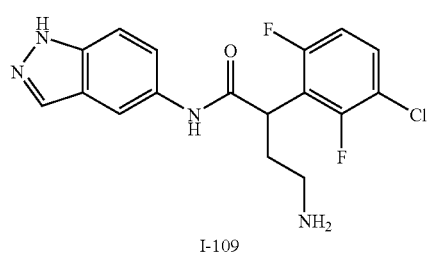
I-109
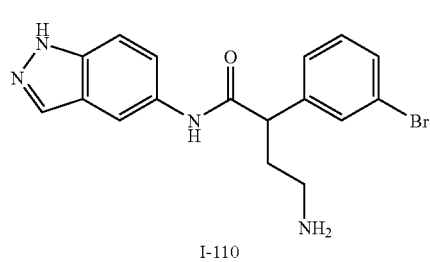
I-110
TABLE 1-continued
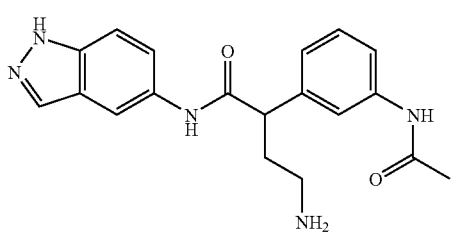
I-111
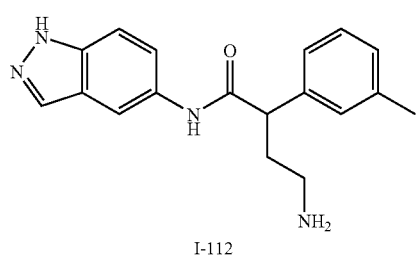
I-112
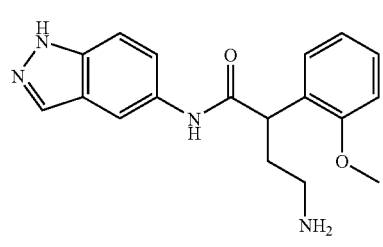
I-113
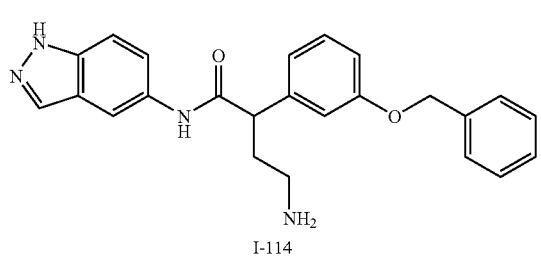
I-114
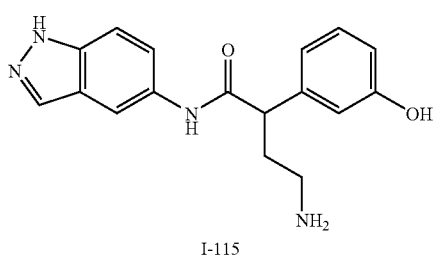
I-115
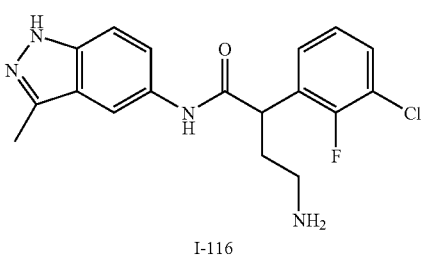
I-116

TABLE 1-continued
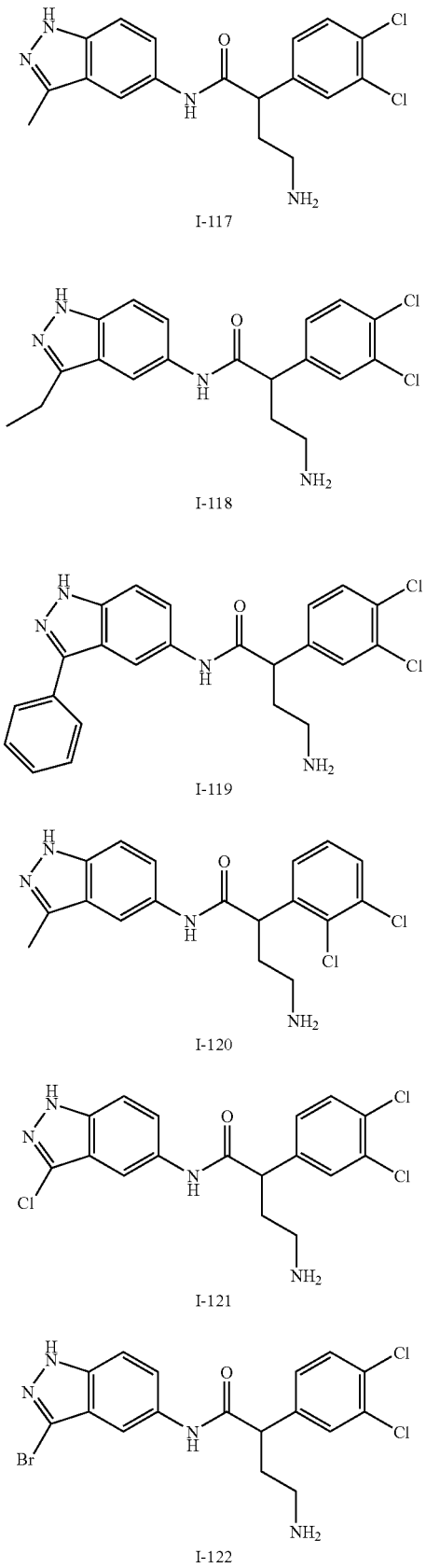
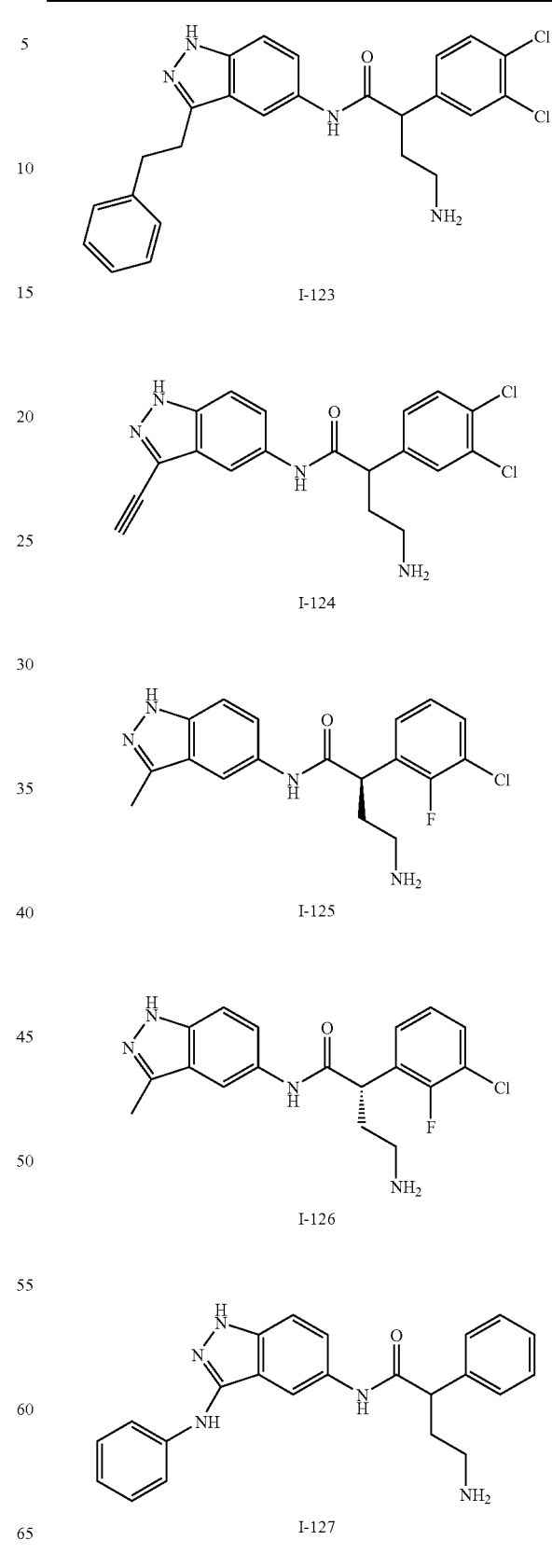

TABLE 1-continued
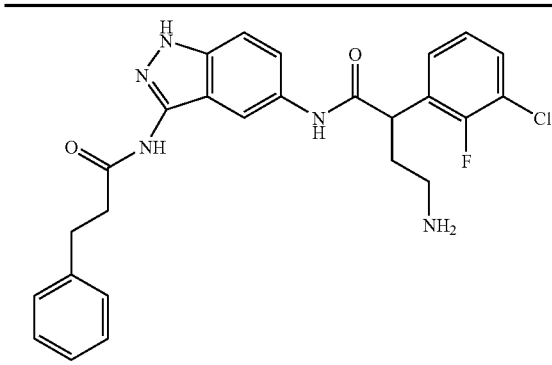
I-128
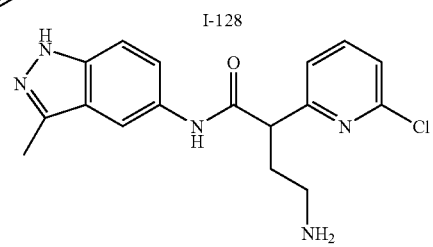
I-129
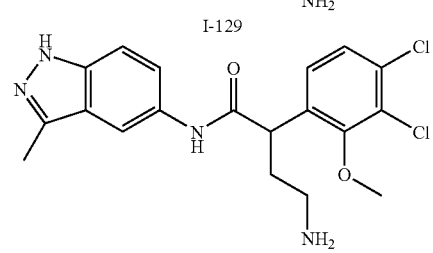
I-130
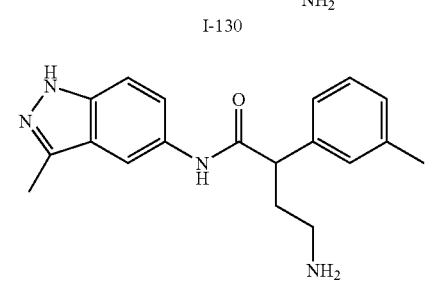
I-131
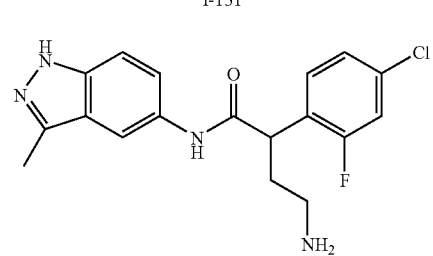
I-132
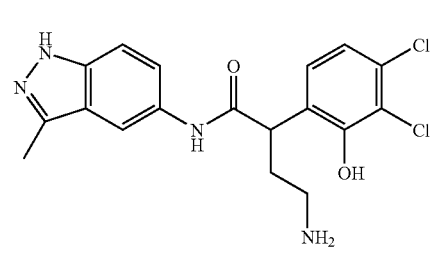
I-133
TABLE 1-continued
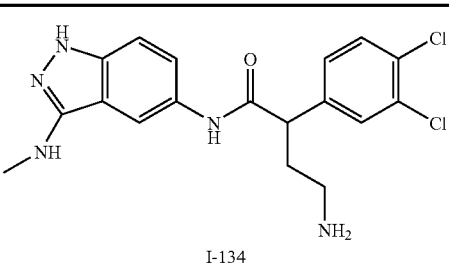
I-134
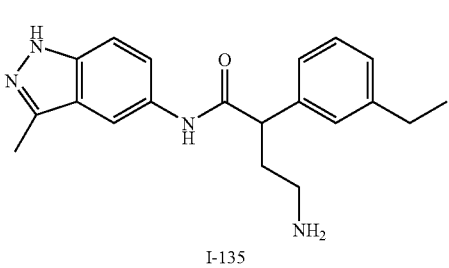
I-135
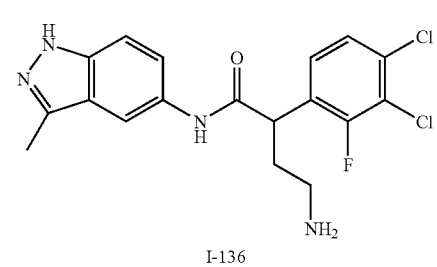
I-136
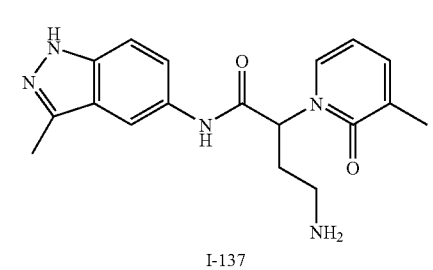
I-137
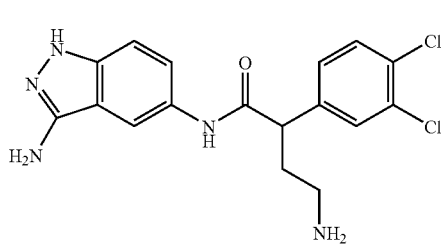
I-138
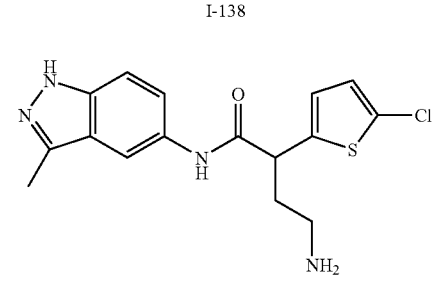
I-139

TABLE 1-continued
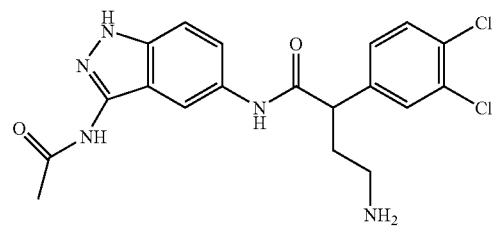
I-140
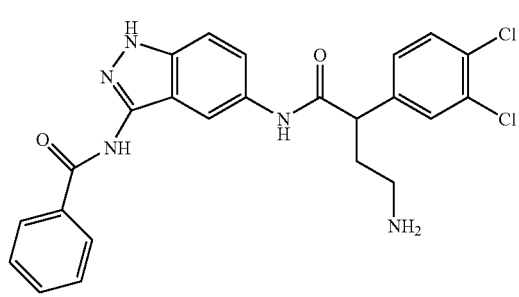
I-141
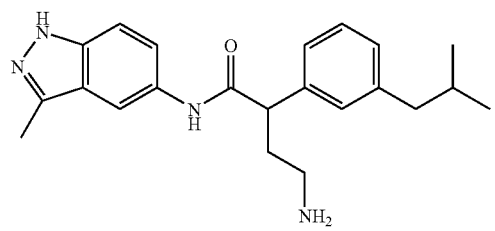
I-142
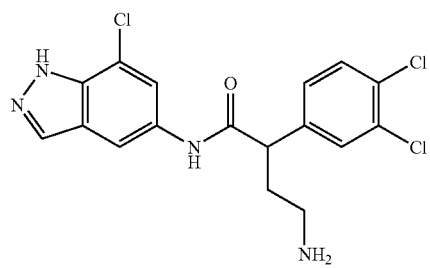
I-143
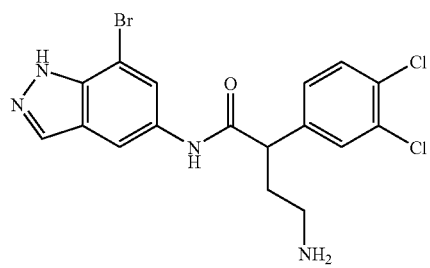
I-144
TABLE 1-continued
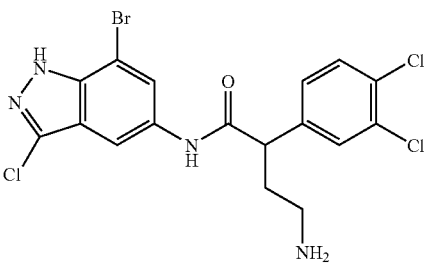
I-145
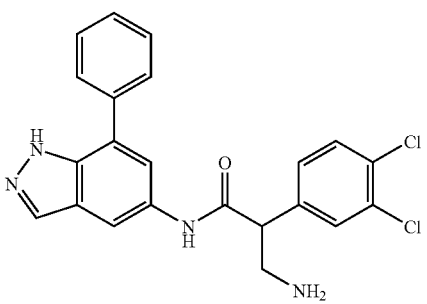
I-146
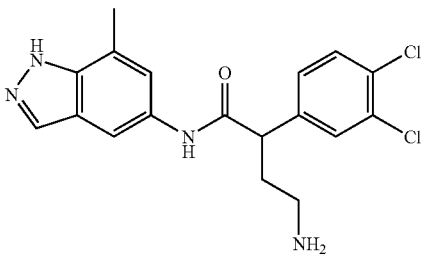
I-147
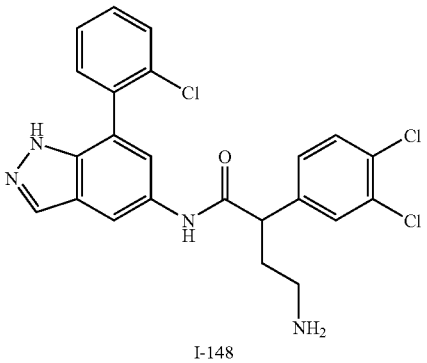
I-148
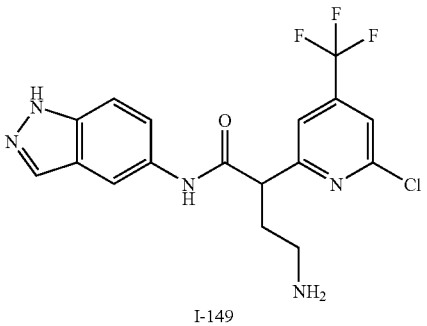
I-149

TABLE 1-continued
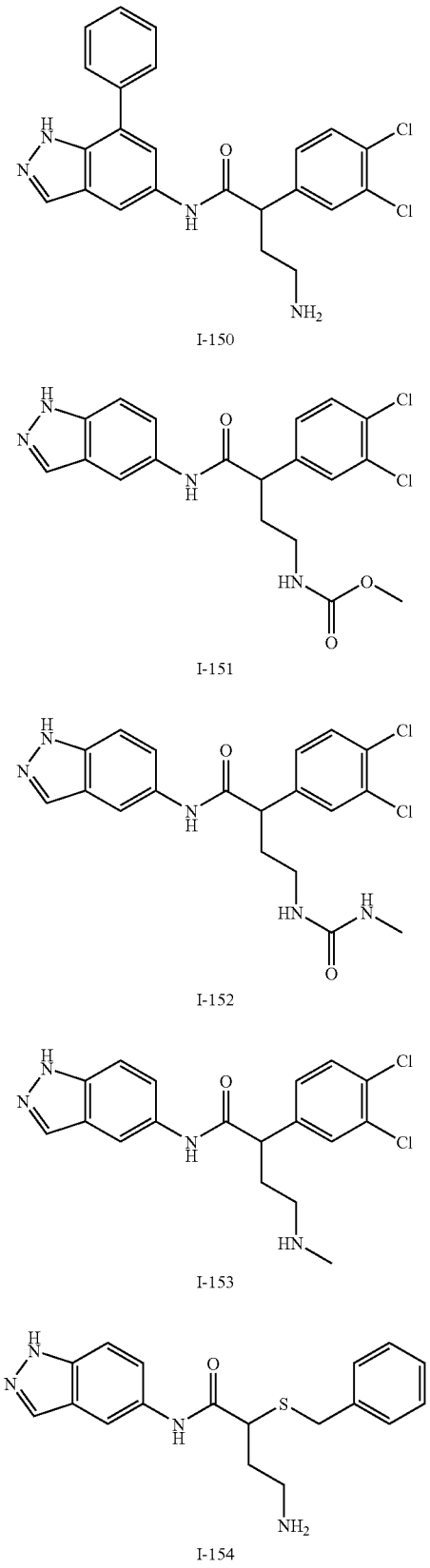
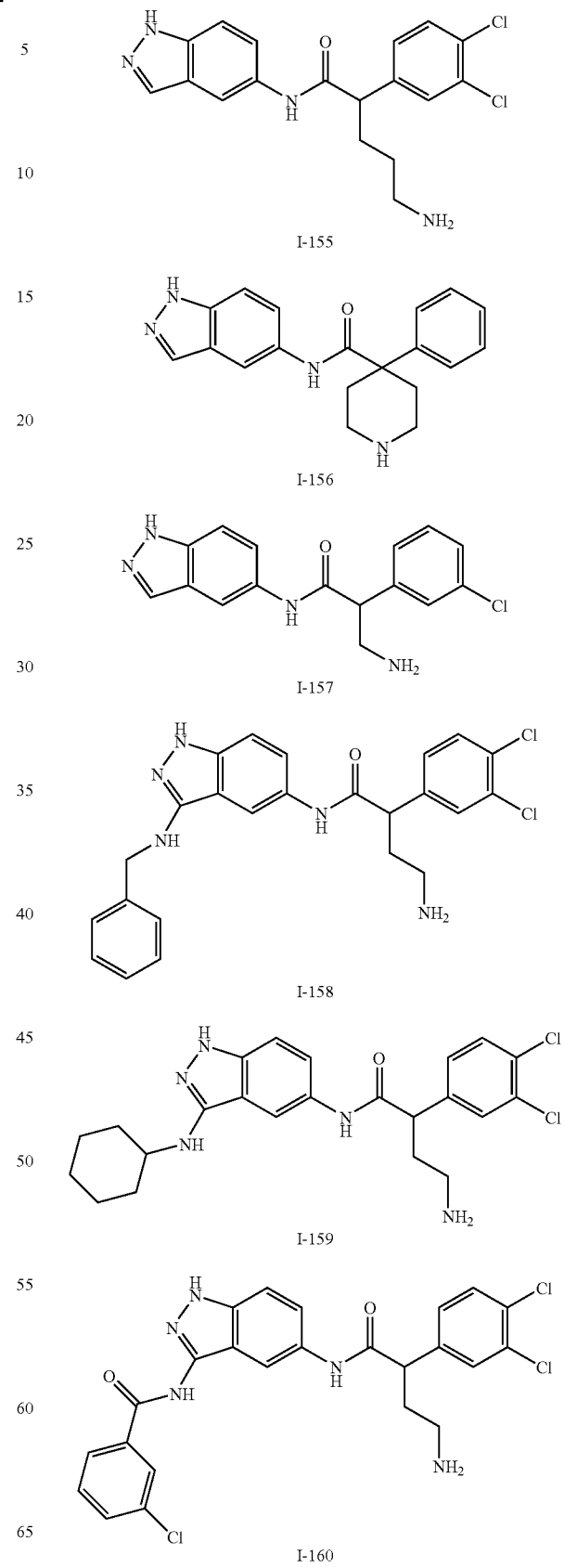

TABLE 1-continued
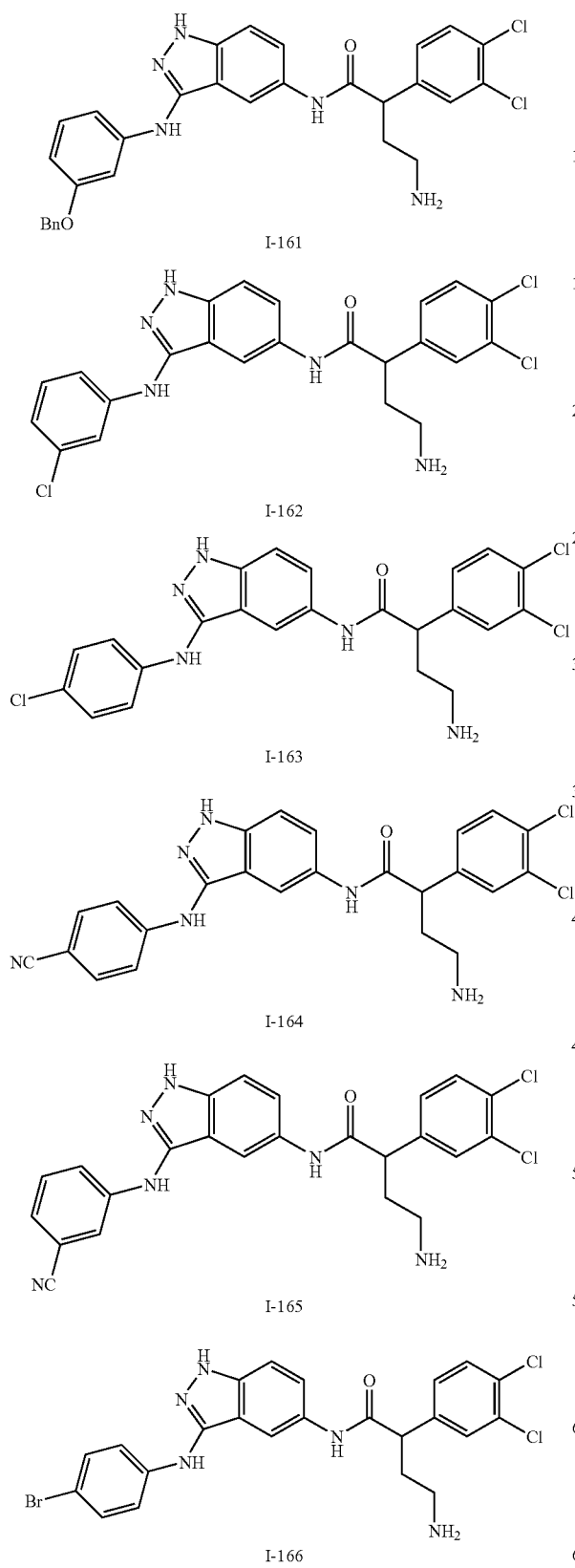
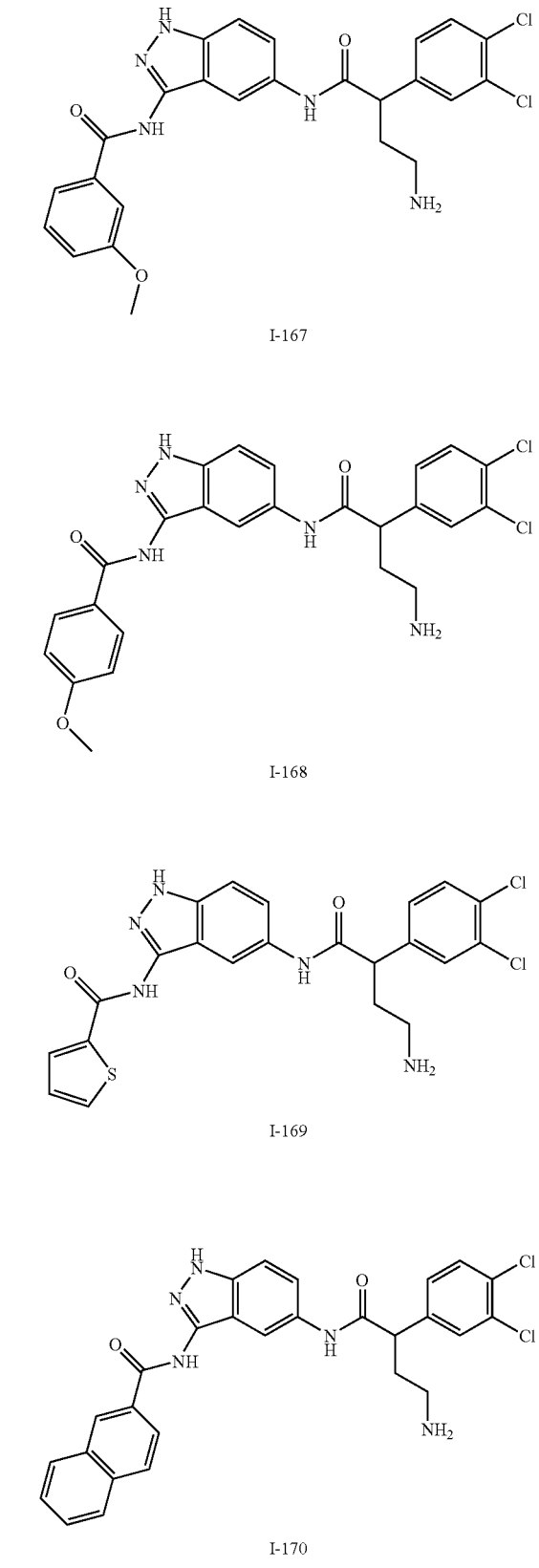

TABLE 1-continued
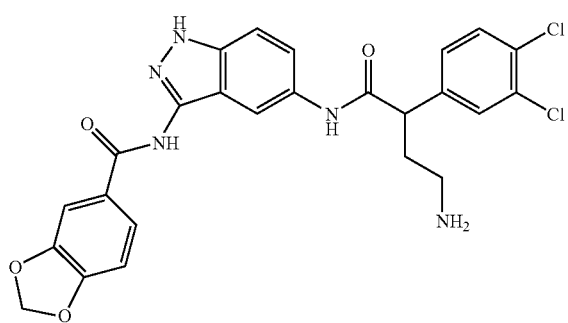
I-171
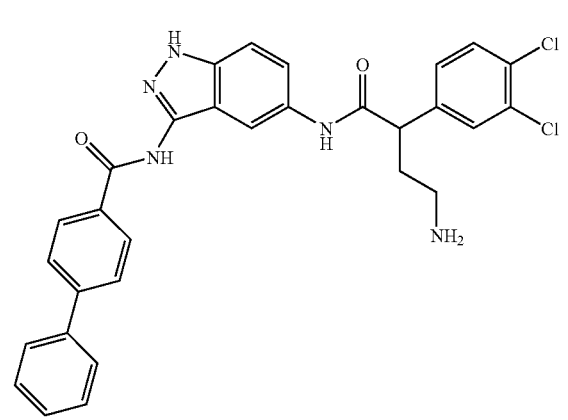
I-172
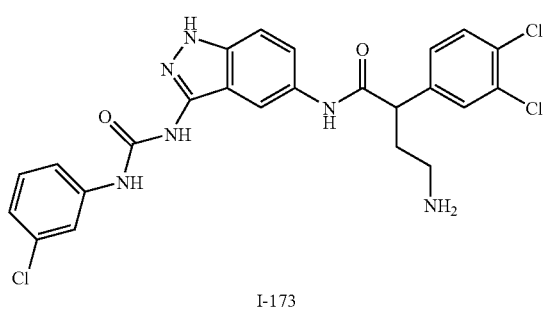
I-173
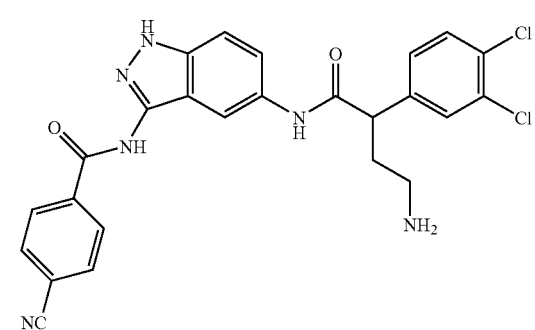
I-174
TABLE 1-continued
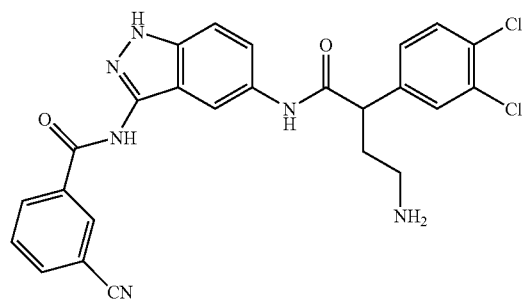
I-175
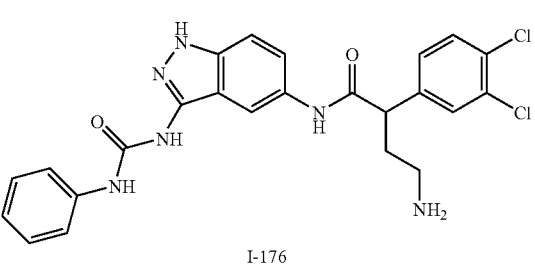
I-176
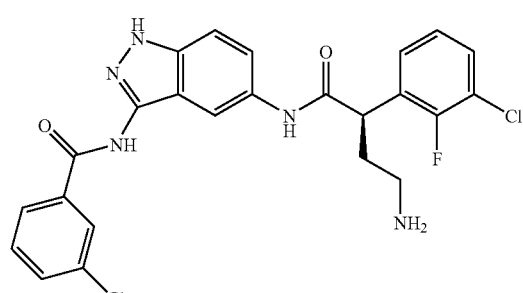
I-177
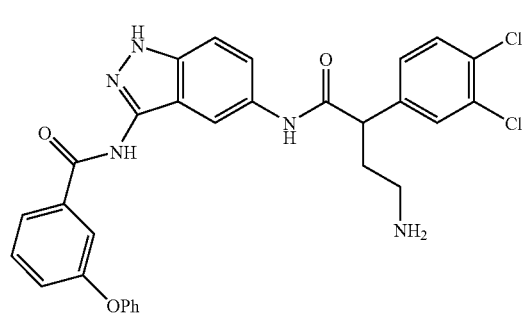
I-178
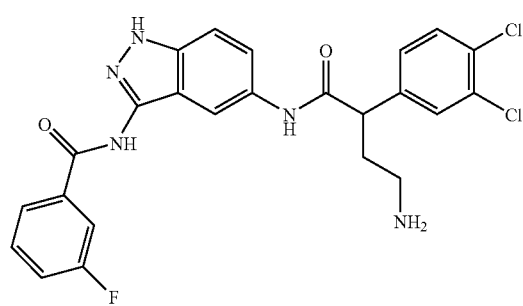
I-179

TABLE 1-continued
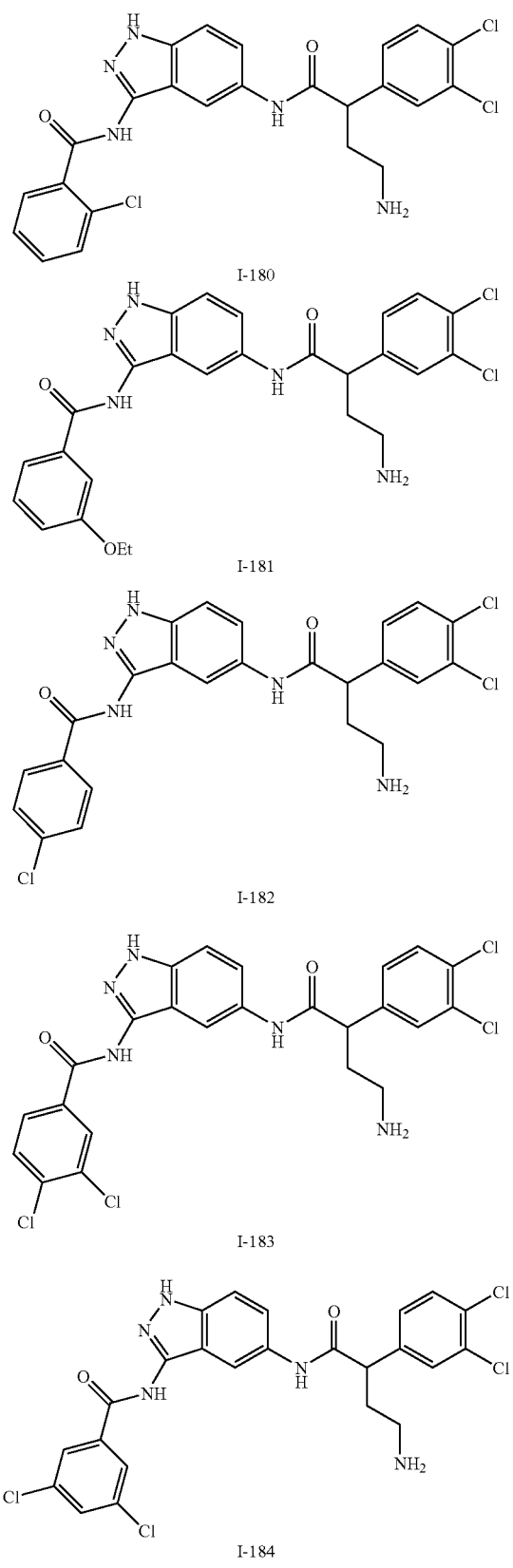
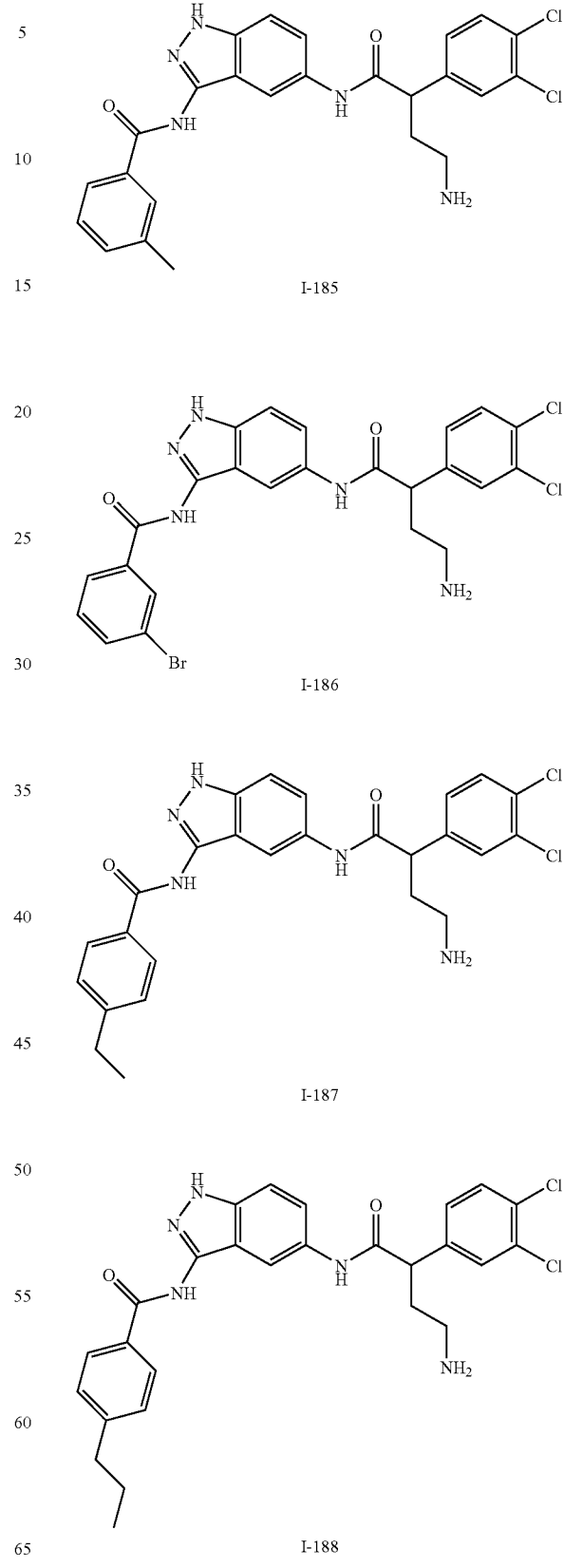

TABLE 1-continued
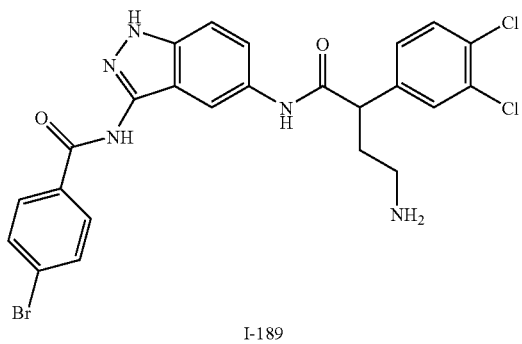
I-189
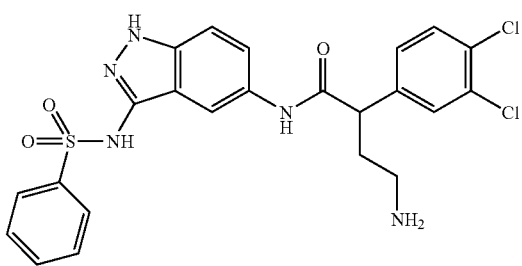
I-190
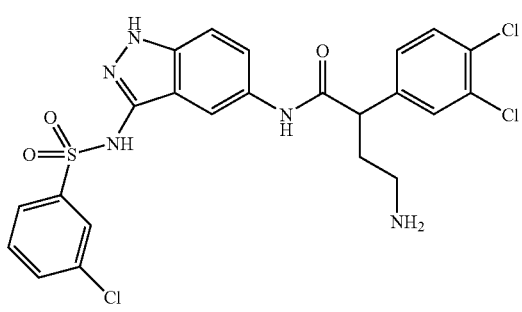
I-191
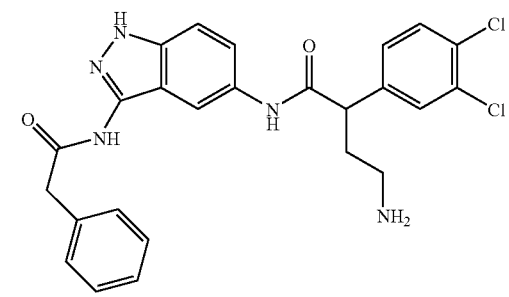
I-192
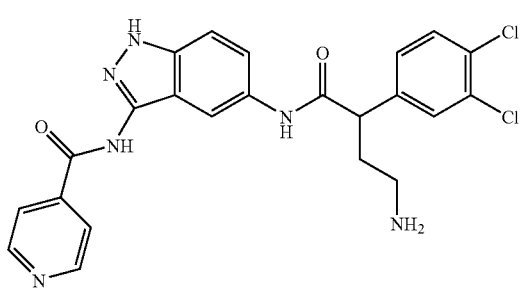
I-193
TABLE 1-continued
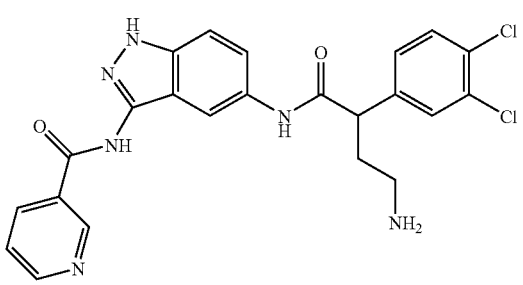
I-194
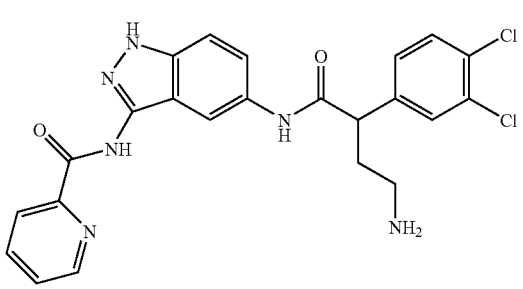
I-195
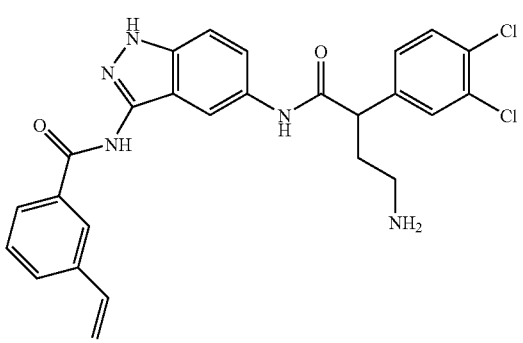
I-196
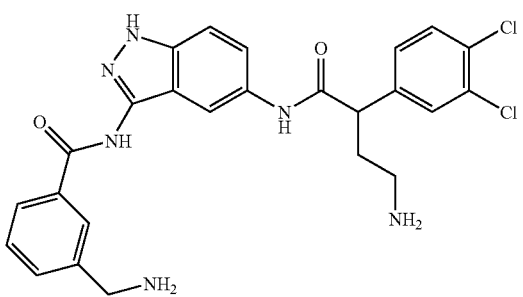
I-197

TABLE 1-continued
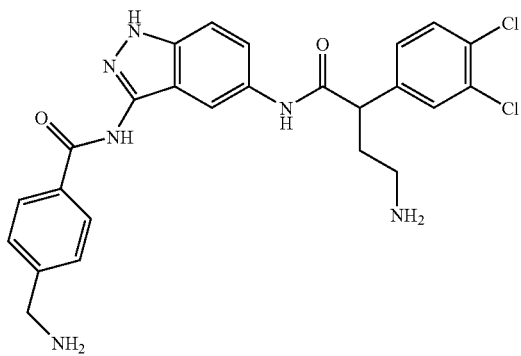
I-198
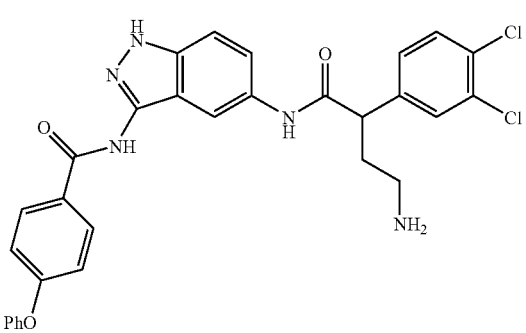
I-199
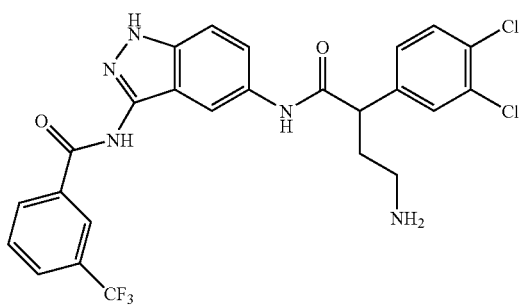
I-200
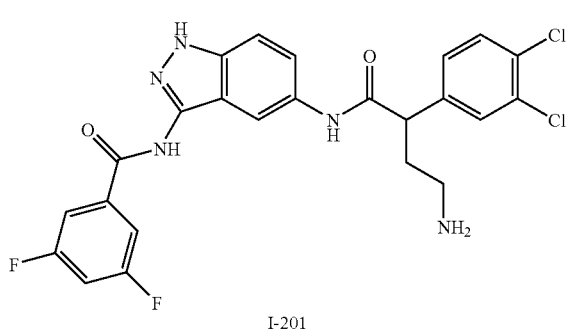
I-201
TABLE 1-continued
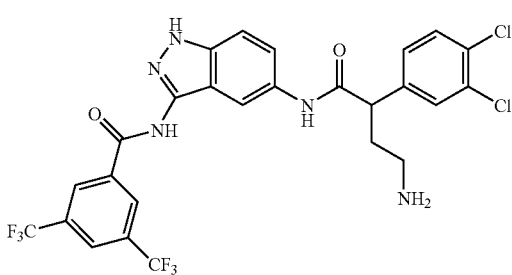
I-202
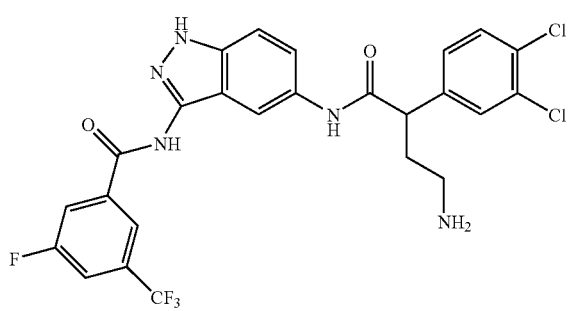
I-203
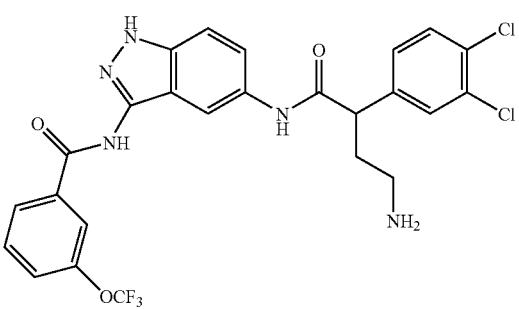
I-204
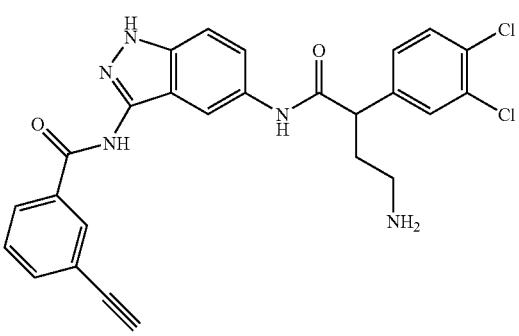
I-205

TABLE 1-continued
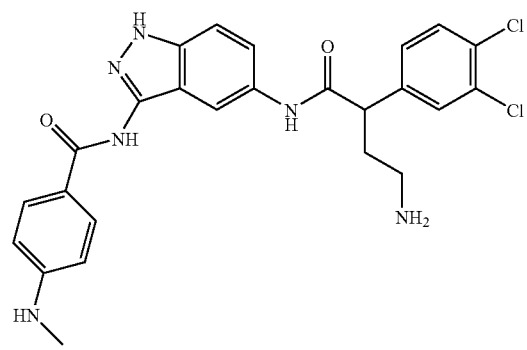
I-206
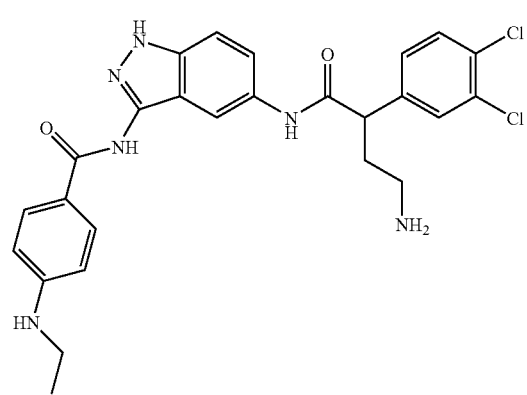
I-207
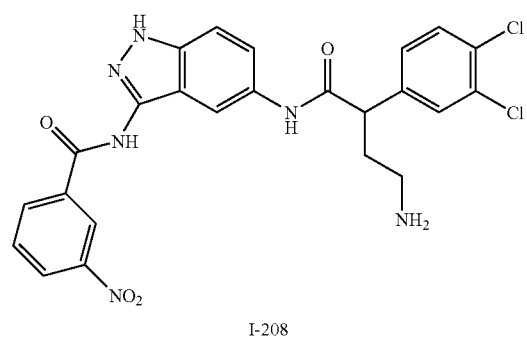
I-208
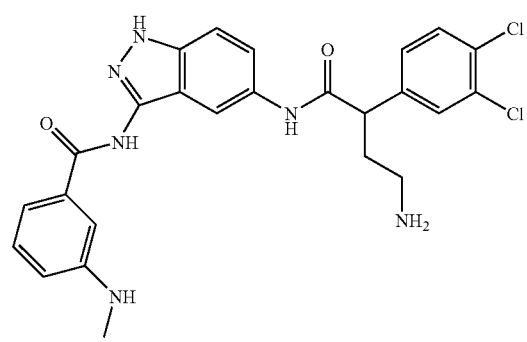
I-209
TABLE 1-continued
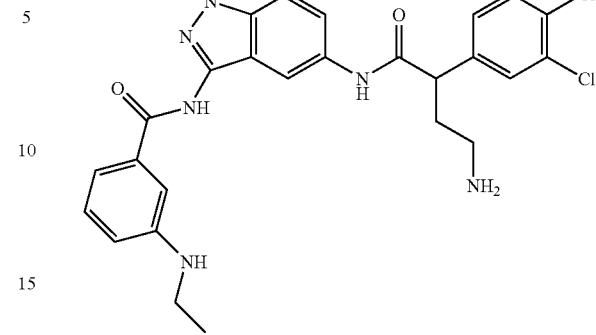
I-210
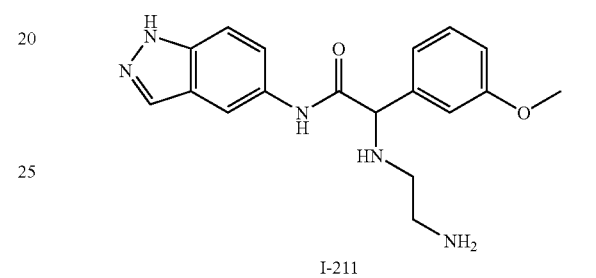
I-211
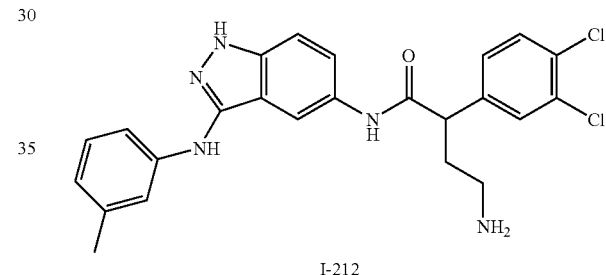
I-212
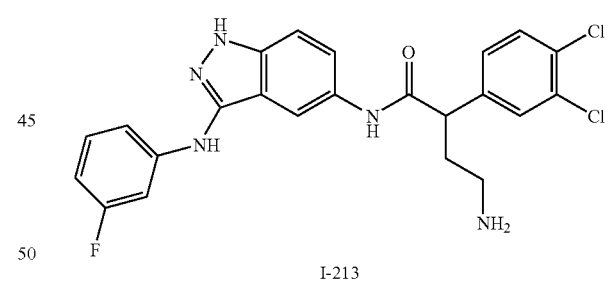
I-213
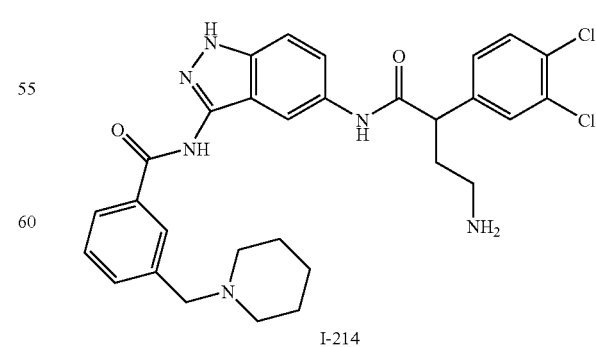
I-214

TABLE 1-continued
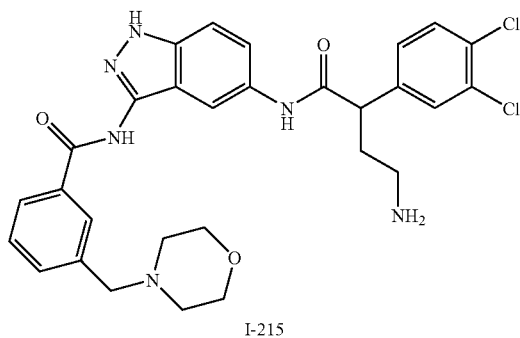
I-215
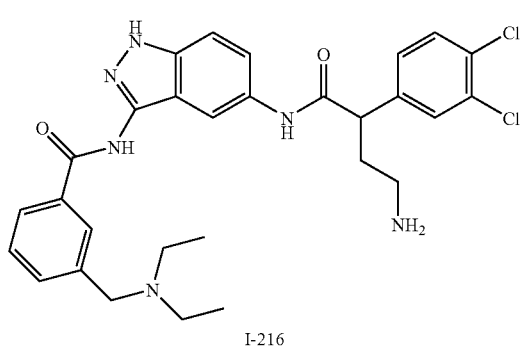
I-216
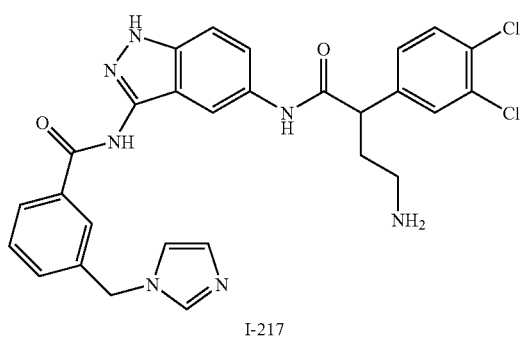
I-217
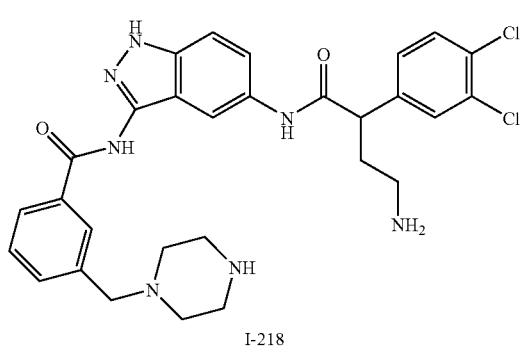
I-218
TABLE 1-continued
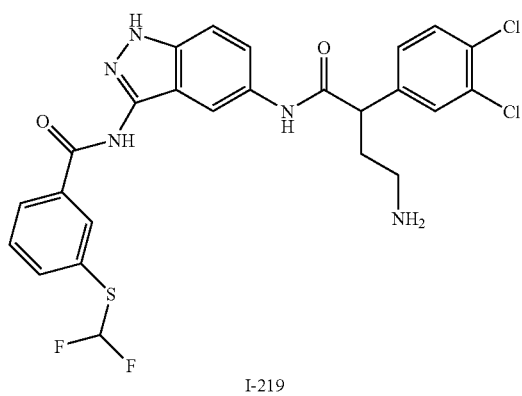
I-219
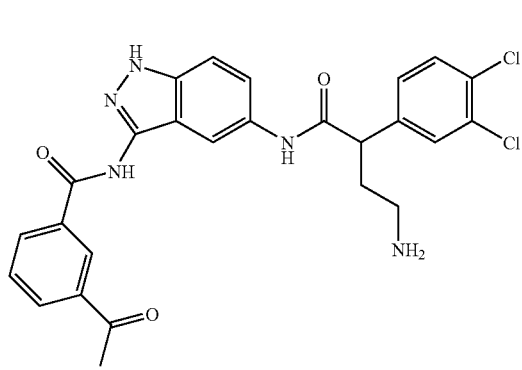
I-220
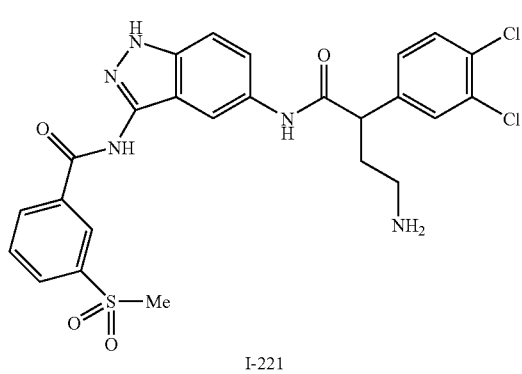
I-221
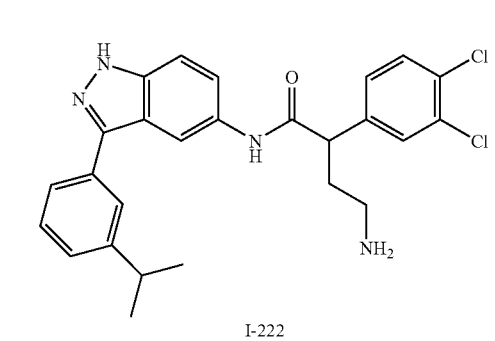
I-222

TABLE 1-continued
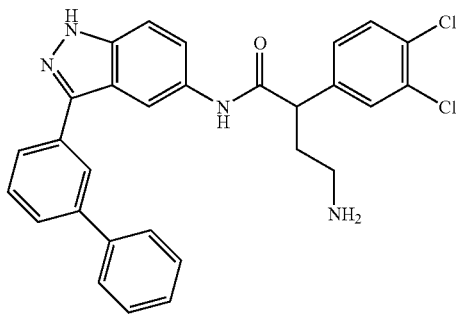
I-223
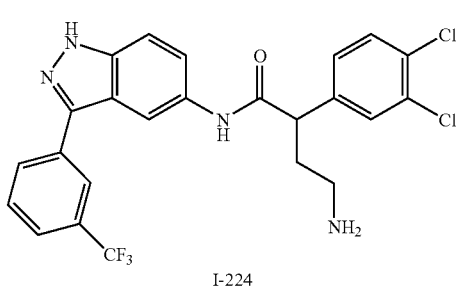
I-224
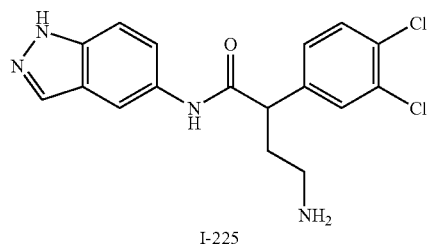
I-225
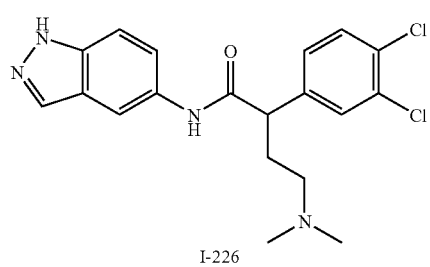
I-226
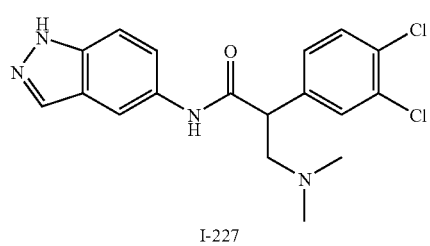
I-227
TABLE 1-continued
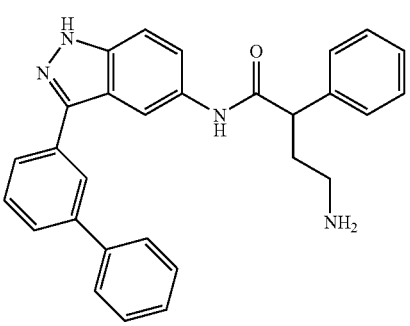
I-228
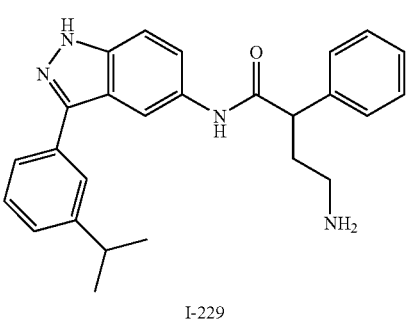
I-229
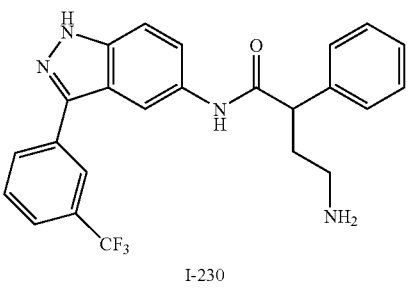
I-230
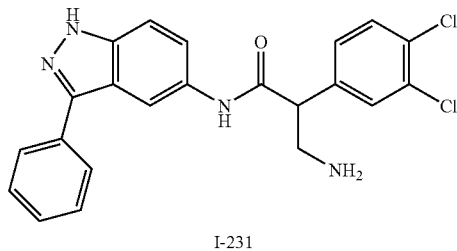
I-231
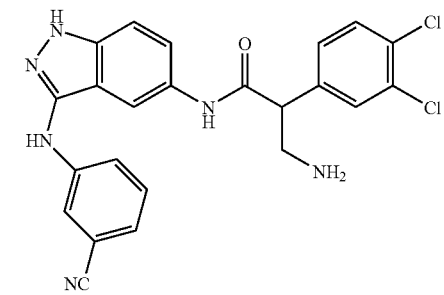
I-232

TABLE 1-continued
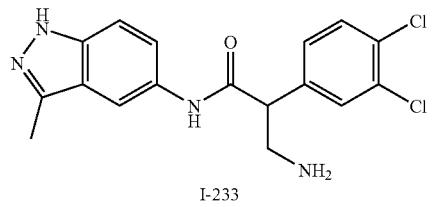
I-233
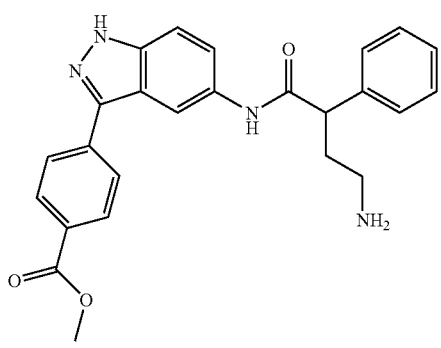
I-234
I-235
I-236
I-237
TABLE 1-continued
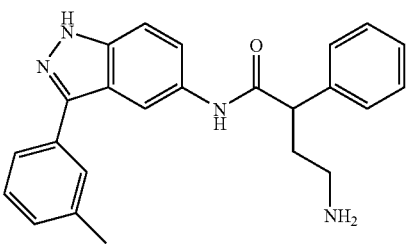
I-238
I-239
I-240
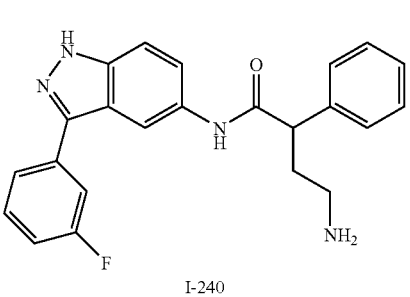
I-241
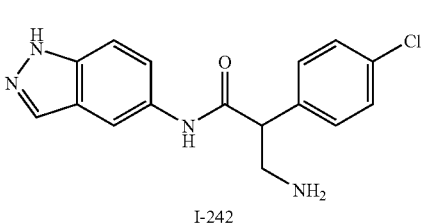
I-242
I-243

TABLE 1-continued
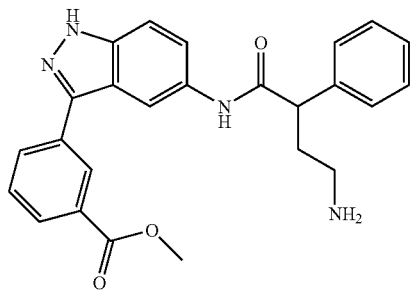
I-244
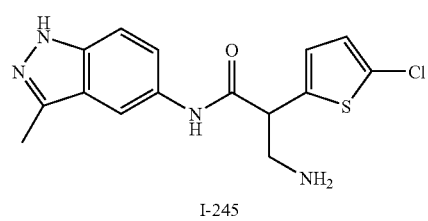
I-245
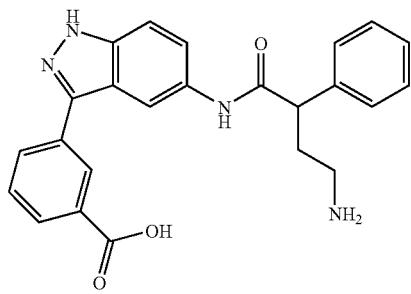
I-246
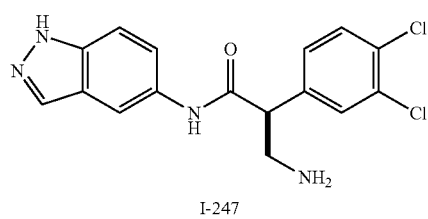
I-247
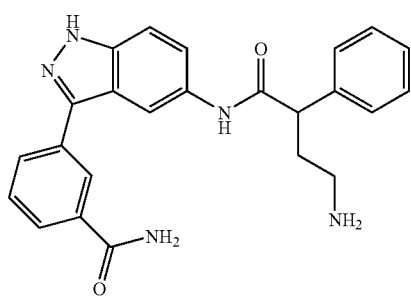
I-248
TABLE 1-continued
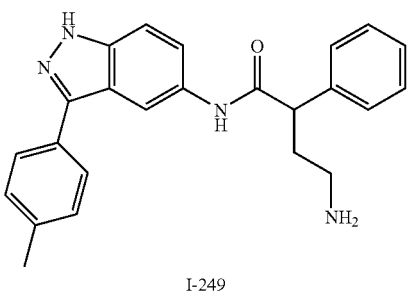
I-249
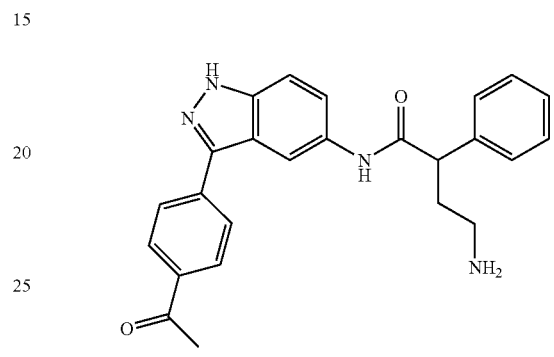
I-250
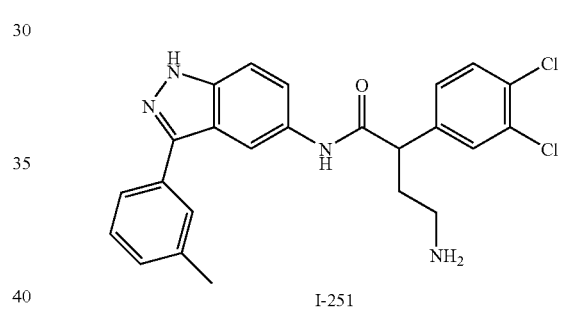
I-251
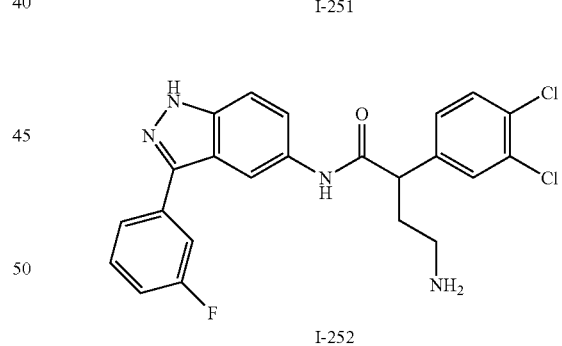
I-252
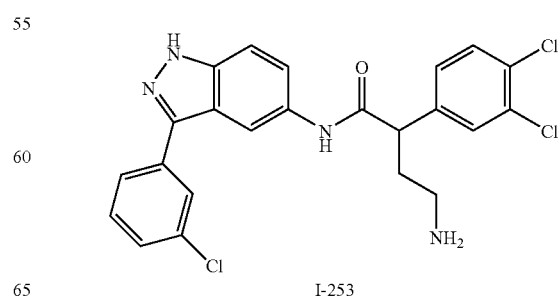
I-253

TABLE 1-continued
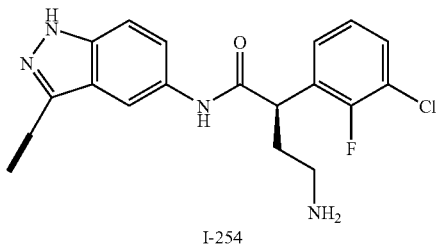
I-254
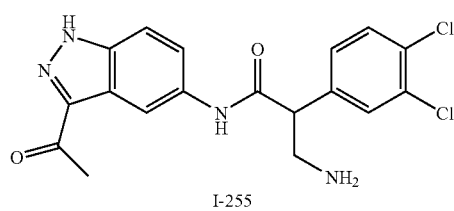
I-255
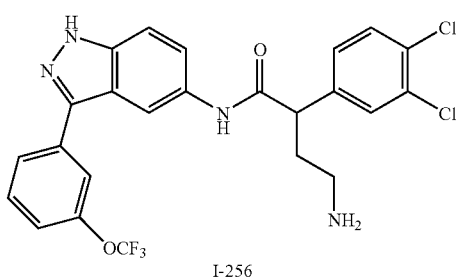
I-256
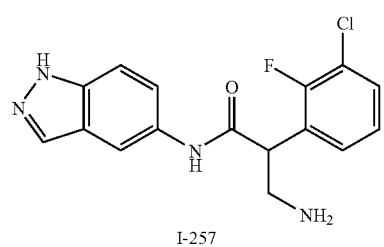
I-257
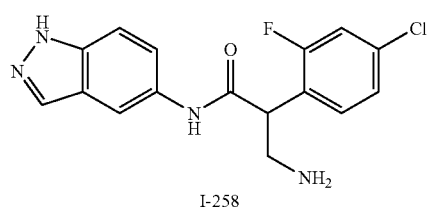
I-258
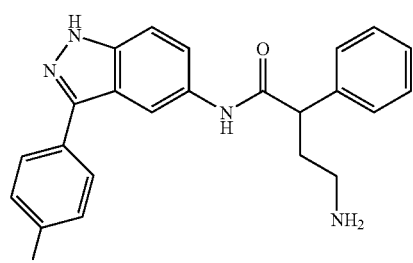
I-259
TABLE 1-continued
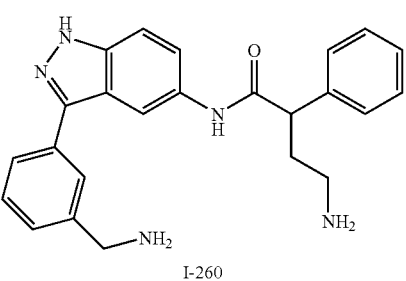
I-260
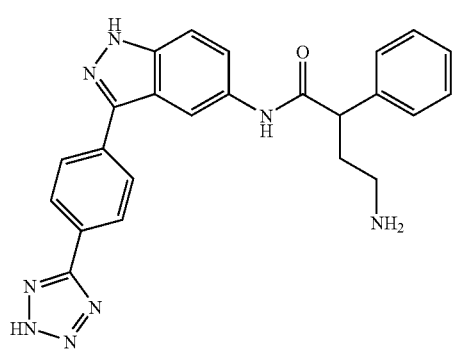
I-261
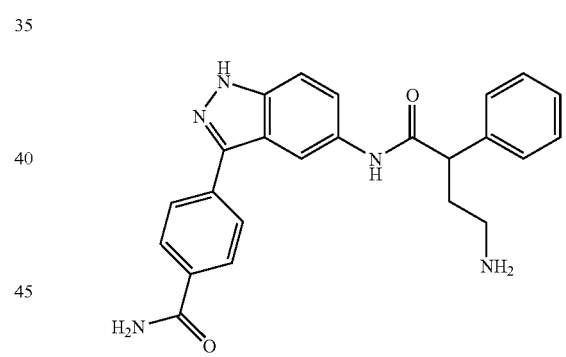
I-262
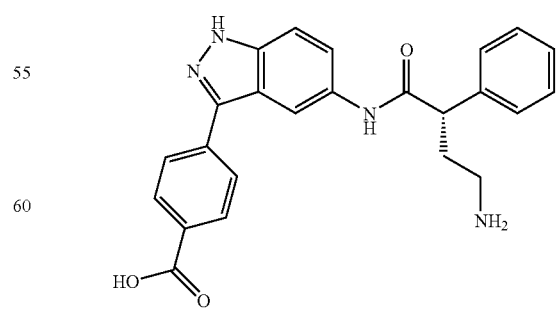
I-263

TABLE 1-continued
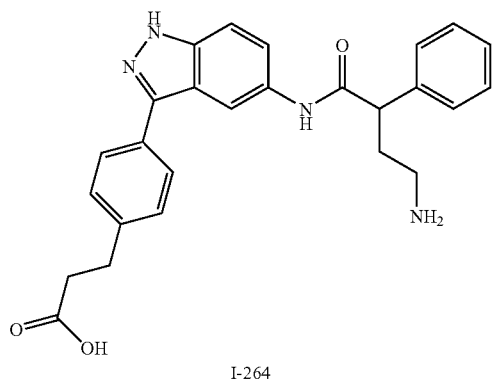
I-264
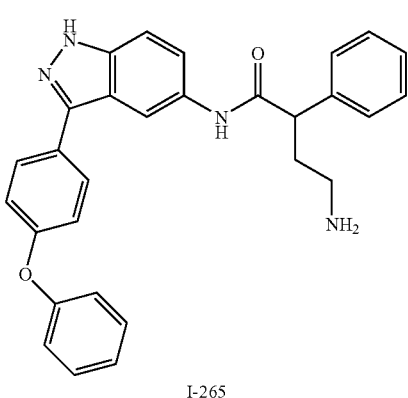
I-265
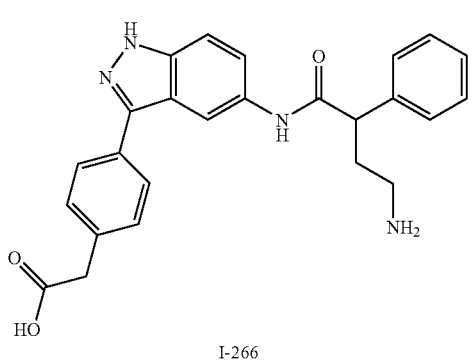
I-266
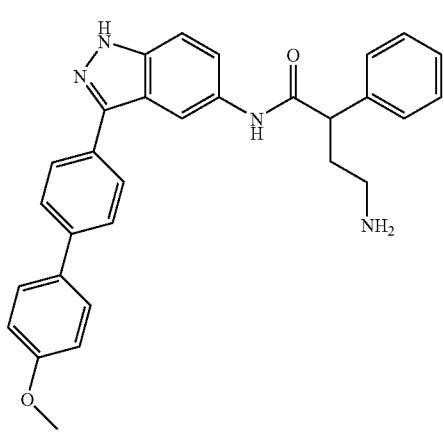
I-267
TABLE 1-continued
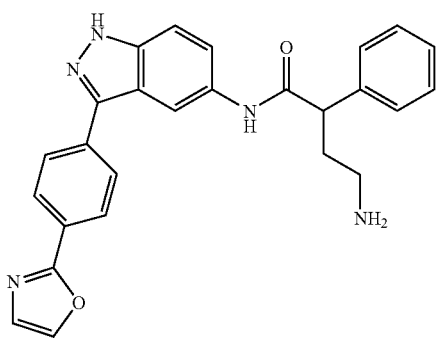
I-268
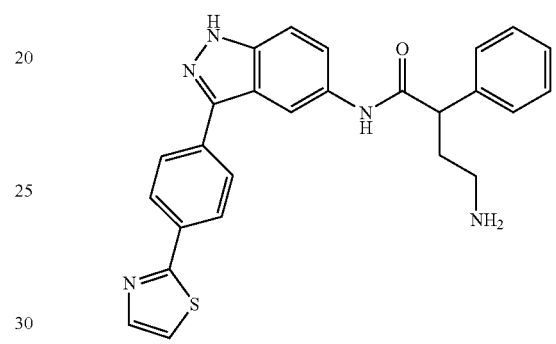
I-269
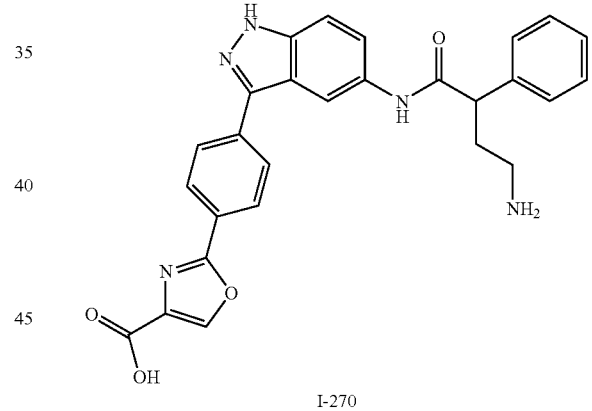
I-270
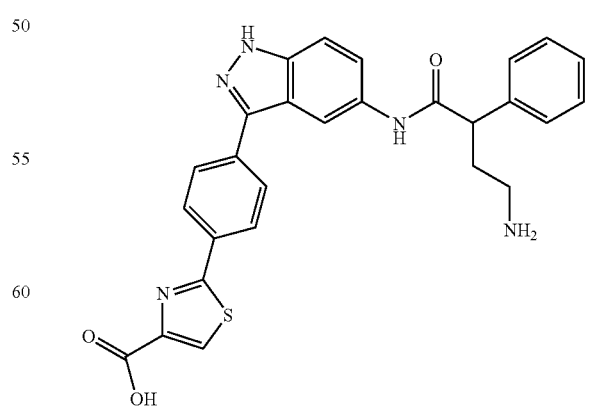
I-271

TABLE 1-continued
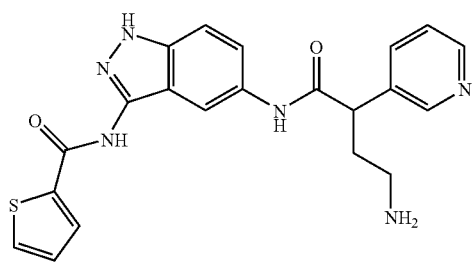
I-272
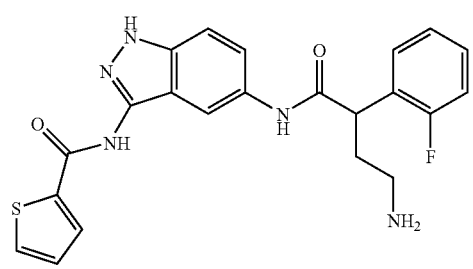
I-273
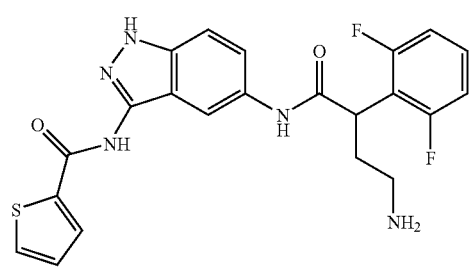
I-274
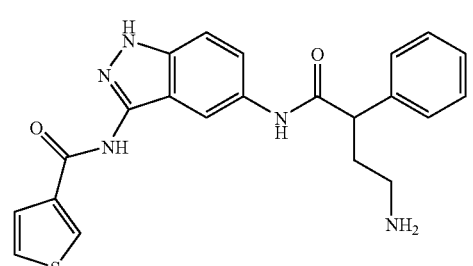
I-275
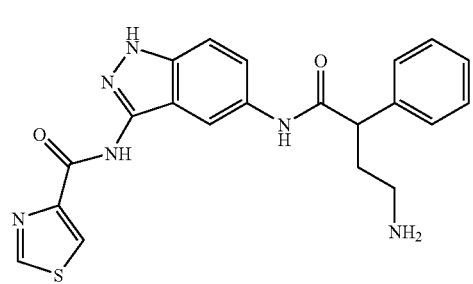
I-276
TABLE 1-continued
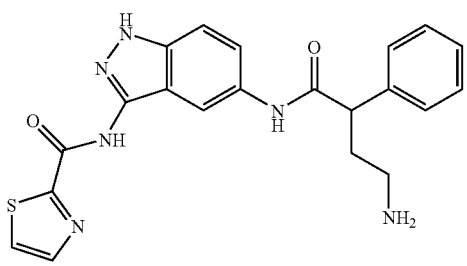
I-277
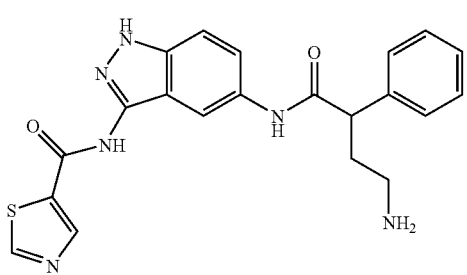
I-278
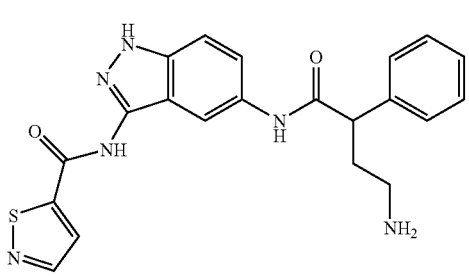
I-279
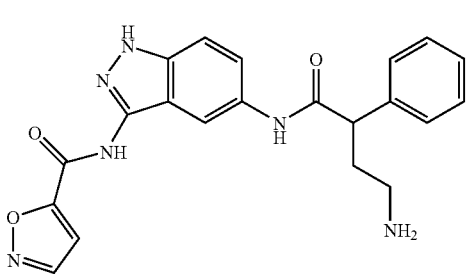
I-280
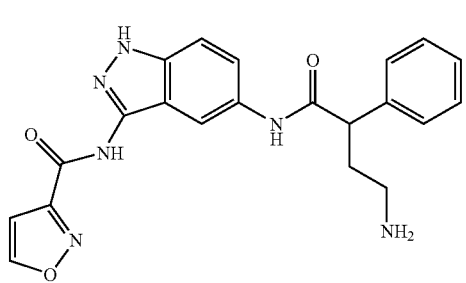
I-281

TABLE 1-continued
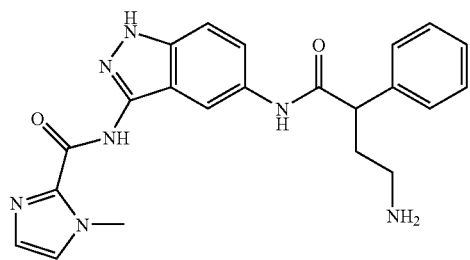
I-282
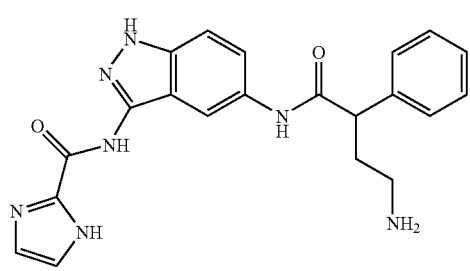
I-283
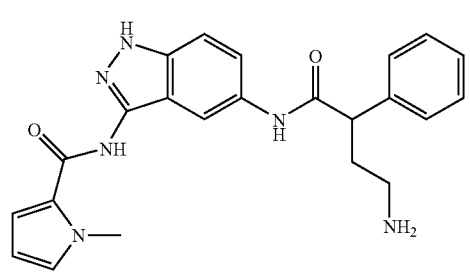
I-284
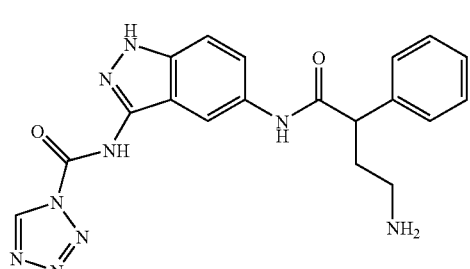
I-285
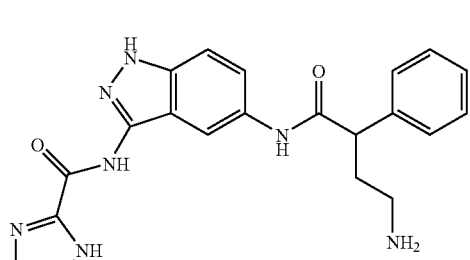
I-286
TABLE 1-continued
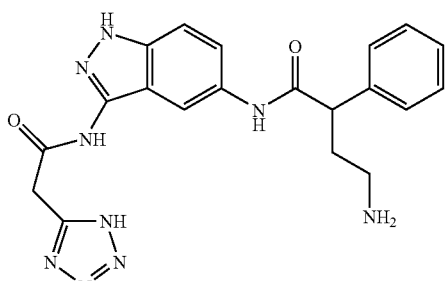
I-287
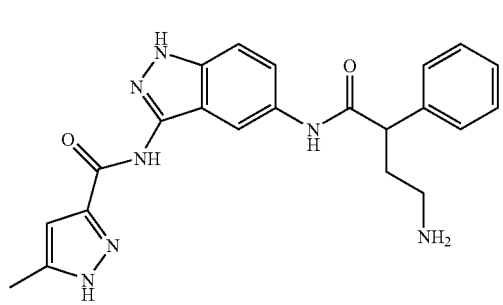
I-288
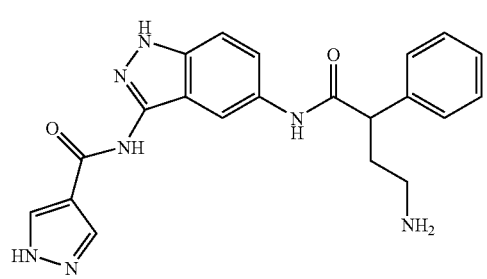
I-289
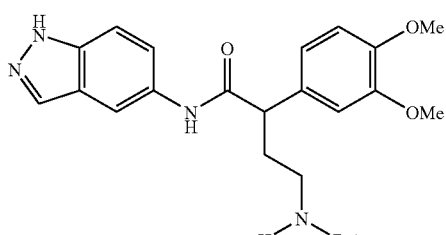
I-1000
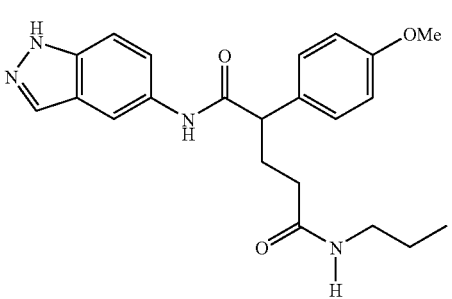
I-1001

TABLE 1-continued
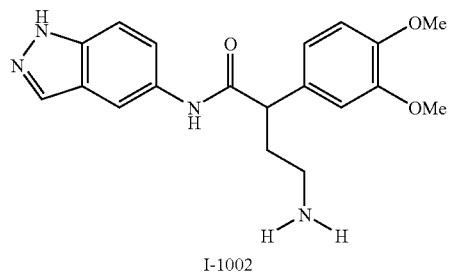
I-1002
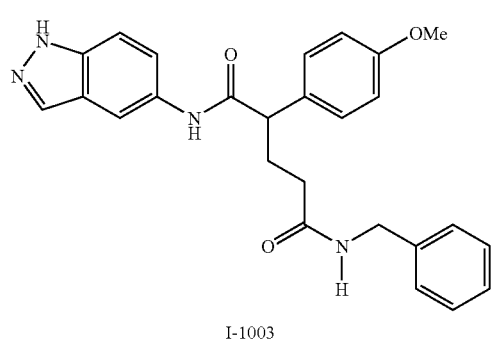
I-1003
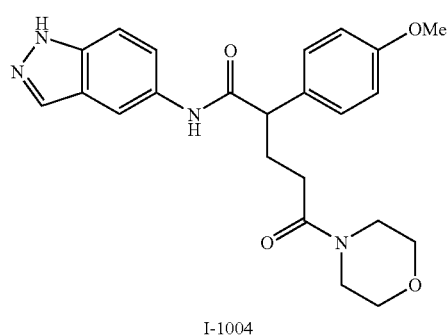
I-1004
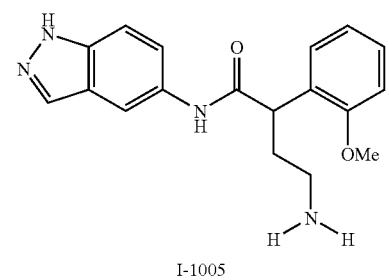
I-1005
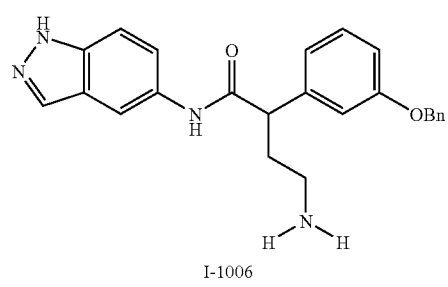
I-1006
TABLE 1-continued
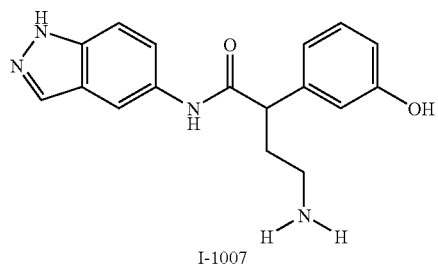
I-1007
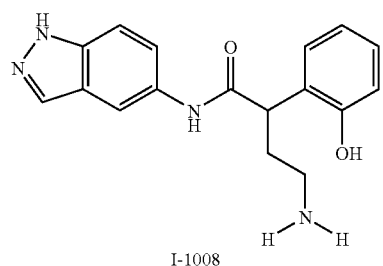
I-1008
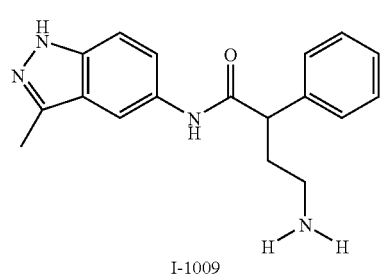
I-1009
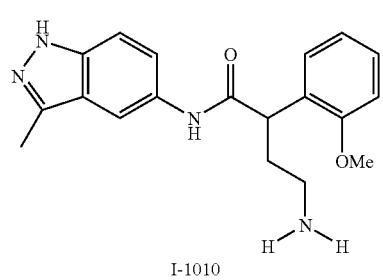
I-1010
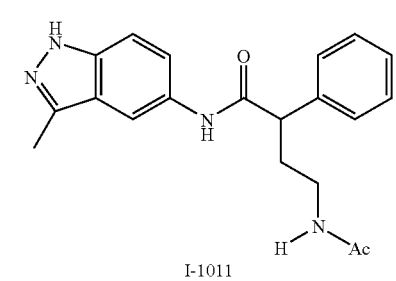
I-1011
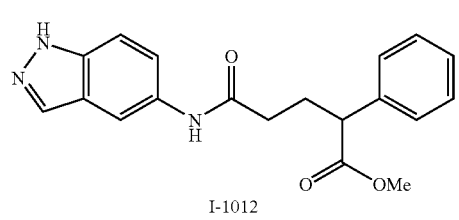
I-1012

TABLE 1-continued
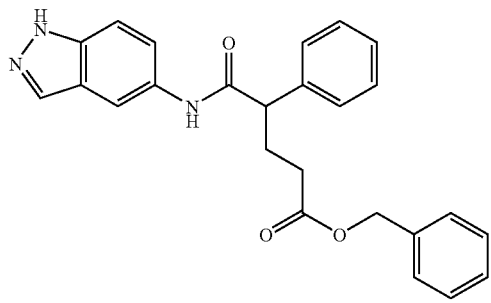
I-1013
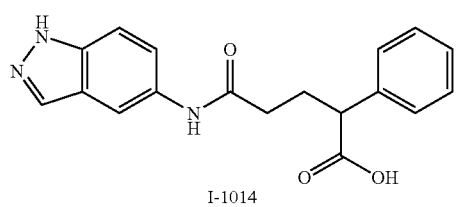
I-1014
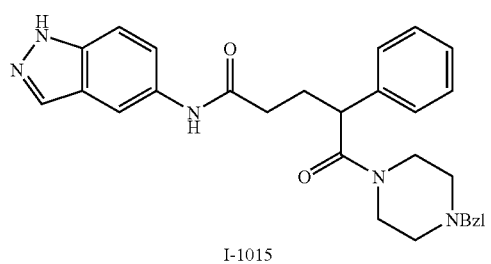
I-1015
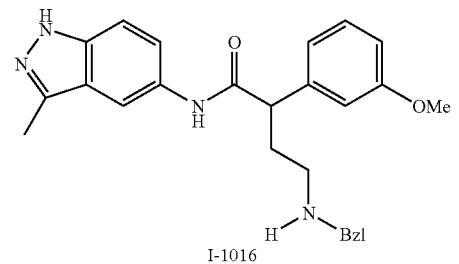
I-1016
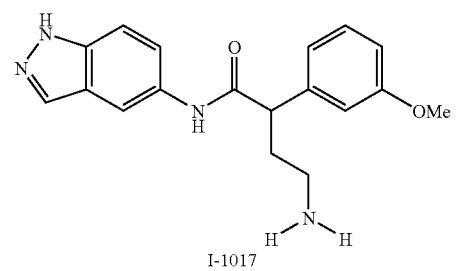
I-1017
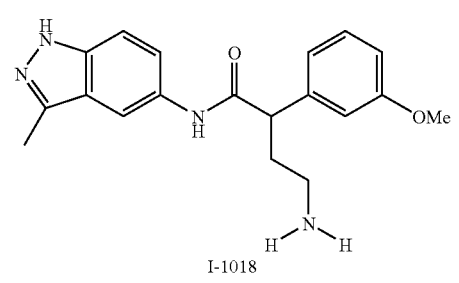
I-1018
TABLE 1-continued
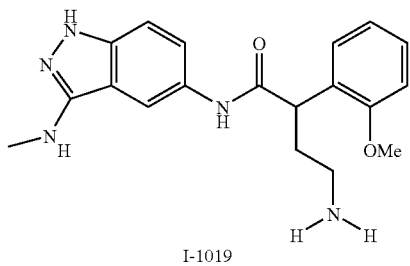
I-1019
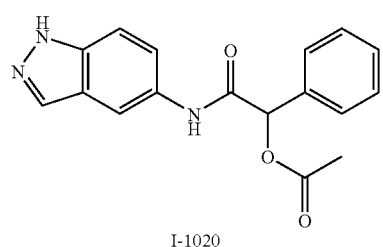
I-1020
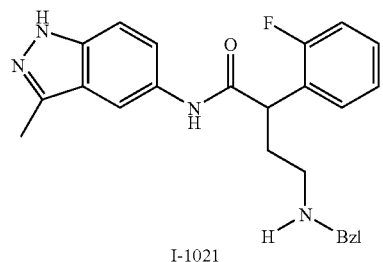
I-1021
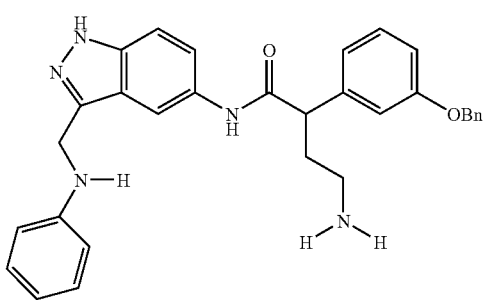
I-1022
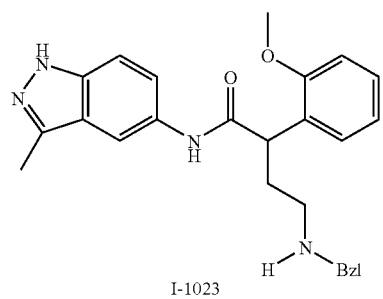
I-1023
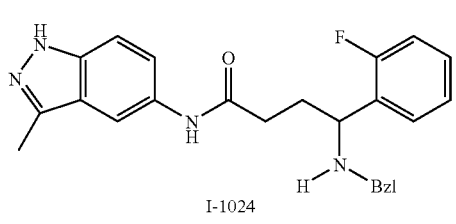
I-1024

TABLE 1-continued
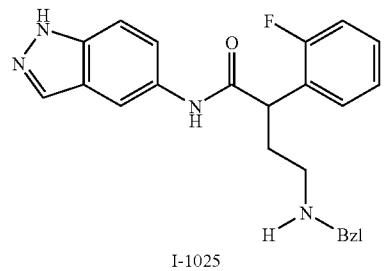
I-1025
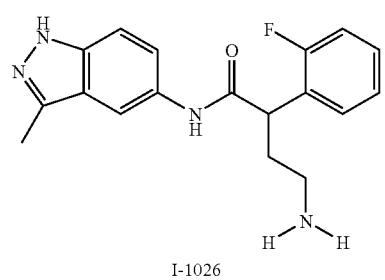
I-1026
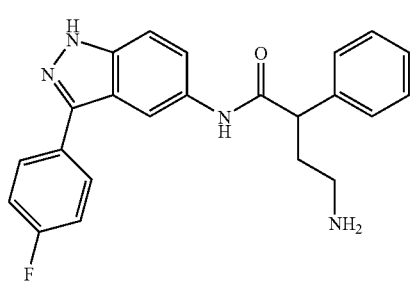
I-1027
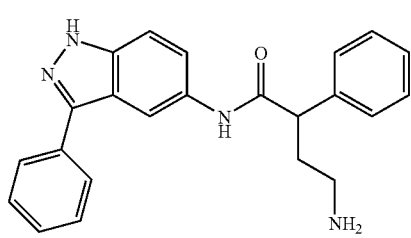
I-1028
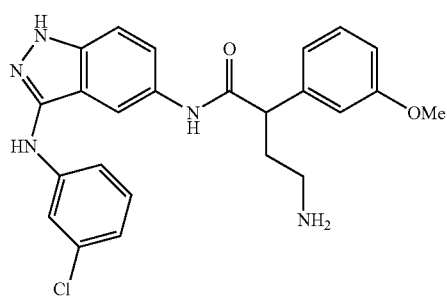
I-1029
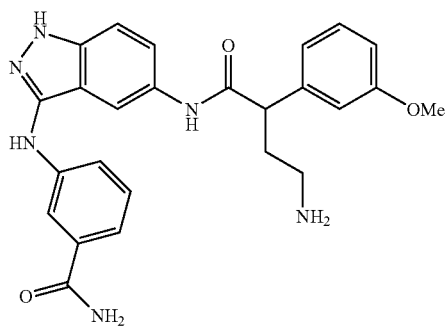
I-1030
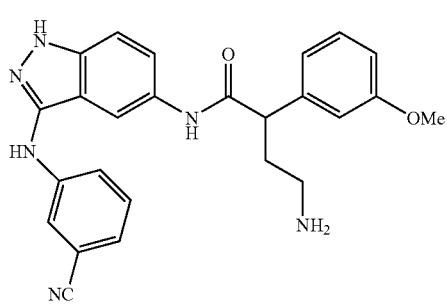
I-1031
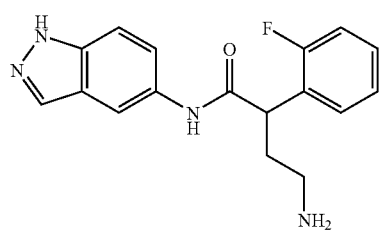
I-1032
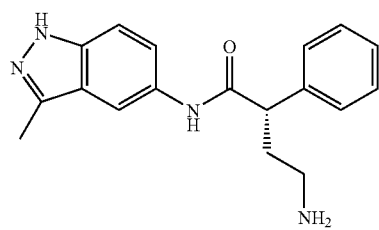
I-1033
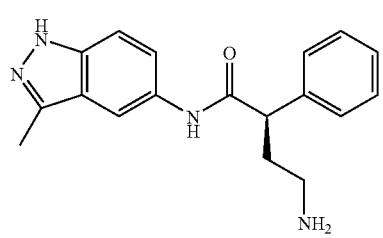
I-1034

TABLE 1-continued
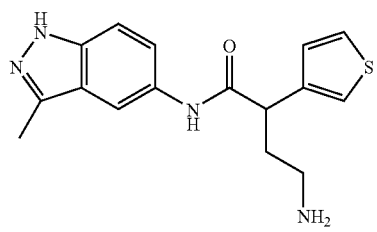
I-1035
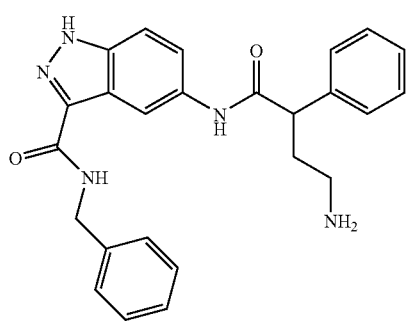
I-1036
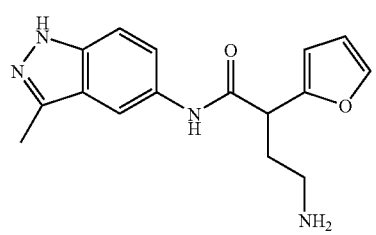
I-1037
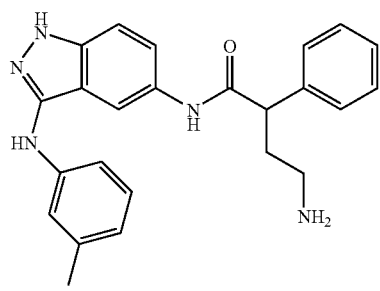
I-1038
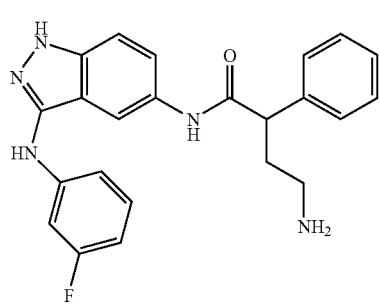
I-1039
TABLE 1-continued
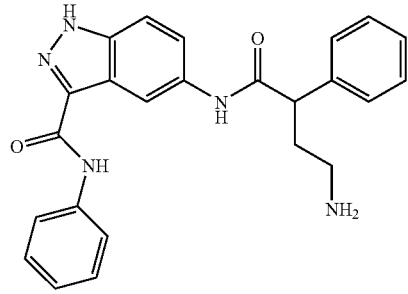
I-1040
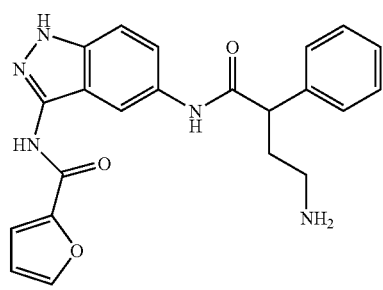
I-1041
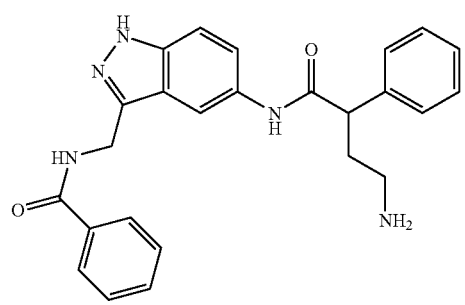
I-1042
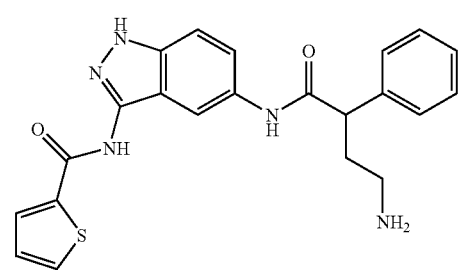
I-1043
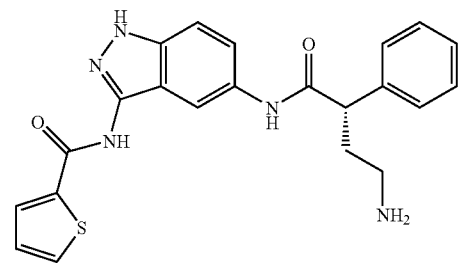
I-1044

TABLE 1-continued
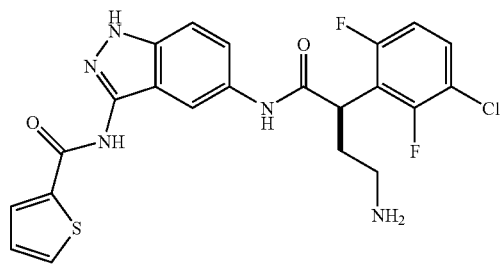
I-1045
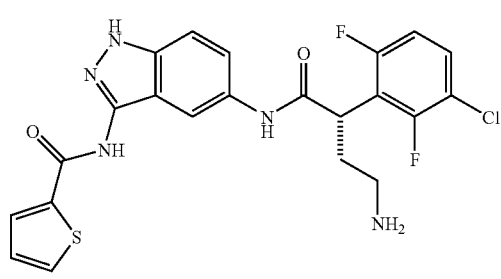
I-1046
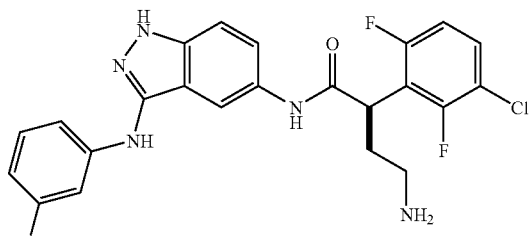
I-1047
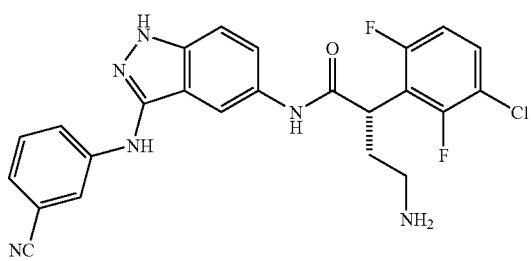
I-1048
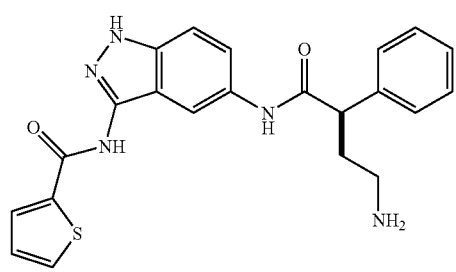
I-1049
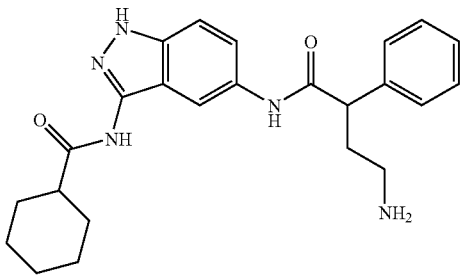
I-1050
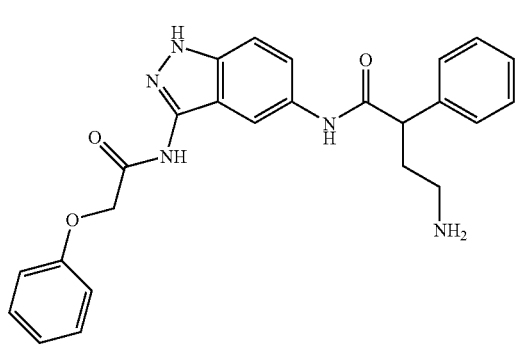
I-1051
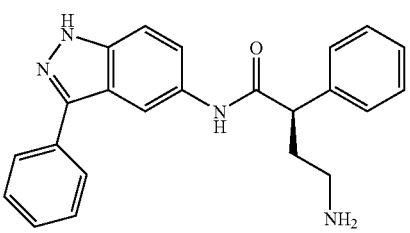
I-1052
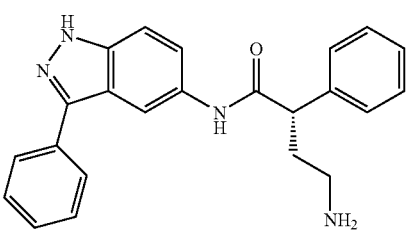
I-1053
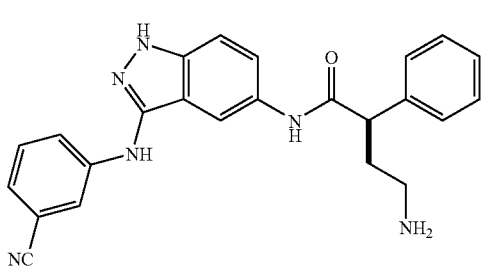
I-1054

TABLE 1-continued
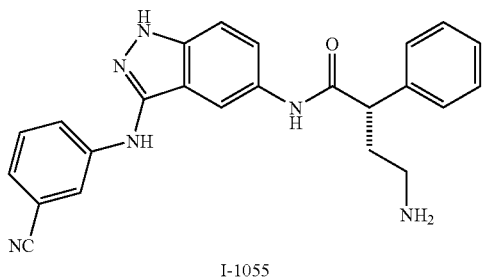
I-1055
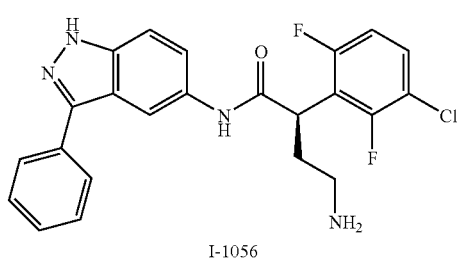
I-1056
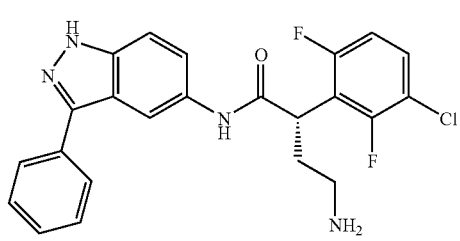
I-1057
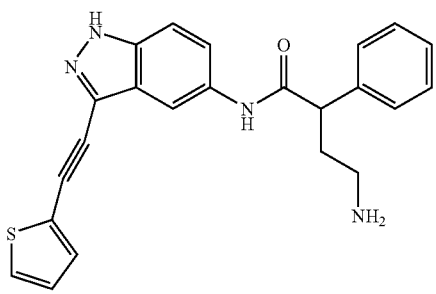
I-1058
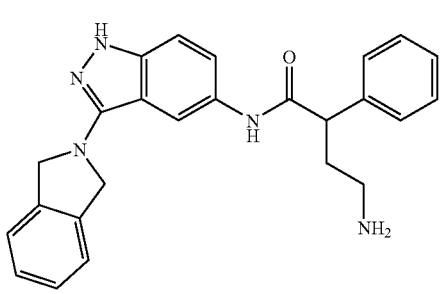
I-1059
TABLE 1-continued
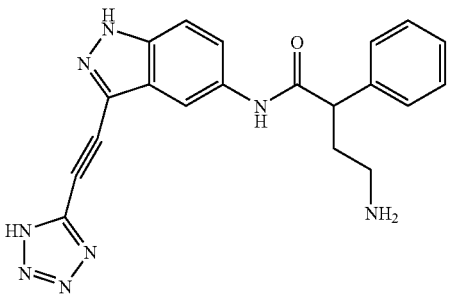
I-1060
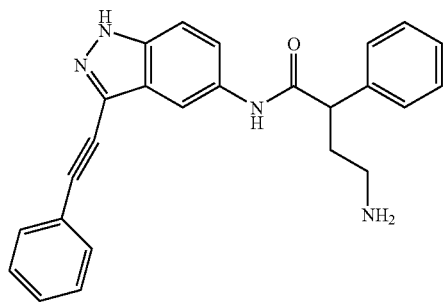
I-1061
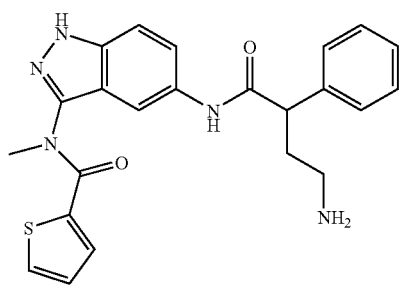
I-1062
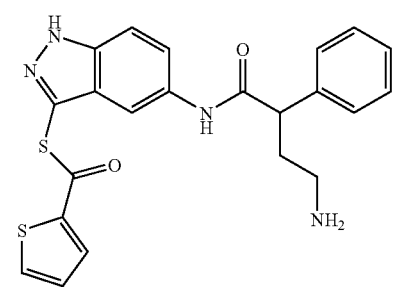
I-1063
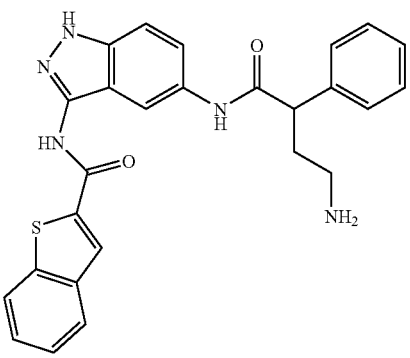
I-1064

TABLE 1-continued

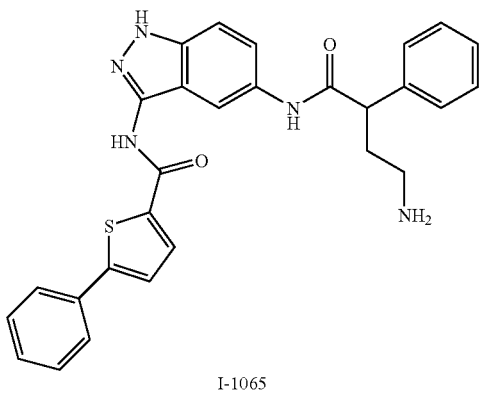

I-1065

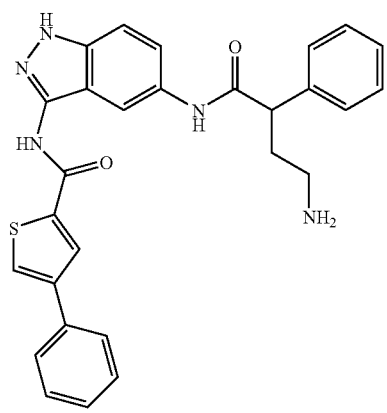

I-1066

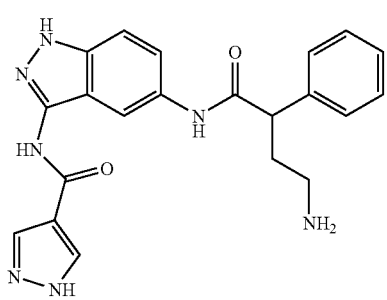

I-1067

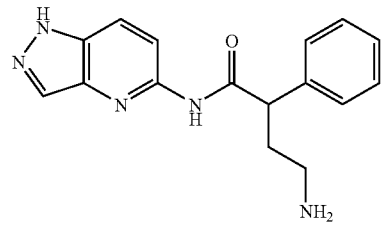

I-1068

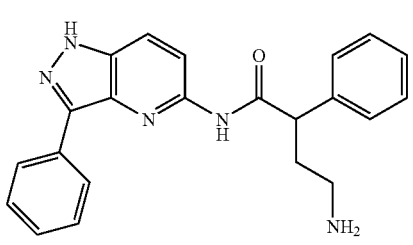

I-1069

TABLE 1-continued

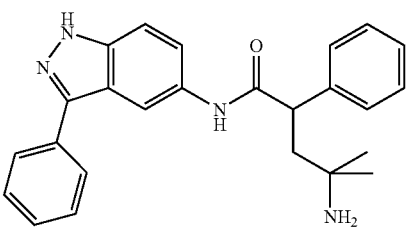

I-1070

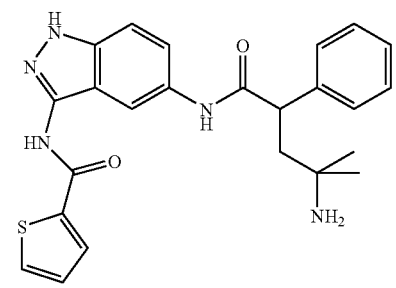

I-1071

The compounds of the present invention may be prepared as illustrated by the Schemes I–XVII below, by the Synthetic Examples described herein, and by general methods known to those of ordinary skill in the art.

Scheme I

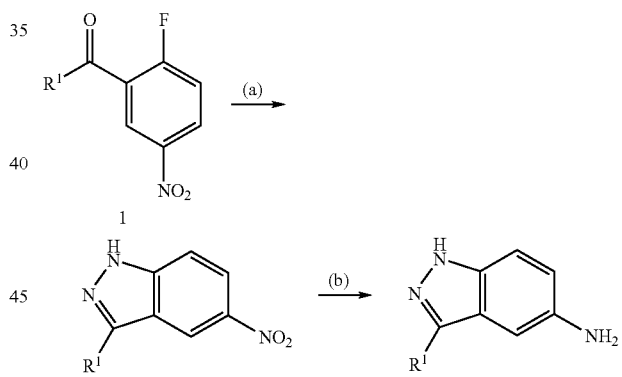

Reagents:
(a) N$_2$H$_4$·H$_2$O, BuOH, reflux;
(b) SnCl$_2$·2H$_2$O, BuOH, reflux.

Scheme I above shows a general method for preparing the aminoindazole compounds 3 where R$^1$ is other than hydrogen. When R$^1$ is an alkyl or aryl group, the nitro-indazole compound 2 may be prepared by methods substantially similar to those described by Henke, et al, *J. Med. Chem.*, 1997, 40, 2706. The reduction of the nitro group at step (b) to afford compound 3 is achieved by the methods described by Bellamy, et al, *Tetrahedron Lett.*, 1984, 25, 839. Alternatively, reduction of the nitro group of compound 2 can be achieved by treating 2 with hydrogen gas in the presence of Pd/C by methods substantially similar to those described by Boyer, et al, *J. Chem. Res. Miniprint*, 1990, 11, 2601. Another alternative method for achieving the reduction of the nitro group of compound 2 is by hydrolysis using a method substantially similar to that described by Lee, et al, *Synthesis,* 2001, 1, 81.

Scheme II

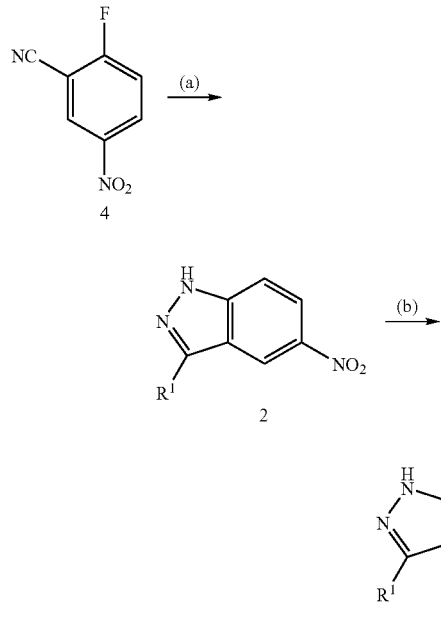

Reagents:
(a) N₂H₄·H₂O, BuOH, reflux;
(b) SnCl₂·2H₂O, BuOH, reflux.

Scheme II above shows a general method for preparing the aminoindazole compounds 3 where $R^1$ is an amino or alkylamino group. The nitro-indazole compound 2 may be prepared from 2-fluoro-5-nitro-benzonitrile (1) by methods substantially similar to those describe by Parnell, et al, *J. Chem. Soc.,* 1959, 2363. Amino-indazole compound 3 may then be prepared from compound 2 as described above for Scheme I.

Scheme III

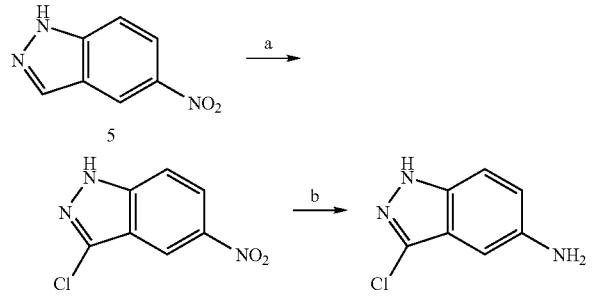

Reagents:
(a) Cl₂, acetic acid;
(b) H₂, Pd/C

Scheme III above shows a method for preparing compounds of formula I where $R^1$ is halogen. For example, 5-nitro-1H-indazole (5) may be chlorinated to afford 3-chloro-5-nitro-1H-indazole (6) using the methods described by v. Auwers, et al, *Justus Liebigs Ann. Chem.,* 1927, 451, 295. Alternatively, the nitroindazole 5 can be treated with N-chlorosucciniimide to form a 3-chloro nitroindazole 6. The reduction of 6 to form the amino compound 7 may be achieved by following the methods described by Boyer, et al., *J. Chem. Res. Miniprint,* 1990, 11, 2601.

Scheme IV

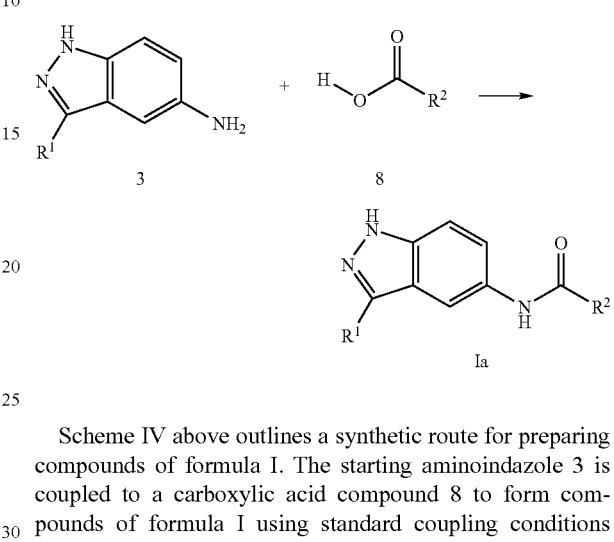

Scheme IV above outlines a synthetic route for preparing compounds of formula I. The starting aminoindazole 3 is coupled to a carboxylic acid compound 8 to form compounds of formula I using standard coupling conditions known in the art. Where necessary, reactive functional groups of $R^2$ may be protected before coupling. In certain cases, the yield of the coupling reaction has been improved by protecting the indazole ring NH, with a Boc group.

Scheme V

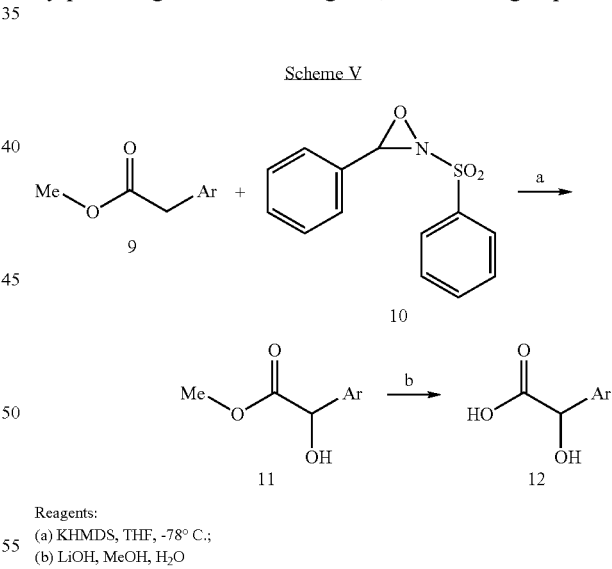

Reagents:
(a) KHMDS, THF, -78° C.;
(b) LiOH, MeOH, H₂O

Scheme V above shows a general method for preparing α-hydroxy acids 12 used for preparing compounds of formula Ib, where $R^3$ is OH, according to the methods described in Scheme IV. The formation of the α-hydroxy ester compound 11 front 9 and 10 was achieved by methods substantially similar to those described by Hernandez, et al, *J. Org. Chem.,* 1995, 60, 2683. The oxaziridine reagent 10 can be prepared according to the procedure described by Davies, et al., *J. Org. Chem.,* 1988, 53, 2087.

Scheme VI

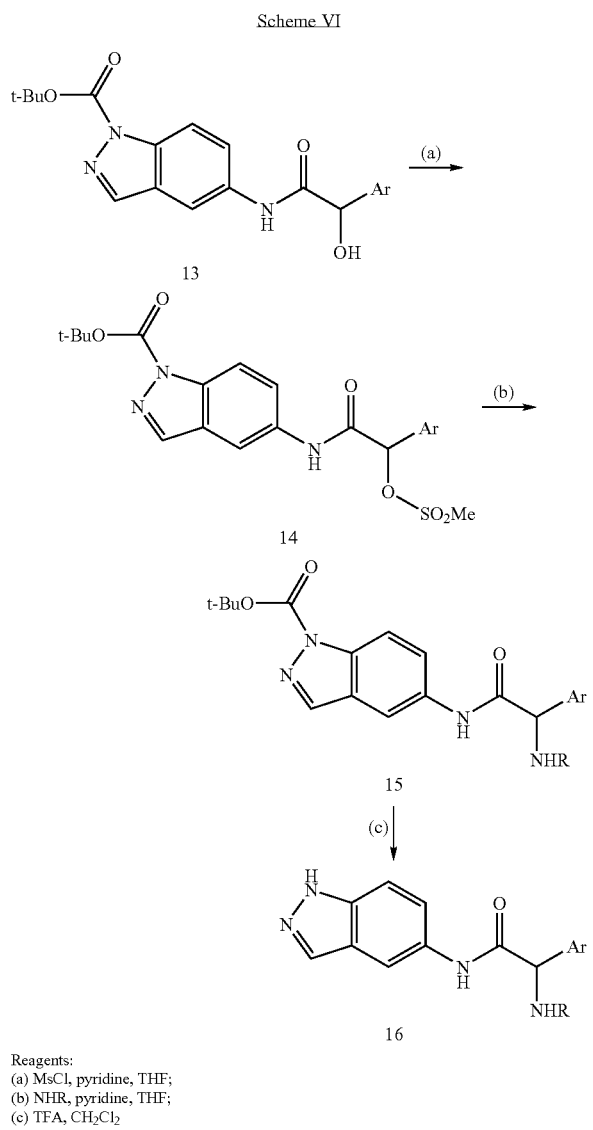

Reagents:
(a) MsCl, pyridine, THF;
(b) NHR, pyridine, THF;
(c) TFA, CH$_2$Cl$_2$ Scheme VI shows a general method for preparing compounds of formula Ib where R$^3$ is a variety of amino groups from compounds of formula Ib where R$^3$ is a hydroxy group as described above in Scheme V. Compound 13 may be treated with methanesulfonyl chloride and pyridine in THF to afford the mesyl derivative 14. The mesyl group may then be displaced by the desired amino group to afford compound 15. Removal of the Boc protecting group provides compound 16. Each of these steps are well known to one of skill in the art.

Scheme VII

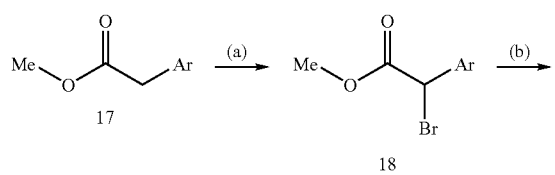

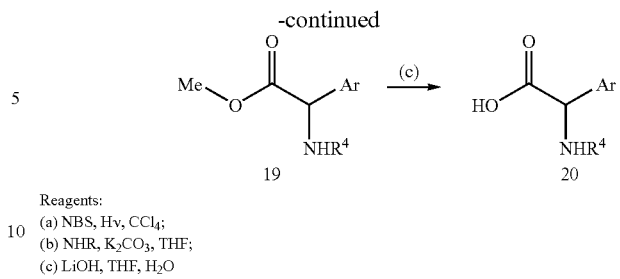

Reagents:
(a) NBS, Hv, CCl$_4$;
(b) NHR, K$_2$CO$_3$, THF;
(c) LiOH, THF, H$_2$O Scheme VII above shows a method for preparing carboxylic acid intermediates useful for preparing compounds of formula Ib where R$^3$ is an amino group. This method may be used to prepare compounds of formula Ib where R$^3$ is a variety of amino groups of formula N(R$^4$)$_2$, N(R)COT$_n$N(R$^4$)$_2$, or N(R)T$_n$N(R$^4$)$_2$. Each of the above steps is well known to one of skill in the art. Carboxylic acid compound 20 may then be coupled to the amino-indazole according to Scheme IV to afford compounds of formula Ib.

Scheme VIII

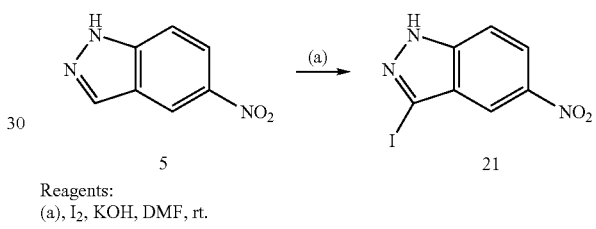

Reagents:
(a), I$_2$, KOH, DMF, rt.

Scheme VIII above shows the preparation of 3-iodo-5-nitroindazole (21) from 5-nitroindazole (5) according to methods substantially similar to that described in published PCT application number WO 02/10137.

Scheme IX

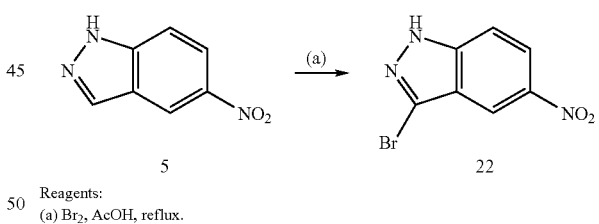

Reagents:
(a) Br$_2$, AcOH, reflux.

Scheme IX above shows a method for the preparation of 3-bromo-5-nitroindazole, by a method substantially similar to that described by Benchidimi, et al, *J Het. Chem.*, 1979, 16, 1599.

Scheme IX

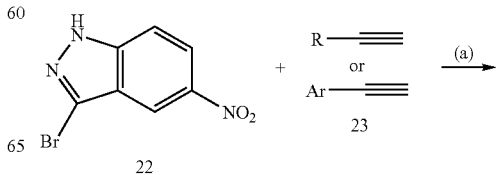

-continued

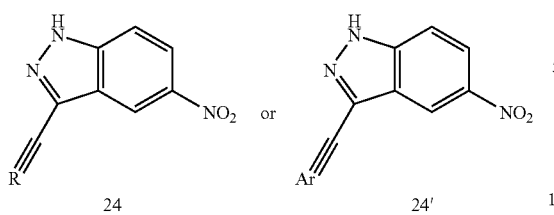

Reagents:
(a) Pd(PPh₃)₂Cl₂, CuI, Et₃N, DMF, 50° C.

Scheme IX above shows a general method for the preparation of compounds of formula I where $R^1$ is an alkynyl group. The bromoindazole (22) is coupled with propyne (23), by the Sonograshira coupling method, to afford 5-nitro-3-prop-1-ynyl-1H-indazole (24). One of skill in the art would recognize that a variety of alkynes are amenable to the above reaction and are useful for the preparation of a variety of compounds of formula I wherein the T moiety of the $R^1$ group is an alkynyl group.

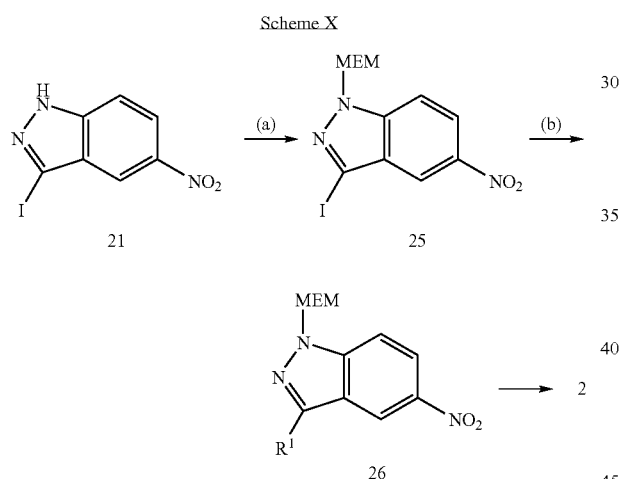

Reagents:
(a) MEMCl, NaHMDS, THF, rt;
(b) RB(OH)₂, Pd(dppf)₂Cl₂, K₂PO₄, DME, rt.

Scheme X above shows an alternative method for the preparation of nitroindazoles (2). The NH-group of the iodoindazole compound 21 may be protected. Although use of the MEM-protecting group is depicted above, one of skill in the art would recognize that a variety of protecting groups would be suitable for the above reaction. Other amino protecting groups are well known in the art and are described in detail in *Protecting Groups in Organic Synthesis*, Theodora W. Greene and Peter G. M. Wuts, 1991, published by John Wiley and Sons. The amino-protected iodoindazole (25) is coupled to a boronic acid using the Suzuki coupling methods that are well known in the art. One of ordinary skill in the art would recognize that a variety of boronic acids may be used in the Suzuki coupling thereby resulting in a variety of indazoles (26) where $R^1$ is alkyl or aryl.

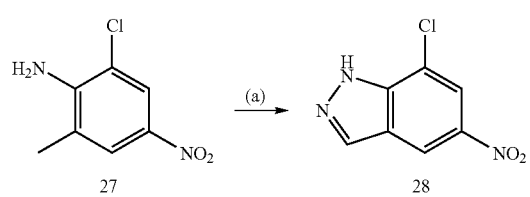

Reagents:
(a) NaNO₂, AcOH, reflux.

Scheme XI above shows a general method for the preparation of 7-chloro-5-nitroindazole (28) by treating 2-chloro-6-methyl-4-nitro-phenylamine (27) with sodium nitrate in the presence of acetic acid.

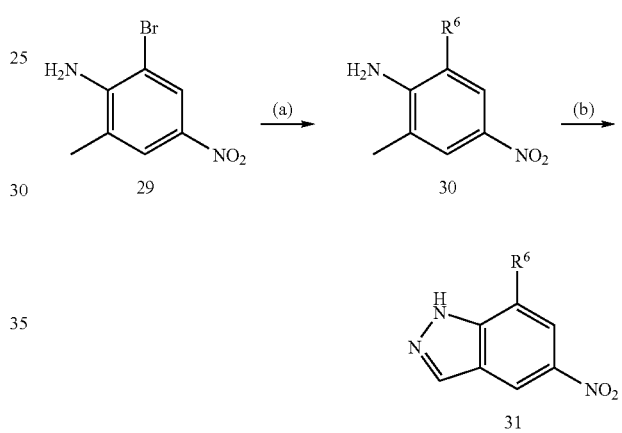

Reagents:
(a) R⁶B(OH)₂, Pd(PPh₃)₄, Na₂CO₃, DME, aq. EtOH;
(b) NaNO₂, AcOH, reflux.

Scheme XII above shows a general method for preparing compounds of formula I having an $R^6$ substituent at the 7-position (31). At step (a), 2-bromo-6-methyl-4-nitro-phenylamine (29) is coupled with a boronic acid using Suzuki coupling conditions to form the intermediate compound (30). One of ordinary skill in the art would recognize that a variety of boronic acids are suitable for the above reaction and would be useful in preparing a variety of compounds of formula I having an $R^6$ substituent at the 7-position of the indazole ring (31). The indazole ring is formed at step (b) by treating intermediate (30) with sodium nitrate and acetic acid at reflux.

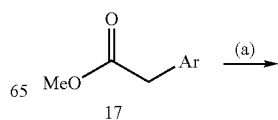

-continued

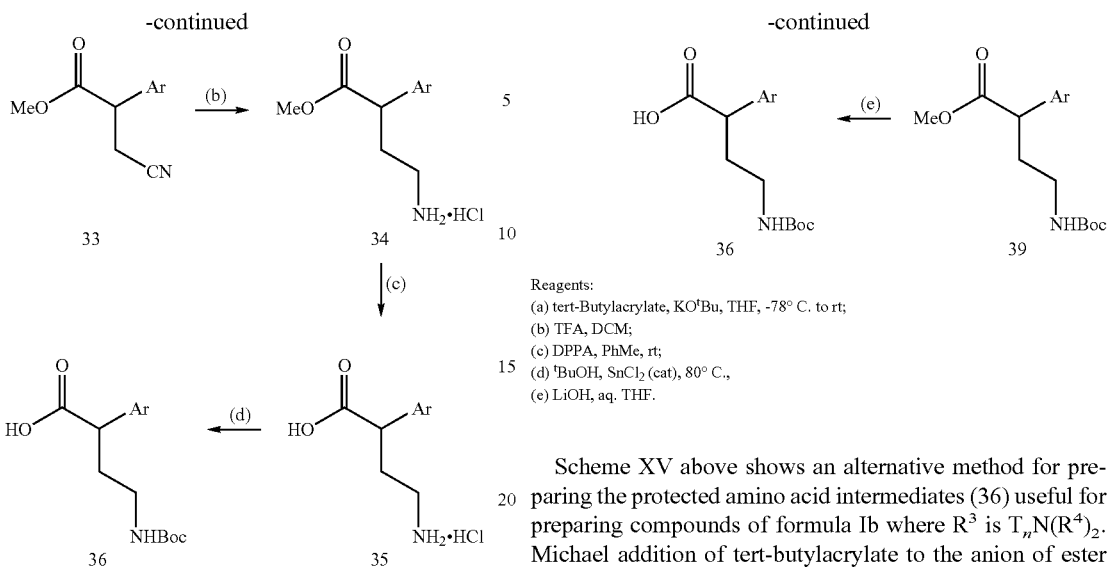

Reagents:
(i) LDA, -78° C.
(ii) ICH₂CN, -78° C. to ambient temperature, THF;
(b) H₂, PtO₂, HCl, MeOH;
(c) 8M HCl, reflux;
(d) (Boc)₂O, Na₂CO₃, aq. THF, ambient temperature.

Scheme XIV above shows a general method for preparing the protected amino acid intermediates (36) useful for preparing compounds of formula Ib where $R^3$ is $T_nN(R^4)_2$. The cyano compound (33) is prepared by treating the ester (17) with lithiumdiisopropylamide (LDA) at −78° C. then adding iodoacetonitrile. The nitrile is reduced using hydrogen in the presence of a platinum catalyst by a method substantially similar to that described by Prager, et al, *Aust. J. Chem.*, 1997, 50, 813. The resulting amine (34) is hydrolyzed to form the acid compounds 35. The amino groups is then protected with a BOC group by treating 35 with BOC-anhydride in the presence of aqueous sodium carbonate in tetrahydrofuran. Other amino protecting groups are well known in the art and are described in detail in *Protecting Groups in Organic Synthesis*, Theodora W. Greene and Peter G. M. Wuts, 1991, published by John Wiley and Sons.

Scheme XV

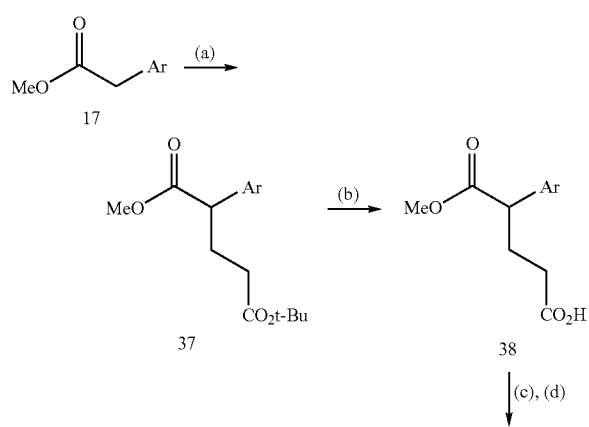

Reagents:
(a) tert-Butylacrylate, KO$^t$Bu, THF, -78° C. to rt;
(b) TFA, DCM;
(c) DPPA, PhMe, rt;
(d) $^t$BuOH, SnCl₂ (cat), 80° C.,
(e) LiOH, aq. THF.

Scheme XV above shows an alternative method for preparing the protected amino acid intermediates (36) useful for preparing compounds of formula Ib where $R^3$ is $T_nN(R^4)_2$. Michael addition of tert-butylacrylate to the anion of ester 17 affords the diester 37. The tert-butyl ester of compound 37 is selectively cleaved to afford the acid intermediate 38. The mono-ester 38 is then treated sequentially with diphenylphosphorylazide and tert-butanol to afford the BOC-protected amino ester 39. Hydrolysis of ester affords the desired protected amino acid intermediate (36).

Scheme XVI

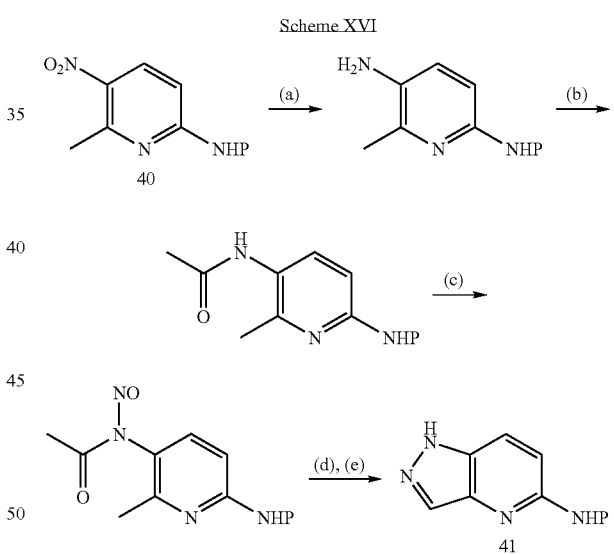

Reagents:
(a) H₂, Pd/C;
(b) Ac₂O;
(c) NOCl;
(d) benzene, reflux;
(e) KOH, ethanol, reflux Scheme XVI above shows a general method for preparing compounds of the present invention where $V^3$ is N. The pyridopyrazole intermediate 41, useful for the preparation of compounds of the present invention where $V^3$ is N, is prepared from the amino protected pyridine compound 40 by methods substantially similar to those described by Foster, H. E. et. al., J. Chem. Soc., Perkin Trans 1, 1973, 2901.

Scheme XVIII

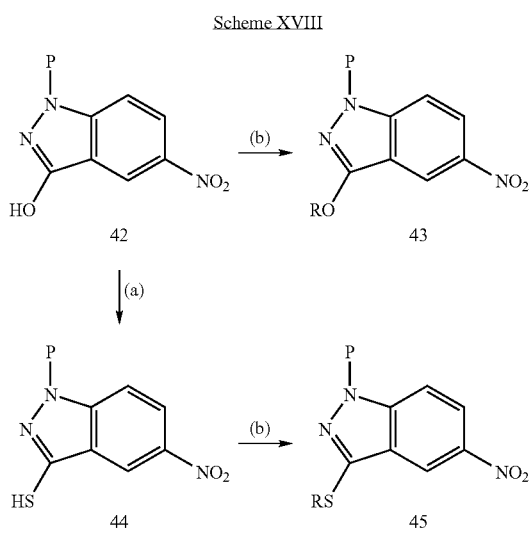

Reagents:
(a) P$_2$S$_5$, xylene, reflux;
(b) NaNH$_2$, RCl

Scheme XVI above shows a general method for preparing compounds of the present invention wherein a methylene unit of the T moiety of the R$^1$ group of formula I is replaced by either —O— or —S—. The formation of the indazole 42 was achieved by methods substantially similar to those described by Pfannstiel, K. et. al., Ber1942, 75B, 1096 and Vicente, J et al., *Heterocycles,* 1997, 45 (1), 129. Indazole 45 was synthesized from compound 42 following a procedure outlined by Kuroda, T et al in JP50130759.

Scheme XVIII

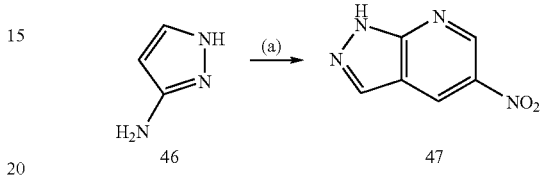

Scheme XVIII above shows a general scheme for preparing compounds of formula I where V$^1$ is nitrogen by methods substantially similar to that described by Fanta, *Org. Synth. Coll.,* 4, 844.

Scheme XIX

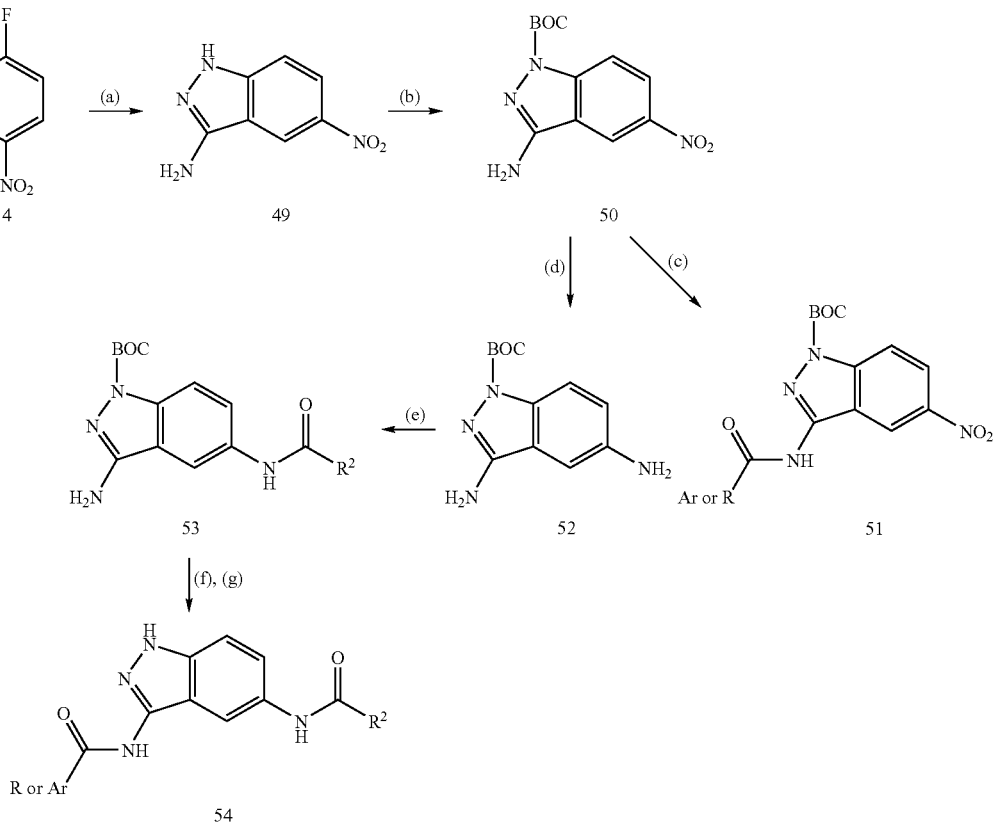

Reagents:
(a) N$_2$H$_4$·H$_2$O, BuOH, reflux;
(b) (Boc)$_2$O, Et$^i$Pr$_2$N, DMAP (cat), THF, rt;
(c) RC(O)Cl, Py;
(d) H$_2$, Pd/C, MeOH, rt;
(e) R$^2$CO$_2$H, PyBroP, DCM;
(f) RC(O)Cl, Et$^i$Pr$_2$N, DCM;
(g) TFA, DCM.

Scheme XVIII above shows a synthetic route for preparing compounds of the present invention where $R^1$ is $NH_2$, NHC(O)R, or NHC(O)Ar. Nitrile 4 may be treated with hydrazine to afford 3-aminoindazole 49. Selective Boc-protection of the endocyclic nitrogen, followed by acylation of the exocyclic nitrogen affords 5-nitroindazole 51. The nitro group may be reduced by hydrogenation (Scheme III) and the resulting amino group coupled with an acid 8 as in Scheme IV. Alternatively, hydrogenation of 5-nitroindazole 50 affords 3,5-diaminoindazole 52. Selective acylation with acid 8 yields the indazole 53, which may be elaborated as shown to provide indazole 54. All of the methods used are known to those skilled in the art.

The activity of a compound utilized in this invention as an inhibitor of AKT, PKA, PDK1, p70S6K, or ROCK kinase may be assayed in vitro, in vivo or in a cell line according to methods known in the art. In vitro assays include assays that determine inhibition of either the phosphorylation activity or ATPase activity of activated AKT, PKA, PDK1, p70S6K, or ROCK. Alternate in vitro assays quantitate the ability of the inhibitor to bind to AKT, PKA, PDK1, p70S6K, or ROCK. Inhibitor binding may be measured by radiolabeling the inhibitor prior to binding, isolating the inhibitor/AKT, inhibitor/PKA, inhibitor/PDK1, inhibitor/p70S6K, or inhibitor/ROCK complex and determining the amount of radiolabel bound. Alternatively, inhibitor binding may be determined by running a competition experiment where compounds are incubated with AKT, PKA, PDK1, p70S6K, or ROCK bound to known radioligands. Detailed conditions for assaying a compound utilized in this invention as an inhibitor of AKT, PKA, PDK1, p70S6K, or ROCK kinase are set forth in the Examples below.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that is effective to measurably inhibit a protein kinase, particularly AKT, PKA, PDK1, p70S6K, or ROCK kinase, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "measurably inhibit", as used herein means a measurable change in AKT, PKA, PDK1, p70S6K, or ROCK activity between a sample comprising said composition and a AKT, PKA, PDK1, p70S6K, or ROCK kinase and al equivalent sample comprising AKT, PKA, PDK1, p70S6K, or ROCK kinase in the absence of said composition.

A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a AKT, PKA, PDK1, p70S6K, or ROCK family kinase.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}$ alkyl$)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tarcolimus, rapamycin, mycophenolate mofetil, interferons, corticosteroids, cyclophophamide, azathioprine, and sulfasalizine; neurotrophic factors Such as acetylcholinesterase inhibitors, MAO inhibitors, interferons, anti-convulsants, ion channel blockers, riluzole, and anti-Parkinisonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

According to another embodiment, the invention relates to a method of inhibiting AKT, PKA, PDK1, p70S6K, or ROCK kinase activity in a biological sample comprising the step of contacting said biological sample with a compound of this invention, or a composition comprising said compound. Preferably, the method comprises the step of contacting said biological sample with a preferred compound of the present invention, as described herein supra.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of AKT, PKA, PDK1, p70S6K, or ROCK kinase activity in a biological sample is useful for a variety of purposes that are known to one of skill in the art. Examples of such purposes include, but are not limited to, blood transfusion, organ-transplantation, biological specimen storage, and biological assays.

Another aspect of this invention relates to a method for treating an AKT-, PKA-, PDK1-, p70S6K-, or ROCK-mediated disease in a patient, which method comprises administering to a patient in need thereof, a therapeutically effective amount of a compound of the present invention, or a pharmaceutically acceptable composition comprising said compound. According to a preferred embodiment, the invention relates to administering a compound of formula I', or a pharmaceutically acceptable composition comprising said compound. A more preferred embodiment relates to administering a preferred compound of formula I', as described herein supra, or a pharmaceutically acceptable composition comprising said compound.

According to another embodiment, the present invention relates to a method for treating an AKT-, PKA-, PDK1-, p70S6K-, or ROCK-mediated disease in a patient, which method comprises administering to a patient in need thereof, a therapeutically effective amount of a compound of formula IIa, IIb, or V, or a pharmaceutically acceptable composition comprising said compound. According to another embodiment, said method comprises administering to a patient in need thereof, a therapeutically effective amount of a preferred compound of formula IIa, IIb, or V, as described herein supra, or a pharmaceutically acceptable composition comprising said compound.

According to another embodiment, the present invention relates to a method for treating an AKT-, PKA-, PDK1-, p70S6K-, or ROCK-mediated disease in a patient, which method comprises administering to a patient in need thereof, a therapeutically effective amount of a compound of formula III or IV, or a pharmaceutically acceptable composition comprising said compound. According to another embodiment, said method comprises administering to a patient in need thereof, a therapeutically effective amount of a preferred compound of formula III, or IV, as described herein supra, or a pharmaceutically acceptable composition comprising said compound.

According to another embodiment, the invention provides a method for treating or lessening the severity of an AKT-mediated disease or condition in a patient comprising the step of administering to said patient a composition according to the present invention.

The term "AKT-mediated condition" or "disease", as used herein, means any disease or other deleterious condition in which AKT is known to play a role. The term "AKT-mediated condition" or "disease" also means those diseases or conditions that are alleviated by treatment with an AKT inhibitor. AKT-mediated diseases or conditions include, but are not limited to, proliferative disorders, cancer, cardiovascular disorders, rheumatoid arthritis, and neurodegenerative disorders. Preferably, said cancer is selected from pancreatic, prostate, or ovarian cancer.

According to another embodiment, the invention provides a method for treating or lessening the severity of a PKA-mediated disease or condition in a patient comprising the step of administering to said patient a composition according to the present invention.

The term "PKA-mediated condition" or "disease", as used herein, means any disease or other deleterious condition in which PKA is known to play a role. The term "PKA-mediated condition" or "disease" also means those diseases or conditions that are alleviated by treatment with a PKA inhibitor. PKA-mediated diseases or conditions include, but are not limited to, proliferative disorders and cancer. According to another embodiment, the invention provides a method for treating or lessening the severity of a PDK1-mediated disease or condition in a patient comprising the step of administering to said patient a composition according to the present invention.

According to another embodiment, the invention provides a method for treating or lessening the severity of an PDK1-mediated disease or condition in a patient comprising the step of administering to said patient a composition according to the present invention.

The term "PDK1-mediated condition" or "disease", as used herein, means any disease or other deleterious condition in which PDK1 is known to play a role. The term "PDK1-mediated condition" or "disease" also means those diseases or conditions that are alleviated by treatment with a PDK1 inhibitor. PDK1-mediated diseases or conditions include, but are not limited to, proliferative disorders, and cancer. Preferably, said cancer is selected from pancreatic, prostate, or ovarian cancer.

According to another embodiment, the invention provides a method for treating or lessening the severity of a p70S6K-mediated disease or condition in a patient comprising the step of administering to said patient a composition according to the present invention.

The term "p70S6K-mediated condition" or "disease", as used herein, means any disease or other deleterious condition in which p70S6K is known to play a role. The term "p70S6K-mediated condition" or "disease" also means those diseases or conditions that are alleviated by treatment with a p70S6K inhibitor. p70S6K-mediated diseases or conditions include, but are not limited to, proliferative disorders, such as cancer and tuberous sclerosis.

According to another embodiment, the invention provides a method for treating or lessening the severity of a ROCK-mediated disease or condition in a patient comprising the step of administering to said patient a composition according to the present invention.

The term "ROCK-mediated condition" or "disease", as used herein, means any disease or other deleterious condition in which ROCK is known to play a role. The term "ROCK-mediated condition" or "disease" also means those diseases or conditions that are alleviated by treatment with a ROCK inhibitor. Such conditions include, without limitation, hypertension, angina pectoris, cerebrovascular contraction, asthma, peripheral circulation disorder, premature birth, cancer, arteriosclerosis, spasm, retinopathy, inflammatory disorders, autoimmune disorders, AIDS, and osteoporosis.

According to another embodiment, the present invention relates to a method for treating or lessening the severity of a disease or condition selected from a proliferative disorder, a cardiac disorder, an inflammatory disorder, an autoimmune disorder, a viral disease, or a bone disorder, wherein said method comprises the step of administering an effective amount of a compound of the present invention. Preferably, said method comprises the step of administering an effective amount of a preferred compound of the present invention.

According to a preferred embodiment, the present invention relates to a method for treating or lessening the severity of a disease or condition selected from cancer, rheumatoid arthritis, asthma, HIV, angina pectoris, peripheral circulation disorder, hypertension, arteriosclerosis, or osteoporosis.

Preferably, the present invention relates to a method for treating or lessening the severity of a cancer.

More preferably, the present invention relates to a method for treating or lessening the severity of a cancer selected from brain (gliomas), breast, colon, head and neck, kidney, lung, liver, melanoma, ovarian, pancreatic, prostate, sarcoma, or thyroid.

Most preferably, the present invention relates to a method for treating or lessening the severity of pancreatic, prostate, or ovarian cancer.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutical compositions thereof may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound of this invention. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

SYNTHETIC EXAMPLES

As used herein, the term "$R_t$(min)" refers to the HPLC retention time, in minutes, associated with the compound. Unless otherwise indicated, the HPLC method utilized to obtain the reported retention time is as follows:

Column: XTerra C8 column, 4.6×150 mm
Gradient: 0–100% acetonitrile+methanol 60:40 (20 mM Tris phosphate)
Flow rate: 1.51 mL/minute
Detection: 225 nm.

Example 1

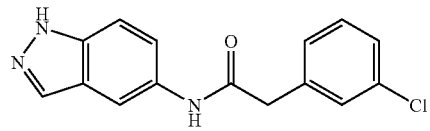

I-6

2-(3-Chloro-phenyl)-N-(1H-indazol-5-yl)-acetamide (I-6): To a solution of 5-aminoindazole (1 mmol), HOBt (1 mmol) and 3-chlorophenylacetic acid (1.1 mmol) in DMF (4 mL) was added N-methylmorpholine (1.1 mmol). After stirring for 10 minutes, EDC-HCl (1.1 mmol) was added and the reaction mixture stirred overnight at ambient temperature. The reaction mixture was concentrated and the residue purified by reverse phase preparative HPLC [Waters Delta-Pak C18, 15 uM, 100Å column, gradient 10%–100% B (solvent A: 0.05% TFA in water; solvent B: $CH_3CN$) over 10 minutes at 25 mL/min] to afford compound I-6 (79 mg, 42%). $^1$H NMR (400 MHz, DMSO-d6) δ 3.68 (2H, s), 7.12–7.73 (6H, m), 8.00 (1H, s), 8.11 (1H, s), 10.10 (1H, s), 12.97 (1H, bs); MS (ES+): m/e=(M+H) 286.

Example 2

We have prepared other compounds of formula I by methods substantially similar to those described in Example 1. The characterization data for these compounds is summarized in Table 2 below and includes HPLC, LC/MS (observed) and $^1$H NMR data.

$^1$H NMR data is summarized in Table 2 below wherein $^1$H NMR data was obtained at 400 MHz in deuterated DMSO, unless otherwise indicated, and was found to be consistent with structure. Compound numbers correspond to the compound numbers listed in Table 1.

TABLE 2

Characterization Data for Selected Compounds of Formula I

| Compound No I- | M+1(obs) | $R_t$(min) | $^1$H NMR |
| --- | --- | --- | --- |
| 1 | — | 6.65 | 2.61–2.67(2H, m), 2.91–2.95(2H, m), 7.19(1H, m), 7.27–7.29(4H, m), 7.37 (1H, d), 7.46(1H, d), 8.00(1H, s), 8.11 (1H, s), 9.89(1H, s), 12.95(1H, brs). |
| 2 | 320 | 7.90 | 3.8(2H, s), 7.3–7.7(6H, m), 8.0(1H, s), 8.2(1H, s), 10.3(1H, s), 13.0(1H, s) |

TABLE 2-continued

Characterization Data for Selected Compounds of Formula I

| Compound No I- | M+1(obs) | $R_t$(min) | $^1$H NMR |
|---|---|---|---|
| 3 | 295 | 6.90 | 3.4(3H, s), 3.5(2H, m), 6.7(2H, d), 7.2(2H, d), 7.4(2H, q), 8.1(1H, s), 8.2(1H, s), 10.1(1H, s), 13.0(1H, s). |
| 4 | 286 | 7.17 | 3.85(2H, s), 7.29–7.49(6H, m), 8.00 (1H, s), 8.10(1H, s), 10.20(1H, s), 13.00(1H, brs). |
| 5 | 286 | 7.48 | 3.66(2H, s), 7.36–7.49(6H, m), 8.00 (1H, s), 8.11(1H, s), 10.18(1H, s) 13.00(1H, brs). |
| 7 | 268 | 6.25 | 3.61(2H, s), 6.75–6.81(2H, m), 7.05 (1H, t), 7.15(1H, m), 7.44–7.45(2H, m), 8.00(1H, s), 8.12(1H, s), 9.54(1H, s), 10.06(1H, s), 13.00(1H, brs). |
| 8 | 268 | 5.75 | 4.54(2H, s), 6.63(1H, d), 6.76(2H, m), 7.09–7.13(1H, m), 7.40–7.49(2H, m), 8.00(1H, s), 8.12(1H, s), 10.12(1H, s), 13.00(1H, brs). |
| 9 | 268 | 5.51 | 3.51(2H, s), 6.68(2H, d), 7.14(2H, d), 7.42–7.45(2H, m), 8.00(1H, s), 8.11 (1H, s), 9.26(1H, s), 10.06(1H, s), 12.96(1H, brs). |
| 10 | 302 | 7.67 | 4.16(2H, s), 7.46–7.57(6H, m), 7.85 (1H, d), 7.94(1H, d), 7.99(1H, s), 8.11 (1H, s), 8.17(1H, d), 10.33(1H, s), 12.97(1H, brs). |
| 11 | 302 | 7.76 | 3.83(2H, s), 7.46–7.54(5H, m), 7.85–90 (4H, m), 8.00(1H, s), 8.14(1H, s), 10.25(1H, s), 12.98(1H, brs). |
| 12 | 352 | 8.39 | 3.7(2H, s), 7.3–7.6(4H, m), 7.7(2H, d), 8.0(1H, s), 8.2(1H, s), 10.3(1H, s), 13.0(1H, s). |
| 13 | 344 | 8.10 | 3.7(2H, s), 6.8(1H, d), 6.9(2H, d), 7.0–7.5(8H, m), 8.0(1H, s), 8.1(1H, s), 10.1(1H, s), 13.0(1H, s). |
| 14 | 358 | 8.14 | 3.7(2H, s), 5.1(2H, s), 6.9(1H, dt), 7.0(1H, d), 7.2–7.5(9H, m), 8.0(1H, s), 8.1(1H, s), 10.1(1H, s), 13.0(1H, s). |
| 15 | 344 | 8.21 | 3.6(2H, s), 7.0(4H, d), 7.1(1H, t), 7.3–7.5 (6H, m), 8.0(1H, s), 8.2(1H, s), 10.2(1H, s), 13.0(1H, s). |
| 16 | 321 | 7.99 | 3.69(2H, s), 7.34(1H, d), 7.40(1H, d), 7.48(1H, d), 7.55–7.62(2H, m), 8.00 (1H, s), 8.10(1H, s), 10.20(1H, s), 12.98(1H, s) |
| 17 | 288 | 7.20 | 3.67(2H, s), 7.19(1H, m), 7.38–7.49 (4H, m), 8.00(1H, s), 8.10(1H, s), 10.18(1H, s), 12.98(1H, brs). |
| 18 | 288 | 7.23 | 3.71(1H, s), 7.07–7.13(3H, m), 7.40 (1H, d), 7.48(1H, d), 8.00(1H, s), 8.10 (1H, s), 10.19(1H, s), 12.98(1H, brs). |
| 19 | 304 | 7.57 | 3.68(2H, s), 7.36–7.42(3H, m), 7.47 (1H, d), 7.56(1H, m), 8.00(1H, s), 8.10(1H, s), 10.18(1 H, s), 12.98(1H, brs). |
| 20 | 304 | 7.41 | 3.7(2H, s), 7.3(1H, m), 7.4–7.6(4H, m), 8.0(1H, s), 8.2(1H, s), 10.2(1H, s), 13.1(1H, s) |
| 21 | 296 | 6.67 | 3.6(2H, s), 6.0(2H, s), 6.7–6.9(3H, m), 7.4–7.5(2H, m), 8.0(1H, s), 8.2 (1H, s), 10.2(1H, s), 13.0(1H, bs) |
| 22 | 356, 354 | 8.13 | 3.5(2H, s), 7.3–7.5(2H, q), 7.7(2H, dd), 7.8(1H, s), 8.0(1H, s), 8.2(1H, s), 10.4(1H, s), 13.0(1H, s). |
| 23 | 253 | 5.40 | 3.71(2H, s), 7.36–7.49(3H, m), 7.75 (1H, m), 8.00(1H, s), 8.10(1H, s), 8.46 (1H, m), 8.54(1H, s), 10.23(1H, s), 12.98(1H, brs). |
| 24 | 291 | 6.88 | 3.74(2H, s), 6.98(1H, t), 7.07(1H, t), 7.27(1H, s), 7.35(1H, d), 7.44–7.46 (2H, m), 7.63(1H, d), 8.00(1H, s), 8.12(1H, s), 10.10(1H, s), 10.91(1H, brs), 12.98(1H, brs). |

TABLE 2-continued

Characterization Data for Selected Compounds of Formula I

| Compound No I- | M+1(obs) | R$_t$(min) | $^1$H NMR |
|---|---|---|---|
| 25 | 308 | 7.90 | 3.94(2H, s), 7.38–7.47(4H, m), 7.61 (1H, s), 7.92(1H, d), 7.99(2H, m), 8.12(1H, s), 10.29(1H, s), 12.97(1H, brs). |
| 26 | 258 | 6.67 | 3.66(2H, s), 7.11(1H, m), 7.33(1H, s), 7.42–7.50(3H, m), 8.00(1H, s), 8.12 (1H, s), 10.13(1H, s), 12.97(1H, brs). |
| 27 | 258 | 7.90 | 3.87(2H, s), 6.98(2H, m), 7.39–7.42 (2H, m), 7.48(1H, m), 8.01(1H, s), 8.12(1H, s), 10.20(1H, s), 12.98(1H, brs). |
| 28 | 244 | 7.49 | 1.16–1.23(2H, m), 1.51–1.61(4H, m), 1.74–1.76(2H, m), 2.23–2.31(3H, m), 7.39(1H, d), 7.45(1H, d), 7.99(1H, s), 8.12(1H, s), 9.83(1H, s), 12.98(1H, brs). |
| 29 | 258 | 8.00 | 0.96–1.02(2H, m), 1.12–1.24(3H, m), 1.60–1.78(6H, m), 2.18(2H, m), 7.38 (1H, d), 7.45(1H, d), 7.99(1H, s), 8.12 (1H, s), 9.83(1H, s), 12.95(1H, brs). |
| 30 | 272 | 8.47 | 1.18–1.26(2H, m), 1.39–1.72(12H, m), 2.01(1H, m), 2.22(2H, d), 7.39(1H, d), 7.45(1H, d), 7.99(1H, s), 8.13 (1H, s), 9.84(1H, s), 12.97(1H, brs). |
| 31 | 268 | 6.02 | 5.11(1H, m), 6.41(1H, m), 7.29(1H, m), 7.34–7.38(2H, m), 7.45–7.58(4H, m), 8.00(1H, s), 8.15(1H, s), 9.93(1H, s), 12.97(1H, brs). |
| 32 | 268 | 6.02 | 5.11(1H, m), 6.41(1H, m), 7.29(1H, m), 7.34–7.38(2H, m), 7.45–7.58(4H, m), 8.00(1H, s), 8.15(1H, s), 9.93(1H, s), 12.97(1H, brs). |
| 33 | 310 | 6.93 | 2.17(3H, s), 6.00(1H, s), 7.38–7.49 (5H, m), 7.57(2H, m), 8.00(1H, s), 8.07(1H, s), 10.33(1H, s), 12.99(1H, brs). |
| 34 | 286 | 6.29 | 5.12(1H, m), 6.47(1H, m), 7.19(2H, t), 7.45(1H, d), 7.54–7.58(3H, m), 8.00 (1H, s), 8.14(1H, s), 9.95(1H, s), 12.97(1H, brs). |
| 35 | 302 | 6.95 | 5.14(1H, m), 6.52(1H, m), 7.42–7.47 (3H, m), 7.54–7.56(3H, m), 8.00(1H, s), 8.14(1H, s), 9.56(1H, s), 12.98 (1H, brs). |
| 36 | 336 | 7.46 | 5.24(1H, m), 6.67(1H, m), 7.46(1H, d), 7.55(1H, d), 7.72–7.75(4H, m), 8.00(1H, s), 8.14(1H, s), 10.03(1H, s), 12.98(1H, brs). |
| 37 | 347 | 7.07 | 5.11(1H, m), 6.52(1H, m), 7.44–7.57 (6H, m), 8.00(1H, s), 8.13(1H, s), 9.96 (1H, s), 12.98(1H, brs). |
| 38 | 298 | 5.97 | 3.73(3H, s), 5.04(1H, m), 6.29(1H, m), 7.42–7.46(3H, m), 7.54(1H, m), 8.00 *1H, s), 8.15(1H, s), 9.88(1H, s), 12.98(1H, brs). |
| 39 | 302 | 6.33 | 5.48(1H, m), 6.64(1H, m), 7.33–7.37 (2H, m), 7.44–7.48(2H, m), 7.57–7.60 (2H, m), 8.00(1H, s), 8.16(1H, s), 10.05(1H, s), 12.99(1H, brs). |
| 40 | 302 | 6.91 | 5.15(1H, d), 6.59(1H, d), 7.35–7.56 (6H, m), 7.94(1H, s), 8.00(1H, s), 9.86 (1H, s), 12.98(1H, s) |
| 41 | 314 | 4.99 | 3.73(3H, s), 4.95(1H, m), 6.20(1H, m), 6.88(2H, m), 6.94(1H, s), 7.45 (1H, d), 7.55(1H, d), 8.00(1H, s), 8.15 (1H, s), 8.95(1H, s), 9.83(1H, s), 12.97(1H, brs). |
| 42 | 304 | 6.72 | 5.15(1H, m), 6.62(1H, m), 7.38–7.47 (3H, m), 7.53–7.55(2H, m), 8.00(1H, s), 8.13(1H, S), 9.97(1H, S), 12.98 (1H, S). |
| 43 | 304 | 6.78 | 5.18(1H, m), 6.71(1H, m), 7.17–7.25 (3H, m), 7.46(1H, d), 7.54(1H, d), 8.00(1H, s), 8.13(1H, s), 9.99(1H, s), 12.99(1H, brs). |

TABLE 2-continued

Characterization Data for Selected Compounds of Formula I

| Compound No I- | M+1(obs) | $R_t$(min) | $^1$H NMR |
|---|---|---|---|
| 44 | 307 | 5.85 | 5.35(1H, d), 6.07(1H, d), 7.01–7.08 (1H, m), 7.10–7.18(1H, m), 7.36(3H, m), 7.46(1H, d), 7.58(1H, d), 7.75 (1H, d), 8.00(1H, s), 8.18(1H, s), 9.94 (1H, s), 11.01(1H, d), 12.96(1H, s). |
| 45 | 318 | 7.15 | 5.30(1H, d), 6.58(1H, d), 7.44–7.59 (4H, m), 7.69(1H, d), 7.89–7.93(2H, m), 7.99(1H, s), 8.04(1H, s), 8.16(1H, s), 10.01(1H, s), 12.97(1H, s). |
| 46 | 367 | 8.14 | 1.40(9H, s), 5.37(1H, m), 7.28–7.40 (4H, m), 7.46–7.52(4H, m), 8.00(1H, s), 8.09(1H, s), 10.25(1H, s), 12.98 (1H, brs). |
| 47 | 367 | 8.14 | 1.40(9H, s), 5.37(1H, m), 7.28–7.40 (4H, m), 7.46–7.52(4H, m), 8.00(1H, s), 8.09(1H, s), 10.25(1H, s), 12.98 (1H, brs). |
| 48 | 267 | 5.80 | 5.07(1H, brs), 7.37(1H, d), 7.44–7.53 (4H, m), 7.60(2H, m), 8.05(1H, s), 8.09(1H, s), 8.73(3H, brs), 10.58(1H, s), 13.06(1H, brs). TFA salt |
| 49 | 267 | 5.80 | 5.07(1H, brs), 7.37(1H, d), 7.44–7.53 (4H, m), 7.60(2H, m), 8.05(1H, s), 8.09(1H, s), 8.73(3H, brs), 10.58(1H, s), 13.06(1H, brs). TFA salt |
| 50 | 301 | 6.71 | 5.1(1H, s), 7.35(1H, d), 7.45–7.65 (5H, m), 8.10(2H, d), 8.8(3H, bs), 10.6(1H, bs), 13.1(1H, bs) TFA salt |
| 51 | 301 | 6.69 | 5.13(1H, s), 7.36(1H, d), 7.51–7.55 (4H, m), 7.56(1H, s), 7.72(1H, s), 8.06–8.13 (1H, m), 8.78(3H, brs), 10.62 (1H, s), 13.08(1H, s) TFA salt |
| 52 | 347 | 6.78 | 3.61(2H, brs), 4.60(1H, s), 7.30(2H, m), 7.41(4H, br m), 7.60(1H, s), 7.96 (1H, s), 8.09(1H, s), 8.16(1H, s), 10.11 (1H, brs,), 12.95(1H, s). TFA salt |
| 53 | 335 | 7.19 | 3.10(2H, brs), 4.68(1H, s), 7.44(2H, m), 7.59(2H, br m), 7.75(1H, s), 7.88 (1H, s), 8.00(1H, s), 8.16(1H, s), 10.18 (1H, brs,), 12.99(1H, s). TFA salt |
| 54 | 335 | 7.39 | 5.16(1H, s), 7.36(1H, d), 7.51–7.58 (2H, m), 7.81(1H, d), 7.88(1H, s), 8.06 (2H, m), 8.78(3H, brs), 10.60(1H, s), 13.08(1H, brs) TFA salt |
| 55 | 319 | 6.93 | 5.19(1H, s), 7.37(1H, d), 7.51–7.61 (3H, m), 7.85(1H, m), 8.06–8.10 (2H, m), 8.83(3H, brs), 10.60(1H, s), 13.15(1H, brs) TFA salt |
| 56 | M−H 304 | 5.54 | — |
| 57 | 279 | 6.70 | .7(2H, AB quartet), 5.6(1H, s), 7.4–7.7 (6H, m), 8.10(2H, s), 9.5(1H, bs), 10.2 (1H, bs), 11.05(1H, s), 13.1(0.5H, bs) TFA salt |
| 58 | 317 | 6.93 | 5.30(1H, d), 7.40–7.45(1H, m), 7.50–7.55 (1H, m), 7.60–7.65(2H, m), 7.69 (1H, m), 7.89–7.93(2H, m), 7.99(2H, s), 8.05–8.1(2H, m), 8.95(2H, s), 10.75 (1H, s), 13.0(1H, brs). TFA salt |
| 76 | 316 | 7.22 | 2.42(3H, s), 5.14(1H, m), 6.57(1H, m), 7.37–7.40(3H, m), 7.48–7.53(2H, m), 7.59(1H, s), 8.07(1H, s), 9.95(1H, s), 12.55(1H, brs). |
| 77 | 333 | 7.17 | 2.45(3H, s), 5.15(1H, brs), 7.37(1H, d), 7.44(1H, d), 7.61(2H, m) 7.84 (1H, d), 7.95(1H, s), 8.76(3H, brs), 10.58(1H, s), 12.66(1H, s) TFA salt |
| 78 | 336 | 7.80 | 5.16(1H, d), 6.63(1H, d), 7.40(2H, m), 7.50(2H, m), 7.56(1H, s), 7.67(1H, m), 8.14(1H, s), 10.14(1H, s), 13.23(1H, s) |

TABLE 2-continued

Characterization Data for Selected Compounds of Formula I

| Compound No I- | M+1(obs) | $R_t$(min) | $^1$H NMR |
|---|---|---|---|
| 79 | 330 | 7.55 | 1.28(3H, t), 2.85(2H, q), 5.14(1H, d), 6.58(1H, d), 7.35–7.42(3H, m), 7.48–7.52 (2H, m), 7.59(1H, s), 8.11(1H, s), 9.95(1H, s), 12.55(1H, s). |
| 80 | 344 | 7.91 | 1.33(6H, d), 3.25(1H, sep), 5.14(1H, d), 6.59(1H, d), 7.37–7.42(3H, m), 7.49(1H, d), 7.54–7.59(2H, m), 8.17 (1H, s), 9.95(1H, s), 12.51(1H, s). |
| 81 | 378 | 8.30 | 5.15(1H, d), 6.63(1H, d), 7.36–7.42 (3H, m), 7.52–7.54(4H, m), 7.60(1H, s), 7.73(1H, d), 7.91(2H, d), 8.52(1H, s), 10.09(1H, s), 13.19(1H, s). |
| 82 | 301 | 6.87 | 3.65(2H, s), 5.25(2H, brs), 7.16(1H, d), 7.26(1H, d), 7.32–7.37(3H, m), 7.43(1H, s), 7.94(1H, s), 10.05(1H, s), 11.29(!H, brs). |
| 83 | 336 | 7.54 | 3.66(2H, s), 5.24(2H, brs), 7.15(1H, d), 7.25(1H, d), 7.33(1H, m), 7.59–7.61 (2H, m), 7.94(1H, s), 10.06(1H, s)<11.29(1H, brs). |
| 84 | 282 | 6.15 | 3.56–3.58(1H, m), 3.82–3.86(1H, m), 4.07–4.09(1H, m), 4.96(1H, m), 7.25 (1H, m), 7.31–7.35(2H, m), 7.39–7.47 (4H, m), 7.99(1H, s), 8.16(1H, s), 10.10(1H, s), 12.95(1H, brs). |
| 85 | 336, 334 | 7.13 | 3.6(1H, m), 3.87(1H, m), 4.00(1H, m), 5.01(1H, bs), 7.35–7.4(3H, m), 7.47(1H, d), 7.6(1H, d), 8.0(1H, s), 8.15(1H, s), 10.18(1H, s) |
| 86 | 266 | 7.23 | 1.4(3H, d), 3.8(1H, q), 7.2–7.5(7H, m), 8.0(1H, s), 8.2(1H, s), 10.1(1H, s), 13.0(1H, s) |
| 87 | 370 | 8.07 | 1.5(3H, d), 3.9(1H, q), 7.3–7.7(10H, m), 7.8(1H, s), 8.0(1H, s), 8.2(1H, s), 10.2(1H, s), 13.0(1H, s). |
| 88 | 320 | 8.68 | 0.8–1.9(9H, m), 2.6(1H, m), 7.2–7.5 (7H, m), 8.0(1H, s), 8.2(1H, s), 10.1 (1H, s), 13.0(1H, s) |
| 89 | 328 | 8.29 | 5.1(1H, s), 7.2–7.5(12H, m), 8.0(1H, s), 8.2(1H, s), 10.4(1H, s), 13.1(1H, s) |
| 90 | 292 | 6.09 | 2.9(2H, d), 4.45(1H, t), 7.4–7.5(3H, m), 7.7–7.8(3H, m), 8.0(1H, s), 8.1 (1H, d), 10.6(1H, s), 13.0(1H, s). |
| 91 | 317 | 7.7 | 2.7(2H, t), 4.3(2H, t), 7.0(2H, d), 7.3–7.5 (4H, m), 8.0(1H, s), 8.2(1H, s), 10.1(1H, s), 13.0(1H, s). |
| 92 | 280 | 7.5 | 1.87(2H, q), 2.3(2H, t), 2.6(2H, t), 7.1–7.3(5H, m), 7.4–7.5(2H, q), 8.0 (1H, s), 8.1(1H, s), 9.9(1H, s), 13.0 (1H, s). |
| 93 | 304 | 7.45 | 3.7(2H, s), 7.2(1H, t), 7.3–7.6(4H, m), 8.0(1H, s), 8.1(1H, s), 10.3(1H, s), 13.0(1H, s). |
| 94 | 362, 360 | 7.68 | 3.6(2H, s), 3.8(3H, s), 7.0(1H, t), 7.4–7.5 (4H, m), 8.0(1H, s), 8.1(1H, s), 10.1(1H, s), 13.0(1H, s). |
| 95 | 351, 349 | 7.46 | 3.07(2H, m), 3.21(2H, m), 4.15(1H, m), 7.26(1H, d, J=8.0Hz), 7.34(1H, d, J=8.7Hz), 7.53(2H, m), 7.60(1H, m), 8.06(2H, d, J=7.45Hz), 8.30(3H, brs), 10.46(1H, s), 13.09(1H, s) TFA salt |
| 96 | 351, 349 | 7.46 | 3.08(2H, m), 3.21(2H, m), 4.16(1H, m), 7.26(1H, d, J=8.4Hz), 7.35(1H, d, J=8.5Hz), 7.50(2H, m), 7.69(1H, m), 8.06(2H, d, J=6.6Hz), 8.25(3H, brs), 10.46(1H, s), 13.09(1H, s). TFA salt |

Example 3

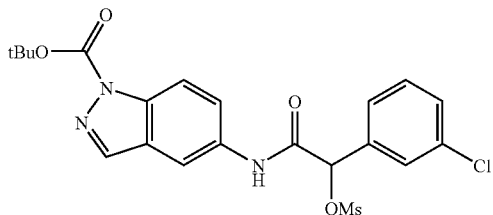

5-[2-(3-Chloro-phenyl)-2-methanesulfonyloxy-acetylamino]-indazole-1-carboxylic acid tert-butyl ester: 5-Amino-indazole-1-carboxylic acid tert-butyl ester was prepared following the procedure outlined by S. J. Brickner, WO9002744. 5-Amino-indazole-1-carboxylic acid tert-butyl ester was then coupled with 2-(3-chlorophenyl)-2-hydroxyacetic acid following the procedure as described in Example 1 to afford 5-[2-(3-chloro-phenyl)-2-hydroxyacetylamino]-indazole-1-carboxylic acid tert-butyl ester. To a solution of 5-[2-(3-chloro-phenyl)-2-hydroxy-acetylamino]-indazole-1-carboxylic acid tert-butyl ester (7.47 mmol) in dry THF (20 mL) at 0° C. was added pyridine (37.33 mmol, 5 equivalents) followed by methanesulfonyl chloride (22.40 mmol, 3 equivalents) added in a dropwise fashion. The resultant solution was stirred at ambient temperature overnight. The reaction mixture was then concentrated in vacuo and the resulting oil was partitioned between EtOAc and brine. The organic layer was washed with brine (thrice), dried over sodium sulphate, filtered and concentrated in vacuo to afford the title compound (3.58 g, qunatitative yield), which was used without further purification.

Example 4

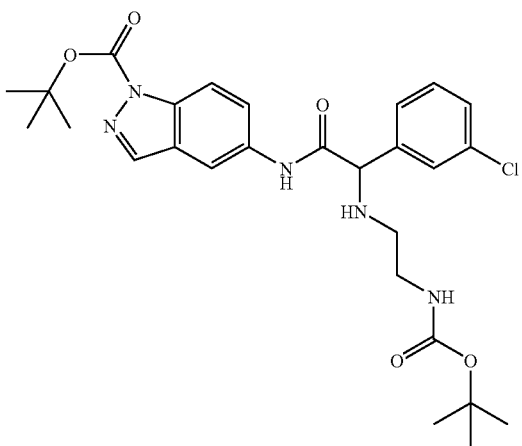

5-[2-(2-tert-Butoxycarbonylamino-ethylamino)-2-(3-chloro-phenyl)-acetylamino]-indazole-1-carboxylic acid tert-butyl ester: To a solution of 5-[2-(3-chloro-phenyl)-2-methanesulfonyloxy-acetylamino]-indazole-1-carboxylic acid tert-butyl ester (1.49 mmol) in dry THF (4 mL) was added pyridine (4.48 mmol, 3 equivalents) followed by followed by a dry THF solution of (2-amino-ethyl)-carbamic acid tert-butyl ester (3 equivalents, ~0.5 mL/mmol). The resulting solution was refluxed at 60° C. overnight. The reaction mixture was then concentrated in vacuo and the resulting oil was partitioned between EtOAc and brine. The organic layer was washed with brine (thrice), dried over sodium sulphate, filtered and concentrated under reduced pressure. The residue was purified by silica gel chromatography using eluting with EtOAc:hexane (60:40) to afford the title compound in 85% yield.

Example 5

I-59

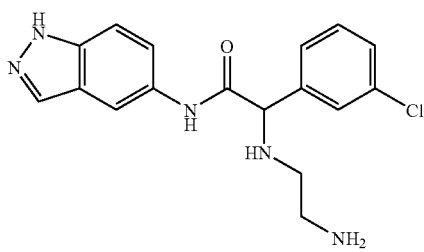

2-(2-Amino-ethylamino)-2-(3-chloro-phenyl)-N-(1H-indazol-5-yl)-acetamide (I-59): To 5-[2-(2-tert-butoxycarbonylamino-ethylamino)-2-(3-chloro-phenyl)-acetylamino]-indazole-1-carboxylic acid tert-butyl ester (1.26 mmol) was added trifluoroacetic acid (5 mL) and the reaction mixture was stirred for 1.5 hours. The reaction mixture was concentrated in vacuo and the residue purified by reverse phase preparative HPLC [Waters Delta Pak C18, 15 uM, 100A column, gradient 10%–100% B (solvent A: 0.05% TFA in water; solvent B: $CH_3CN$) over 10 minutes at 25 mL/min] to afford compound the title compound (172 mg, 82%). $^1$H NMR (400 MHz, DMSO-d6) δ 2.5–5.5(9H, br m), 6.9–7.3 (1H, m), 7.4–8.2(8H, m), 9.2–10.8(1H, br m), 13.0(1H, br s); MS (ES+): m/e=344.4(100%), 346.4(40%)

Example 6

We have prepared other compounds of formula I by methods substantially similar to those described in Examples 1, 3, 4, and 5. The characterization data for these compounds is summarized in Table 3 below and includes HPLC, LC/MS (observed) and $^1$H NMR data.

$^1$H NMR data is summarized in Table 3 below wherein $^1$H NMR data was obtained at 400 MHz in deuterated DMSO, unless otherwise indicated, and was found to be consistent with structure. Compound numbers correspond to the compound numbers listed in Table 1.

TABLE 3

Characterization Data for Selected Compounds of Formula I

| Compound No | M+1 (obs) | $R_t$(min) | $^1$H NMR |
|---|---|---|---|
| 60 | — | 6.0 | 2.0(2H, m), 2.8–3.2(4H, m), 5.2(1H, brs), 7.4(1H, m), 7.6(4H, m), 7.8(4H, m), 8.1(1H, m), 9.6–9.8(2H, brs), 10.8(1H, brs), 12.9–13.3(1H, brs) TFA salt |
| 61 | 358 | 5.8 | 2.6–2.7(3H, s), 2.9–3.4(4H, m), 5.1(1H, brs), 7.4(1H, m), 7.5–7.6 (4H, m), 7.7(1H, s), 8.1(2H, m), 10.5–10.7(1H, brs), 12.7–13.3(1H, brs) TFA salt |

TABLE 3-continued

Characterization Data for Selected Compounds of Formula I

| Compound No | M+1 (obs) | R$_t$(min) | $^1$H NMR |
|---|---|---|---|
| 62 | 372.5 | 6.1 | 2.8–3.4(10H, m), 4.7–4.9(1H, brs), 7.3–7.7(6H, m), 8.0–8.2(2H, m), 10.2–10.5(1H, brs), 12.7–13.3(1H, brs) TFA salt |
| 63 | 372 | 6.0 | 1.2(3H, m), 2.8–3.3(6H, m), 5.0(1H, brs), 7.4(1H, m), 7.6(4H, m), 7.7(1H, s), 8.0–8.1(2H, m), 10.5–10.8(1H, brs), 12.8–13.3(1H, brs) TFA salt |
| 64 | 434 | 7.5 | 2.8–3.4(4H, m), 4.2–4.3(2H, s), 4.7–5.1(1H, brs), 7.3–7.6(10H, m), 7.7(1H, s), 8.1(2H, m), 10.4–10.6 (1H, brs), 12.9–13.1(1H, brs) TFA salt |
| 65 | 392 | 7.6 | 4.2–4.4(2H, m), 5.2(1H, s), 7.3(1H, m), 7.4–7.6(6H, m), 7.7(1H, m), 7.9(1H, m), 8.0–8.1(2H, m), 8.7(1H, m), 9.6–10.5(1H, brs), 10.6(1H, s), 12.9–13.2(1H, brs) TFA salt |
| 66 | 406 | 7.7 | 3.2(3H, brs), 3.4(1H, brs), 5.2(1H, s), 7.5(3H, m), 7.6(4H, m), 7.8(2H, m), 8.1(2H, m), 8.6(1H, s), 9.6–9.9 (1H, brs), 10.7(1H, s), 12.8–13.2 (1H, brs) TFA salt |
| 67 | 372 | 6.0 | 3.2(3H, brs), 3.4(1H, brs), 5.2(1H, s), 7.5(3H, m), 7.6(4H, m), 7.8(2H, m), 8.1(2H, m), 8.6(1H, s), 9.6–9.9 (1H, brs), 10.7(1H, s), 12.8–13.2 (1H, brs) TFA salt |
| 68 | 400 | 6.6 | 0.9–1.0(3H, m), 1.5–1.6(2H, m), 2.0(2H, m), 2.7–3.1(6H, m), 5.2(1H, brs), 7.4(1H, m), 7.6(5H, m), 7.7–7.8 (1H, m), 8.1(2H, m), 8.4–8.6(2H, brs), 9.7–9.9(1H, m), 12.9–13.1 (1H, brs) TFA salt |

Example 7

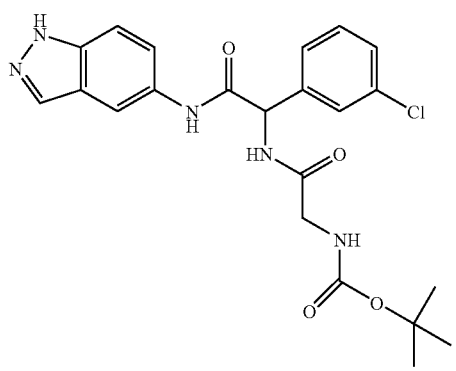

({[(3-Chloro-phenyl)-(1H-indazol-5-ylcarbamoyl)-methyl]-carbamoyl}-methyl)-carbamic acid tert-butyl ester: To a solution of 2-amino-2-(3-chloro-phenyl)-N-(1H-indazol-5-yl)-acetamide (0.17 mmol) and tert-butoxycarbonylamino-acetic acid (0.17 mmol) in THF (2 mL) was added HOBt (0.18 mmol). The reaction mixture was cooled to 0° C. and EDC (0.18 mmol) was added and the reaction mixture was left to stir overnight. The reaction mixture was then concentrated in vacuo and the residue was was partitioned between EtOAc and brine. The organic layer was washed with brine, dried over sodium sulphate, filtered and concentrated under reduced pressure. The residue was purified by silica gel chromatography eluting with EtOAc:hexanes (80: 20) to give the title compound in 55% yield.

Example 8

I-74

2-(2-Amino-acetylamino)-2-(3-chloro-phenyl)-N-(1H-indazol-5-yl)-acetamide (I-74): To a solution of ({[(3-chloro-phenyl)-(1H-indazol-5-ylcarbamoyl)-methyl]-carbamoyl}-methyl)-carbamic acid tert-butyl ester (0.09 mmol) in dichloromethane (2.5 mL) at 0° C. was added trifluoroacetic acid (2.5 mL) and the reaction mixture was stirred for 1 hour. The reaction mixture was concentrated in vacuo to afford compound the title compound (9 mg, 24%). $^1$H NMR (400 MHz, DMSO-d6) δ 3.8(2H, m), 5.8(1H, m), 7.4–7.7(5H, m), 7.9–8.2(4H, m), 9.3–9.4(1H, m), 10.6 (1H, s), 13.0(1H, br s); MS (ES+): m/e=358.3(40%), 134.3(100%).

Example 9

We have prepared other compounds of formula I by methods substantially similar to those described in Examples 7 and 8. The characterization data for these compounds is summarized in Table 4 below and includes HPLC, LC/MS (observed) and $^1$H NMR data.

$^1$H NMR data is summarized in Table 4 below wherein $^1$H NMR data was obtained in at 400 MHz deuterated DMSO, unless otherwise indicated, and was found to be consistent with structure. Compound numbers correspond to the compound numbers listed in Table 1.

TABLE 4

Characterization Data for Selected Compounds of Formula I

| Compound No I- | M+1(obs) | R$_t$(min) | $^1$H NMR |
|---|---|---|---|
| 75 | 344, 346 | 7.22 | 2.3–2.4(2H, m), 2.8(2H, m), 3.7(1H, s), 7.3–7.6(6H, m), 8.0–8.2(2H, m), 8.8–9.0(1H, brs), 10.4(1H, m), 12.8–13.0(1H, brs) |

Example 10

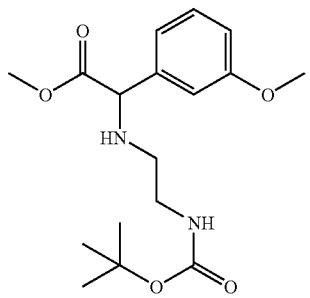

(2-tert-Butoxycarbonylamino-ethylamino)-(3-methoxy-phenyl)-acetic acid methyl ester: To a solution of (3-methoxy-phenyl)-acetic acid methyl ester (19.6 mmol) in CCl$_4$ was added N-bromosuccinimide (19.6 mmol) and the reaction mixture was irradiated for 2 hours. The reaction mixture was then concentrated in vacuo to afford the intermediate bromo-(3-methoxy-phenyl)-acetic acid methyl ester. To a solution of bromo-(3-methoxy-phenyl)-acetic acid methyl ester in THF (30 mL) under an atmosphere of nitrogen was added a solution of (2-amino-ethyl)-carbamic acid tert-butyl ester (20.6 mmol) in THF (20 mL) followed by K$_2$CO$_3$ (39.2 mmol, 2 equivalents). The reaction mixture was stirred for 2 hours at room temperature. The reaction mixture was partitioned between water (50 mL) and EtOAc (2×50 mL), the combined organics were dried (sodium sulfate) and concentrated in vacuo to afford an oil. The oil was purified by silica gel column chromatography using as eluent EtOAc:petrol (1:1) to give the title compound as an oil in 53% yield.

Example 11

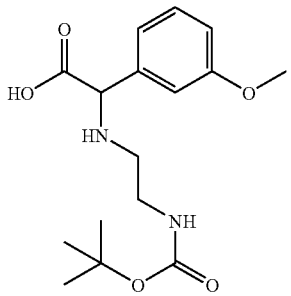

(2-tert-Butoxycarbonylamino-ethylamino)-(3-methoxy-phenyl)-acetic acid: To a solution of (2-tert-butoxycarbonylamino-ethylamino)-(3-methoxy-phenyl)-acetic acid methyl ester (10.4 mmol) in TiAF:H$_2$O (3:1, 40 mL) was added LiOH (10.9 mmol) and the reaction mixture was stirred for 3 hours at room temperature. The reaction mixture was concentrated in vacuo then diluted with H$_2$O and neutralised with 2M HCl solution and the resulting precipitate was collected by filtration to afford the title compound in 46% yield.

Example 12

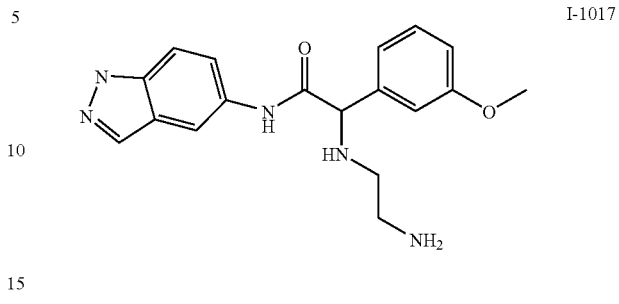

I-1017

2-(2-Amino-ethylamino)-N-(1H-indazol-5-yl)-2-(3-methoxy-phenyl)-acetamide (I-1017): 5-Aminoindazole was coupled with (2-tert-butoxycarbonylamino-ethylamino)-(3-methoxy-phenyl)-acetic acid according to the method described in Example 1. The BOC protecting group was then removed according to the method described in Example 8 to afford compound I-1017. $^1$H NMR (400 MHz, DMSO-d6) δ 3.02–3.14 (4H, m), 3.80 (3H,s), 4–5 (1H, vbr s), 5.11 (1H, brs), 7.05 (1H,d), 7.20 (2H,m), 7.40 (2H,m), 7.52 (1H,d), 7.5–8 (2H, brs), 8.05 (1H,s), 8.07 (1H,s), 8.2–10.1 (1H, brs), 10.68 (1H,brs), 13.15 (1H,brs); MS (ES+): m/e=340.

Example 13

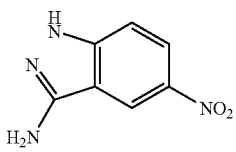

5-Nitro-1H-indazole-3-ylamine: Hydrazine monohydrate (17.5 mL, 362 mmol) was added to a hot (50° C.) solution of 2-fluoro-5-nitrobenzonitrile (30 g, 181 mmol) in EtOH (500 mL). The mixture was heated at reflux for 4 hours then allowed to cool to room temperature, whereupon the product precipitated from solution. The filtrate was concentrated and the residue partitioned between EtOAc and saturated ammonium chloride solution. The organic phase was separated, dried over magnesium sulfate and concentrated to obtain further product. The combined product (32.2 g, quant.) was taken on to the following step without further purification.

Example 14

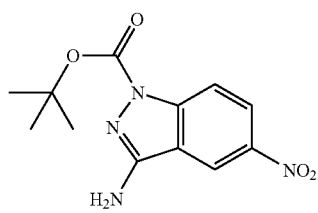

3-Amino-5-nitroindazole-1-carboxylic acid tert-butyl ester: Dimethylaminopyridine (4 g, 36 mmol) was added to a solution of 5-nitro-1H-indazol-3-ylamine (32.2 g, 181 mmol), tert-butyldicarbonate (39.4 g, 181 mmol) and triethylamine (25 mL, 181 mmol) in THF (1 L) at room temperature under nitrogen. After stirring for 30 minutes, the reaction mixture was concentrated and the residue partitioned between EtOAc and saturated ammonium chloride solution. The layers were separated and the organic phase washed with brine, dried (MgSO₄), and concentrated to an orange solid. Recrystallisation from ethyl acetate provided the title product as a yellow solid (25 g, 50%). $^1$H NMR (400 MHz, DMSO) 1.60 (9H, s), 6.75 (2H, brs), 8.10 (1H, d), 8.36 (1H, d), 8.96 (1H, s); MS (ES−) m/e=277.

Example 15

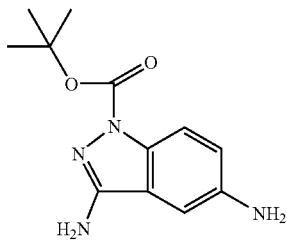

3,5-Diamino-indazole-1-carboxylic acid tert-butyl ester: 3-Amino-5-nitroindazole-1-carboxylic acid tert-butyl ester (3 g, 10.8 mmol) was dissolved in MeOH (50 mL) and the solution degassed (3× alternating vacuum/nitrogen purges). Palladium on charcoal 10% w/w (300 mg) was added and the nitrogen atmosphere replace by hydrogen. After 3 hours, the mixture was filtered through a pad of Celite® and the filtrate concentrated to afford the title compound as a highly viscous oil (2.17 g, 81%). $^1$H NMR (400 MHz, DMSO)1.55 (9H, s), 5.07 (2H, brs), 6.04 (2H, brs), 6.79–6.82 (2H, m), 7.62 (1H, brs). MS (ES+) m/e=249.

Example 16

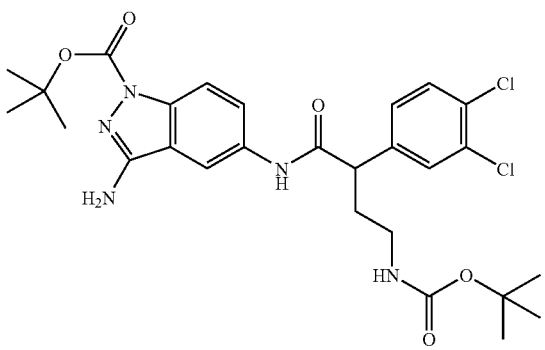

3-Amino-5-[4-tert-butoxycarbonylamino-2-(3,4-dichlorophenyl)-butyrylamino]-indazole-1-carboxylic acid tert-butyl ester: To a stirred solution of 3,5-diamino-indazole-1-carboxylic acid tert-butylester (2.17 g, 8.75 mmol), PyBroP (4.1 g, 8.75 mmol) and 4-tert-butoxycarbonylamino-2-(3,4-dichloro-phenyl)-butyric acid (3 g, 8.75 mmol) in dichloromethane (100 mL) was added diisopropylethylamine (3.0 mL, 17.5 mmol) at 0° C. The resulting mixture was allowed to warm to room temperature over 4 hours then was concentrated and the residue partitioned between EtOAc and ammonium chloride (saturated, aqueous). The organic phase was separated and washed with sodium bicarbonate (saturated, aqueous), then dried (sodium sulfate) and concentrated to a brown foam. Purification by column chromatography (silica, 20% petroleum ether-EtOAc gave the title compound as a light brown solid (2.92 g, 58%); $^1$H NMR (400 MHz, DMSO) 1.36 (9H, s), 1.56 (9H, s), 1.80–1.90 (1H, m), 2.10–2.20 (1H, m), 2.89 (2H, m), 6.29 (2H, brs), 6.87 (1H, t), 7.38 (1H, d), 7.45 (1H, d), 7.61–7.65 (2H, m), 7.90 (1H, m), 8.19 (1H, s), 10.30 (1H, s); MS (ES+) m/e=578.

Example 17

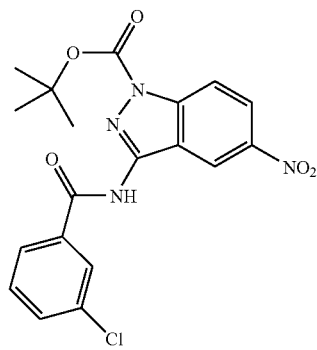

3-(3-Chlorobenzoylamino)-5-nitroindazole-1-carboxylic acid tert-butyl ester: 3-Amino-5-nitroindazole-1-carboxylic acid tert-butyl ester (600 mg, 2 mmol) was dissolved in dry pyridine (15 mL) under nitrogen. The solution was cooled on an ice bath and 3-chlorobenzoyl chloride (0.3 mL, 2 mmol) added. After 6 hours, the mixture was diluted with EtOAc, washed with 1M hydrochloric acid solution (×3) and brine then dried over magnesium sulfate and concentrated to a solid. Purification by column chromatography (silica, 7:3 petrol)-EtOAc) afforded the title compound as a solid (300 mg, 39%); $^1$H NMR (400 MHz, CDCl₃) 1.77 (9H, s), 7.52 (1H, t), 7.62 (1H, d), 7.90 (1H, d), 8.07 (1H, m), 8.32 (1H, d), 8.45 (1H, d), 9.22 (1H, brs), 9.32 (1H, s); MS (ES+) m/e=417.

Example 18

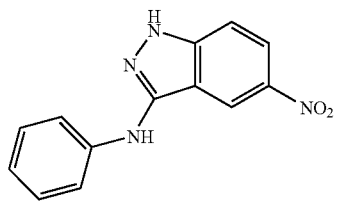

(5-Nitro-1H-indazol-3-yl)-phenylamine: 2-Fluoro-5-nitro-N-phenyl benzamide (100 mg, 0.38 mmol) was suspended in EtOH (10 mL) and the mixture heated to 50° C. To the resulting solution was added hydrazine monohydrate (0.1 mL, 1.9 mmol). The mixture was heated at reflux for 30 minutes, at which time LC-MS showed complete conversion to the aryl hydrazine (ES+m/e=273). The mixture was allowed to cool to room temperature, concentrated and the residue partitioned between EtOAc and saturated ammonium chloride solution. The layers were separated and the organic phase was dried over sodium sulfate and concentrated to a yellow foam. The residue was dissolved in phosphorous oxychloride (5 mL) and the mixture heated at 90° C. for 30 minutes, then allowed to cool to room temperature and stirred overnight. The reaction mixture was concentrated and the residue partitioned between EtOAc and saturated sodium bicarbonate. The organic phase was dried over sodium sulfate and concentrated to afford the title compound as a red solid (80 mg, 83%); $^1$H NMR (400 MHz, DMSO) 6.88 (1H, t), 7.31 (2H, t), 7.51 (1H, d), 7.74 (2H, t), 8.17 (1H, dd), 9.24 (1H, s), 9.42 (1H, s), 12.74 (1H, s); MS (ES+) m/e=255.

Example 19

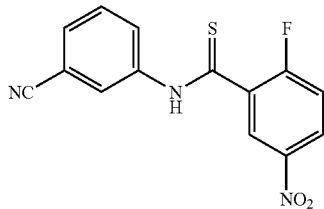

N-(3-Cyano-phenyl)-2-fluoro-5-nitro-thiobenzamide: To a solution of N-(3-Cyano-phenyl)-2-fluoro-5-nitro-benzamide (10.0 g; 0.035 mol) in toluene (100 mL) was added Lawson's reagent (7.84 g; 0.019 mol) and the solution refluxed for 16 hours. The reaction mixture was concentrated in vacuo and purified by flash chromatography, eluting with 30% ethyl actetate/petroleum ether to afford the title compound as a yellow solid (8.56 g; 81%). $^1$H NMR (400 MHz, CDCl$_3$) $\delta_H$ 7.60–7.75 (2H, m), 7.80 (1H, m), 8.15 (1H, d), 8.40–8.50 (1H, m), 8.50 (1H, s), 8.50–8.55 (1H, n), 12.45 (1H, br). Mass Spectrum (ES−) m/e=300.22.

Example 20

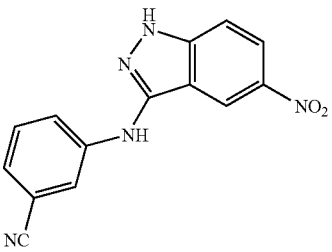

3-(5-Nitro-1H-indazol-3-ylamino)-benzonitrile: To a solution of N-(3-Cyano-phenyl)-2-fluoro-5-nitro-thiobenzamide (8.56 g; 0.028 mol) in n-butanol (300 mL) was added hydrazine hydrate (2.54 mL; 0.053 mol) and the solution refluxed for 3 hours. The reaction mixture was concentrated in vacuo and triturated with hot ethanol to afford the title compound as a red solid (4.93 g; 62%). $^1$H NMR (400 MHz, DMSO-d6) $\delta_H$ 7.30 (1H, d), 7.45–7.60 (2H, m), 7.90 (1H, d), 8.20 (1H, d), 8.25 (1H, s), 9.20 (1H, s), 9.85 (1H, s). Mass Spectrum (ES−) m/e=278.28.

Example 21

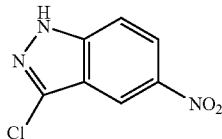

3-Chloro-5-nitroindazole: 5-Nitroindazole (5 g, 30.7 mmol) was suspended in glacial AcOH (150 mL) and the mixture heated to 50° C. N-Chlorosuccinimide (4.9 g, 36.8 mmol) was added and the mixture heated at relux (solution forms) for 1 hour. The reaction mixture was concentrated and partitioned between EtOAc and brine. The organic phase was washed with saturated sodium bicarbonate, dried over sodium sulfate and concentrated to a yellow solid. Recrystallisation from EtOH provided the title compound as a pale yellow solid (2.63 g, 43%); $^1$H NMR (400 MHz, DMSO) $\delta$ 7.73 (1H, d), 8.21 (1H, dd), 8.51 (1H, d), 13.97 (1H, brs); MS (ES−) m/e=196.

Example 22

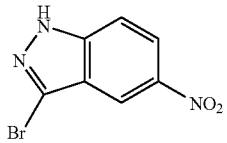

3-Bromo-5-nitroindazole: 5-Nitroindazole (10 g, 61.3 mmol) was dissolved in acetic acid (170 mL) and the mixture heated to 80° C. Bromine (3.1 mL, 60.7 mmol) was added slowly and the mixture heated to reflux. After 2 hours, the reaction mixture was allowed to cool to room temperature, and the resulting precipitate filtered off. Additional product was isolated by concentrating the filtrate, partitioning the residue between chloroform and saturated sodium bicarbonate solution, separating and drying the organic phase over sodium sulfate. Concentration gave a solid which was combined with the original precipitate to give the title compound as a yellow solid (11.4 g, 77%). $^1$H NMR $\delta$ 7.74 (1H, d), 8.21 (1H, dd), 8.40 (1H, d), 14.06 (1H, brs); MS (ES−) m/e=240.

Example 23

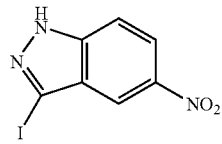

3-iodo-5-nitro-1H-indazole: To a solution of 5-nitro-1H-indazole (10.0 g, 62.3 mmol) in DMF (120 ml) was added potassium hydroxide (12.9 g, 230.4 mmol) followed by iodine (31.1 g, 122.6 mmol) portion wise over 5 minutes. The resulting mixture was stirred at room temperature for 14 hours and then poured onto 10% sodium metabisulfite (100 ml) and extracted into ethyl acetate (3×50 ml). The combined organic extracts were washed with brine (50 ml), dried (Na$_2$SO$_4$) and concentrated in vacuo to afford the title compounds as a pale orange solid (17.5 g). $^1$H NMR (400 MHz, DMSO-d6) δ 7.77 (1H, d), 8.26 (1H, d), 8.34 (1H, s), 14.15 (1H, s). MS (ES+) m/e=290.

Example 24

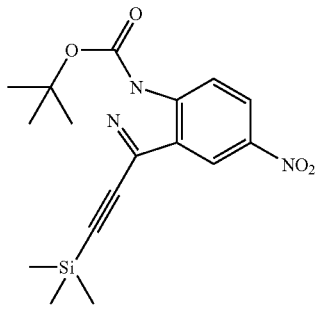

5-Nitro-3-(trimethylsilylethynyl)-indazole-1 carboxylic acid tert-butyl ester: 3-Bromo 5-nitro-indazole-1-carboxylic acid tert-butyl ester (2 g, 5.8 mmol) was dissolved in dry DMF (30 mL) under nitrogen and triethylamine (1.6 mL, 1.6 mmol) added. Copper iodide (20 mg, 0.12 mmol), trimethylsilylacetylene (2.5 mL, 17.4 mmol) palladium bis-triphenylphosphine dichloride (84 mg, 0.12 mmol) and a further 1.6 mL of triethylamine were added and the mixture heated at 50° C. overnight. The reaction mixture was allowed to cool to room temperature and concentrated. The residue was taken up in EtOAc and filtered through a plug of Celite®. The filtrate was washed with saturated ammonium chloride solution and dried over sodium sulfate then concentrated to a black foam. Purification by chromatography (silica, 1:1 petrol-EtOAc) gave the title compound as a black solid (940 mg, 45%); MS (ES+) m/e=360.

Example 25

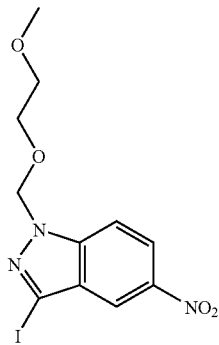

3-iodo-1-(2-methoxyethoxymethyl)-5-nitro-1-H-indazole: To a solution of 3-iodo-5-nitro-1H-indazole (10.0 g, 34.6 mmol) in THF (50 ml) was added sodium bis(trimethylsilyl)amide (1M in THF, 48.4 mmol, 48.4 ml) and the solution stirred at room temperature for 20 minutes. 2-methoxyethoxymethyl chloride (4.9 g, 39.1 mmol, 4.5 ml) was added and the solution stirred at room temperature for 15 hours. The reaction was quenched with ammonium chloride (30 ml, saturated aqueous) and extracted into ethyl acetate (3×50 ml). The combined organic extracts were dried (Na$_2$SO$_4$) and concentrated in vacuo. The resulting residue was purified by flash column chromatography on silica gel (1:1 EtOAc:hexanes) to give the title compound as an orange solid (6.0 g). $^1$H NMR (400 MHz, CDCl$_3$) δ 3.35 (3H, s), 3.50–3.52 (2H, m), 3.68–3.70 (2H, m), 5.86 (1H, s), 7.69 (1H, d), 8.38 (1H, d), 8.53 (1H, s). MS (ES+) m/e=378.

Example 26

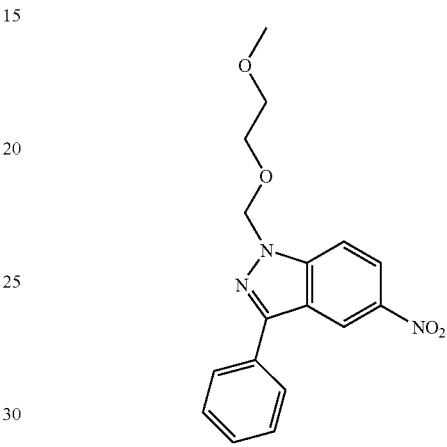

3-iodo-1-(2-methoxyethoxymethyl)-5-nitro-3-phenyl-1H-indazole: To a mixture of 3-iodo-1-(2-methoxyethoxymethyl)-5-nitro-1H-indazole (0.50 g, 1.32 mmol), phenyl boronic acid (0.22 g, 1.80 mmol), potassium phosphate (1.26 g, 5.94 mmol) and 1,1'-Bis(diphenylphosphino)ferrocenedichloropalladium(II), complex with dichloromethane (0.15 g, 0.18 mmol) was added dry dimethoxyethane (8.0 ml) and then heated at 85° C. for 18 hours. Ammonium chloride solution (30 ml, saturated aqueous) was added and extracted into ethyl acetate (3×30 ml). The combined organic extracts were dried (Na$_2$SO$_4$) and concentrated in vacuo. The residue was purified by flash column chromatography on silica gel (3% MeOH in DCM) to afford the title compound as a yellow solid (0.35 g, 81%). $^1$H NMR (400 MHz, CDCl$_3$) δ 3.37 (3H, s), 3.51–3.53 (2H, m), 3.73–3.75 (2H, m), 5.93 (1H, s), 7.50–7.54 (1H, m), 7.57–7.61 (2H, m), 7.73 (1H, d), 7.98 (2H, dd), 8.37 (1H, dd), 9.00 (1H, s).

Example 27

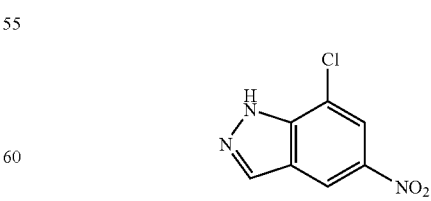

7-Chloro-5-nitro-1H-indazole: To a solution of 2-chloro-6-methyl-4-nitroaniline (5.49 g, 29.4 mmole) in acetic acid (150 mL) was added sodium nitrite (2.03 g, 29.4 mmole) pre-dissolved in water (5 mL). The resulting brown slurry was stirred overnight at room temperature, then at 60° C. for a further 4 hours. The bulk of the solvent was removed by evaporation in-vacuo and the resulting black residue re-dissolved in EtOAc (100 mL) and washed in brine (2×70 mL). The organic layer was dried (MgSO$_4$), filtered and concentrated to give a mixture of starting material and product 91 mg(1.49 g). The crude mixture was taken through to the next step; $^1$H NMR (400 MHz, DMSO) δ 8.25(1H, s), 8.50(1H, s), 8.85(1H, s), 14.30(1H, br s).MS (ES+): m/e=198 (minus Boc).

Example 28

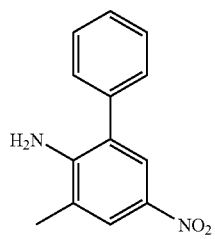

3-Methyl-5-nitro-biphenyl-2-ylamine: A mixture of 2-bromo-6-methyl-4-nitroaniline (100 mg, 0.43 mmole), phenyl boronic acid (81 mg, 0.66 mmole), 2M Na$_2$CO$_{3(aq)}$ (660 μL), Pd(PPh$_3$)$_4$ (4 mg, 0.0033 mmole) in DME(2.4 mL) containing 1.0:1.3 EtOH/H$_2$O (1.4 mL) was placed in a microwave tube and degassed for 5 minutes. The tube was then capped and irradiated with microwaves (CEM Discover) for 20 minutes at 110° C. The crude reaction mixture was diluted with dichloromethane (10 mL) and washed with saturated NaHCO$_3$ solution (3×20 mL). The organic layer was dried (MgSO$_4$), filtered and concentrated in-vacuo to afford a crude solid, this was then purified further by flash chromatography (100% dichloromethane) to yield the desired pure (91 mg) as a bright yellow solid. $^1$H NMR (400 MHz, CDCl$_3$) δ 2.25(3H, s), 4.42(2H, br s), 7.39(3H, m), 7.50(2H, m), 7.97(1H, s), 8.12(1H, s). MS (ES+): m/e=229, (ES−): m/e=227.

Example 29

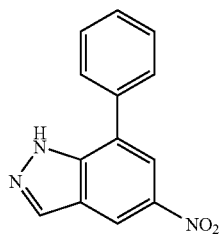

5-Nitro-7-phenyl-1H-indazole: To a solution of 3-Methyl-5-nitro-biphenyl-2-ylamine (91 mg, 0.39 mmole) in pre-heated glacial acetic acid (4 mL) was added 0.44M sodium nitrite solution (1 mL), in a dropwise fashion. The resulting mixture was stirred overnight at room temperature. The crude product was concentrated in-vacuo and the residue re-dissolved in EtOAc (20 mL) and washed with saturated NaHCO$_3$ (2×20 mL) and brine (1×20 mL). The organic layer was separated, dried (MgSO$_4$), filtered and concentrated in-vacuo to yield the desired product (67 mg) as a yellow powder. $^1$H NMR (400 MHz, CDCl3) δ 7.50(1H, m), 7.58(2H, m), 7.69(2H, m), 8.33 (2H, m), 8.75(1H, s), 10.55(br s). MS (ES+): m/e=240, (ES−): m/e=238.

Example 30

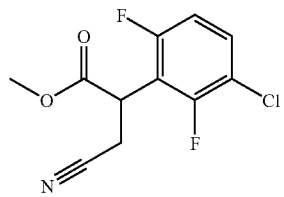

2-(3-Chloro-2,6-difluorophenyl)-3-cyanopropionic acid methyl ester: Butyllithium (4.1 mL of 2.5M solution in hexanes, 10.3 mmol) was added to a solution of diisopropylamine (1.4 mL, 10.3 mmol) in THF (15 mL) under nitrogen at 0° C. After 15 minutes the reaction mixture was cooled to −78° C. and a solution of 3-chloro-2,6-difluorophenylacetic acid methyl ester (2.15 g, 9.8 mmol) in THF (15 mL) was added. After 30 minutes, iodoacetonitrile (3.5 mL, 49 mmol) was added rapidly to the reaction mixture. The reaction mixture was allowed to warm to 0° C. and ammonium chloride solution added (10 mL, saturated aqueous). The reaction mixture was concentrated and the residue partitioned between EtOAc and brine. The aqueous phase was extracted with EtOAc and the combined organics were dried over magnesium sulfate then concentrated to afford a black oil. The crude product was purified by column chromatography (silica, 25% EtOAc-petrol to EtOAc) to afford the title compound as a pale yellow oil (1.51 g, 59%); $^1$H NMR (400 MHz, DMSO) δ 3.06 (1H, dd), 3.19 (1H, dd), 3.67 (3H, s), 4.64 (1H, dd), 7.29 (1H, t), 7.70 (1H, m).

Example 31

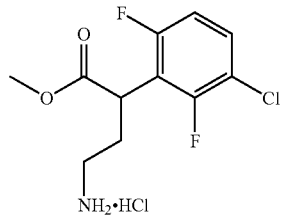

4-Amino-2-(3-chloro-2,6-difluorophenyl)-butyric acid methyl ester hydrochloride: To a solution of 2-(3-Chloro-2,6-difluorophenyl)-3-cyanopropionic acid methyl ester (784 mg, 3.0 mmol) and concentrated hydrochloric acid (0.63 mL, 7.55 mmol) in MeOH (5 mL) was added platinum dioxide (69 mg, 0.3 mmol) under nitrogen. The reaction mixture was degassed (5× vacuum cycles) and the nitrogen atmosphere replaced with hydrogen (5× vacuum cycles). The mixture was stirred for 3.5 hours, then filtered through a pad of Celite®, washing with MeOH. The filtrate was concentrated and used in the next step without further purification.

Example 32

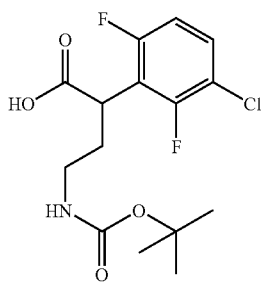

4-tert-Butylcarbonylamino-2-(3-chloro-2,6-difluorophenyl)-butyric acid:

4-Amino-2-(3-chloro-2,6-difluorophenyl)-butyric acid methyl ester hydrochloride (685 mg, 2.28 mmol) was dissolved in 8M hydrochloric acid solution (10 mL) and the mixture heated at reflux overnight. The mixture was allowed to cool to room temperature, then concentrated. The residue was dissolved in a solution of sodium bicarbonate (1.2 g, 11.4 mmol) in water (15 mL) and THF added (15 mL). The mixture was cooled to 0° C. and di-tert-butyldicarbonate (648 mg, 2.97 mmol) was added. The reaction mixture was allowed to warm to room temperature and stirred for 5.5 hours, then concentrated. After dilution with water, the mixture was extracted with ether, then the aqueous phase acidified to pH 4.5 using 2M HCl. The acidified aqueous phase was extracted with EtOAc (×3) and the combined extracts dried (magnesium sulfate) and concentrated. The residue was purified by chromatography (silica, 5% MeOH-DCM) to afford the title compound as a wax (512 mg, 65% two steps); MS (ES−) m/e=348.

Example 33

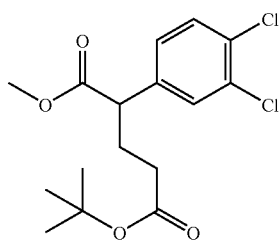

2-(2,4-Dichlorophenyl)-pentanedioic acid 5-tert-butyl ester 1-methyl ester:

Potassium tert-butoxide (767 mg, 6.85 mmol) was added to a solution of methyl 3,4-dichlorophenylacetate (15 g, 68 mmol) in THF (100 mL) at 0° C. under nitrogen. After 15 minutes, the resulting yellow solution was cooled to −78° C. and tert-butylacrylate (11.0 mL, 75 mmol) added over 10 minutes. The reaction mixture was allowed to reach room temperature and stirred overnight. The mixture was concentrated and partitioned between EtOAc and saturated ammonium chloride solution. The aqueous phase was extracted with EtOAc and the combined organics washed with brine, dried (magnesium sulfate) and concentrated to a yellow oil. Purification by column chromatography (silica, 5% ether-petrol) gave the title compound as a pale yellow oil (15.5 g, 65%).

Example 34

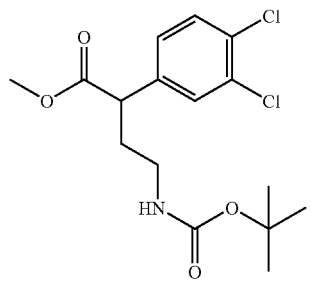

4-tert-Butoxycarbonylamino-2-(3,4-dichlorophenyl)-butyric acid methyl ester: 2-(2,4-Dichlorophenyl)-pentanedioic acid 5-tert-butyl ester 1-methyl ester (13 g, 45 mmol) was dissolved in toluene (130 mL) at 0° C. under nitrogen. Diphenylphosphoryl azide (10.6 mL, 49 mmol) and triethylamine (6.8 mL, 49 mmol) were added and the mixture allowed to warm to room temperature over 3 hours. After a further 2 hours, the reaction mixture was concentrated and the residue taken up in EtOAc. The organic phase was washed with 1 w/w % citric acid solution and brine then dried over magnesium sulfate. Concentration at 30° C. gave the acyl azide as a yellow oil which was immediately dissolved in tert-butanol (130 mL) at room temperature. Tin tetrachloride (0.31 mL, 2.68 mmol) was added and the mixture heated at 80° C. for 45 minutes, during which time nitrogen gas was evolved. Upon cooling to room temperature, saturated sodium bicarbonate solution (30 mL) was added and the reaction mixture concentrated. The residue was extracted EtOAc (×3) and the combined extracts washed with brine, dried over magnesium sulfate and concentrated to a yellow oil. Purification by column chromatography (silica, 20% EtOAc-petrol) gave the title compound as a colourless oil (12.8 g, 79%); MS (ES−) m/e=360.

Example 35

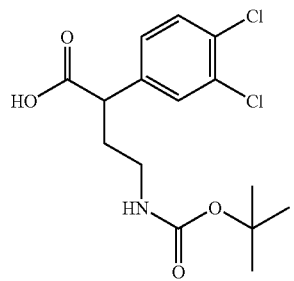

4-tert-Butoxycarbonylamino-2-(3,4-dichlorophenyl)-butyric acid: To a solution of 4-tert-butoxycarbonylamino-2-(3,4-dichlorophenyl)-butyric acid methyl ester (12.3 g, 34 mmol) in THF (80 mL)/water (20 mL) was added lithium hydroxide (1.63 g, 68 mmol) at 0° C. The reaction mixture was allowed to warm to room temperature and stirred overnight. The reaction mixture was concentrated and the residue diluted with water. After extraction with EtOAc, the aqueous phase was acidified to pH 5 by the addition of 2M aqueous hydrochloric acid solution. The aqueous phase was extracted with EtOAc and the extracts dried over magnesium sulfate. Concentration gave the title compound as a pale brown foam (11.54 g, 98%); $^1$H NMR (400 MHz, DMSO) δ 1.35 (9H, s), 1.74–1.81 (1H, m), 2.03–2.10 (1H, m), 2.81 (2H, m), 3.61 (1H, t), 6.86 (1H, m), 7.28 (1H, dd), 7.54 (1H, dd), 7.59 (1H, d), 12.60 (1H, brs); MS (ES–) m/e=346.

Example 36

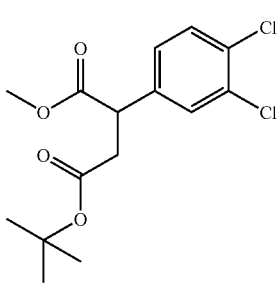

(3,4-Dichloro-phenyl)-succinic acid 4-tert-butyl ester 1-methyl ester: 2.5M $^n$Butyllithium in hexanes (37.5 ml, 0.094 mol) was added, in a dropwise fashion, to a solution of diisopropylamine (14.45 ml, 0.103 mol) in tetrahydrofuran (300 ml) at 0° C. The solution was stirred at 0° C. for 20 minutes. The mixture was then cooled to −70° C. and a solution of (3,4-dichloro-phenyl)-acetic acid methyl ester (20.54 g, 0.094 mol) in tetrahydrofuran (50 ml) was added dropwise via cannula. The reaction mixture was stirred at −70° C. for 30 minutes. After this time, tert-butyl bromoacetate (45.42 ml, 0.281 mol) was added in a dropwise fashion. The cooling bath was removed and the reaction mixture was allowed to warm up to room temperature. The reaction mixture was quenched with a saturated solution of $NH_4Cl$ (100 ml). THF was partially removed in vacuo and the mixture was extracted with EtOAc (3×200 ml). The combined organic extrats were washed with brine, dried ($MgSO_4$) and concentrated in vacuo. The crude mixture was purified by silica gel column chromatography using as eluent petrol: ether (9:1) to give the title compound in 92% yield.). $^1$H NMR (400 MHz, DMSO-d6) δ 1.34 (9H, s), 2.65 (1H, dd), 2.98 (1H, dd), 3.60 (3H, s), 4.08 (1H, m), 7.31 (1H, m), 7.58–7.62 (2H, m); MS (ES$^+$): m/e=333.2 (5%); MS (ES$^-$): m/e=331.2 (100%), 333.2 (65%), 335.2 (10%).

Example 37

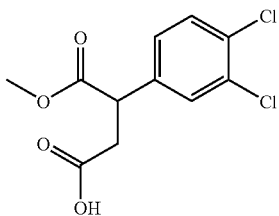

2-(3,4-Dichloro-phenyl)-succinic acid 1-methyl ester: Trifluoroacetic acid (100 ml) was added to a mixture of 2-(3, 4-dichloro-phenyl)-succinic acid 4-tert-butyl ester 1-methyl ester (23.64 g, 0.071 mol) and dichloromethane (100 ml). The reaction mixture was stirred at room temperature for 3 hours then concentrated in vacuo. The crude mixture was kept under vacuo for several hours before being used without further purification in the next step.). $^1$H NMR (400 MHz, DMSO-d6) δ 2.66 (1H, dd), 3.01 (1H, dd), 3.59 (3H, s), 4.08 (1H, m), 7.30 (1H, m), 7.56–7.61 (2H, m); MS (ES$^+$): m/e=277.1 (100%), 279.1 (65%), 281.0 (10%); MS (ES$^-$): m/e=275.1 (50%), 277.1 (30%), 279.1 (5%).

Example 38

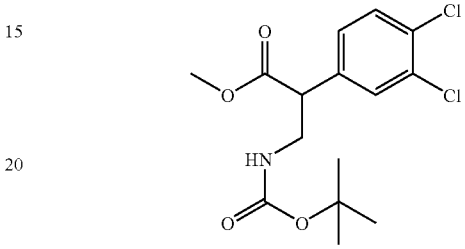

3-tert-Butoxycarbonylamino-2-(3,4-dichloro-phenyl)-propionic acid methyl ester: To a solution of 2-(3,4-dichlorophenyl)-succinic acid 1-methyl ester (0.071 mol) in toluene (200 ml) at 0° C. were successively added diphenylphosphoryl azide (16.82 ml, 0.078 mol) and triethylamine (14.83 ml, 0.106 mol). The mixture was stirred at room temperature for 3 hours. The reaction mixture was diluted with 1% citric acid (100 ml) and extracted with EtOAc (3×150 ml). The combined organic extracts were washed with brine, dried ($MgSO_4$) and concentrated in vacuo. The resulting oil was dissolved in tert-butanol (200 ml). Tin(IV) chloride (0.5 ml, 0.004 mol) was added and the mixture was heated to 80° C. for 1 hour ($N_2$ evolving). The reaction mixture was cooled down to room temperature, quenched with a saturated solution of $NaHCO_3$. Tert-Butanol was removed in vacuo and the mixture was extracted with EtOAc (3×150 ml). The combined organic extracts were washed with brine, dried ($MgSO_4$) and concentrated in vacuo. The crude mixture was purified by silica gel column chromatography using as eluent petrol: EtOAc (9:1) to give the title compound (17.35 g) in 70% yield.). $^1$H NMR (400 MHz, DMSO-d6) δ 1.31 (9H, s), 3.25–3.40 (1H, m), 3.41–3.52 (1H, m), 3.61 (3H, s), 3.90 (1H, t), 6.95 (1H, t), 7.26 (1H, m); 7.52 (1H, s), 7.60 (1H, d); MS (ES$^+$): m/e 348.2 (7%); MS (ES$^-$): m/e=457.2 (100%), 459.2 (70%), 461.2 (15%).

Example 39

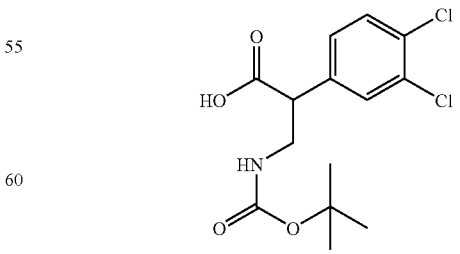

3-tert-Butoxycarbonylamino-2-(3,4-dichloro-phenyl)-propionic acid: To 3-tert-Butoxycarbonylamino-2-(3,4-dichloro-phenyl)-propionic acid methyl ester (17.11 g, 0.049 mol) in tetrahydrofuran-water (200 ml of each) was added lithium hydroxide (1.18 g, 0.049 mol). The reaction mixture was stirred at room temperature for 6 hours. THF was removed in vacuo and the pH was adjusted to pH 4 with 2M hydrochloric acid. The aqueous phase was extracted with EtOAc (3×100 ml). The combined organic phases were dried (MgSO$_4$) and concentrated in vacuo. The title compound was obtained as a foam in 89% yield (14.67 g). $^1$H NMR (400 MHz, DMSO-d6) δ 1.30 (9H, s), 3.22–3.35 (1H, m), 3.35–3.50 (1H, m), 3.76 (1H, t), 6.84 (1H, t), 7.24 (1H, m); 7.48 (1H, s), 7.58 (1H, d), 12.85 (1H, s); MS (ES$^+$): m/e=334.2 (8%); MS (ES$^-$): m/e=332.2 (100%), 334.1 (65%), 336.1 (10%).

Example 40

We have prepared other compounds of formula I by methods substantially similar to those described in Examples 1 through 39. The characterization data for these compounds is summarized in Table 5 below and includes HPLC, LC/MS (observed) and $^1$H NMR data.

$^1$H NMR data is summarized in Table 5 below wherein $^1$H NMR data was obtained at 400 MHz in deuterated DMSO, unless otherwise indicated, and was found to be consistent with structure. Compound numbers correspond to the compound numbers listed in Table 1.

TABLE 5

Characterization Data for Selected Compounds of Formula I

| Compound No | M+1(obs) | R$_t$(min) | $^1$H NMR |
|---|---|---|---|
| 69 | 376 | 6.56 | 2.9–3.3(4H, m), 4.8(1H, brs), 7.45–7.50(1H, m), 7.55–7.65(2H, m), 7.70–7.75(1H, d), 7.80(1H, s), 7.90–7.95(3H, m), 8.08(1H, s), 8.1(1H, s), 10.6–10.7(1H, brs), 13.0–13.2(1H, brs) TFA salt |
| 70 | 344 | 5.88 | 3.1–3.3(4H, m), 5.2(1H, brs), 7.3–7.4(2H, m), 7.6–7.7(2H, s), 7.7–7.9(2H, brs), 8.15–8.2(2H, d), 9.7–10.0(1H, brs), 10.6–10.7 (1H, brs), 13.1–13.3(1H, brs) TFA salt |
| 71 | 374 | 5.68 | 2.99(1H, brs), 3.11(3H, brs), 3.88(3H, s), 5.09(1H, brs), 7.29(1H, d), 7.38(1H, d), 7.53 (2H, m), 7.69, (1H, s), 7.85(3H, brs), 8.06(1H, s), 8.09(1H, s), 9.75(1H, v brs), 10.69(1H, brs), 13.08(1H, brs) TFA salt |
| 72 | 436 | 7.31 | 3.1–3.3(4H, m), 5.2(1H, brs), 7.0–7.1(2H, m), 7.15–7.30(2H, m), 7.40–7.50(2H, m), 7.52–7.60 (2H, m), 7.80(1H, s), 8.0–8.1(3H, m), 8.08(1H, s), 8.1(1H, s), 8.17(1H, s), 10.6–10.7(1H, brs), 13.0–13.2(1H, brs) TFA salt |
| 73 | 360 | 6.28 | 3.1–3.3(4H, m), 5.3(1H, brs), 7.3–7.7(8H, m), 8.0–8.1(3H, m), 8.08(1H, s), 8.1(2H, m), 8.17(1H, s), 9.6–9.8(2H, brs), 10.7–10.8(1H, brs), 13.0–13.2(1H, brs) TFA salt |

Example 41

We have prepared other compounds of formula I by methods substantially similar to those described in Examples 1 through 39 and by the general synthetic Schemes I–XV. The characterization data for these compounds is summarized in Table 6 below and includes HPLC, LC/MS (observed), IR, and $^1$H NMR data.

$^1$H NMR data is summarized in Table 6 below wherein $^1$H NMR data was obtained at 400 MHz in deuterated DMSO, unless otherwise indicated, and was found to be consistent with structure. Compound numbers correspond to the compound numbers listed in Table 1.

TABLE 6

Characterization data for Selected Compounds of Formula I

| Compd. No | M+1 (obs) | R$_t$ | $^1$H NMR | IR (cm$^{-1}$) |
|---|---|---|---|---|
| 97 | 317 | 6.0 | 1.2–2.0(2H, brs), 2.8–2.9(1H, m), 3.2–3.3 (1H, m), 3.7–3.8(1H, m), 7.2–7.6(6H, m), 8.0–8.2(2H, m), 10.0–10.3(1H, brs), 12.8–13.1(1H, brs) | 1648.3 |

TABLE 6-continued

Characterization data for Selected Compounds of Formula I

| Compd. No | M+1 (obs) | R$_t$ | $^1$H NMR | IR (cm$^{-1}$) |
|---|---|---|---|---|
| 98 | 296 | 5.2 | 1.3(1H, m), 1.8–1.9(1H, m), 2.1–2.2(1H, m), 2.6–2.9(1H, m), 3.7–3.9(1H, m), 7.2–7.5 (7H, m), 7.9–8.0(1H, s), 8.0–8.1(1H, s), 10.0–10.1(1H, m), 12.9–13.1(1H, brs) | 1655.1 |
| 99 |  | 6.8 | 1.7–2.4(2H, brs), 2.8(1H, m), 3.3(1H, m), 3.7–3.8(1H, m), 7.3–7.5(3H, m), 7.6–7.7(2H, m), 8.0(1H, s), 8.2(1H, s), 10.1–10.3 (1H, brs), 12.8–13.1(1H, brs) | 1646.6 |
| 100 | 331 | 5.9 | 1.7–1.8(1H, m), 2.0–2.3(1H, m), 2.5–2.6 (2H, m), 3.9(1H, m), 7.2–7.6(6H, m), 8.0(1H, s), 8.1(1H, s), 10.0–10.3(1H, br m), 12.6–13.2(1H, brs) | 1646.1 |
| 101 | 347 | 5.84 | 1.94–2.00(1H, m), 2.28–2.32(1H, m), 2.76–2.85(2H, m), 4.12(1H, t), 7.27 (1H, t), 7.36–7.53(3H, m), 7.55(1H, t), 7.74(3H, brs), 8.02(1Hs), 8.11(1H, s), 10.19(1H, s), 13.05(1H, brs) | 3291, 1671, 1509, 1458, 1200, 1136, 837, 799, 722 |
| 102 | 345 | 6.4 | 1.6–2.2(2H, br m), 1.8–2.0(1H, m), 2.2–2.3 (1H, m), 2.6(2H, m), 4.0–4.1(1H, m), 7.3–8.2(1H, m), 10.1–10.2(1H, brs), 12.6–1.32(1H, brs) | 1651 |
| 103 | 382 | 6.7 | 1.8–2.0(1H, m), 2.1–2.3(1H, m), 2.4–2.5 (2H, m), 4.0(1H, m), 7.4–7.6(3H, m), 7.7–7.9(2H, m), 8.0–8.2(2H, m), 10.1–10.3 (1H, brs), 12.6–13.4(1H, brs) | 1655 |
| 104 | 364 | 6.4 | 1.7–1.9(1H, m), 2.1–2.3(1H, m), 2.4–3.6 (2H, m), 4.0(1H, m), 7.4–7.8(6H, m), 7.9–8.1(2H, m), 10.1–10.3(1H, brs), 12.8–13.2(1H, brs) | 1655 |
| 105 | 429 | 7.52 | 2.01–2.14(1H, m), 2.30–2.42(1H, m), 2.60–3.73(1H, m), 2.75–2.86(1H, m), 4.08(1H, t), 7.37(1H, d), 7.48(1H, d), 8.01(1H, s), 8.05–8.15(4H, m), 10.38 (1H, s), 13.03(1H, brs) | 3279, 3045, 1681, 1647, 1550, 1447, 1380, 1306, 1277, 1181, 1141, 1125, 947, 898, 872, 845. |
| 106 | 363 | 6.2 | 1.7–1.9(1H, m), 2.1–2.3(1H, m), 2.6–2.7 (2H, m), 3.0–3.2(1H, m), 4.2–4.4(1H, m), 7.3–7.6(5H, m), 7.9–8.2(2H, m), 10.0–10.4(1H, br m), 12.8–13.2(1H, brs) | 1648 |
| 107 | 308 | 4.24 | 1.80–1.95(1H, m), 2.12–2.25(1H, m), 2.60–2.80(2H, m), 3.57(1H, t), 5.11 (2H, s), 6.44(1H, m), 6.54(1H, d), 6.59 (1H, s), 6.80–7.20(3H, m), 7.35–7.50 (2H, m), 8.00(1H, s), 8.13(1H, s), 10.01(1H, s), 12.98(1H, brs) | 670, 1599, 1558, 1539, 1504, 1201, 1135, 847, 837, 801. |
| 108 | 339 | 5.89 | 1.87–2.05(1H, m), 2.22–2.35(1H, m), 2.60–2.85(2H, m), 3.72(1H, t), 6.95–7.50 (7H, m), 7.71(3H, brs), 8.01(1H, s), 8.11(1H, m), 8.00(1H, s), 10.13 (1H, s), 13.00(1H, brs) TFA salt | 3263, 3056, 2918, 1669, 1590, 1509, 1475, 1436, 1377, 1197, 1136, 949, 879, 841. |
| 109 | 363 | 5.61 | 1.82–1.95(1H, m), 2.30–2.80(3H, m), 4.10–4.23(1H, m), 7.15–7.25(1H, m), 7.30–740(1H, m), 7.46(1H, d), 7.55–7.68 (1H, m), 8.00–8.05(2H, m), 9.98 (1H, brs), 12.99(1H, brs) | 3258, 2942, 1672, 1597, 1557, 1507, 1473, 1443, 1313, 1276, 1201, 1134, 1010, 946, 877, 834, 804. |
| 110 | 375 | 6.01 | 1.95–2.10(1H, m), 2.40–2.50(1H, m), 2.70–2.90(2H, m), 4.06–4.10(1H, m), 7.14(1H, t, J 8.0Hz), 7.30–7.43(3H, m), 7.57(1H, s), 7.83(1H, s), 8.19(1H, s), 10.12(1H, s), 12.29(1H, br). | 1672.2, 1508.3, 1201.4, 1136.1 |
| 111 | 352 | 4.43 | 1.40–2.90(9H, m), 3.70(1H, t), 7.00–8.10 (8H, m), 9.90–10.15(2H, m), 12.90–13.00(1H, m) | 3254, 2958, 2931, 2863, 1727, 1670, 1648, 1605, 1557, 1506, 1489, 1442, 1377, 1273, 1228, 1200, 1178, 1131, 1070, 997, 946, 881, 830 |
| 112 | 309 | 5.68 | (CDCl$_3$) 1.91–2.01(1H, m), 2.22–2.32 (1H, m), 2.31(3H, s), 2.62–2.78(2H, m), 3.75(1H, t, J 7.2Hz), 7.08–7.10(1H, m), 7.20–7.27(3H, m), 7.38–7.47(2H, m), 8.00(1H, s), 8.12(1H, s), 10.10 (1H, br), 12.97(1H, br) | 1673.4, 1507.4, 1201.6, 1137.97 |

TABLE 6-continued

Characterization data for Selected Compounds of Formula I

| Compd. No | M+1 (obs) | R$_t$ | $^1$H NMR | IR (cm$^{-1}$) |
|---|---|---|---|---|
| 113 | 325 | 5.33 | 1.78–1.90(1H, m), 2.08–2–20(1H, m), 2.60–2.74(2H, m), 3.85(3H, s), 4.10–4.19 (1H, m), 4.95(2H, br hump), 6.85 (1H, t), 7.05(1H, d), 7.29(1H, t), 7.36–7.50 (3H, m), 8.00(1H, s), 8.12(1H, s), 9.95(1H, s), 13.00(1H, brs) | 1673, 1598, 1563, 1507, 1464, 1291, 1245, 1202, 1132, 1025, 946, 874, 838, 801, 754, 738 |
| 114 | 401 | 6.96 | 1.77–1.87(H, m), 2.15–2.25(1H, m), 2.50–2.70(2H, m), 3.75–3.81(1H, m), 4.25(2H, br hump), 5.09(2H, s), 6.92 (1H, d), 7.01(1H, d), 7.08(1H, s), 7.20–7.50(8H, m), 7.98(1H, s), 8.10 (1H, s), 10.09(1H, s), 13.00(1H, brs) | 1660, 1596, 1563, 1507, 1484, 1451, 1316, 1262, 1202, 1026, 946, 879, 838, 801, 762, 737, 721, 678 |
| 115 | 311 | 4.47 | 1.85–1.96(1H, m), 2.18–2.30(1H, m), 2.60–2.82(2H, 2xm), 3.62–3.70(1H, m), 6.66(1H, d), 6.79–6.85(2H, m), 7.10(1H, t), 7.24(2H, brs), 7.42 (1H, d), 7.48(1H, d), 7.99(1H, s), 8.10 (1H, s), 9.48(1H, brs), 10.07(1H, s), 13.04(1H, brs) | 1673, 1631, 1591, 1510, 1462, 1201, 1137, 949, 874, 839, 800, 723 |
| 116 | 361 | 5.90 | 1.95–2.00(1H, m), 2.28–2.32(1H, m), 2.43(3H, s), 2.77–2.85(2H, m), 4.11 (1H, t), 7.27(1H, t), 7.33–7.46(3H, m), 7.55(1H, t), 7.72(3H, brs), 8.06(1H, s), 10.18(1H, s), 12.60(1H, brs). TFA salt | 3037, 1741, 1712, 1474, 1364, 1283, 1155, 1107, 912 |
| 117 | 377 | 6.99 | 1.99–2.04(1H, m), 2.26–2.32(1H, m), 2.42(3H, s), 2.67–2.70(1H, m), 2.76–2.80 (1H, m), 3.78(1H, t), 7.31–7.40 (3H, m), 7.62–7.71(5H, m), 8.04(1H, s), 10.19(1H, s), 12.6(1H, brs). TFA salt | 3039, 1670, 1199, 1134, 1032, 839, 789, 722 |
| 118 | 391 | 7.35 | 1.28(3H, t), 1.99–2.02(1H, m), 2.26–2.29 (1H, m), 2.67–2.70(1H, m), 2.77–2.82 (1H, m), 2.85(2H, q), 3.78(1H, t), 7.33–7.41(3H, m), 7.66–7.71(5H, m), 8.06(1H, s), 10.18(1H, s), 12.6(1H, brs). TFA salt | 2981, 1670, 1510, 1200, 1135, 1033, 799, 723 |
| 119 | 439 | 8.07 | 1.99–2.02(1H, m), 2.28–2.31(1H, m), 2.67–2.70(1H, m), 2.77–2.81(1H, m), 3.81(1H, t), 7.41(2H, m), 7.49–7.56 (4H, m), 7.66–7.68(2H, m), 7.73(3H, brs), 7.89(2H, d), 8.45(1H, s), 10.31 (1H, s), 13.2(1H, brs). TFA salt | 2922, 1670, 1497, 1201, 1134, 1033, 799, 722 |
| 120 | 379 | 6.4 | 1.7–1.9(1H, m), 2.1–2.3(1H, m), 2.5(3H, s), 2.6–2.7(2H, m), 3.0(1H, m), 4.2–4.4 (1H, m), 7.3–7.4(3H, m), 7.5–7.6(2H, m), 8.1(1H, s), 10.1–10.5(1H, br m), 12.4–12.8(1H, brs) | 1649.6 cm−1 |
| 121 | 397 | 7.35 | 1.74–1.80(1H, m), 2.09–2.16(1H, m), 3.92(1H, t), 7.39–7.52(3H, m), 7.58–8.12 (2H, m), 8.13(1H, s), 10.39(1H, brs). | 3271, 1648, 1472, 1431, 1303, 1029, 789 |
| 122 | 441 | 7.49 | 1.77–1.80(1H, m), 2.13–2.15(1H, m), 2.90–2.92(1H, m), 3.96(1H, t), 7.40–7.52 (4H, m), 7.60–7.66(2H, m), 8.06 (1H, s), 10.42(1H, brs). | 2921, 1661, 1498, 1471, 1033, 805 |
| 123 | 476 | 8.22 | 1.75–1.77(1H, m), 2.08–2.49(1H, m), 3.01–3.04(2H, m), 3.12–3.16(2H, m), 3.91(1H, t), 7.15–7.25(1H, m), 7.26–7.7.27 (4H, m), 7.38–7.41(3H, m), 7.63 (1H, d), 7.65(1H, s), 8.07(1H, s), 10.22 (1H, brs), 12.7(1H, brs). | 3277, 1646, 1560, 1507, 1059, 1032 |
| 124 | 387 | 7.09 | 1.81–1.90(1H, m), 2.16–2.33(1H, m), 2.91(1H, m), 3.96(1H, t), 4.50(1H, s), 7.40–7.45(2H, m), 7.51–7.53(1H, m), 7.60–7.67(2H, m), 8.21(1H, s), 10.45 (1H, brs). | 3278, 1660, 1559, 1495, 1471, 1033, 1133, 808 |
| 125 | 363 | 6.1 | 1.3–1.7(2H, brs), 1.7–1.8(1H, m), 2.1–2.2 (1H, m), 2.4(3H, s), 2.5–2.6(2H, m), 4.2(1H, m), 7.2(1H, m), 7.4(2H, m), 7.5–7.6 (2H, m), 8.1(1H, s), 10.1–10.3(1H, brs), 12.4–12.7(1H, brs) | — |
| 126 | 363 | 6.1 | 1.3–1.7(2H, brs), 1.8(1H, m), 2.1–2.2 (1H, m), 2.4–2.5(3H, s), 2.5–2.7(2H, m), 4.2(1H, m), 7.2–7.7(5H, m), 8.1(1H, s), 10.1–10.4(1H, brs), 12.4–12.7(1H, brs) | 1646.2 |

TABLE 6-continued

Characterization data for Selected Compounds of Formula I

| Compd. No | M+1 (obs) | $R_t$ | $^1$H NMR | IR (cm$^{-1}$) |
|---|---|---|---|---|
| 127 | 454 | 7.81 | 1.76–1.99(1H, m), 2.14–2.16(1H, m), 3.88–3.92(1H, m), 6.78(1H, t), 7.27 (4H, m), 7.28–7.29(1H, m), 7.61–7.67 (4H, m), 8.32(1H, s), 8.84(1H, s), 10.14(1H, brs), 11.93(1H, brs). | 3290, 1658, 1602, 1553, 1497, 1473, 1317, 1030, 807, 749 |
| 128 | 510 | 7.50 | .74–1.77(1H, m), 2.07–2.3(1H, m), 2.69 (2H, t), 2.94(2H, t), 3.17(3H, m), 3.90 (1H, t), 4.11(1H, m) 7.18(1H, m), 7.29–7.41 (6H, m), 7.47(1H, m), 7.61–7.65 (2H, m), 7.97(1H, m), 10.18(1H, brs), 10.28(1H, s), 13.2(1H, brs). | 3256, 1660, 1555, 1497, 1471, 1317, 1023, 698 |
| 129 | 344 | 5.36 | 1.88–1.97(1H, m), 2.12–2.21(1H, m), 2.43(3H, s), 2.54–2.59(2H, m), 4.02 (1H, dd), 7.37–7.42(3H, m), 7.51(1H, d), 7.85(1H, t), 8.08(1H, s), 10.23(1H, brs), 12.52(1H, brs) | 3247, 2925, 1665, 1578, 1557, 1516, 1440, 1306, 1158, 1127, 984, 810, 769 |
| 130 | 407 | 6.99 | 1.81–1.90(1H, m), 2.15–2.24(1H, m), 2.43(3H, s), 2.66(2H, t), 3.88(3H, s), 4.17(1H, dd), 7.39(2H, s), 7.46(1H, d), 7.52(1H, d), 8.03(1H, s), 10.11(1H, brs), 12.53(1H, brs) | 3257, 2904, 1650, 1552, 1506, 1465, 1393, 1312, 1204, 1189, 1132, 1015, 861, 799 |
| 131 | 323 | 5.90 | (CDCl$_3$) 1.88–1.98(1H, m), 2.21–2.31 (1H, m), 2.31(3H, s), 2.43(3H, s), 2.60–2.75 (2H, m), 3.75(1H, t, J 7.2Hz), 7.08–7.10(1H, m), 7.20–7.27(3H, m), 7.37(2H, s), 8.06(1H, s), 10.08(1H, br), 12.53(1H, br). | 670.7, 1511.7, 1136.6 |
| 132 | 359 | 6.22 | 1.85(1H, m), 2.25(1H, m), 2.6–2.8(2H, m), 4.15(1H, m), 4.2–4.6(2H, brs), 7.30(1H, m), 7.40(2H, s), 7.55(1H, m), 7.65(1H, m), 8.10(1H, s), 10.25(1H, s) | 1665, 1487, 1308, 898, 666 |
| 133 | 393 | 6.60 | 1.91–1.99(1H, m), 2.16–2.23(1H, m), 2.43(3H, s), 2.84–2.87(1H, m), 4.09 (1H, dd), 6.41(1H, brs), 6.92(1H, d), 7.32–7.37(2H, m), 8.08(1H, s), 12.46 (1H, brs) | 3380, 3288, 1675, 1568, 1516, 1475, 1440, 1399, 1322, 1291, 1184, 1137, 922, 805, 764 |
| 134 | 392 | 6.46 | 1.95–2.06(1H, m), 2.22–2.35(1H, m), 2.62–2.71(1H, m), 2.74–2.82(1H, m), 2.82(3H, d), 3.78(1H, t), 7.17(1H, d), 7.23(1H, dd), 7.39(1H, dd), 7.62(2H, brs), 7.64–7.68(2H, m), 7.93(1H, s), 10.03(1H, s), 11.31(1H, s) | 3265, 3015, 2970, 2933, 1736, 1671, 1561, 1518, 1470, 1365, 1304, 1229, 1202, 1133, 1031, 953, 874, 836. |
| 135 | 337 | 6.45 | (CDCl$_3$) 1.19(3H, t, J 7.6Hz), 1.91–2.03 (1H, m), 2.27–2.33(1H, m), 2.43(3H, s), 2.62(2H, q, J 7.6Hz), 2.68–2.83(2H, m), 3.73(1H, t, J 7.9Hz), 7.13–7.40 (6H, m), 7.69(3H, br), 8.05(1H, s), 10.08(1H, s), 12.53(1H, br). TFA salt | 1673.1, 1201.4, 1137.4 |
| 136 | 387 | 7.0 | 1.7–1.9(1H, m), 2.1–2.3(1H, m), 2.4–2.5 (3H, s), 2.6–2.7(2H, m), 4.2(1H, m), 7.4(2H, m), 7.5–7.6(2H, m), 8.0–8.1(1H, s), 10.1–10.4(1H, brs), 12.4–12.7(1H, brs) | 652.7, 1727.2 |
| 137 | 340 | 4.84 | (D$_4$-MeOH) 2.19(3H, s), 2.26–2.35 (1H, m), 2.54(3H, s), 2.54–2.62(1H, m), 2.91–3.03(2H, m), 5.73(1H, t), 6.44(1H, t), 7.39–7.47(3H, m), 7.64 (1H, d), 8.01(1H, s) | 3237, 3053, 1660, 1644, 1542, 1501, 1434, 1373, 1317, 1204, 1127, 835, 794, 764, 718 |
| 138 | 378 | 6.15 | 1.8–1.95(1H, m), 2.15–2.3(1H, m), 2.55–2.7 (2H, m), 3.8–3.85(1H, m), 5.25(2H, s), 5.55(2H, brs), 7.15(1H, d), 7.25(1H, d), 7.4(1H, d), 7.6–7.7(2H, m), 7.9(1H, s), 10.1(1H, brs), 12.4–12.7(1H, brs) | 1659, 1535, 1201 |
| 139 | 349 | 6.19 | 1.8–1.95(1H, m), 2.1–2.3(1H, m), 2.4–2.5 (3H, s), 2.6–2.7(2H, m), 4.1(1H, m), 6.85(1H, m), 6.95(1H, m), 7.3–7.4(2H, m), 8.0–8.05(1H, s), 10.1–10.2(1H, brs), 12.4–12.7(1H, brs) | 3237, 1655, 1511, 1183 |
| 140 | 420 | 6.16 | 1.8–1.95(1H, m), 2.1–2.3(1H, m), 2.4–2.5 (3H, s), 2.5–2.7(2H, m), 4.0–4.1(1H, m), 7.3–7.4(2H, m), 7.45–7.5(1H, m), 7.6–7.75(2H, m), 7.95–8.0(1H, s), 10.1–10.15 (1H, brs), 10.35–10.4(1H, brs), 12.5–12.8(1H, brs) | 3200, 1661, 1558, 799 |

TABLE 6-continued

Characterization data for Selected Compounds of Formula I

| Compd. No | M+1 (obs) | $R_t$ | $^1$H NMR | IR (cm$^{-1}$) |
|---|---|---|---|---|
| 141 | 482 | 7.24 | 1.7–1.85(1H, m), 2.1–2.25(1H, m), 2.5–2.7 (2H, m), 3.9–4.0(1H, m), 7.3–7.4(2H, m), 7.45–7.7(5H, m), 7.95–8.0(1H, s), 8.0–8.1(2H, m), 10.1–10.2(1H, brs), 10.7–10.85(1H, brs), 12.5–12.8(1H, brs) | 3250, 1637, 1536, 1313, 799 |
| 142 | 365 | 7.34 | (CDCl$_3$) 0.86–0.88(6H, m), 1.79–1.85 (1H, m), 1.91–2.00(1H, m), 2.2.25–2.33 (1H, m), 2.43(3H, s), 2.43–2.46(2H, m), 2.64–2.78(2H, m), 3.30(2H, br), 3.74 (1H, t, J 7.4Hz), 7.06–7.37(6H, m), 8.03(1H, s), 10.07(1H, s), 12.53(1H, br). | 1673.3, 1201.6, 1183.8, 1137.6 |
| 143 | 398 | 7.29 | 1.92–2.04(1H, m), 2.16–2.32(1H, m), 2.52–2.67(1H, m), 2.70–2.80(1H, m), 3.73(1H, t, J=7.4Hz), 7.34(1H, m), 7.52–7.76 (6H, br m), 7.93(1H, s), 8.12(1H, s), 10.26(1H, s), 13.60(1H, brs). | 1670, 1512, 1201, 1135 |
| 144 | 443 | 7.23 | 1.75–1.83(1H, m), 2.07–2.20(1H, m), 2.40–2.58(2H, m), 3.92(1H, m), 7.37(1H, d, J=8.4Hz), 7.59(1H, d, J=8.3Hz), 7.61(1H, s), 7.73(1H, s), 8.00(1H, s), 8.12(1H, s), 10.20–10.59(1H, br m), 13.19–13.59(1H, brs). | 1654, 1582, 1545, 1506, 1472, 1031 |
| 145 | 477 | 7.93 | 1.80(1H, m), 2.18(1H, m), 2.50–2.68 (2H, br m), 3.80(1H, m), 7.35(1H, m), 7.59(3H, m), 7.80(1H, s), 8.01(1H, s). | 1670, 1585, 1549, 1502, 1472 |
| 146 | 427 | 8.05 | 3.04(1H, dd, J=6.2, 12.7Hz), 3.31(1H, m), 3.91(1H, m), 6.12(2H, brs), 7.35–7.48 (2H, m), 7.51(3H, m), 7.66(4H, m), 8.10(2H, d, J=12.7), 10.31(1H, s), 13.12(1H, brs). | 1672, 1600, 1562, 1202, 1135 |
| 147 | 377 | 6.81 | 1.85–2.10(1H, m), 2.20–2.30(1H, m), 2.47(3H, s), 2.55–2.80(2H, m), 3.77 (1H, t), 7.16(1H, s), 7.38(1H, dd), 7.60–7.73 (4H, m), 7.90(1H, s), 7.99(1H, s), 10.10(1H, s), 13.09(1H, s) | 3255, 2922, 1704, 1677, 1651, 1553, 1513, 1473, 1322, 1195, 1135, 1085, 1032, 942, 866, 841 |
| 148 | 473 | 7.91 | 1.95–2.05(1H, m), 2.20–2.35(1H, m), 2.60–2.85(2H, m), 3.79(1H, t), 7.34 (1H, m), 7.39(1H, dd), 7.43–7.75(8H, m), 8.09(1H, s), 8.13(1H, m), 10.26 (1H, s), 12.93(1H, s) | 3073, 2943, 1671, 1561, 1508, 1472, 1419, 1326, 1202, 1135, 1058, 1033, 945, 874, 835. |
| 149 | 398 | 6.34 | 2.15–2.24(1H, m), 2.35–2.44(1H, m), 2.78–2.86(2H, m), 4.12(1H, t), 7.39 (1H, dd), 7.49(1H, d), 7.72(3H, brs), 7.86(1H, s), 8.02(1H, d), 8.09(1H, s), 10.27(1H, s), 13.03(1H, brs) TFA salt | 3268, 3099, 2950, 1670, 1563, 1506, 1404, 1327, 1178, 1143, 943, 881, 840, 799, 71 |
| 150 | 440 | 7.74 | 1.85(1H, m), 2.18(1H, m), 2.52–2.70 (2H, m), 3.88(1H, m), 7.40(2H, m), 7.43(3H, m), 7.64(4H, m), 8.09(2H, s,), 10.31(1H, brs), 13.10(1H, brs). | 1667, 1600, 1558, 1492 |
| 151 | 421 | 8.11 | 1.79–1.89(1H, m), 2.24–2.30(1H, m), 3.09–3.22(2H, m), 3.55(3H, s), 3.60–3.63 (1H, m), 5.85(1H, br), 7.20–7.35 (4H, m), 7.47(1H, s), 7.85(1H, s), 8.00 (1H, s), 9.36(1H, br), 11.87(1H, br). | 3291.5, 1691.3, 1652.8, 1551.8, 1509.1, 1272.7 |
| 152 | 420 | 7.55 | 1.50–1.55(1H, m), 1.90–1.99(1H, m), 2.35(3H, d, J 4.6Hz), 2.74–2.79(1H, m), 2.91–2.96(1H, m), 3.38–3.42(1H, m), 5.10–5.20(1H, br), 5.35–5.45(1H, br), 6.90–7.15(4H, m), 7.20–7.30(1H, s), 7.53(1H, s), 7.77(1H, s), 9.74(1H, s), 9.36(1H, br), 12.13(1H, br). | 1737.4, 1647.81, 1580.0, 1365.6 |
| 153 | 378 | 6.59 | 1.91(1H, m), 2.21(1H, m), 2.41(3H, s), 2.53–2.70(2H, br m), 3.88(1H, m), 6.59–7.10(1H, brs), 7.38(2H, m), 7.43(1H, m), 7.62(2H, m), 7.99(1H, s), 8.09(1H, s), 10.31(1H, brs), 12.98(1H, brs). | 1666, 1597, 1561, 1506, 1469 |
| 154 | 341 | 5.80 | 1.94–2.00(1H, m), 2.28–2.32(1H, m), 2.76–2.95(2H, m), 3.58(1H, t), 3.85 (2H, d), 7.20–7.40(4H, m), 7.38(1H, d), 7.55(1H, d), 7.75(3H, brs), 8.02(1Hs), 8.11(1H, s), 10.19(1H, s), 13.05(1H, brs). | 1666, 1198, 1135, 830, 799, 718 |

TABLE 6-continued

Characterization data for Selected Compounds of Formula I

| Compd. No | M+1 (obs) | R$_t$ | $^1$H NMR | IR (cm$^{-1}$) |
|---|---|---|---|---|
| 155 | 381 | 6.8 | 1.1–1.4(2H, m), 1.6–1.8(1H, m), 2.0–2.1 (1H, m), 2.4–3.6(2H, m), 3.7–3.8(1H, m), 7.3–7.7(5H, m), 7.9–8.2(2H, m), 10.1–10.2(1H, m), 12.8–13.2(1H, brs) | — |
| 156 | 321 | 5.17 | 1.80–1.95(2H, m), 2.50–2.65(2H, m), 2.68–2.80(2H, m), 2.85–2.98(2H, m), 7.22–7.28(1H, m), 7.35–7.50(5H, m), 7.95–8.02(2H, m), 9.25(1H, brs), 12.99(1H, brs) | 1649, 1597, 1503, 1446, 1239, 944 |
| 157 | 316 | 5.71 | 3.17(1H, m), 3.43–3.61(1H, m), 4.08(1H, m), 7.37–7.41(4H, br m), 7.89(3H, brs), 8.12(1H, s), 8.49(1H, s), 8.56(1H, s), 10.58(1H, s), 11.60(1H, brs). | 1672, 1511, 1201, 1135 |
| 158 | 468 | 7.89 | 1.75–1.95(1H, m), 2.10–2.25(1H, m), 2.57–2.70 (1H, m), 2.90–3.10(1H, m), 3.83(1H, t), 4.43(2H, d), 6.48(1H, t), 7.10–7.23(3H, m), 7.29(2H, t), 7.37–7.47(3H, m), 7.58–7.67 (2H, m), 8.06(1H, s), 10.02(1H, s), 11.29(1H, s) | 3277, 3097, 2938, 2884, 1647, 1553, 1509, 1474, 1436, 1399, 1356, 1311, 1236, 1203, 1183, 1134, 1073, 1030, 991, 958, 873, 833, 811. |
| 159 | 460 | 8.9 | 1.15–1.30(6H, m), 1.55–1.65(1H, m), 1.65–1.90 (3H, m), 1.95–2.05(2H, m), 2.10–2.20 (1H, m), 2.53–2.60(1H, m), 3.42–3.47(1H, m), 3.83(1H, t), 5.62(1H, d), 7.10–7.20 (2H, m), 7.39(1H, dd), 7.60–7.66(2H, m), 8.03(1H, s), 9.98(1H, s), 11.20(1H, s) | 3288, 2928, 2853, 1662, 1557, 1470, 1449, 1317, 1201, 1182, 1132, 1031, 840, 805 |
| 160 | 516 | 7.78 | 1.75–1.9(1H, m), 2.1–2.25(1H, m), 2.5–2.65 (2H, m), 3.85–3.9(1H, m), 7.35–7.45 (2H, m), 7.45–7.75(5H, m), 7.95–8.0 (1H, s), 8.0–8.05(1H, m), 8.10(1H, s), 10.3(1H, brs), 10.8–10.95(1H, brs), 12.7–12.8 (1H, brs | 1662, 1546, 741 |
| 161 | 561 | 8.90 | 1.78(1H, m), 2.11(1H, m), 2.48(1H, m), 2.93(1H. br m), 3.88(1H, m), 5.07(2H, s), 6.44(1H, m), 7.11(2H, br m), 7.27(3H, br m), 7.40(6H, br m), 7.60(2H, m), 8.30(1H, s), 8.82(1H, s), 10.09(1H, s), 11.94(1H, brs) | 1603, 1558, 1533, 1474 |
| 162 | 490 | 8.57 | 1.78(1H, m), 2.12(1H, m), 2.50(2H, m), 3.90(1H, m), 6.81(1H, m), 7.20(2H, br m), 7.30(1H, m), 7.38(1H, m), 7.46(1H, m), 7.59(1H, m), 7.67(1H, m), 7.87(1H, s), 8.34(1H, s), 9.11(1H, s), 10.13(1H, brs), 12.04(1H, brs) | 1598, 1541, 1480 |
| 163 | 490 | 8.58 | 1.85–1.95(1H, m), 2.15–2.3(1H, m), 2.5–2.7 (2H, m), 3.87–3.95(1H, m), 5.7–6.2(2H, brs), 7.20–7.35(4H, m), 7.4–7.45(1H, m), 7.6–7.75(4H, s), 8.35(1H, s), 9.05(1H, s), 10.3(1H, brs), 12.7–12.8(1H, brs | 1660, 1548, 1491 |
| 164 | 479 | 7.82 | 2.00–2.08(1H, m), 2.24–2.33(1H, m), 2.64–2.69 (1H, m), 2.75–2.82(1H, m), 3.80(1H, t, J 7.5Hz), 7.32–7.41(3H, m), 7.65–7.73 (6H, m), 8.33(1H, s), 9.56(1H, s), 10.22 (1H, br), 12.32(1H, br) | 2220.9, 1670.9, 1606.7, 1541.7, 1201.2, 1183.8, 1135.5 |
| 165 | 479 | 8.03 | 1.78–1.90(1H, m), 2.12–2.21(1H, m), 2.53–2.61 (2H, m), 3.89(1H, t, J 7.7Hz), 7.20–7.45 (5H, m), 7.63–7.68(2H, m), 7.84–7.86 (1H, m), 8.18(1H, m), 8.39(1H, m), 9.36 (1H, s), 10.19(1H, br), 12.14(1H, br). | 2229.9, 1668.8, 1602.4, 1559.8, 1476.3, 1201.5, 1134.4 |
| 166 | 534 | 8.60 | 1.83–1.92(1H, m), 2.15–2.24(1H, m), 2.53–2.67 (2H, m), 3.86(1H, t, J 7.5Hz), 7.29–7.41 (5H, m), 7.60–7.67(4H, m), 8.32(1H, s), 9.05(1H, s), 10.17(1H, br), 12.03(1H, br) | 2220.9, 1669.3, 1548.0, 1488.5 |
| 167 | 512 | 7.40 | 1.93–2.03(1H, m), 2.21–2.30(1H, m), 2.63–2.79(2H, m), 3.77(H, t), 3.85(3H, s), 7.19(1H, dd), 7.37(1H, dd), 7.43–7.48 (2H, m), 7.54(1H, dd), 7.63–7.70(7H, m), 7.94(1H, d), 10.22(1H, s), 10.77(1H, s), 12.79(1H, s) TFA salt | 3247, 3063, 1685, 1537, 1470, 1434, 1317, 1291, 1189, 1143, 1040, 846, 799, 718 |

TABLE 6-continued

Characterization data for Selected Compounds of Formula I

| Compd. No | M+1 (obs) | $R_t$ | ¹H NMR | IR (cm⁻¹) |
|---|---|---|---|---|
| 168 | 512 | 7.30 | 1.93–2.02(1H, m), 2.20–2.30(1H, m), 2.61–2.79(2H, m), 3.77(1H, t), 3.85(3H, s), 7.07–7.10(2H, m), 7.37(1H, dd), 7.43 (1H, d), 7.54(1H, dd), 7.63–7.70(5H, m), 7.92(1H, d), 8.06(1H, d), 10.21(1H, s), 10.61(1H, s), 12.75(1H, s). TFA salt | 3196, 3058, 1670, 1639, 1598, 1542, 1511, 1470, 1321, 1260, 1204, 1184, 1132, 1040, 830, 794 |
| 169 | 488 | 7.13 | 1.94–2.03(1H, m), 2.21–2.31(1H, m), 2.61–2.80(2H, m), 3.78(1H, t), 7.24–7.27 (1H, m), 7.38(1H, dd), 7.43(1H, d), 7.56 (1H, dd), 7.64–7.70(5H, m), 8.80(1H, dd), 7.95(1h, d), 10.23(1H, s), 10.87(1H, s), 12.81(1H, s) TFA salt | 3222, 3088, 1670, 1562, 1475, 1419, 1332, 1286, 1194, 1132, 1030, 840, 794, 712 |
| 170 | 532 | 8.10 | 1.87–2.00(1H, m), 2.15–2.38(1H, m), 2.60–2.77 (2H, m), 3.79(1H, t), 6.56(1H, s), 7.35–7.39(1H, m), 7.42–7.47(1H, m), 7.54–7.70 (6H, m), 8.00–8.16(5H, m), 8.72(1H, s), 10.24(1H, s), 10.94(1H, s), 12.80(1H, s) | 3257, 3226, 1658, 1541, 1472, 1322, 1294, 1233, 1202, 1133, 1031, 958, 867, 830. |
| 171 | 526 | 7.31 | 1.93–2.02(1H, m), 2.18–2.31(1H, m), 2.62–2.80 (2H, m), 3.77(1H, t), 6.15(2H, s), 6.55(1H, s), 7.08(1H, d), 7.35–7.44(2H, m), 7.51–7.70(6H, m), 7.91(1H, s), 10.21 (1H, s), 10.60(1H, s), 12.76(1H, s) | 3265, 1655, 1605, 1541, 1503, 1473, 1439, 1400, 1359, 1324, 1294, 1259, 1133, 1037, 931, 875, 812. |
| 172 | 558 | 8.46 | 1.94–2.04(1H, m), 2.18–2.32(1H, m) 2.58–2.70 (1H, m), 2.70–2.83(1H, m), 3.78(1H, t), 7.37(1H, dd), 7.42–7.47(2H, m), 7.50–7.56 (3H, m), 7.62–7.71(5H, m), 7.79(2H, d), 7.87(2H, d), 7.97(1H, d), 8.17(2H, d), 10.23(1H, s), 10.83(1H, s), 12.80(1H, s) TFA salt | 1736, 1673, 1637, 1544, 1374, 1365, 1228, 1216, 1205, 1137. |
| 173 | 531 | 8.38 | 1.78–1.80(1H, m), 2.10–2.14(1H, m), 2.89 (1H, m), 3.77(0.5H, t), 3.93(0.5H, t), 7.05 (1H, m), 7.31–7.41(5H, m), 7.48(1H, m), 7.60–7.65(1H, m), 7.66(1H, s), 7.78(1H, s), 8.14(1H, m), 9.40(1H, brs), 9.67(1H, brs), 10.2(0.5H, brs), 10.25(0.5H, brs), 12.6(1H, brs) | 3257, 1672, 1593, 1529, 1477, 1312, 774 |
| 174 | 507 | 7.22 | 1.94–2.02(1H, m), 2.20–2.30(1H, m), 2.61–2.79 (2H, m), 3.78(1H, t, J 7.5Hz), 7.36–7.67 (5H, m), 7.97–8.22(5H, m), 10.23(1H, br), 11.08(1H, br), 12.86(1H, br). | 2232.8, 1667.8, 1546.7, 1201.5, 1134.8 |
| 175 | 507 | 7.22 | 1.91–1.99(1H, m), 2.20–2.30(1H, m), 2.60–2.76 (2H, m), 3.81(1H, t, J 7.6Hz), 7.36–7.81 (6H, m), 7.98–8.49(4H, m), 8.32(1H, s), 10.26(1H, br), 11.03(1H, br), 12.84(1H, br). | 2232.0, 1667.9, 1547.6, 1202.0, 1134.5 |
| 176 | 497 | 7.83 | 1.75–1.78(1H, m), 2.09–2.15(1H, m), 2.80–2.89 (1H, m), 3.92(1H, t), 7.00(1H, t), 7.29–7.41(4H, m), 7.47–7.52(3H, m), 8.17 (1H, s), 9.29(1H, brs), 9.57(1H, brs), 10.22 (1H, brs), 12.45(1H. brs). | 3263, 1638, 1560, 1497, 1312, 1031, 692 |
| 177 | 500 | 7.38 | 1.75–1.90(1H, m), 2.10–2.25(1H, m), 2.50–2.65 (2H, m), 4.10–4.15(1H, m), 7.18–7.25 (1H, m), 7.35–7.7(6H, m), 7.6–7.75(4H, brs), 7.95–8.15(3H, m), 10.2(1H, br), 10.9 (1H, br), 12.8(1H, br). | 1663, 1541, 1458 |
| 178 | 574 | 8.54 | 1.70–1.90(1H, m), 2.05–2.18(1H, m), 2.40–2.60 (2H, m), 3.72–3.92(1H, m), 7.10(2H, d), 7.19(1H, t), 7.28(1H, d), 7.35–7.46(4H, m), 7.50–7.70(5H, m), 7.86(1H, d), 7.92 (1H, s), 10.24(1H, s), 10.78(1H, s), 12.76 (1H, s) | 3491, 3291, 3069, 2954, 2871, 1674, 1647, 1549, 1488, 1474, 1439, 1325, 1296, 1279, 1232, 1198, 1133, 1032, 954, 892, 879. |
| 179 | 500 | 7.47 | 1.78(1H, m), 2.05(1H, m), 3.90(1H, m), 7.35(1H, d, J=8.30Hz), 7.42(1H, d, J=8.9Hz) 7.46(2H, m), 7.60(3H, m), 7.83 (1H, m), 7.90(3H, m), 10.20(1H, brs), 10.70–10.8(1H, s), 12.56–12.94(1H, brs). | 1587, 1551, 1473, 1324, 1270 |
| 180 | 518 | 7.39 | 1.75–1.93(1H, m), 2.10–2.22(1H, m), 2.38–2.65 (2H, m), 3.75–3.95(1H, m), 7.37–7.70 (9H, m), 8.05–8.10(1H, m), 10.19–10.27 (1H, m), 10.82(1H, s), 12.74(1H, s) | 3183, 1654, 1593, 1541, 1499, 1470, 1434, 1388, 1330, 1203, 1185, 1134, 1049, 1032, 958, 905, 876, 838. |

TABLE 6-continued

Characterization data for Selected Compounds of Formula I

| Compd. No | M+1 (obs) | $R_t$ | $^1$H NMR | IR (cm$^{-1}$) |
|---|---|---|---|---|
| 181 | 526 | 7.85 | 1.36(3H, t), 1.72–1.90(1H, m), 2.05–2.20 (1H, m), 2.38–2.60(2H, m), 3.72–3.92(1H, m), 4.12(2H, q), 7.16(1H, d), 7.35–7.68 (8H, m), 7.92–7.96(1H, m), 10.19–10.28 (1H, m), 10.71(1H, s), 12.75(1H, s) | 3242, 2919, 1666, 1645, 1597, 1518, 1502, 1491, 1473, 1438, 1390, 1329, 1301, 1281, 1235, 1047, 1030, 911, 823. |
| 182 | 516 | 7.93 | 1.75–1.90(1H, m), 2.05–2.20(1H, m), 2.38–2.65 (2H, m), 3.85–3.95(1H, m), 7.35–7.70 (7H, m), 7.95–8.02(1H, m), 8.05–8.1(2H, m), 10.2–10.27(1H, m), 10.8(1H, brs), 12.8(1H, s) | 1655, 1553, 1473 |
| 183 | 550 | 8.44 | 1.75–1.90(1H, m), 2.05–2.20(1H, m), 2.38–2.65 (2H, m), 3.9–3.95(1H, m), 7.35–7.65 (7H, m), 7.80–7.85(1H, m), 8.00–8.1(2H, m), 8.30(1H, s), 10.3(1H, brs), 10.9(1H, brs), 12.8(1H, s) | 1643, 1536, 1307 |
| 184 | 550 | 8.46 | 1.78(1H, m), 2.11(1H, m), 3.31(2H, m), 3.90(1H, br m), 7.39(2H, br m), 7.50(1H, br m), 7.60(2H, br m), 7.92(1H, m), 7.98(1H, m), 8.08(2H, m), 10.85–13.10(1H, brs), 12.79(1H, brs). | 1664, 1643, 1554, 1473 |
| 185 | 496 | 7.72 | 1.70(1H, m), 2.05(1H, m), 2.41(3H, s), 3.30(2H, m), 3.85(1H, br m), 7.27–7.44 (4H, br m), 7.51(1H, m), 7.60(2H, m), 7.85(2H, m), 7.93(1H, s), 10.18(1H, m), 10.61(1H, brs), 12.70(1H, brs). | 1641, 1587, 1545, 1470 |
| 186 | 560 | 8.04 | 1.78(1H, m), 2.16(1H, m), 3.30(2H, br m), 3.88(1H, m), 7.32(2H, m), 7.32(1H, m) 7.41(1H, m), 7.50(2H, m), 7.60(2H, m), 7.85(1H, m), 7.95(1H, s), 8.05(1H, m), 8.21(1H, m), 10.20(1H, m), 10.59–11.09 (1H, brs), 12.37–12.92(1H, brs). | 1644, 1528, 1475 |
| 187 | 510 | 8.12 | 1.10(3H, t), 1.70(1H, m), 2.10(1H, m), 3.32 (2H, br m), 2.70(2H, q), 3.87(1H, m), 7.35(4H, m), 7.32(1H, m), 7.50(2H, m), 7.60(2H, m), 7.90(1H, s), 7.95(1H, m), 10.20(1H, s), 10.60(1H, s), 12.57–12.88 (1H, brs). | 1653, 1542, 1472 |
| 188 | 524 | 8.55 | 0.91(3H, t), 1.62(2H, m), 1.74(1H, m), 2.10 (1H, m), 3.30(2H, m), 2.60(2H, q), 3.88(1H, m), 7.35(4H, m), 7.41(1H, m), 7.59(2H, m), 7.93(3H, br m), 10.20(1H, s), 10.59(1H, s), 12.58–12.90(1H, brs). | 1654, 1541, 1491 |
| 189 | 560 | 8.00 | 1.70(1H, m), 2.10(1H, m), 3.29(2H, m), 3.87(1H, m), 7.32(1H, m), 7.41(1H, m), 7.58(2H, m), 7.77(2H, m), 7.91(1H, m), 7.80(2H, m), 10.65–11.00(1H, brs), 12.50–12.96 (1H, brs). | 1655, 1541, 1472 |
| 190 | 518 | 7.15 | 1.82(1H, m), 2.19(1H, m), 2.58(2H, m), 3.89(1H, m), 7.16(1H, m), 7.29(1H, m), 7.40(4H, m), 7.65(2H, m), 7.77(2H, m), 7.96(1H, m), 10.19(1H, s), 11.55–12.27(1H, brs). | 654, 1541, 1507 |
| 191 | 554 | 7.46 | 1.85(1H, m), 2.19(1H, m), 2.61(2H, m), 3.89(1H, m), 7.06(1H, m), 7.18(1H, m), 7.30–7.40(3H, m), 7.61(2H, m), 7.78(1H, m), 7.85(1H, m), 9.97(1H, s), 11.02–11.41 (1H, brs). | 1653, 1558, 1507 |
| 192 | 496 | 7.49 | 1.82(1H, m), 2.12(1H, m), 3.25(2H, m), 3.75(2H, s), 3.89(1H, m), 7.20(1H, m), 7.34(6H, br m), 7.51(1H, m), 7.60(2H, m), 7.93(1H, s), 10.20(1H, brs), 10.51(1H, s), 12.10–13.10(1H, brs). | 1655, 1600, 1471 |
| 193 | 483 | 6.49 | (D$_4$-MeOH) 2.09–2.14(1H, m), 2.40–2.44 (1H, m), 2.85–2.90(1H, m), 2.95–3.01 (1H, m), 3.79(1H, t), 7.38–7.40(1H, m), 7.48(2H, s), 7.55–7.57(1H, m), 7.60–7.65 (1H, m), 8.03(2H, d), 8.12(1H, s), 8.83(2H, s) TFA salt | 3242, 3083, 1675, 1557, 1511, 1465 1184, 1132, 846, 974, 722 |
| 194 | 483 | 6.54 | (D$_4$-MeOH) 2.02–2.05(1H, m), 2.30–2.36 (1H, m), 2.70–2.80(2H, m), 3.76(1H, t), 7.38–7.54(4H, m), 7.65(2H, s), 8.10(1H, d), 8.46(1H, d), 8.80(1H, s), 9.20(1H, s) | 3191, 1660, 1542, 1465, 1306, 1117, 1030 |

TABLE 6-continued

Characterization data for Selected Compounds of Formula I

| Compd. No | M+1 (obs) | R$_t$ | $^1$H NMR | IR (cm$^{-1}$) |
|---|---|---|---|---|
| 195 | 483 | 7.27 | (D$_4$-MeOH) 1.99–2.06(1H, m), 2.30–2.39 (1H, m), 2.70–2.82(2H, m), 3.78(1H, t), 7.39–7.54(4H, m), 7.65–7.68(2H, m), 8.07(1H, t), 8.20(1H, s), 8.27(1H, d), 8.77 (1H, d) | 3268, 1670, 1542, 1465, 1317, 1122, 799, 738 |
| 196 | 508 | 7.94 | 1.80–1.91(1H, m), 2.10–2.25(1H, m), 2.50–2.70 (2H, m), 3.85(1H, m), 5.38(1H, d, J 11.0Hz), 5.55(1H, d J 17.7Hz), 6.81–6.88 (1H, m), 7.37–7.73(7H, m), 7.97(2H, s), 8.20(1H, s), 10.26(1H, br), 10.80(1H, br), 12.78(1H, br). | 2232.0, 1669.1, 1602.3, 1573.0, 1535.7, 1443.5, 1244.62, 1203.3, 1154 |
| 197 | 511 | 6.75 | 1.90–2.10(1H, m), 2.20–2.30(1H, m), 2.60–2.82 (2H, m), 3.79(1H, t J 7.3Hz), 4.15 (2H, s), 7.00–7.45(4H, m), 7.58–7.80(6H, s), 8.00–8.30(6H, m), 10.27(1H, br), 10.80 (1H, br), 12.83(1H, br). TFA salt | 1669.8, 1547.8, 1200.8, 1134.9 |
| 198 | 511 | 6.45 | 1.92–2.04(1H, m), 2.20–2.31(1H, m), 2.60–2.82 (2H, m), 3.78(1H, t J 7.0Hz), 4.15 (2H, s), 7.36–7.52(3H, m), 7.61–7.66(3H, s), 7.74(3H, br), 7.98(1H, s), 8.00–8.30 (6H, m), 8.11(2H, d, J 7.6Hz), 8.29(3H, br), 10.25(1H, br), 10.82(1H, br), 12.82 (1H, br). TFA salt | 1669.6, 1547.8, 1200.8, 1134.6 |
| 199 | 574 | 8.55 | 1.95(1H, m), 2.21(1H, m), 2.67(1H, s), 2.73(1H, m), 3.73(1H, m), 7.07(2H, d, J=8.6Hz), 7.13(2H, d, J=8.5Hz), 7.33(1H, m), 7.32(1H, m), 7.35–7.52(4H, br m), 7.55–7.76(5H, br m), 7.91(1H, s), 8.05 (2H, d, J=8.6Hz), 10.20(1H, s), 10.70(1H, s), 12.73(1H, s). | 1597, 1573, 1533, 1300, 1142 |
| 200 | 550 | 8.14 | 1.78(1H, m), 2.10(1H, m), 3.85(1H, m), 7.31(1H, d, J=9.0Hz), 7.37(1H, d, J=9.0Hz) 7.49(1H, m), 7.58(2H, m), 7.79 (2H, m), 7.95(2H, m), 8.31(1H, m), 8.36 (1H, s), 10.18(1H, s), 10.89–11.18(1H, br s), 12.68–12.89(1H, brs). | 1587, 1555, 1324, 1128 |
| 201 | 518 | 7.72 | 1.80(1H, m), 2.11(1H, m), 2.55(2H, m), 3.81(1H, m), 5.11–5.97(2H, brs), 7.30 (1H, d, J=8.3Hz), 7.39(1H, d, J=9.0Hz) 7.50(1H, m), 7.57(3H, m), 7.75(2H, m), 7.91(1H, s), 10.20(1H, s), 10.72–10.10 (1H, brs), 12.81(1H, s). | 1598, 1552, 1472, 1330, 1125 |
| 202 | 616 | 8.93 | 1.78(1H, m), 2.10(1H, m), 3.85(1H, m), 7.35(1H, d, J=8.3Hz), 7.41(1H, d, J=9.0Hz) 7.50(1H, m), 7.58(3H, m), 8.01 (1H, s), 8.41(1H, s), 8.70(2H, s), 10.25(1H, s), 12.68–13.01 | 1557, 1473, 1320, 1195 |
| 203 | 568 | 8.37 | 1.85(1H, m), 2.07(1H, m), 2.49–2.71(2H, br m), 3.81(1H, m), 6.09–7.89(2H, brs), 7.35(1H, d, J=8.3Hz), 7.43(1H, d, J=9.0Hz), 7.51(1H, m), 7.60(2H, m), 7.94 (1H, s), 8.02(1H, m), 8.21(1H, m), 8.29(1H, s), 10.23(1H, s), 10.93–11.41(1H, brs), 12.82(1H, s). | 1551, 1470, 1551, 1328, 1124 |
| 204 | 566 | 8.29 | 1.78(1H, m), 2.08(1H, m), 3.89(1H, m), 7.32(1H, d, J=8.3Hz), 7.42(1H, d, J=9.0Hz) 7.51(1H, m), 7.60(3H, m), 7.70 (1H, m), 7.95(1H, m), 8.01(1H, m), 8.10(1H, m), 10.23(1H, s), 10.78–11.01 (1H, brs), 12.75(1H, s). | 1586, 1552, 1474, 1260, 1162 |
| 205 | 506 | 7.63 | 1.90–2.04(1H, m), 2.20–2.31(1H, m), 2.60–2.82 (2H, m), 3.77(1H, t J 7.4Hz), 4.35 (1H, s), 7.36–7.74(9H, m), 7.96(1H, s), 8.08(1H, d, J 7.64Hz), 8.16(1H, s), 10.23 (1H, br), 10.88(1H, br), 12.81(1H, br). TFA salt | 1669.1, 1550.1, 1474.0, 1202.4, 1133.3 |
| 206 | 511 | 7.08 | (D$_4$-MeOH) 2.02–2.07(1H, m), 2.33–2.40 (1H, m), 2.72–2.87(2H, m), 2.87(3H, s), 3.81(1H, t), 6.67(2H, d), 7.39–7.53(4H, m), 7.65(1H, s), 7.87(2H, d), 8.01(1H, s) | 3247, 2950, 1655, 1598, 1537, 1475, 1322, 1271, 1184, 1132, 825, 753 |

TABLE 6-continued

Characterization data for Selected Compounds of Formula I

| Compd. No | M+1 (obs) | R$_t$ | $^1$H NMR | IR (cm$^{-1}$) |
|---|---|---|---|---|
| 207 | 525 | 7.45 | (D$_4$-MeOH) 1.29(3H, t), 2.03–2.10(1H, m), 2.37–2.43(1H, m), 2.78–2.90(2H, m), 3.23(2H, q), 3.79(1H, t), 6.68(2H, d), 7.38–7.54(4H, m), 7.64(1H, s), 7.86(2H, d), 8.02(1H, s) | 3263, 2966, 1665, 1603, 1527, 1475, 1327, 1265, 1184, 1132, 825, 794, 769 |
| 208 | 528 | 7.58 | 1.72–1.80(1H, m), 2.10–2.16(1H, m), 3.90(1H, t), 7.38(1H, d), 7.43(1H, d), 7.51–7.62(4H, m), 7.87(1H, t), 8.00(1H, s), 8.49(1H, t), 8.90(1H, s), 10.28(1H, s), 12.94(1H, s) | 3217, 1639, 1521, 1465, 1347, 1322, 1296, 1127, 876, 810 |
| 209 | 511 | 7.29 | 1.90–2.03(1H, m), 2.20–2.31(1H, m), 2.58–2.80(2H, m), 2.74(3H, s), 3.77(1H, t), 6.70–6.80(1H, m), 7.15–7.28(3H, m), 7.35–7.45(2H, m), 7.50–7.55(1H, m), 7.60–7.75(5H, m), 7.93(1H, s), 10.21(1H, s), 10.56(1H, s), 12.74(1H, s) TFA salt | 3252, 3047, 1671, 1604, 1547, 1472, 1431, 1326, 1201, 1135, 1031, 839. |
| 210 | 525 | 7.68 | 1.19(3H, t), 1.90–2.05(1H, m), 2.14–2.32(1H, m), 2.55–2.80(2H, m), 3.11(2H, q), 3.76(1H, t), 6.70–6.85(1H, m), 7.18–7.28(3H, m), 7.32–7.45(2H, m), 7.50–7.53(1H, m), 7.60–7.73(5H, m), 7.93(1H, s), 10.20(1H, s), 10.55(1H, s), 12.74(1H, s) TFA salt | 3236, 3035, 1671, 1548, 1472, 1434, 1327, 1201, 1134, 1031, 953, 835. |
| 212 | 468 | 8.57 | 1.80–1.92(1H, m), 2.16–2.28(1H, m), 2.26(3H, s), 2.50–2.67(2H, m), 3.90(1H, t J 7.3Hz), 6.58–6.60(1H, m), 7.00–7.70(8H, m), 8.30(1H, s), 8.76(1H, s), 10.21(1H, br), 11.92(1H, br). | 1665.6, 1611.2, 1560.2, 1473.4, 1201.3 |
| 213 | 472 | 8.53 | 1.80–1.90(1H, m), 2.12–2.25(1H, m), 2.50–2.65(2H, m), 3.92(1H, m), 6.56(1H, m), 7.21–7.42(5H, m), 7.62–7.68(3H, m), 8.35(1H, s), 9.15(1H, br), 10.25(1H, br), 12.06(1H, br). | 1664.7, 1616.5, 1554.4, 1533.1, 1492.2, 1143.5 |
| 214 | 579 | 7.49 | 1.40(2H, m), 1.51(4H, m), 1.80(1H, m), 2.13(4H, m), 3.50(2H, s), 3.88(1H, t), 7.36–7.42(2H, m), 7.46–7.54(3H, m), 7.58–7.63(2H, m), 7.94(1H, s), 7.96(2H, s), 10.27(1H, s), 10.72(1H, s), 12.75(1H, brs). | 1662, 1545, 1470, 1324, 1032 |
| 215 | 581 | 7.22 | 1.78(1H, m), 2.11(1H, m), 2.39(4H, m), 3.55(2H, s), 3.59(4H, m), 7.36–7.42(2H, m), 747–7.62(5H, m), 7.95–7.99(3H, m), 10.20(0.5H, brs), 10.29(0.5H, brs), 10.73(1H, brs), 12.75(1H, brs). | 3227, 1661, 1545, 1437, 1113 |
| 216 | 567 | 7.07 | 0.99(6H, t), 1.73(1H, m), 2.09(1H, m), 3.30(2H, s), 3.76(0.5H, t), 3.69(0.5H, t), 7.25–7.61(7H, m), 7.92–7.99(3H, m), 10.20(1H, brs), 10.71(1H, brs), 12.75(1H, brs). | 2967, 1655, 1557, 1472, 1323, 1055, 1013, 811 |
| 217 | 562 | 6.85 | 1.78(1H, m), 2.11(1H, m), 2.88(1H, m), 3.76(0.5H, t), 3.86(0.5H, t), 5.30(2H, s), 6.92(1H, s), 7.25(1H, s), 7.35–7.43(2H, m), 7.49–7.61(5H, m), 7.81(1H, s), 7.92–8.02(3H, m), 10.19(1H, brs), 10.79(1H, brs), 12.75(1H, brs). | 2981, 1668, 1540, 1473, 1323, 1054, 1013, 815, 722 |
| 218 | 580 | 6.37 | 1.80(1H, m), 2.12(1H, m), 2.32(4H, m), 2.71(4H, m), 2.87(1H, m), 3.51(2H, s), 3.75(0.5H, t), 3.90(o.5H, m), 7.36–7.43(2H, m), 7.46–7.52(5H, m), 7.94–7.97(3H, m), 10.20(0.5H, brs), 10.29(0.5H, brs), 10.71(1H, brs), 12.75(1H, brs). | 1662, 1550, 1469, 1324, 1134, 1031. |
| 219 | 564 | 8.20 | 1.75(1H, m), 2.08(1H, m), 2.85(1H, m), 3.90(1H, m), 7.33(2H, m), 7.51(1H, m), 7.53–7.60(4H, br m), 7.82(1H, d), 7.95(1H, m), 8.15(1H, d), 8.26(1H, s), 10.27(1H, s), 10.90(1H, brs), 12.74(1H, brs). | 1657, 1546, 1469, 1324 |
| 220 | 524 | 7.09 | 1.75(1H, m), 2.09(1H, m), 2.78(3H, s), 2.83(1H, m), 3.89(1H, m), 7.35(1H, d), 7.40(1H, d), 7.50(1H, m), 7.59(2H, m), 7.68(1H, t), 7.95(1H, m), 8.15(1H, d), 8.30(1H, d), 8.61(1H, s), 10.28(1H, s), 10.95(1H, brs), 12.73(1H, brs). | 1660, 1545, 1491, 1324 |

TABLE 6-continued

Characterization data for Selected Compounds of Formula I

| Compd. No | M+1 (obs) | $R_t$ | $^1$H NMR | IR (cm$^{-1}$) |
|---|---|---|---|---|
| 221 | 560 | 6.93 | 1.75(1H, m), 2.10(1H, m), 2.48(2H, m), 2.81(1H, m), 3.84(1H, m), 7.31(1H, d), 7.41(1H, d), 7.50(1H, m), 7.59(2H, m), 7.80(1H, t), 7.98(1H, m), 8.15(1H, d), 8.35(1H, d), 8.66(1H, s), 10.25(1H, s), 11.05(1H, brs), 12.78(1H, brs). | — |
| 222 | 479 | 9.28 | (D$_4$-MeOH) 1.35(6H, d), 1.99–2.04 (1H, m), 2.30–2.39(1H, m), 2.67–2.80 (2H, m), 3.00–3.07(1H, m), 3.79(1H, t), 7.31(1H, d), 7.41–7.54(5H, m), 7.67–7.73(2H, m), 7.79(1H, s), 8.36 (1H, s) | 1675, 1557, 1496, 1470, 1189, 1132, 794 |
| 223 | 515 | 9.55 | (D$_4$-MeOH) 2.00–2.05(1H, m), 2.35–2.40 (1H, m), 2.72–2.82(2H, m), 3.78 (1H, t), 7.38–7.49(2H, m), 7.50–7.57 (5H, m), 7.60–7.71(3H, m), 7.75–7.77 (2H, m), 7.91(1H, d), 8.17(1H, s), 8.44(1H, s) | 3226, 1670, 1562, 1495, 1470, 1321, 1137, 1029, 810 |
| 224 | 507 | 9.11 | (D$_4$-MeOH) 2.10–2.18(1H, m), 2.42–2.51 (1H, m), 2.86–3.03(2H, m), 3.82 (1H, t), 7.42(1H, d), 7.51–7.58(3H, m), 7.68(1H, s), 7.73–7.74(2H, m), 8.22(2H, s), 8.41(1H, s) TFA salt | 3206, 3068, 1665, 1557, 1501, 1475, 1327, 1301, 1184, 1122, 794 |
| 225 | 365 | 13.7 | 1.7–1.8(1H, m), 2.1–2.2(1H, m), 2.8–3.4 (2H, m), 3.9–4.0(1H, m), 7.3–7.7 (5H, m), 7.9–8.2(2H, m), 10.1–10.4 (1H, brs), 12.7–13.3(1H, brs) | 1644.2 |
| 226 | 391 | 7.54 | 2.06–2.12(1H, m), 2.35–2.50(1H, m), 2.79(6H, s), 2.92–3.06(2H, m), 3.76 (1H, t J 7.5Hz), 7.36–7.49(3H, m), 7.66–7.70(2H, m), 8.01(1H, s), 8.11 (1H, s), 9.52(1H, br), 10.26(1H, br), 13.02(1H, br). | 1670.8, 1199.7, 1132.7 |
| 227 | 377 | 8.75 | 3.47–3.51(1H, m), 3.85–3.93(1H, m), 4.29(1H, t J 7.2Hz), 7.36–7.51(3H, m), 7.67–7.77(2H, m), 8.03(1H, s), 8.09(1H, s), 9.39(1H, br), 10.43(1H, br), 13.04(1H, br). TFA salt | 1671.4, 1200.1, 1132.3 |
| 228 | 447 | 8.48 | 2.01–2.10(1H, m), 2.32–2.41(1H, m), 2.66–2.81(2H, m), 3.78(1H, t), 7.27–7.31(1H, d), 7.35–7.42(3H, m), 7.48–7.56(6H, m), 7.60–7.64 (1H, m), 7.70(1H, d), 7.75(2H, d), 7.90(1H, d), 8.16(1H, s), 8.42(1H, s) D$_4$-MeOH | 3211, 1665, 1598, 1562, 1496, 1312, 805, 764 |
| 229 | 413 | 8.10 | 2.04–2.13(1H, m), 2.34–2.43(1H, m), 2.71–2.86(2H, m), 3.02–3.07 (1H, m), 3.79(1H, t), 7.28–7.53(9H, m), 7.71(1H, d), 7.79(1H, s), 8.36 (1H, s) D$_4$-MeOH | 3227, 2966, 1660, 1598, 1557, 1491, 1312, 1199, 1184, 1132, 794 |
| 230 | 439 | 8.12 | 2.14–2.22(1H, m), 2.41–2.51(1H, m), 2.85–3.02(2H, m), 3.82(1H, t), 7.31–7.35(1H, m), 7.41(2H, t), 7.47–7.57 (4H, m), 7.72–7.74(2H, m), 8.22(2H, s), 8.40(1H, s) D$_4$-MeOH | — |
| 231 | 425 | 8.90 | — | — |
| 232 | 465 | 8.93 | 2.91(1H, dd), 3.24(1H, dd), 3.78(1H, t), 7.21(1H, d), 7.29(1H, d), 7.37(2H, t), 7.44(1H, t), 7.60–7.65(2H, m), 7.84 (1H, d), 8.17(1H, s), 8.40(1H, s), 9.36 (1H, s), 10.24(1H, s), 12.14(1H, s). | 3267, 1649, 1613, 1564, 1538, 1493, 1474, 1405, 1330, 1265, 1241, 1204, 1134, 1031, 877, 859 |
| 233 | 363 | 7.50 | 2.43(3H, s), 2.86(1H, dd), 3.21(1H, dd), 3.74(1H, t), 7.30–7.38(3H, m), 7.59–7.62(2H, m), 8.08(1H, s), 10.21 (1H, s), 12.54(1H, s). | 3242, 2918, 1655, 1596, 1560, 1510, 1473, 1375, 1308, 1261, 1181, 1133, 1064, 1031, 989, 949, 870, 844. |
| 234 | 457 | 8.59 | 1.81(1H, m), 2.15(1H, m), 2.52(1H, m), 2.99(1H, m), 3.91(1H, m), 7.45 (3H, m), 7.60(2H, s), 7.69(1H, m), 7.75(1H, s), 7.91(2H, m), 8.43(1H, s), 10.35(1H, s), 12.77–13.56(1H, brs). | 1662, 1609, 1560, 1494, 1282 |

TABLE 6-continued

Characterization data for Selected Compounds of Formula I

| Compd. No | M+1 (obs) | $R_t$ | $^1$H NMR | IR (cm$^{-1}$) |
|---|---|---|---|---|
| 235 | 429 | 7.32 | 1.79(1H, m), 2.18(1H, m), 2.50(1H, m), 2.89(1H, m), 3.72(1H, m), 3.89 (3H, s), 7.18(1H, m), 7.28(2H, m), 7.40(2H, m), 7.55(2H, m), 8.01(2H, d, J=8.0Hz), 8.08(2H, d, J=8.2Hz), 8.45 (1H, s), 10.24(1H, s), 12.92–13.45(1H, brs). | 1654, 1610, 1493, 1281 |
| 236 | 447 | 8.57 | 1.79(1H, m), 2.18(1H, m), 2.51(1H, m), 2.92(1H, m), 3.88(1H, m), 7.20 (1H, m), 7.30(2H, m), 7.40(3H, m), 7.50(4H, m), 7.74(2H, d, J=7.9Hz), 7.81(2H, d, J=8.1Hz), 7.99(2H, d, J=7.4Hz), 8.53(1H, s), 10.24(1H, s), 12.70–13.48(1H, brs). | 1660, 1557, 1492, 1320 |
| 237 | 415 | 5.21 | 1.99(1H, m), 2.26(1H, m), 2.63(1H, m), 2.78(1H, m), 3.73(1H, m), 7.22 (1H, m), 7.36(4H, m), 7.57(2H, s), 7.55(2H, m), 7.66(3H, brs), 7.99(2H, d, J=8.1Hz), 8.08(2H, d, J=8.2Hz), 8.45(1H, s), 10.20(1H, s), 13.33(1H, s). TFA salt | 1667, 1591, 1493, 1325 |
| 238 | 385 | 7.46 | 2.05–2.11(1H, m), 2.32–2.42(1H, m), 2.47(3H, s), 2.68–2.80(2H, m), 3.78(1H, t), 7.24–7.31(2H, m), 7.36–7.42 (3H, m), 7.47–7.53(4H, m), 7.69(1H, d), 7.73(1H, s), 8.35(1H, s) D$_4$-MeOH | 3267, 1665, 1588, 1562, 1491, 1312, 1173, 789 |
| 239 | 455 | 8.26 | 2.02–2.11(1H, m), 2.35–2.41(1H, m), 2.67–2.82(2H, m), 3.79(1H, t), 7.27–7.39(4H, m), 7.48–7.55(4H, m), 7.83(1H, s), 7.96(1H, d), 8.38 (1H, s) D$_4$-MeOH | 3227, 1665, 1547, 1501, 1265, 1219, 1163, 805 |
| 240 | 389 | 7.27 | 2.03–2.11(1H, m), 2.33–2.42(1H, m), 2.69–2.84(2H, m), 3.79(1H, t), 7.14–7.18(1H, m), 7.28–7.31(1H, m), 7.38(2H, t), 7.47–7.57(5H, m), 7.66(1H, d), 7.77(1H, d), 8.40(1H, s) D$_4$-MeOH | 3237, 1660, 1588, 1552, 1491, 1465, 1306, 1194, 861 |
| 241 | 405 | 7.76 | 2.15–2.22(1H, m), 2.42–2.51(1H, m), 2.85–3.01(2H, m), 3.82(1H, t), 7.31–7.35(1H, m), 7.39–7.55(8H, m), 7.87(1H, d), 7.93(1H, s), 8.37 (1H, s) D$_4$-MeOH, TFA salt | 3048, 1655, 1486, 1214, 1143, 799 |
| 242 | 315 | 6.30 | 2.84(1H, dd), 3.22(1H, dd), 3.75(1H, t), 7.37–7.47(6H, m), 7.99(1H, s), 8.13 (1H, s), 10.19(1H, s), 12.97(1H, s). | 3281, 1644, 1597, 1547, 1492, 1442, 1341, 1309, 1234, 1093, 1048, 1014, 944, 896, 880, 860, 823. |
| 243 | 349 | 7.15 | 2.93(1H, dd), 3.27(1H, dd), 3.81(1H, t), 7.35–7.40(2H, m), 7.47(1H, d), 7.61–7.64(2H, m), 8.00(1H, s), 8.12 (1H, s), 10.24(1H, s), 12.99(1H, s). | 3280, 2926, 1670, 1597, 1560, 1507, 1473, 1369, 1310, 1290, 1236, 1202, 1133, 1079, 1031, 945, 878, 855, 838, 819. |
| 244 | 429 | 7.32 | 2.02–2.12(1H, m), 2.33–2.43(1H, m), 2.70–2.85(2H, m), 3.79(1H, t), 3.98(3H, s), 7.28–7.32(1H, m), 7.38 (2H, t), 7.48–7.56(4H, m), 7.66(1H, t), 8.07(1H, d), 8.18(1H, d), 8.36(1H, s), 8.59(1H, s) D$_4$-MeOH | 3232, 1711, 1650, 1547, 1486, 1424, 1271, 1250, 1184, 805 |
| 245 | 335 | 6.76 | 2.44(3H, s), 2.86–2.90(1H, m), 3.12–3.17 (1H, m), 3.97(1H, t J 6.5Hz), 6.88(1H, m), 6.98(1H, m), 7.34–7.41 (2H, m), 8.09(1H, s), 10.29(1H, br), 12.57(1H, br). | 1654.4, 1566.6, 1510.9, 1307.4 |
| 246 | 415 | 5.49 | 2.14–2.22(1H, m), 2.41–2.49(1H, m), 2.87–3.01(2H, m), 3.83(1H, t), 7.31–7.35(1H, m), 7.41(2H, t), 7.47–7.56 (4H, m), 7.65(1H, t), 8.09(1H, d), 8.16(1H, d), 8.34(1H, s), 8.59 (1H, s) D$_4$-MeOH, TFA salt | 3063, 1680, 1557, 1491, 1189, 1143 |

TABLE 6-continued

Characterization data for Selected Compounds of Formula I

| Compd. No | M+1 (obs) | $R_t$ | $^1$H NMR | IR (cm$^{-1}$) |
|---|---|---|---|---|
| 247 | 349 | 7.17 | 2.89(1H, dd), 3.22(1H, dd), 3.77(1H, t), 7.35–7.40(2H, m), 7.46(1H, d), 7.60–7.63(2H, m), 8.00(1H, s), 8.12 (1H, s), 10.23(1H, s), 12.98(1H, s). | 3278, 2928, 1650, 1597, 1558, 1507, 1473, 1338, 1311, 1236, 1200, 1133, 1077, 1031, 945, 877. |
| 248 | 414 | 5.90 | 2.08–2.15(1H, m), 2.37–2.42(1H, m), 2.74–2.90(2H, m), 3.80(1H, t), 7.29–7.32(1H, m), 7.39(2H, t), 7.47–7.54 (4H, m), 7.63(1H, t), 7.92(1H, d), 8.17(1H, d), 8.34(1H, s), 8.45 (1H, s) D$_4$-MeOH | 3263, 1644, 1547, 1486, 1383, 1317, 1204, 1137, 799 |
| 249 | 385 | 7.49 | 1.99(1H, m), 2.29(1H, m), 2.65(3H, s), 2.69(1H, m), 2.80(1H, m), 3.60 (1H, m), 7.29(1H, m), 7.21–7.43(4H, br m), 7.55(2H, m), 7.69(2H, brs), 8.05(2H, m), 8.11(2H, m), 8.53(1H, s), 10.28(1H, s), 13.4(1H, brs). | 1671, 1606, 1202 |
| 250 | 413 | 6.87 | — | — |
| 251 | 453 | 8.64 | 1.98–2.06(1H, m), 2.31–2.39(1H, m), 2.47(3H, s), 2.67–2.83(2H, m), 3.78(1H, t), 7.25(1H, d), 7.39–7.42 (2H, m), 7.49–7.54(3H, m), 7.67–7.73 (3H, m), 8.35(1H, s) D$_4$-MeOH | 3217, 1644, 1568, 1496, 1465, 1312, 1199, 1178, 1127, 974 |
| 252 | 457 | 8.55 | 2.01–2.15(1H, m), 2.31–2.40(1H, m), 2.59–2.83(2H, m), 3.78(1H, t), 7.16(1H, d), 7.41(1H, d), 7.48–7.57 (4H, m), 7.65–7.67(2H, m), 7.77(1H, d), 8.41(1H, s) D$_4$-MeOH | 3227, 1650, 1588, 1557, 1485, 1470, 1312, 1137, 1040, 876 |
| 253 | 475 | 9.04 | 2.11–2.18(1H, m), 2.45–2.51(1H, m), 2.82–3.03(2H, m), 3.81(1H, t), 7.41–7.45(2H, m), 7.50–7.58(4H, m), 7.67(1H, s), 7.87(1H, d), 7.94 (1H, s), 8.39(1H, s) D$_4$-MeOH | 3227, 1680, 1491, 1465, 1194, 1137, 846, 805 |
| 254 | 371 | 6.55 | 1.95–2.01(1H, m), 2.28–2.33(1H, m), 2.70–2.83(2H, m), 4.13(1H, t), 4.52 (1H, s), 7.27(1H, t), 7.40–7.45(2H, m), 7.53–7.58(2H, m), 7.72(3H, brs), 8.22 (1H, s), 10.30(1H, s), 13.40(1H, s). TFA salt | 3291, 3068, 2924. 1670, 1554, 1498, 1459, 1306, 1201 1137, 1063, 959, 840, 801. |
| 255 | 391 | 7.56 | 2.67(3H, s), 3.15–3.27(1H, m), 3.45–3.53 (1H, m), 4.07(1H, t), 7.37–7.43 (2H, m), 7.60–7.71(4H, m), 7.87(3H, brs), 8.54(1H, s), 10.45(1H, s), 13.84 (1H, s). TFA salt | 3016, 1669, 1564, 1497, 1467, 1408, 1364, 1324, 1201, 1135, 1033, 951, 881, 838, 828. |
| 256 | 523 | 9.11 | 2.00–2.05(1H, m), 2.32–2.42(1H, m), 2.70–2.85(2H, m), 3.79(1H, t), 7.34(1H, d), 7.42(1H, d), 7.49–7.57 (3H, m), 7.61–7.68(2H, m), 7.83(1H, s), 7.96(1H, d), 8.40(1H, s) D$_4$-MeOH | 2.00–2.05(1H, m), 2.32–2.42 (1H, m), 2.70–2.85 (2H, m), 3.79(1H, t), 7.34 (1H, d), 7.42(1H, d), 7.49–7.57 (3H, m), 7.61–7.68 (2H, m), 7.83 (1H, s), 7.96(1H, d), 8.40(1H, s) |
| 257 | 333 | 6.13 | 2.87–2.91(1H, m), 3.17–3.22(1H, m), 4.06–4.10(1H, m), 7.19–7.23(1H, m), 7.39–7.52(4H, s), 8.01(1H, s), 8.14 (1H, s), 10.35(1H, br), 12.98(1H, br). | 1664.0, 1507.9, 1457.7 |
| 258 | 333 | 6.24 | 2.83–2.88(1H, m), 3.13–3.19(1H, m), 4.00–4.03(1H, m), 7.27–7.29(1H, m), 7.39–7.52(4H, s), 8.00(1H, s), 8.14 (1H, s), 10.34(1H, br), 12.98(1H, br). | 1738.7, 1365.7, 1216.9 |
| 259 | 396 | 6.67 | 2.03–2.11(1H, m), 2.32–2.41(1H, m), 2.67–2.81(2H, m), 3.78(1H, t), 7.28–7.31(1H, m), 7.38(2H, t), 7.46–7.49 (3H, m), 7.55(1H, d), 7.87(2H, d), 8.15(2H, d), 8.40(1H, s) D$_4$-MeOH | 3283, 2930, 2228, 1655, 1609, 1557, 1496, 1317, 1194, 989, 846 |
| 260 | 400 | 5.26 | 2.16–2.25(1H, m), 2.42–2.51(1H, m), 2.80–2.03(2H, m), 3.84(1H, t), 4.25(2H, s), 7.30–7.56(8H, m), 7.38 (1H, t), 7.99–8.02(2H, m), 8.45(1H, s) D$_4$-MeOH, TFA salt | 3042, 2945, 1670, 1496, 1199, 1132, 820, 794 |

TABLE 6-continued

Characterization data for Selected Compounds of Formula I

| Compd. No | M+1 (obs) | $R_t$ | $^1$H NMR | IR (cm$^{-1}$) |
|---|---|---|---|---|
| 261 | 439 | 5.33 | 2.16–2.24(1H, m), 2.42–2.52(1H, m), 2.83–2.91(1H, m), 2.96–3.02 (1H, m), 3.83(1H, t), 7.32–7.35(1H, m), 7.41(2H, t), 7.47–7.50(3H, m), 7.56(1H, d), 8.17–8.21(4H, m), 8.49 (1H, s) D$_4$-MeOH, TFA salt | 3211, 3063, 1665, 1491, 1194, 1132, 835, 789 |
| 262 | 414 | 5.45 | — | — |
| 263 | 415 | 4.96 | 2.12–2.22(1H, m), 2.42–2.51(1H, m), 2.84–2.92(1H, m), 2.95–3.03 (1H, m), 3.84(1H, t), 7.30–7.34(1H, m), 7.40(2H, t), 7.47–7.54(4H, m), 7.98(2H, d), 8.14(2H, d), 8.40(1H, s) D$_4$-MeOH | 3033, 1657, 1609, 1541, 1495, 1380, 1315, 1262, 1175, 1099, 1016, 995, 955, 865, 842. |
| 264 | 443 | 5.37 | 1.88–1.90(1H, m), 2.32–2.35(1H, m), 2.62–2.64(1H, m), 2.70–2.72(1H, m), 2.90–2.94(2H, m), 4.13–4.17(1H, m), 7.23–7.27(1H, m), 7.32–7.51(8H, m), 7.78–7.83(3H, m), 8.33(1H, s), 11.01 (1H, brs), 13.10(1H, vbrs). | 3036, 1655, 1553, 1495, 1400, 1319, 699 |
| 265 | 463 | 8.19 | 1.88(1H, m), 2.15(1H, m), 2.50(2H, m), 3.87(1H, m), 7.06(2H, m), 7.18(4H, m), 7.29(2H, m), 7.40(4H, m), 7.50(2H, s), 7.90(2H, m), 8.56(1H, s), 10.20(1H, s), 12.75–13.35(1H, brs). | 1661, 1589, 1521, 1490, 1236 |
| 272 | 421 | 4.68 | 1.95–2.04(1H, m), 2.32–2.41(1H, m), 2.66–2.76(2H, m), 3.83(1H, dd), 7.24(1H, t), 7.44–7.53(3H, m), 7.79 (1H, d), 7.98–8.00(2H, m), 8.04(1H, s), 8.47(1H, dd), 8.62(1H, d) D$_4$-MeOH | 3237, 3083, 1665, 1537, 1204, 1137, 840, 810, 728 |

Example 42

We have prepared other compounds of formula I by methods substantially similar to those described in Examples 1 through 39 and by the general synthetic Schemes I–VII. The characterization data for these compounds is summarized in Table 7 below and includes HPLC, LC/MS (observed), IR, and $^1$H NMR data.

$^1$H NMR data is summarized in Table 7 below wherein $^1$H NMR data was obtained at 400 MHz in deuterated DMSO, unless otherwise indicated, and was found to be consistent with structure. Compound numbers correspond to the compound numbers listed in Table 1.

TABLE 7

Characterization data for Selected Compounds of Formula I

| Compd No | M+1 (obs) | $R_t$ | $^1$H NMR | IR (cm$^{-1}$) |
|---|---|---|---|---|
| 1000 | 489 | 7.68 | 1.79–1.83(1H, m), 2.12–2.24(1H, m), 2.95–3.08 (2H, m), 3.64(1H, t, J=7.4Hz), 3.71 (3H, s), 3.76(3H, s), 5.00(2H, s), 6.80–7.49 (9H, m), 7.99(1H, s), 8.10(1H, s), 9.98 (1H, s), 12.90(1H, s). | IR(Solid): 2967, 2865, 1715, 1513, 1459, 1262, 1151, 1081, 1012. |
| 1001 | 395 | 6.93 | 0.72–0.89(3H, m), 1.30–1.50(2H, m), 1.82–2.30(3H, m), 2.90–3.09(2H, m), 3.32–3.65 2H, m), 3.74(3H, s), 6.85–6.95(2H, m), 7.20–7.50(4H, m), 7.58–8.12(3H, m), 10.00(1H, s), 12.90(1H, s). | — |
| 1002 | 355 | 4.80 | 1.69–1.81(1H, m), 2.07–2.19(1H, m), 2.45–2.59 (2H, m), 3.67–3.80(7H, m), 6.82–6.96 (2H, m), 7.01–7.05(1H, m), 7.46–7.49(2H, m), 7.99(1H, s), 8.10(1H, s), 10.00(1H, s), 12.90(1H, brs). | IR(Solid): 1665, 1593, 1551, 1508, 1455, 1269, 1231, 1141, 1026. |
| 1003 | 443 | 7.55 | 1.90–2.30(4H, m), 3.50–3.70(1H, m), 3.71–3.75 (3H, m), 4.18–4.32(2H, m), 6.86–6.93 (2H, m), 7.10–7.49(8H, m), 7.95–8.02(1H, m), 8.08–8.14(1H, m), 8.23–8.50(1H, m), 9.78–10.05(1H, m), 12.92(1H, brs). | IR(Solid): 1651, 1546, 1508, 1455, 1246, 1174, 1026. |

TABLE 7-continued

Characterization data for Selected Compounds of Formula I

| Compd No | M+1 (obs) | $R_t$ | $^1$H NMR | IR (cm$^{-1}$) |
|---|---|---|---|---|
| 1004 | 423 | 6.49 | 1.85–1.97(1H, m) 2.16–2.33(3H, m), 3.25–3.58 (8H, m), 3.63–3.69(1H, m), 3.72(3H, s), 6.90(2H, d, J=11.58Hz,), 7.31(2H, d, J= 11.4Hz), 7.36–7.49(2H, m), 7.99(1H, s), 8.11(1H, s), 10.00(1H, s), 12.90(1H, s). | IR(Solid): 1655, 1627, 1503, 1465, 1431, 1246, 1112. |
| 1005 | 311 | 4.85 | 1.92–2.05(1H, m), 2.20–2.32(1H, m), 2.78–2.88 (2H, m), 4.07–4.13(1H, m), 6.81(1H, t), 6.89(1H, d), 7.11(1H, t), 7.29(1H, d), 7.38–7.50 (2H, m), 8.00(1H, s), 8.12(1H, s), 9.82 (1H, s), 9.95(1H, s), 13.00(1H, brs) | 1672, 1511, 1457, 1193, 1137, 838, 816, 800, 756, 723 |
| 1006 | 309 | 5.26 | 1.90–2.08(1H, m), 2.27–2.38(1H, m), 2.43 (3H, s), 2.65–2.75(1H, m), 2.75–2.85(1H, m), 3.75–3.82(1H, m), 7.20–7.50(8H, m, + 2H br hump), 8.04(1H, s), 10.10(1H, s), 12.57(1H, brs) | 1672, 1199, 1135, 838, 799, 722, 701 |
| 1007 | 339 | 5.54 | 1.68–1.80(1H, m), 2.04–2.16(1H, m), 2.45 (3H, s), 2.55–2.62(2H, m), 3.85(3H, s), 4.15–4.20(1H, m), 6.95(1H, t), 7.00(1H, d), 7.20–7.25(1H, m), 7.35–7.48(3H, m), 8.08 (1H, s), 9.91(1H, s), 12.48(1H, brs) | 1674, 1492, 1247, 1201, 1135, 752, 672 |
| 1008 | 351 | 6.40 | 1.78(3H, s), 1.80–1.90(1H, m), 2.18–2.29 (1H, m), 2.40(3H, s), 2.97–3.05(2H, m), 3.69–3.77(1H, m), 7.29(1H, t), 7.34–7.40 (4H, m), 7.40–7.45(2H, m), 7.86(1H, br t), 8.05(1H, s), 10.01(1H, s), 12.51(1H, brs). | 3279, 1648, 1553, 1513, 1490, 1449, 1367, 1310, 995, 803, 773, 741, 696 |
| 1009 | 338 | 7.29 | 1.90–2.12(1H, m), 2.21–2.41(3H, m), 3.51 (3H, s), 3.69–3.76(1H, m), 7.22–7.50(6H, m), 8.00(1H, s), 8.09(1H, s), 9.81(1H, s), 12.90(1H, brs). | IR(Solid): 1722, 1651, 1598, 1555, 1508, 1450, 1255, 1155, 945. |
| 1010 | 414 | 8.65 | 1.96–2.12(1H, m), 2.24–2.41(3H, m), 3.69–3.83 (1H, m), 5.05–5.13(2H, m), 7.21–7.48 (6H, m), 7.90(1H, s), 8.11(1H, s), 10.09 (1h, s), 12.91(1H, s). | — |
| 1011 | 324 | 4.95 | — | 3280, 1703, 1655, 1593, 1551, 1503, 1236. |
| 1012 | 338 | 7.29 | 1.90–2.12(1H, m), 2.21–2.41(3H, m), 3.51 (3H, s), 3.69–3.76(1H, m), 7.22–7.50(6H, m), 8.00(1H, s), 8.09(1H, s), 9.81(1H, s), 12.90(1H, brs). | IR(Solid): 1722, 1651, 1598, 1555, 1508, 1450, 1255, 1155, 945. |
| 1013 | 473 | 8.22 | (CDCl$_3$) 1.95–2.08(1H, m), 2.45–2.61(4H, m), 3.23–3.46(2H, m), 3.58–3.65(1H, m), 3.84(3H, s), 4.99–5.19(3H, m), 6.81–7.02 (3H, m), 7.21–7.42(7H, m), 7.92(1H, s), 8.08(1H, s), 9.78(1H, brs) | — |
| 1014 | 325 | 5.34 | 1.69–1.84(1H, m), 2.06–2.21(1H, m), 2.44–2.58 (2H, m), 3.75(3H, s), 3.78–3.83(1H, m), 6.78–6.84(1H, m), 6.95–7.01(2H, m), 7.21–7.27(1H, m), 7.35–7.41(1H, m), 7.41–7.47 (1H, m), 7.99(1H, brs), 8.11(1H, brs), 10.08(1H, s), 12.96(1H, brs). | — |
| 1015 | 339 | 5.56 | 1.68–1.80(1H, m), 2.06–2.20(1H, m), 2.41 (3H, s), 2.42–2.59(2H, m), 3.75(3H, s), 3.78–3.83(1H, m), 6.75–6.83(1H, m), 6.91–7.02 (2H, m), 7.19–7.28(1H, m) 7.31–7.43 (2H, m), 8.09(1H, m), 10.10(1H, s), 12.53 (1H, s). | 1651, 1593, 1555, 1508, 1484, 1303, 1260, 1146, 1045. |
| 1016 | — | 5.15 | 1.70–1.82(1H, m), 2.05–2.15(1H, m), 2.55–2.65 (2H, m), 2.82(3H, d), 3.83(3H, s), 4.13–4.28 (1H, m), 5.85(1H, d), 6.92(1H, t), 7.00 (1H, d), 7.11(1H,d), 7.18–7.28(2H, m), 7.38 (1H, t), 8.00(1H, s), 9.84(1H, s), 11.24(1H, s) | 1657, 1599, 1491, 1415, 1303, 1244, 1026, 810, 756, 735, 667 |
| 1017 | 325 | 5.34 | 1.69–1.84(1H, m), 2.06–2.21(1H, m), 2.44–2.58 (2H, m), 3.75(3H, s), 3.78–3.83(1H, m), 6.78–6.84(1H, m), 6.95–7.01(2H, m), 7.21–7.27(1H, m), 7.35–7.41(1H, m), 7.41–7.47 (1H, m), 7.99(1H, brs), 8.11(1H, brs), 10.08(1H, s), 12.96(1H, brs). | — |

TABLE 7-continued

Characterization data for Selected Compounds of Formula I

| Compd No | M+1 (obs) | R_t | ¹H NMR | IR (cm⁻¹) |
|---|---|---|---|---|
| 1018 | 339 | 5.56 | 1.68–1.80(1H, m), 2.06–2.20(1H, m), 2.41 (3H, s), 2.42–2.59(2H, m), 3.75(3H, s), 3.78–3.83(1H, m), 6.75–6.83(1H, m), 6.91–7.02 (2H, m), 7.19–7.28(1H, m)7.31–7.43 (2H, m), 8.09(1H, m), 10.10(1H, s), 12.53 (1H, s). | IR(Solid): 1651, 1593, 1555, 1508, 1484, 1303, 1260, 1146, 1045. |
| 1019 | 487 | 8.69 | 1.36(3H, t), 1.78–1.92(1H, m), 2.08–2.20 (1H, m), 2.43(3H, s), 2.91–3.11(2H,m), 4.06 (2H, q), 5.00(2H, s), 6.85–7.02(2H, m), 7.20 (1H, t), 7.25–7.45(9H, m), 8.09(1H, s), 9.85 (1H, s) | 3280, 1686, 1648, 1601, 1494, 1474, 1453, 1296, 1267, 1248, 1079, 1051, 1009, 771, 750, 694 |
| 1020 | 461 | 8.22 | 1.89–2.08(2H, m), 2.25–2.46(5H, m), 4.86–5.03 (3H, m), 7.10–7.51(11H, m), 7.96–8 | — |
| 1021 | 461 | 8.32 | 1.78–1.93(1H, m), 2.11–2.25(1H, m), 2.42 (3H, s), 2.92–3.12(2H, m), 4.05(1H, brt, J= 6.3Hz), 4.99(2H, s), 7.11–7.59(12H, m), 8.09(1H, s), 10.13(1H, s), 12.55(1H, s). | — |
| 1022 | 327 | 5.54 | 1.70–1.86(1H, m), 2.06–2.20(1H, m), 2.42 (3H, s), 2.42–2.65(2H, m), 4.01–4.18(1H, m), 7.10–7.61(5H, m), 8.09(1H, s), 10.18 (1H, s), 12.51(1H, brs). | — |
| 1023 | 401 | 6.79 | 2.06(1H, m), 2.35(1H, m), 2.67(1H, m), 2.77(1H, m), 3.82(3H, s), 3.98(1H, t), 7.10 (2H, d), 7.25–7.57(7H, m), 7.81(2H, d), 8.13 (3H, s), 8.50(1H, s), 10.60(1H, s) HCl salt | — |
| 1024 | 461 | 8.22 | 1.89–2.08(2H, m), 2.25–2.46(5H, m), 4.86–5.03 (3H, m), 7.10–7.51(11H, m), 7.96–8 | — |
| 1025 | 369 | 5.65 | 1.75–1.87(1H, m), 2.10–2.25(1H, m), 2.44 (3H, s), 2.57–2.70(2H, m), 3.79(3H, s), 3.81 (3H, s), 4.10–4.19(1H, m), 5.20(2H, br hump), 6.92–7.02(1H, m), 7.00–7.09(2H, m), 7.30–7.40(2H, m), 8.08(1H,s), 10.00 (1H, s), 12.50(1H, brs) | 1658, 1586, 1550, 1510, 1478, 1431, 1307, 1278, 1234, 1202, 1172, 1086, 1001, 801, 769, 751 |
| 1026 | 315 | 5.26 | 180–1.95(1H, m), 2.10–2.22(1H, m), 2.45 (3H, s), 2.55–2.65(2H, m), 4.15–4.25(1H, m), 6.93–7.00(1H, m), 7.00–7.05(1H, m), 7.30–7.42(3H, m), 8.07(1H, s), 10.27(1H, s), 12.58 1H, brs) | 1658, 1564, 1511, 1484, 1309, 991, 806, 771, 700 |
| 1027 | 389 | 7.10 | 2.03(1H, m), 2.34(1H, m), 2.67(1H, m), 2.78(1H, m), 3.90(1H, t), 7.28(1H, m), 7.35–7.45(6H, m), 7.51–7.57(2H, m), 7.92 (2H, m), 7.97(3H, s), 8.49(1H, s), 10.48 (1H, s) HCl salt | — |
| 1028 | 371 | 6.86 | 2.03(1H, m), 2.35(1H, m), 2.67(1H, m), 2.78(1H, m), 3.93(1H, t), 7.26–7.58(11H, m), 7.90(2H, d), 8.01(3H, s), 8.52(1H, s), 10.51(1H, s) HCl salt | — |
| 1029 | — | 7.72 | 2.44–2.75(2H, m), 3.09–3.20(2H, m), 4.12–4.20 (4H, m), 7.21–7.30(2H, m), 7.41–7.51 (2H, m), 7.64–7.75(4H, m), 7.88(1H, m), 8.13(1H, m), 8.27(1H, m), 8.73(1H, s), 9.55(1H, s), 10.50(1H, s), 12.50(1H, s) TFA salt | — |
| 1030 | — | 5.82 | 1.99–2.09(2H, m), 2.62–2.67(2H, m), 3.71–3.78 (4H, m), 6.95–6.99(2H, m), 7.26–7.31 (4H, m), 7.68–7.83(3H, m), 8.28–8.33(2H, m), 9.01(1H, s), 10.05(1H, s), 12.02(1H, s) TFA salt | — |
| 1031 | — | 7.19 | 2.26–2.32(2H, m), 2.67–2.78(2H, m), 3.69–3.78 (4H, m), 6.87–6.99(3H, m), 7.20–7.46 (4H, m), 7.70(1H, m), 7.83(1H, d), 8.14 (1H, m), 8.33(1H, m), 9.35(1H, s), 10.09 (1H, s), 12.15(1H, s) TFA salt | — |
| 1032 | 313 | 5.23 | 1.69–1.82(1H, m), 2.05–2.20(1H, m), 2.45–2.61 (2H, m), 4.05–4.19(1H, m), 7.10–7.61 (6H, m), 7.99(1H, s), 8.13(1H, s), 10.18 (1H, s), 12.99(1H, brs). | 1660, 1589, 1555, 1498, 1479, 1227. |

TABLE 7-continued

Characterization data for Selected Compounds of Formula I

| Compd No | M+1 (obs) | R_t | ¹H NMR | IR (cm⁻¹) |
|---|---|---|---|---|
| 1033 | 309 | 5.46 | 1.70–1.88(1H, m), 2.10–2.23(1H, m), 2.42 (3H, s), 2.45–2.62(2H, m), 3.69–3.89(1H, m), 7.20–7.48(7H, m), 8.08(1H, s), 10.15 (1H, brs), 12.50(1H, brs). | 1651, 1593, 1560, 1503, 1479, 1446, 1308. |
| 1034 | 309 | 5.45 | 1.70–1.88(1H, m), 2.10–2.23(1H, m), 2.42 (3H, s), 2.45–2.62(2H, m), 3.69–3.89(1H, m), 7.20–7.48(7H, m), 8.08(1H, s), 10.15 (1H, brs), 12.50(1H, brs). | 1651, 1593, 1560, 1503, 1479, 1446, 1308. |
| 1035 | 315 | 5.25 | 1.75–1.90(1H, m), 2.08–2.24(1H, m), 2.2 (3H, s), 2.53–2.65(2H, m), 3.96–4.02(1H, m), 7.15–7.20(1H, m), 7.30–7.45(3H, m), 7.45–7.53(1H, m), 8.10(1H, s), 10.18(1H, s), 12.61(1H, brs) | 3273, 1656, 1663, 1551, 1511, 1483, 1450, 1309, 1237, 992, 866, 805, 786, 752, 701, 669 |
| 1036 | 428 | 7.07 | 1.70–1.83(1H, m), 2.09–2.23(1H, m), 3.15–3.52 (2H, m), 3.79–3.90(1H, m), 4.42–4.53 (2H, m), 7.15–7.61(11H, m), 8.49(1H, s), 8.84–8.95(1H, m), 10.23(1H, brs). | — |
| 1037 | 299 | 4.85 | 1.83–1.97(1H, m), 2.02–2.14(1H, m), 2.43 (3H, s), 2.54–2.66(2H, m), 3.93–4.02(1H, m), 6.27(1H, s), 6.41(1H, s), 7.25–7.42 (2H,m), 7.56(1H, s), 8.08(1H, s), 10.19(1H, s), 12.57(1H, brs) | 1659, 1566, 1511, 1484, 1449, 1308, 1011, 993, 936, 876, 807, 791, 770, 740 |
| 1038 | 400 | 7.43 | 1.90(1H, m), 2.07–2.25(1H, m), 2.26(3H, s), 2.56–2.67(2H, m), 3.81(1H, m), 6.59 (1H, m), 7.09(1H, m), 7.24–7.48(9H, m), 8.29(1H, s), 8.75(1H, s), 10.10(1H, s), 11.92(1H, s) | — |
| 1039 | 404 | 7.41 | 2.27(1H, m), 2.64–2.72(2H, m), 3.81(1H, m), 4.02(1H, m), 6.56(1H, m), 7.22–7.44(9H, m), 7.62(1H, d), 8.34(1H, s), 9.15(1H, brs), 10.15(1H, brs), 12.07(1H, brs) | — |
| 1040 | 414 | 7.24 | 1.71–1.82(1H, m), 2.12–2.25(1H, m), 2.46–2.61 (2H, m), 3.86(1H, brt, J=6.6Hz), 7.05–7.12 (1H, m), 7.20–7.28(1H, m), 7.29–7.48 (6H, m), 7.52–7.65(2H, m), 7.89(1H, d, J= 8.0Hz), 8.56(1H, s), 10.25(2H, brs). | 1651, 1593, 1527, 1489, 1455, 1308, 1231, 1146. |
| 1041 | 404 | 5.44 | 1.67–1.75(1H, m), 2.06–2.22(1H, m), 2.42–2.60 (2H, m), 3.78–3.88(1H, m), 6.69–6.75 (1H, m), 7.19–7.59(8H, m), 7.90–8.00(2H, m), 10.18(1H, s), 10.60(1H, brs), 12.70 (1H, brs). | — |
| 1042 | 428 | 6.03 | 1.65–1.83(1H, m), 2.10–2.22(1H, m), 2.5 (2H obscured), 3.80–3.88(1H, m), 4.75 (2H, d), 7.20–7.57(10H, m), 7.82–7.95(2H, m), 8.08(1H, s), 9.01(1H, s), 10.13(1H, s), 12.77(1H, brs) | 3277, 1650, 1630, 1602, 1543, 1507, 1489, 1313, 1232, 1202, 1180, 1135, 799, 715, 695, 668 |
| 1043 | 420 | 5.86 | 1.61–1.80(1H, m), 2.08–2.11(1H, m), 3.10–3.60 (2H, m), 3.79–3.88(1H, m), 7.10–7.60 (8H, m), 7.81–8.08(3H, m), 10.18(1H, s), 10.80(1H, brs), 12.76(1H, brs). | — |
| 1044 | 420 | 5.95 | 1.61–1.80(1H, m), 2.08–2.11(1H, m), 3.10–3.60 (2H, m), 3.79–3.88(1H, m), 7.10–7.60 (8H, m), 7.81–8.08(3H, m), 10.18(1H, s), 10.80(1H, brs), 12.76(1H, brs). | 1651, 1536, 1498, 1412, 1322, 1284. |
| 1045 | 490 | 6.42 | 1.78–1.90(1H, m), 2.20–2.36(1H, m), 3.23–3.50 (2H, m), 4.17–4.24(1H, m), 7.09–7.28 (2H, m), 7.32–7.62(3H, m), 7.80–7.91(2H, m), 8.10(1H, s), 10.20(1H, brs), 10.80(1H, brs), 12.75(1H, brs). | 1647, 1546, 1468, 1439, 1422, 1318, 1282 |
| 1046 | 490 | 6.44 | 1.78–1.90(1H, m), 2.20–2.36(1H, m), 3.23–3.50 (2H, m), 4.17–4.24(1H, m), 7.09–7.28 (2H, m), 7.32–7.62(3H, m), 7.80–7.91(2H, m), 8.10(1H, s), 10.20(1H, brs), 10.80(1H, brs), 12.75(1H, brs). | 1647, 1546, 1468, 1439, 1422, 1318, 1282 |

TABLE 7-continued

Characterization data for Selected Compounds of Formula I

| Compd No | M+1 (obs) | R$_t$ | $^1$H NMR | IR (cm$^{-1}$) |
|---|---|---|---|---|
| 1047 | 481 | 7.50 | 1.82–1.96(1H, m), 2.24–2.39(1H, m), 2.52–2.65 (2H, m), 4.20–4.29(1H, m), 7.15–7.26 (2H, m), 7.28–7.40(2H, m), 7.45(1H, t), 7.56–7.67(1H, m), 7.80–7.90(1H, m), 8.20 (1H, s), 8.36(1H, s), 9.36(1H, s), 10.20 (1H, brs), 12.13(1H, s). | 3308, 1669, 1603, 1559, 1535, 1473, 1443, 1328, 1270, 1237, 1218, 1188, 1127, 994, 876, 806, 784, 666 |
| 1048 | 481 | 4.48 | 1.82–1.96(1H, m), 2.24–2.39(1H, m), 2.52–2.65 (2H, m), 4.20–4.29(1H, m), 7.15–7.26 (2H, m), 7.28–7.40(2H, m), 7.45(1H, t), 7.56–7.67(1H, m), 7.80–7.90(1H, m), 8.20 (1H, s), 8.36(1H, s), 9.36(1H, s), 10.20 (1H, brs), 12.13(1H, s). | 3308, 1669, 1603, 1559, 1535, 1473, 1443, 1328, 1270, 1237, 1218, 1188, 1127, 994, 876, 806, 784, 666 |
| 1049 | 420 | 6.00 | 1.61–1.80(1H, m), 2.08–2.11(1H, m), 3.10–3.60 (2H, m), 3.79–3.88(1H, m), 7.10–7.60 (8H, m), 7.81–8.08(3H, m), 10.18(1H, s), 10.80(1H, brs), 12.76(1H, brs). | — |
| 1050 | 420 | 6.59 | 1.13–1.95(11H, m), 2.12–2.25(1H, m), 2.39–2.62(2H, m), 2.84–2.96(1H, m), 3.67–3.88 (1H, m), 7.15–7.61(7H, m), 7.89(1H, s), 10.03–10.15(2H, m), 12.52(1h, brs). | 1651, 1551, 1484, 1441, 1327 |
| 1051 | 444 | 6.60 | 1.69–1.83(1H, m), 2.07–2.23(1H, m), 3.19–3.50 (2H, m), 3.78–3.89(1H, m), 4.80(2H, s), 6.90–7.59(12H, m), 8.01(1H, s), 10.15 (1H, brs), 10.48(1H, brs), 12.68(1H, brs). | 1670, 1646, 1598, 1536, 1489, 1303, 1231. |
| 1052 | 369 | 6.91 | 1.70–1.82(1H, m), 2.11–2.24(1H, m), 2.44–2.59 (2H, m), 3.82–3.91(1H, m), 7.18–7.60 (10H, m), 7.83–7.95(1H, m), 8.50(1H, s), 10.22(1H, s), | 2975, 2885, 1660, 1555, 1489, 1384, 1317, 1255, 1146 |
| 1053 | 369 | 6.94 | 1.70–1.82(1H, m), 2.11–2.24(1H, m), 2.44–2.59 (2H, m), 3.82–3.91(1H, m), 7.18–7.60 (10H, m), 7.83–7.95(1H, m), 8.50(1H, s), 10.22(1H, s), 13.20( 1H, brs). | — |
| 1054 | 411 | 7.25 | 1.77–1.87(1H, m), 2.16–2.27(1H, m), 2.55–2.66 (2H, m), 3.82–3.90(1H, m), 7.12–7.50 (8H, m), 7.81–7.88(1H, m), 8.20(1H, s), 8.43(1H, s), 9.34(1H, s), 10.16(1H, s), 12.15(1H, s). | 1658, 1628, 1602, 1589, 1560, 1533, 1479, 1330, 1307, 1265, 1238, 1202, 1180, 1134, 799, 786, 729, 699, 682. |
| 1055 | 411 | 7.26 | 1.77–1.87(1H, m), 2.16–2.27(1H, m), 2.55–2.66 (2H, m), 3.82–3.90(1H, m), 7.12–7.50 (8H, m), 7.81–7.88(1H, m), 8.20(1H, s), 8.43(1H, s), 9.34(1H, s), 10.16(1H, s), 12.15(1H, s). | 1670, 1603, 1559, 1479, 1329, 1203, 1181, 1137, 799, 723, 700, 675 |
| 1056 | 441 | 7.40 | 1.84–1.93(1H, m), 2.27–2.38(1H, m), 2.55–2.65 (2H, m), 4.20–4.30(1H, m), 7.15–7.25 (1H, m), 7.36–7.44(1H, m), 7.50–7.66(5H, m), 7.87–7.95(2H, m), 8.39(1H, s), 10.30 (1H, brs), 13.20(1H, brs). | 1668, 1560, 1496, 1473, 1443, 1321, 1269, 1218, 993, 957, 825, 807, 777, 749, 720, 698. |
| 1057 | 441 | 7.38 | 1.84–1.93(1H, m), 2.27–2.38(1H, m), 2.55–2.65 (2H, m), 4.20–4.30(1H, m), 7.15–7.25 (1H, m), 7.36–7.44(1H, m), 7.50–7.66(5H, m), 7.87–7.95(2H, m), 8.39(1H, s), 10.30 (1H, brs), 13.20(1H, brs). | 1669, 1559, 1496, 1473, 1443, 1320, 1269, 1218, 1202, 993, 807, 776, 749, 720, 699, 675. |

Example 43

AKT-3 Inhibition Assay

Compounds were screened for their ability to inhibit AKT using a standard coupled enzyme assay (Fox et al., Protein Sci., (1998) 7, 2249). Assays were carried out in a mixture of 100 mM HEPES 7.5, 10 mM MgCl2, 25 mM NaCl, 1 mM DTT and 3% DMSO. Final substrate concentrations in the assay were 170 µM ATP (Sigma Chemicals) and 200 µM peptide (RPRAATF, American Peptide, Sunnyvale, Calif.). Assays were carried out at 30° C. and 45 nM AKT. Final concentrations of the components of the coupled enzyme system were 2.5 mM phosphoenolpyruvate, 300 µM NADH, 30 µg/ML pyruvate kinase and 10 µg/ml lactate dehydrogenase.

An assay stock buffer solution was prepared containing all of the reagents listed above, with the exception of AKT, DTT, and the test compound of interest. 55 µl of the stock solution was placed in a 96 well plate followed by addition of 2 µl of 1 mM DMSO stock containing the test compound (final compound concentration 30 µM). The plate was preincubated for about 10 minutes at 30° C. and the reaction initiated by addition of 10 µl of enzyme (final concentration 45 nM) and 1 mM DTF. Rates of reaction were obtained using a Molecular Devices SpectraMax Plus plate reader over a 15 minute read time at 30° C. Compounds showing greater than 50% inhibition versus standard wells containing the assay mixture and DMSO without test compound were titrated to determine $IC_{50}$ values.

The following compounds were shown to have $K_i$ values less than 1 µM for Akt-3 (Compound numbers correspond to the compound numbers listed in Table 1.): I-59, I-60, I-61, I-62, I-64, I-67, I-70, I-73, I-74, I-97 through I-106, I-108 through I-110, I-112, I-115 through I-122, I-124 through I-127, I-129 through I-136, I-138 through I-141, I-141 through I-145, I-147, I-149, I-153, I-155, I-160 through I-175, I-177 through I-189, I-193 through I-210, I-212 through I-227, I-231 through I-234, I-242, I-243, I-245, I-247, I-251 through I-254, I-256 through I-258, I-1005, I-1006, I-1014, I-1022, I-1043 through I-1047, I-1049 and I-1054.

The following compounds were shown to have $K_i$ values between 1.0 and 10.0 µM for AKT-3 (Compound numbers correspond to the compound numbers listed in Table 1.): I-5, I-16, I-35, I-40, I-43, I-48 through I-51, I-53 through I-56, I-58, I-63, I-68, I-71, I-72, I-76, I-77, I-78, I-83, and 1–85, I-107, I-111, I-113, I-114, I-123, I-128, I-137, I-142, I-150 through I-152, I-154, I-156 through I-159, I-176, I-191, I-192, I-235, I-236, I-241, I-250, I-255, I-259, I-1017, I-1018, I-1023, I-1028, I-1038, I-1039, I-1041, I-1048, I-1050 through I-1052, I-1055 and I-1056.

The following compounds were shown to have $K_i$ values between 10.0 and 20.0 µM for AKT-3 (Compound numbers correspond to the compound numbers listed in Table 1.): I-2, I-37, I-52, I-65, I-66, I-79, I-82, I-94, and I-95, I-146, I-190, I-1040, I-1053 and I-1057.

Example 44

PDK-1 Inhibition Assay

Compounds were screened for their ability to inhibit PDK-1 using a radioactive-phosphate incorporation assay (Pitt and Lee, J. Biomol. Screen., (1996) 1, 47). Assays were carried out in a mixture of 100 mM HEPES (pH 7.5), 10 mM $MgCl_2$, 25 mM NaCl, 2 mM DTT. Final substrate concentrations in the assay were 40 µM ATP (Sigma Chemicals) and 65 µM peptide (PDKtide, Upstate, Lake Placid, N.Y.). Assays were carried out at 30° C. and 25 nM PDK-1 in the presence of ~27.5 nCi/µL of [γ-$^{32}$P]ATP (Amersham Pharmacia Biotech, Amersham, UK). An assay stock buffer solution was prepared containing all of the reagents listed above, with the exception of ATP, and the test compound of interest. 15 µl of the stock solution was placed in a 96 well plate followed by addition of 1 µl of 0.5 mM DMSO stock containing the test compound (final compound concentration 25 µM, final DMSO concentration 5%). The plate was preincubated for about 10 minutes at 30° C. and the reaction initiated by addition of 4 µl ATP (final concentration 40 µM).

The reaction was stopped after 10 minutes by the addition of 100 µL 100 mM phosphoric acid, 0.01% Tween-20. A phosphocellulose 96 well plate (Millipore, Cat no. MAPH-NOB50) was pretreated with 100 µL 100 mM phosphoric acid, 0.01% Tween-20 prior to the addition of the reaction mixture (100 µL). The spots were left to soak for at least 5 minutes, prior to wash steps (4×200 µL 100 mM phosphoric acid, 0.01% Tween-20). Alter drying, 20 µL Optiphase 'SuperMix' liquid scintillation cocktail (Perkin Elmer) was added to the well prior to scintillation counting (1450 Microbeta Liquid Scintillation Counter, Wallac).

Compounds showing greater than 50% inhibition versus standard wells containing the assay mixture and DMSO without test compound were titrated to determine $IC_{50}$ values.

The following compounds were shown to have a $K_i$ of less than 1 µM for PDK-1 (Compound numbers correspond to the compound numbers listed in Table 1.): I-100, I-106, I-109, I-110, I-117, I-119, I-120, I-121, I-123, I-125, I-126, I-127, I-130, I-132, I-136, I-138, I-139, I-141, I-162, I-165, I-167, I-168, I-169, I-171, I-172, I-173, I-174, I-179, I-181, I-182, I-189, I-193, I-194, I-195, I-197, I-198, I-206, I-207, I-230, I-231, I-234 through I-238, I-240, I-241, I-242, I-248 through I-251, I-253, I-259 through I-265, I-272, I-1006, I-1022, I-1023, I-1026, I-1027, I-1028, I-1032, I-1034, I-1035, I-1041, I-1043 through I-1046, I-1048, I-1049, I-1052, I-1053, I-1056 and I-1057.

The following compounds were shown to have a $K_i$ of between 1 µM and 3 µM for PDK-1 (Compound numbers correspond to the compound numbers listed in Table 1.): I-98, I-101, I-107, I-112, I-115, I-118, I-122, I-124, I-129, I-137, I-140, I-147, I-158, I-160, I-164, I-166, I-170, I-175, I-176, I-177, I-180, I-185, I-186, I-187, I-188, I-199, I-108, I-212, I-213, I-225, I-228, I-233, I-239, I-1000, I-1005, I-1007, I-1018, I-1036, I-1038, I-1040, I-1054 and I-1055.

The following compounds were shown to have a $K_i$ of greater than 3 µM for PDK-1 (Compound numbers correspond to the compound numbers listed in Table 1.): I-16, I-33, I-54, I-99, I-102, I-105, I-111, I-113, I-114, I128, I-131, I-133, I-134, I-135, I-142, I-145, I-148, I-150, I-153, I-154, I-155, I-156, I-159, I-161, I-163, I-178, I-183, I-184, I-190, I-191, I-196, I-200, I-201 through I-204, I-222, I-226, I-227, I-229, I-232, I-233, I-247, I-254, I-257, I-258, I-1000, I-1014 through I-1021, I-1024, I-1025, I-1029, I-1030, I-1031, I-1033, I-1037, I-1039, I-1042, I-1047, I-1050, I-1051 and I-1054.

Example 45

ROCK Inhibition Assay

Compounds were screened for their ability to inhibit ROCK using a standard coupled enzyme assay (Fox et al (1998) *Protein Sci* 7, 2249). Reactions were carried out in 100 mM HEPES pH 7.5, 10 mM MgCl2, 25 mM NaCl, 1 mM DTT and 1.5% DMSO. Final substrate concentrations in the assay were 13 μM ATP (Sigma chemicals) and 200 FM peptide (KKRNRTLSV, American Peptide, Sunnyvale, Calif.). Assays were carried out at 30° C. and 200 nM ROCK. Final concentrations of the components of the coupled enzyme system were 2.5 mM phosphoenolpyruvate, 400 μM NADH, 30 μg/ml pyruvate kinase and 10 μg/ml lactate dehydrogenase.

An assay stock buffer solution was prepared containing all of the reagents listed above, with the exception of ROCK, DTT and the test compound of interest. 56 μl of the test reaction was placed in a 384 well plate followed by addition of 1 μl of 2 mM DMSO stock containing the test compound (final compound concentration 30 μM). The plate was pre-incubated for about 10 minutes at 30° C. and the reaction initiated by addition of 10 μl of enzyme (final concentration 100 nM). Rates of reaction were obtained using a BioRad Ultramark plate reader (Hercules, Calif.) over a 5 minute read time at 30° C. Compounds showing >50% inhibition versus standard wells containing DMSO, but no compound, were titrated and IC50's determined using a similar protocol.

The following compounds were shown to have a $K_i$ of less than 1 μM for ROCK (Compound numbers correspond to the compound numbers listed in Table 1.): I-5, I-6, I-8, I-20, I-25, I-35, I-54, I-69, I-98, I-99, I-100, I-103 through I-107, I-109, I-110, I-120, I-123, I-125, I-126, I-129, I-132, I-137, I-136, I-141, I-142, I-144, I-145, I-153, I-1002, I-1005, I-1006, I-1007, I-1008, and I-1018.

The following compounds were shown to have a $K_i$ of between 1 μM and 3 μM for ROCK (Compound numbers correspond to the compound numbers listed in Table 1.): I-4, I-7, I-9, I-24, I-26, I-27, I-31 through I-34, I-38, and I-41.

The following compounds were shown to have a $K_i$ of greater than 3 μM for ROCK (Compound numbers correspond to the compound numbers listed in Table 1.): I-12, I-13, I-15, I-16, I-23, I-28, I-29, I-30, O-102, I-118, I-139, I-140, I-1003, I-1014, and I-1019.

Example 46

PKA Inhibition Assay

Compounds were screened for their ability to inhibit PKA using a standard coupled enzyme assay (Fox et al., Protein Sci., (1998) 7, 2249). Assays were carried out in a mixture of 100 mM HEPES 7.5, 10 mM MgCl2, 25 mM NaCl, 1 mM DTT and 3% DMSO. Final substrate concentrations in the assay were 50 μM ATP (Sigma Chemicals) and 80 μM peptide (Kemptide, American Peptide, Sunnyvale, Calif.). Assays were carried out at 30° C. and 18 nM PKA. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above, with the exception of ATP, and the test compound of interest. 55 μl of the stock solution was placed in a 96 well plate followed by addition of 2 μl of DMSO stock containing serial dilutions of the test compound (typically starting from a final concentration of 5 μM). The plate was preincubated for 10 minutes at 30° C. and the reaction initiated by addition of 5 μl of ATP (final concentration 50 μM). Initial reaction rates were determined with a Molecular Devices SpectraMax Plus plate reader over a 15 minute time course. IC50 and Ki data were calculated from non-linear regression analysis using the Prism software package (GraphPad Prism version 3.0a for Macintosh, GraphPad Software, San Diego Calif., USA).

The following compounds were shown to have a $K_i$ of less than 1 μM for PKA (Compound numbers correspond to the compound numbers listed in Table 1.): I-2, I-35, I-40, I-43, I-48, I-51, I-52, I-54, I-55, I-56, I-59, I60, I-67, I-69, I-73, I-76 through I-78, I-85, I-93, I-97, I-98 through I-110, I-113, I-116 through I-136, I-138 through I-141, I-143 through I-145, I-147, I-149, I-153, I-155 through I-169, I-172, I-174, I-175, I-177 through I-189, I-193 through I-201, I-203 through I-210, I-226, I-227, I-230 through I-237, I-240, I-242 through I-247, I-249, I-252, I-254, I-260, I-261, I-263, I-1006, I-1022, I-1023, I-1026, I-1028, I-1033, I-1034, I-1039, I-1041, I-1043 and I-1044.

The following compounds were shown to have a $K_i$ between 1 μM and 5 μM on PKA (Compound numbers correspond to the compound numbers listed in Table 1.): I-6, I-24, I-84, I-92, I-202 and I-1053

Example 47 p70S6K Inhibition Assay

Compounds were screened for their ability to inhibit p70S6K using a radioactive-phosphate incorporation assay at Upstate Biotechnology (Pitt and Lee, J. Biomol. Screen., (1996) 1, 47). Assays were carried out in a mixture of 8 mM MOPS (pH 7.0), 10 mM MgAcetate, 0.2 mM EDTA. Final substrate concentrations in the assay were 15 μM ATP (Sigma Chemicals) and 100 μM peptide (KKRNRTLTV, Upstate Ltd., Dundee, UK). Assays were carried out at 30° C. and in the presence of p70S6K (5–10 mU, Upstate Ltd., Dundee, UK) and [γ-$^{33}$P]ATP (Specific activity approx. 500 cpm/pmol, Amersham Pharmacia Biotech, Amersham, UK). An assay stock buffer solution was prepared containing all of the reagents listed above, with the exception of ATP, and the test compound of interest. 15 μL of the stock solution was placed in a 96 well plate followed by addition of 1 μL of 40 μM or 8 μM DMSO stock containing the test compound, in duplicate (final compound concentration 2 μM or 0.4 μM, respectively, final DMSO concentration 5%). The plate was preincubated for about 10 minutes at 30° C. and the reaction initiated by addition of 4 μL ATP (final concentration 15 μM).

The reaction was stopped after 10 minutes by the addition of 5 μL 3% phosphoric acid solution. A phosphocellulose 96 well plate (Millipore, Cat no. MAPHNOB50) was pretreated with 100 μL 100 mM phosphoric acid, 0.01% Tween-20 prior to the addition of the reaction mixture (20 μL). The spots were left to soak for at least 5 minutes, prior to wash steps (4×200 μL 100 mM phosphoric acid, 0.01% Tween-20). After drying, 20 μL Optiphase 'SuperMix' liquid scintillation cocktail (Perkin Elmer) was added to the well prior to scintillation counting (1450 Microbeta Liquid Scintillation Counter, Wallac).

Percentage inhibition of compounds at 2 μM and 0.4 μM was calculated by comparing p70S6K activity with standard wells containing the assay mixture and DMSO without test compound.

Compounds showing high inhibition versus standard wells were titrated to determine $IC_{50}$ values.

While we have described a number of embodiments of this invention, it is apparent that our basic examples may be altered to provide other embodiments which utilize the compounds and methods of this invention. Therefore, it will

We claim:
1. A compound of formula IIa:

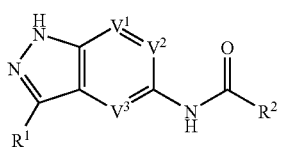

IIa or a pharmaceutically acceptable salt thereof, wherein:
$R^1$ is selected from halogen, CN, $N(R^4)_2$, or T-R;
T is selected from a valence bond or a $C_{1-6}$ alkylidene chain, wherein up to two methylene units of T are optionally, and independently, replaced by —O—, —N(R)—, —S—, —N(R)C(O)—, —C(O)N(R)—, —C(O)—, or —SO$_2$—;
each R is independently selected from hydrogen or an optionally substituted $C_{1-6}$ aliphatic group, or:
two R groups on the same nitrogen, taken together with the nitrogen atom attached thereto, form a 5–7 membered saturated, partially unsaturated, or aromatic ring having 1–3 heteroatoms independently selected from nitrogen, oxygen, or sulfur;
$R^2$ is selected from Q-C(R)(Q-Ar)$R^3$, wherein:
R and $R^3$ optionally form a 5–7 membered saturated or partially unsaturated ring having 0–4 heteroatoms independently selected from nitrogen, oxygen, or sulfur;
each Q is independently selected from a valence bond or a $C_{1-4}$ alkylidene chain;
each Ar is independently an optionally substituted ring selected from a 5–7 membered saturated, partially unsaturated, or fully unsaturated monocyclic ring having 0–4 heteroatoms independently selected from nitrogen, oxygen, or sulfur, or an 8–10 membered saturated, partially unsaturated, or fully unsaturated bicyclic ring having 0–4 heteroatoms independently selected from nitrogen, oxygen, or sulfur;
$R^3$ is selected from R', Ar$^1$, Q-OR$^5$, Q-OC(O)R$^5$, Q-CONHR$^5$, Q-OC(O)NHR$^5$, Q-SR$^5$, Q-N(R$^4$)$_2$, N(R)(Q-Ar), N(R)C(O)Q-N(R$^4$)$_2$, or N(R)Q-N(R$^4$)$_2$;
R' is an optionally substituted $C_{1-6}$ aliphatic group;
each $R^4$ is independently selected from R, COR, CO$_2$R, CON(R)$_2$, SO$_2$R, SO$_2$N(R)$_2$, or Ar$^1$;
each $R^5$ is independently selected from R or Ar;
$V^1$, $V^2$ and $V^3$ are each independently C(R$^6$);
each $R^6$ is independently selected from R, Ar$^1$, halogen, CN, NO$_2$, OR, SR, N(R$^4$)$_2$, N(R)COR, N(R)CON(R$^4$)$_2$, N(R)C(O)OR, CON(R$^4$)$_2$, OC(O)N(R$^4$)$_2$, CO$_2$R, OC(O)R, N(R)SO$_2$R, N(R)SO$_2$N(R$^4$)$_2$, SO$_2$R, or SO$_2$N(R$^4$)$_2$; and
each Ar$^1$ is independently selected from an optionally substituted 5–7 membered saturated, partially unsaturated, or fully unsaturated monocyclic ring having 0–4 heteroatoms independently selected from nitrogen, oxygen, or sulfur;
provided that when $V^1$, $V^2$, and $V^3$ are each CH and $R^1$ is hydrogen then $R^3$ is other than R', Q-OC(O)R$^5$, or OCH$_2$phenyl.

2. The compound according to claim 1, wherein:
$R^1$ is selected from halogen, $N(R^4)_2$, or optionally substituted $C_{1-6}$ aliphatic; and
$R^2$ is Q-C(R)(Q-Ar)R3, wherein:
R and $R^3$ optionally form a 5–7 membered saturated or partially unsaturated ring having 0–4 heteroatoms independently selected from nitrogen, oxygen, or sulfur;
$R^3$ is selected from R', Q-OR$^5$, Q-N(R$^4$)$_2$, Ar$^1$, N(R)C(O)Q-N(R$^4$)$_2$, or N(R)Q-N(R$^4$)$_2$; and
Ar is an optionally substituted 5–6 membered saturated, partially unsaturated, or fully unsaturated monocyclic ring having 0–4 heteroatoms independently selected from nitrogen, oxygen, or sulfur, or all optionally substituted 9–10 membered saturated, partially unsaturated, or fully unsaturated bicyclic ring having 0–4 heteroatoms independently selected from nitrogen, oxygen, or sulfur.

3. The compound according to claim 2, wherein:
$R^1$ is selected from chloro, bromo, fluoro, NH$_2$, NHMe, NHEt, NH-cyclohexyl, methyl, ethyl, propyl, isopropyl, cyclopropyl, acetylenyl, or d t-butyl; and
$R^3$ is selected from CH$_2$OH, OH, NH$_2$, CH$_2$NH$_2$, CH$_2$NHMe, CH$_2$N(Me)$_2$, CH$_2$CH$_2$NH$_2$, CH$_2$CH$_2$NHMe, CH$_2$CH$_2$N(Me)$_2$, CH$_2$CH$_2$NH$_2$, NHCO$_2$t-butyl, phenyl, cyclopentyl, methyl, ethyl, isopropyl, cyclopropyl, NH(CH$_2$)$_3$NH$_2$, NH(CH$_2$)$_2$NH$_2$, CH$_2$C(Me)$_2$NH$_2$, CH$_2$C(Me)$_2$CHMe, NH(CH$_2$)$_2$NHEt, NHCH$_2$pyridyl, NHSO$_2$phenyl, NHC(O)CH$_2$C(O)Ot-butyl, NHC(O)CH$_2$NH$_3$, or NHCH$_2$-imidazol-4-yl.

4. The compound according to claim 1, wherein:
$R^1$ is hydrogen; and
$R^2$ is Q-C(R)(Q-Ar)R$^3$, wherein:
R and $R^3$ optionally form a 5–7 membered saturated or partially unsaturated ring having 0–4 heteroatoms independently selected from nitrogen, oxygen, or sulfur;
$R^3$ is selected from Q-OR$^5$, Q-N(R$^4$)$_2$, Ar$^1$, N(R)C(O)Q-N(R$^4$)$_2$, or N(R)Q-N(R$^4$)$_2$; and
Ar is an optionally substituted 5–6 membered saturated, partially unsaturated, or fully unsaturated monocyclic ring having 0–4 heteroatoms independently selected from nitrogen, oxygen, or sulfur, or an optionally substituted 9–10 membered saturated, partially unsaturated, or fully unsaturated bicyclic ring having 0–4 heteroatoms independently selected from nitrogen, oxygen, or sulfur.

5. The compound according to claim 4, wherein:
$R^3$ is selected from OH, NH$_2$, CH$_2$NH$_2$, CH$_2$NHMe, CH$_2$N(Me)$_2$, CH$_2$CH$_2$NH$_2$, CH$_2$CH$_2$NHMe, CH$_2$CH$_2$N(Me)$_2$, NHCO$_2$t-butyl, phenyl, NH(CH$_2$)$_3$NH$_2$, CH$_2$C(Me)$_2$NH$_2$, CH$_2$C(Me)$_2$CHMe, NH(CH$_2$)$_2$NH$_2$, NH(CH$_2$)$_2$NHEt, NHCH$_2$pyridyl, NHSO$_2$phenyl, NHC(O)CH$_2$C(O)Ot-butyl, NHC(O)CH$_2$NH$_3$, or NHCH$_2$-imidazol-4-yl.

6. The compound according to claim 1, wherein said compound is selected from the group consisting of:

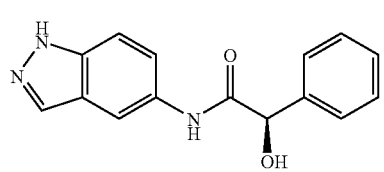

I-31

-continued
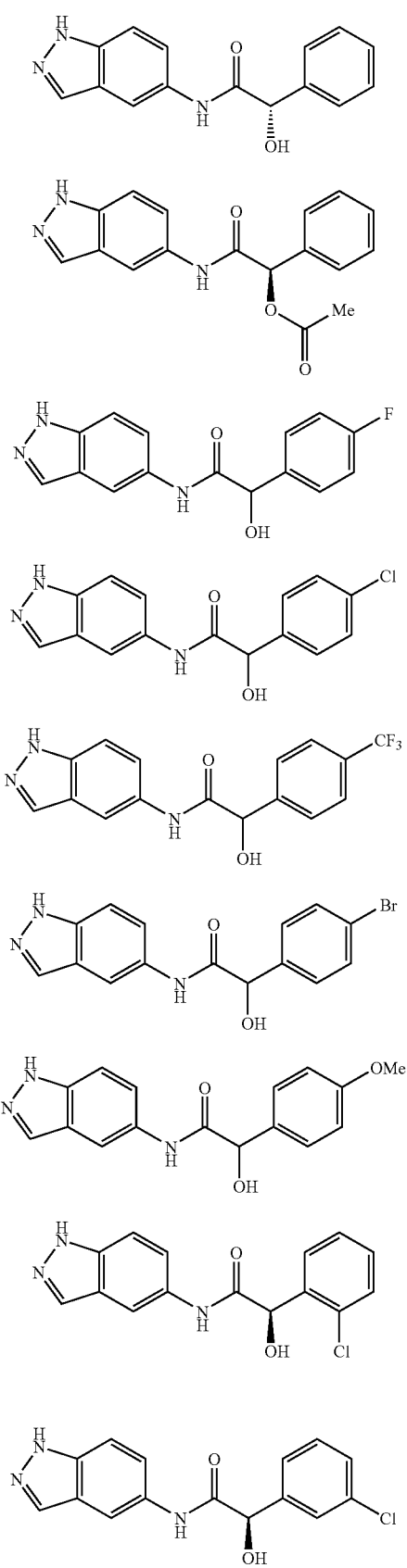
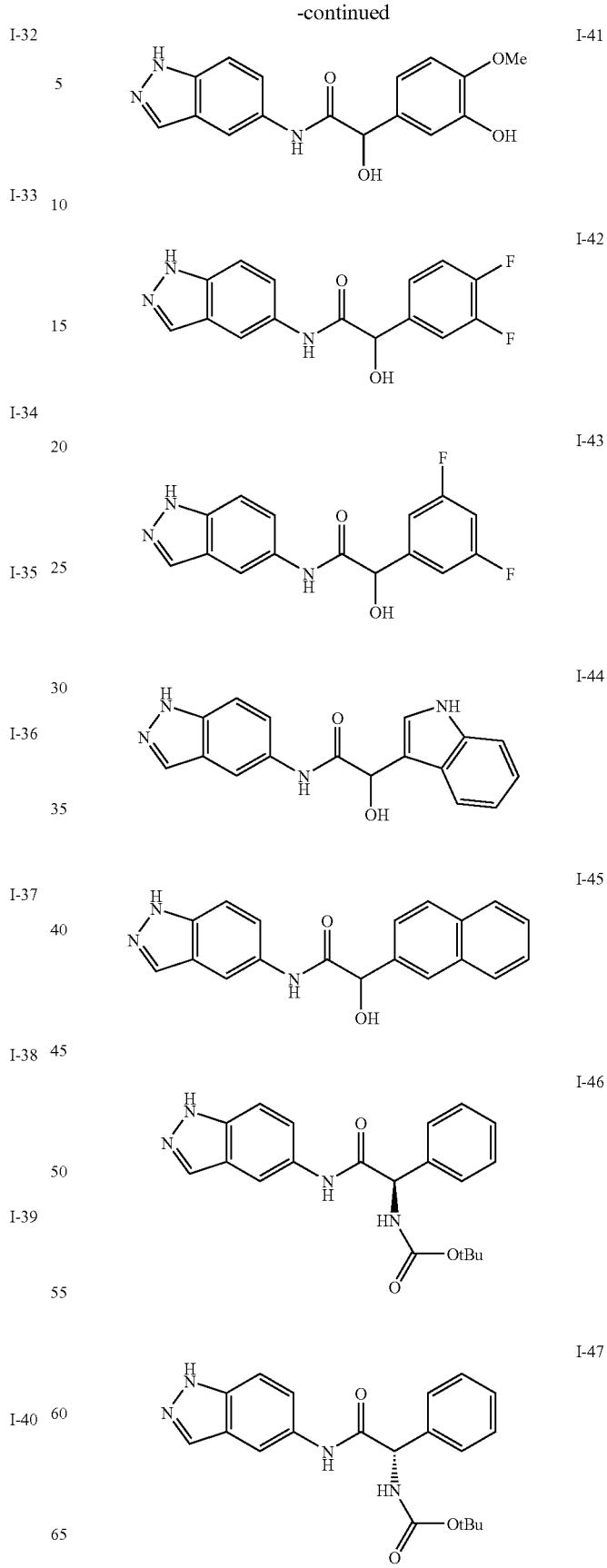

-continued
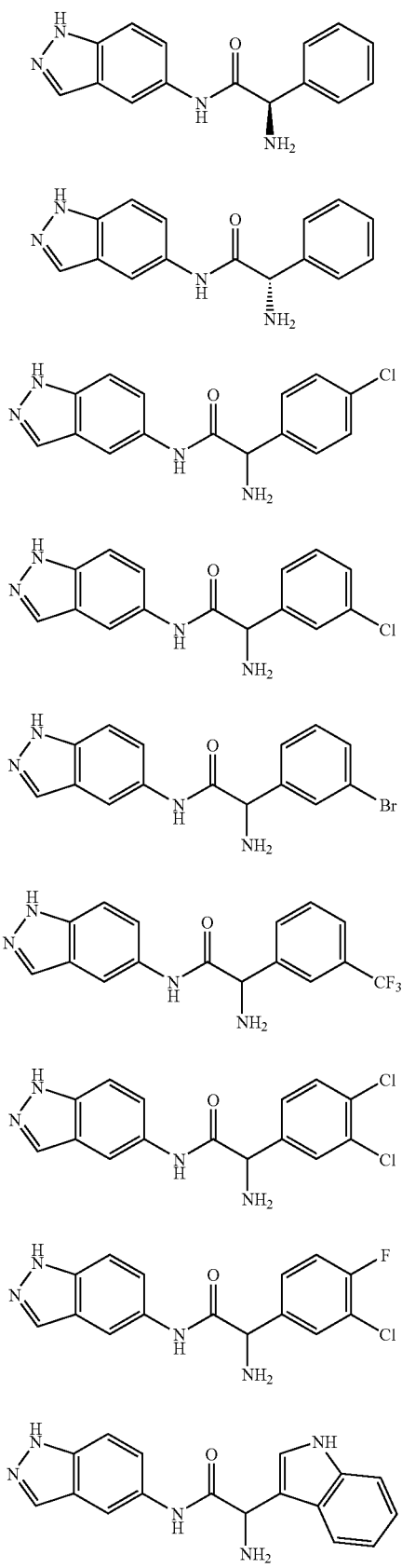
I-48
I-49
I-50
I-51
I-52
I-53
I-54
I-55
I-56
-continued
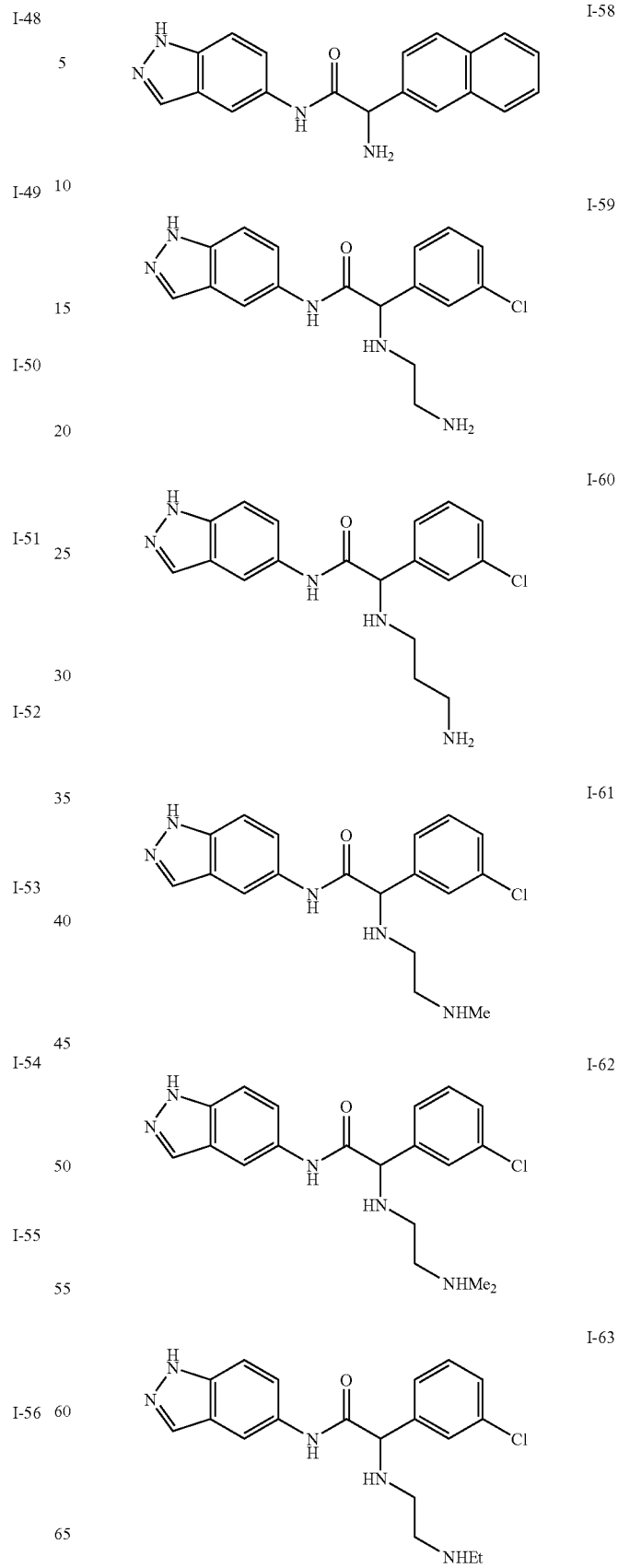
I-58
I-59
I-60
I-61
I-62
I-63

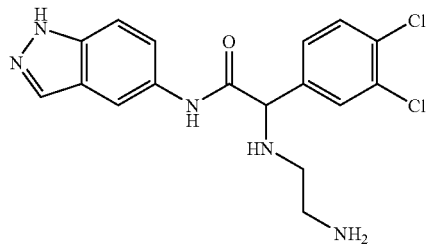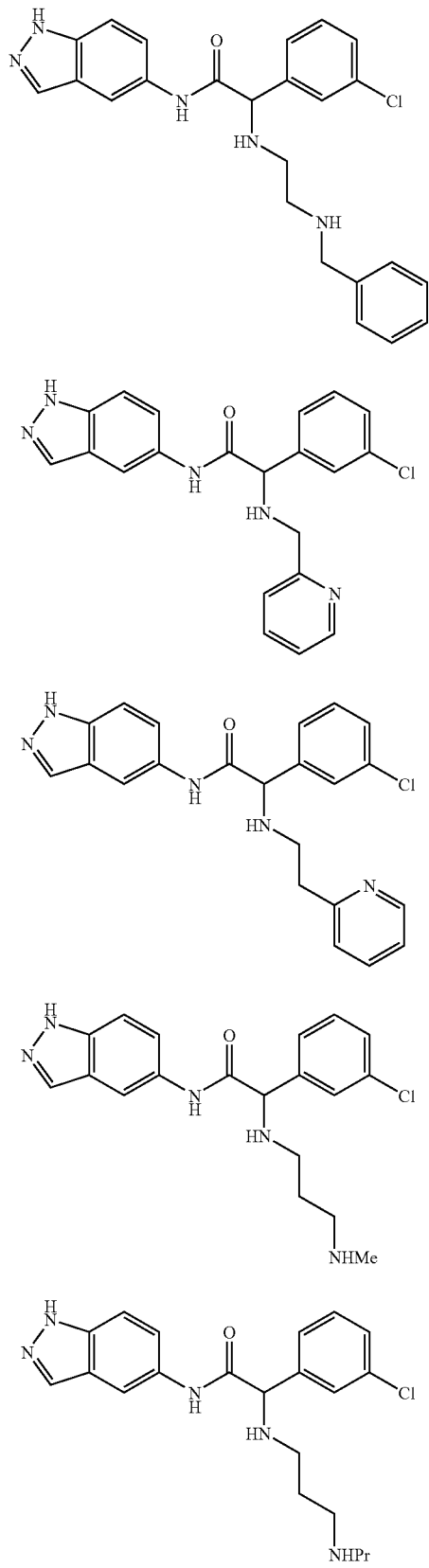

-continued

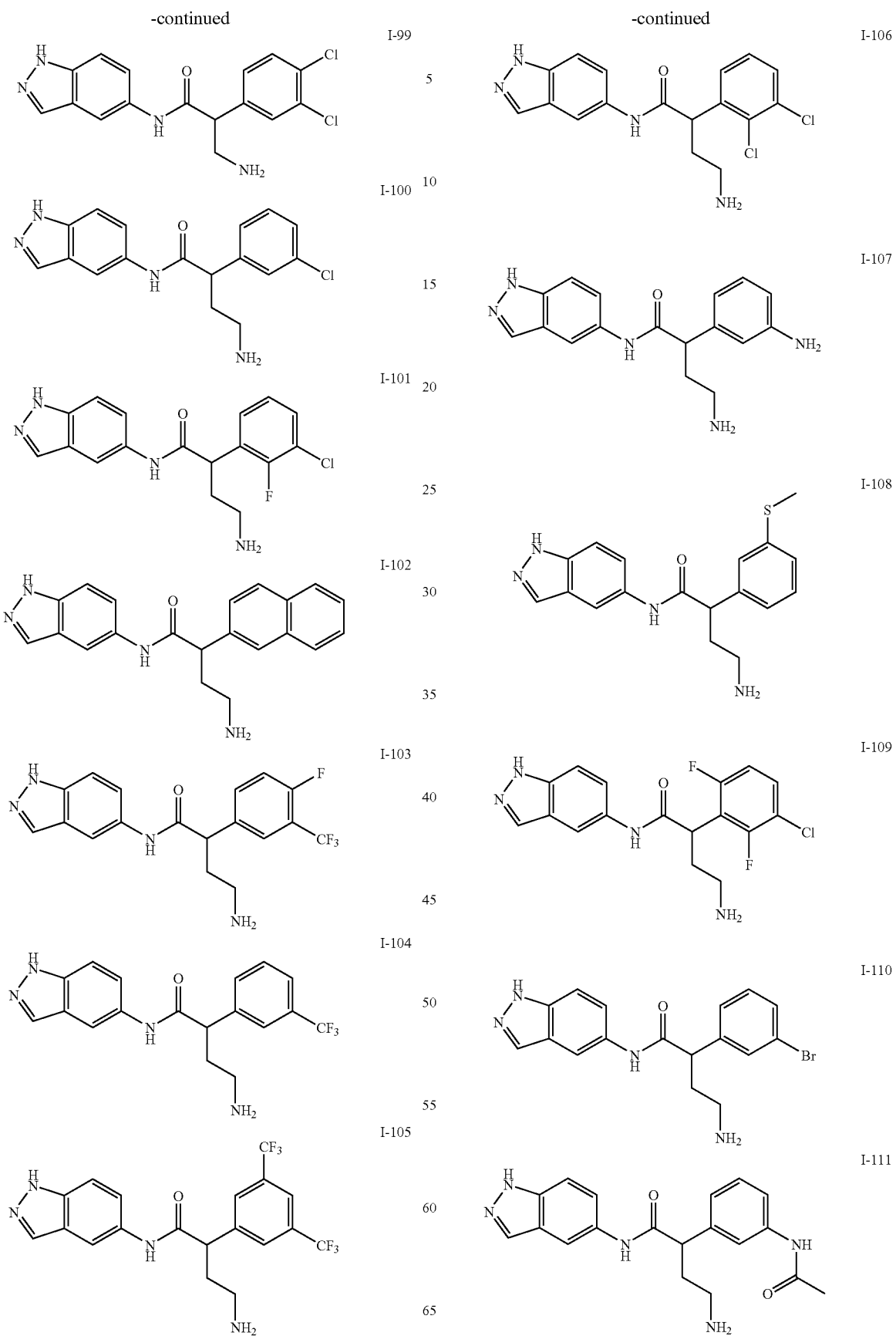

-continued
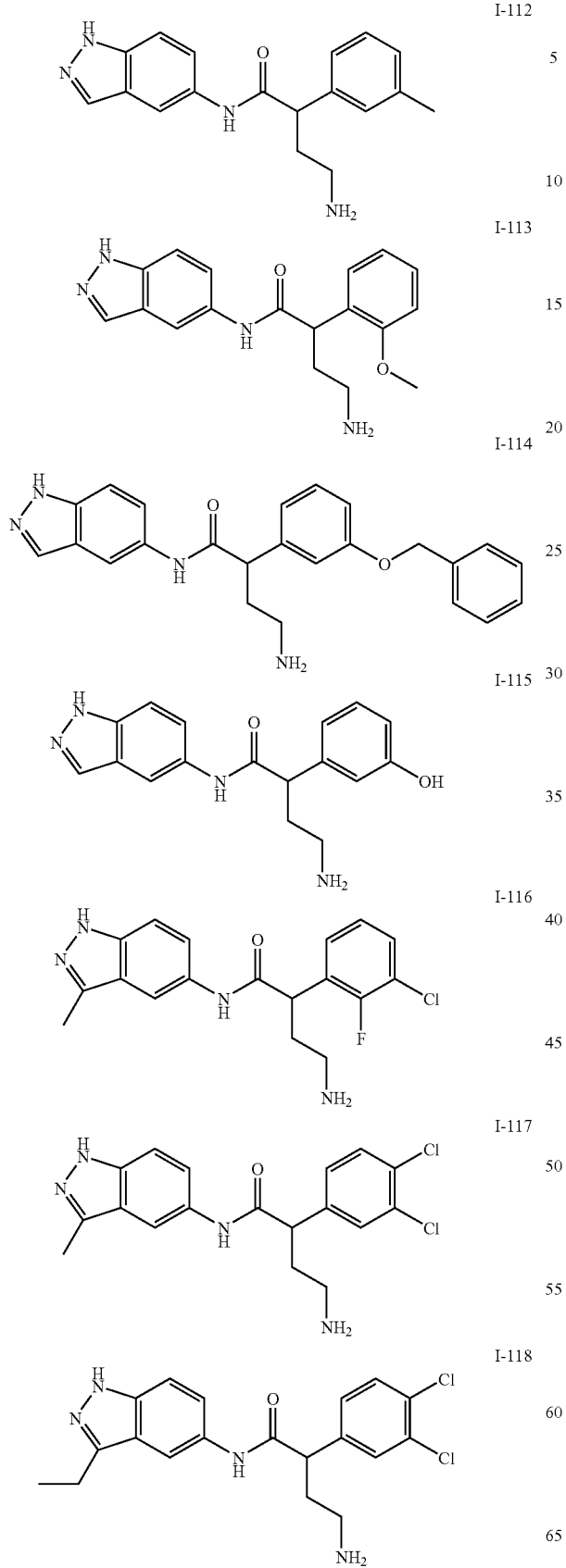
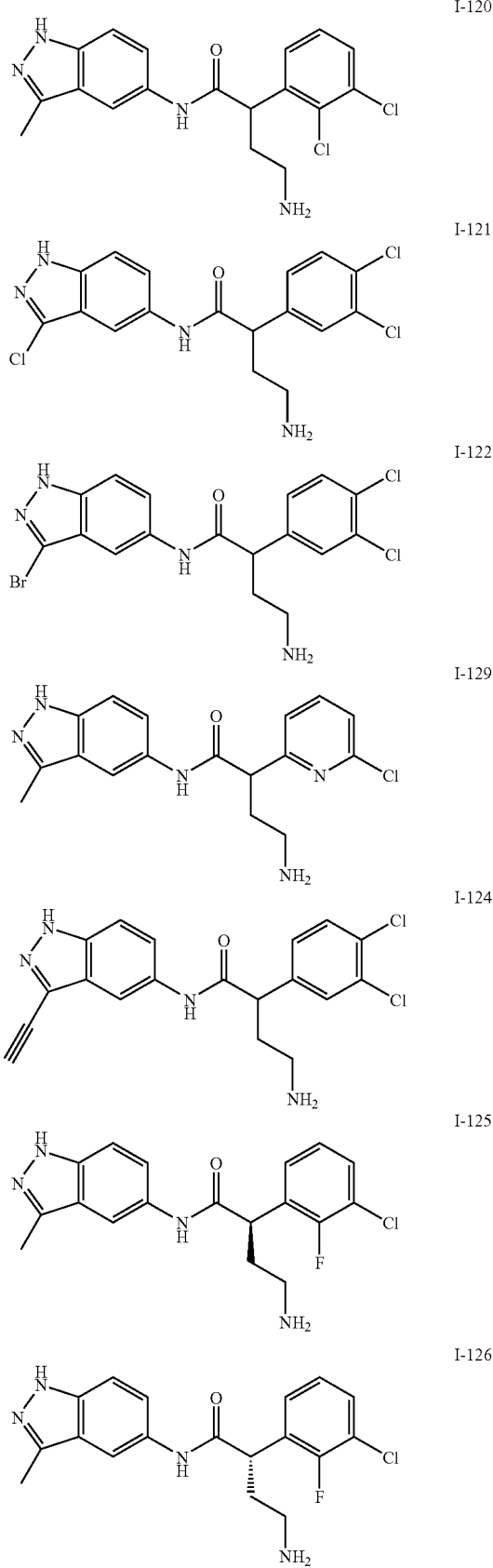

-continued
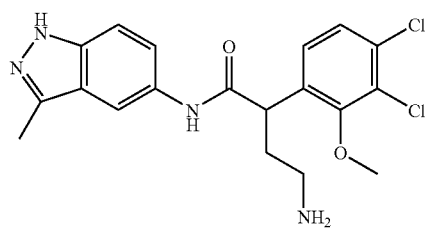  I-130
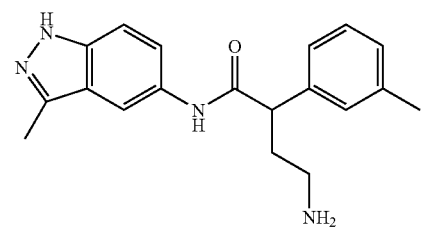  I-131
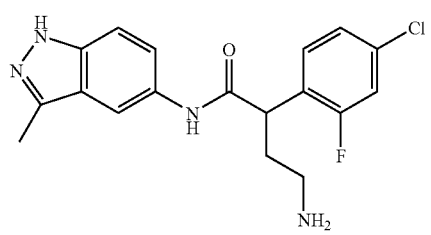  I-132
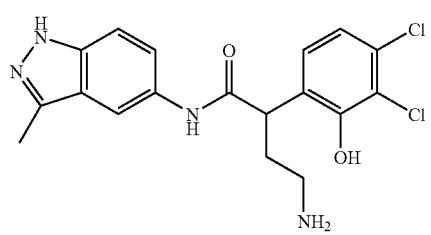  I-133
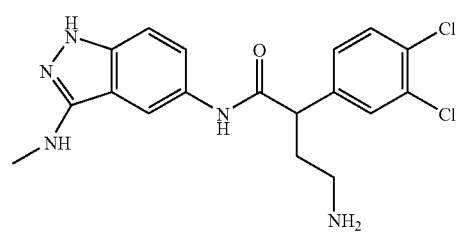  I-134
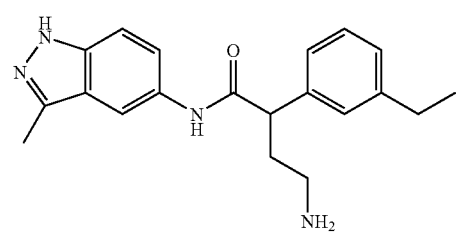  I-135
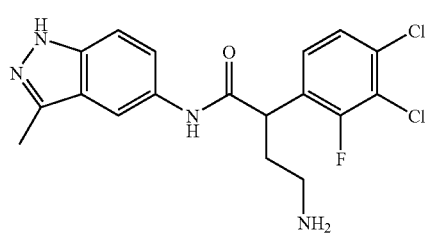  I-136
-continued
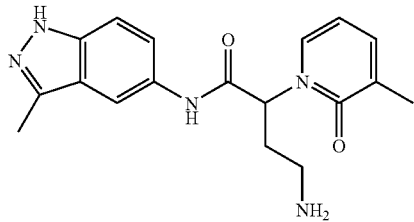  I-137
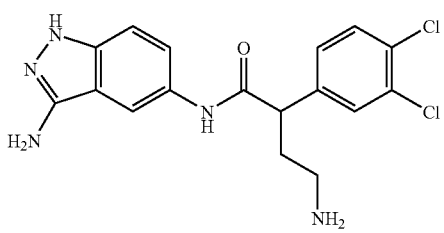  I-138
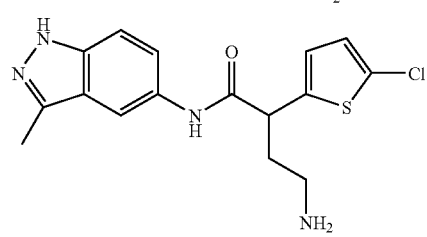  I-139
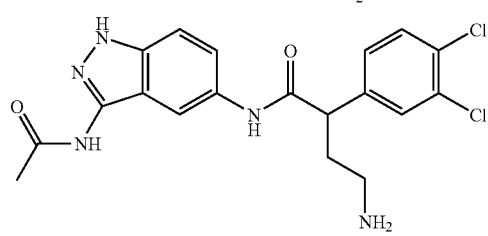  I-140
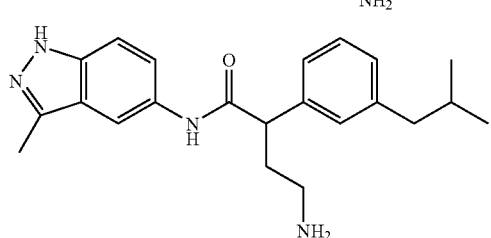  I-142
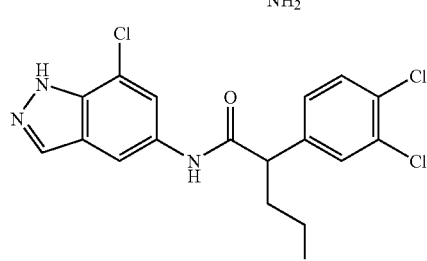  I-143
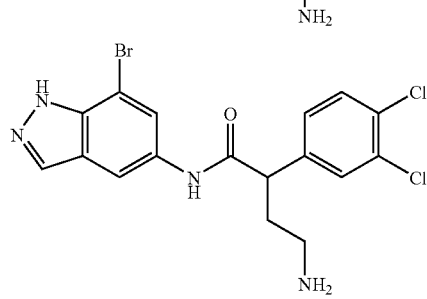  I-144

I-145 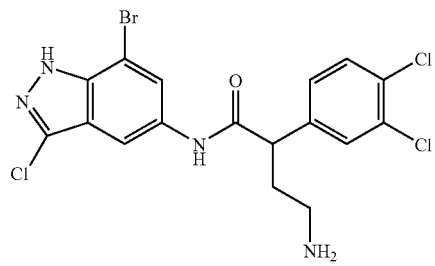
I-146 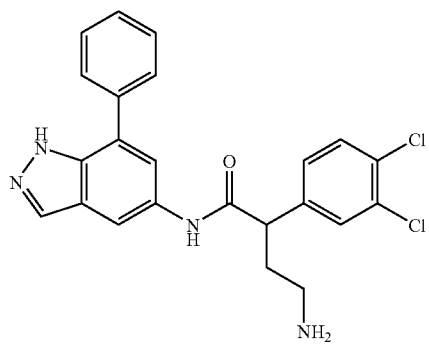
I-147 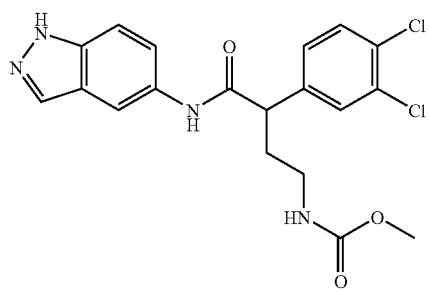
I-148 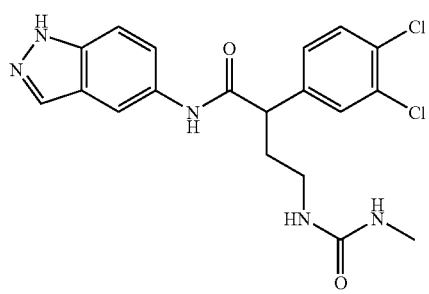
I-149 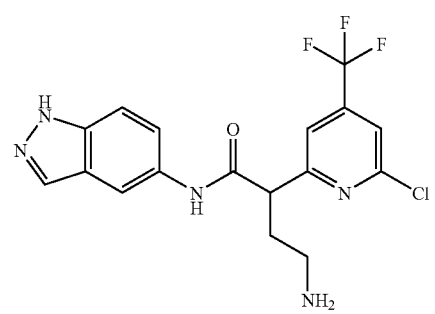
I-150 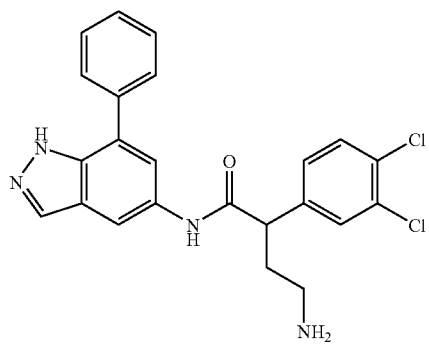
I-151
I-152
I-153
I-154 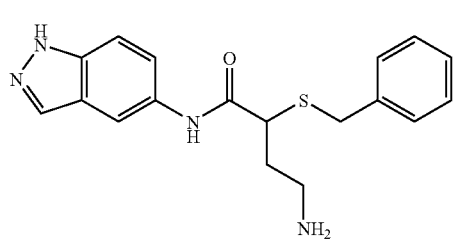

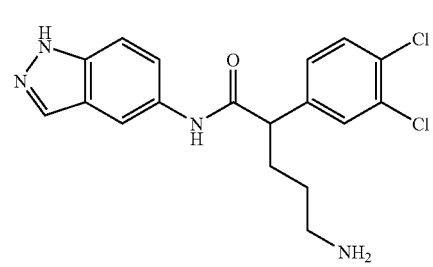
I-155
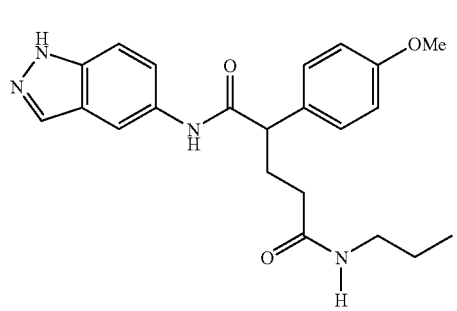
I-1001
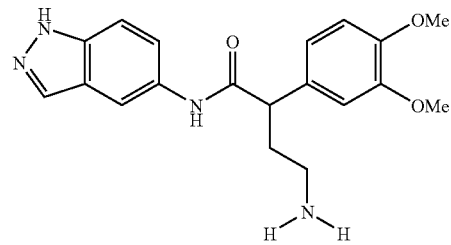
I-1002
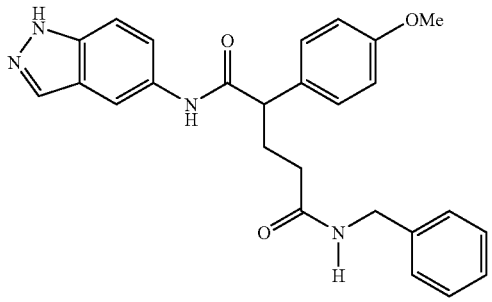
I-1003
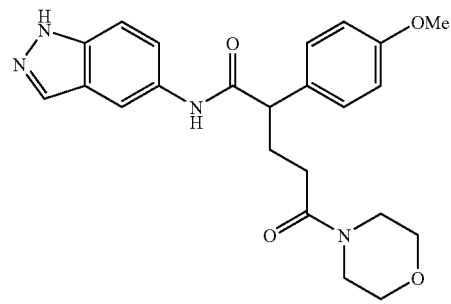
I-1004
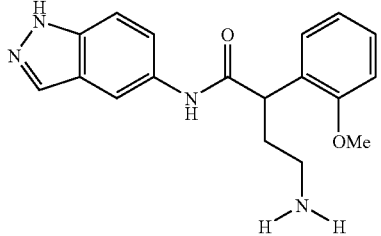
I-1005

-continued
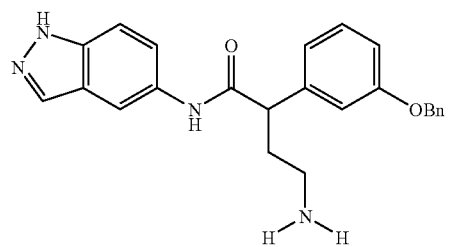
I-1006
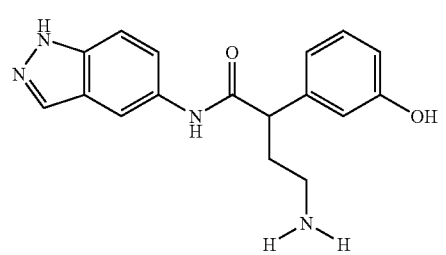
I-1007
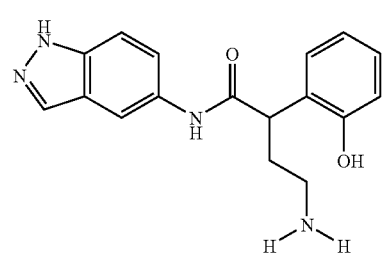
I-1008
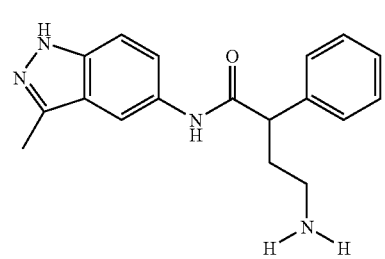
I-1009
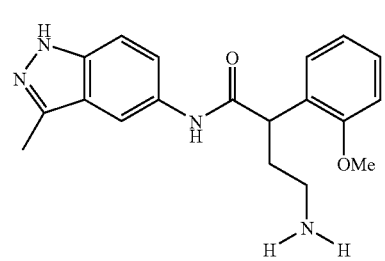
I-1010
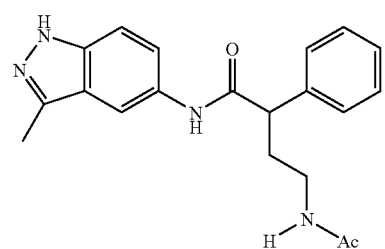
I-1011
-continued
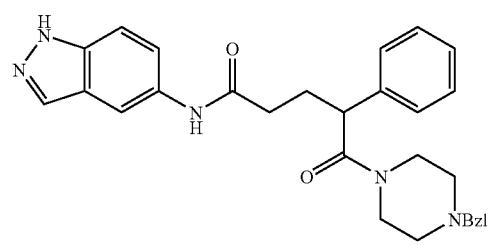
I-1015
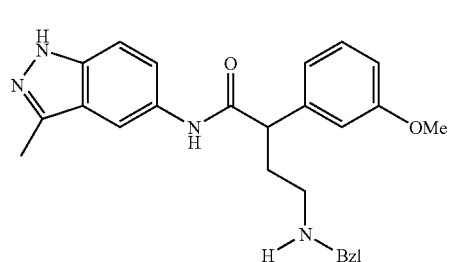
I-1016
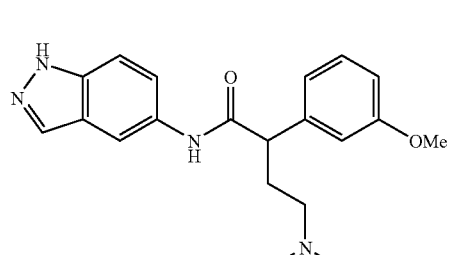
I-1017
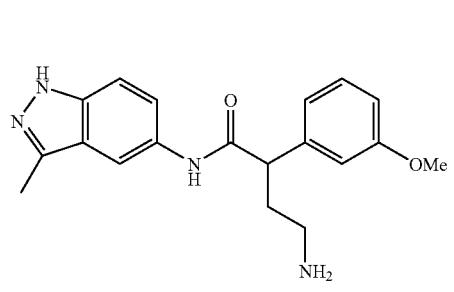
I-1018
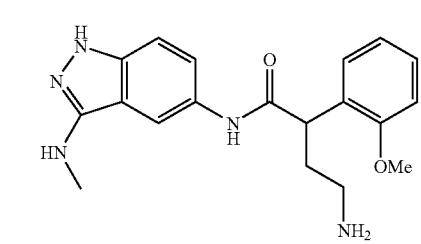
I-1019
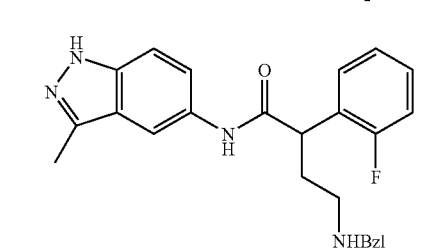
I-1021

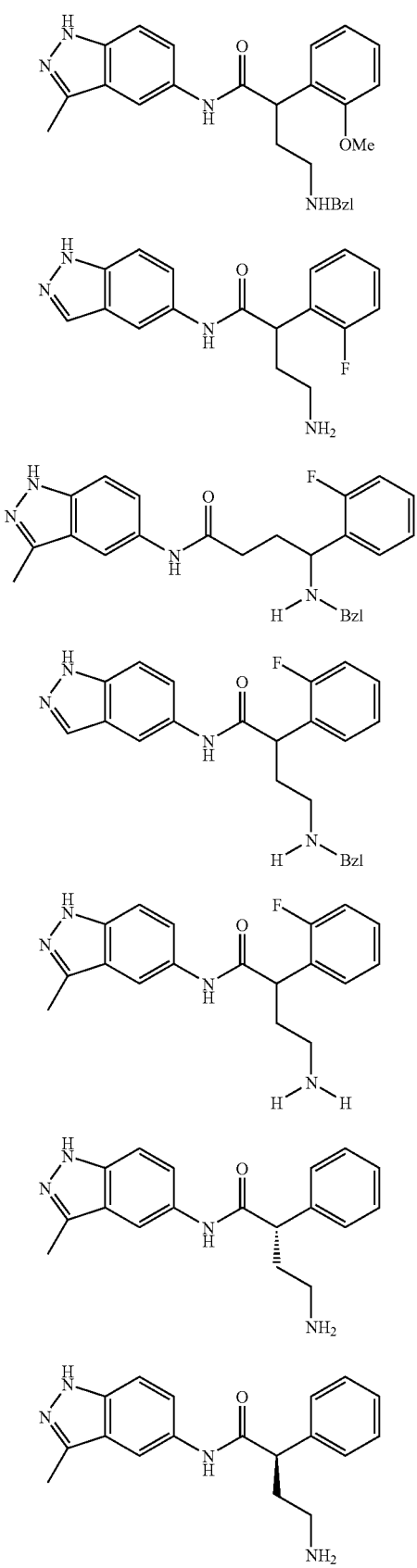

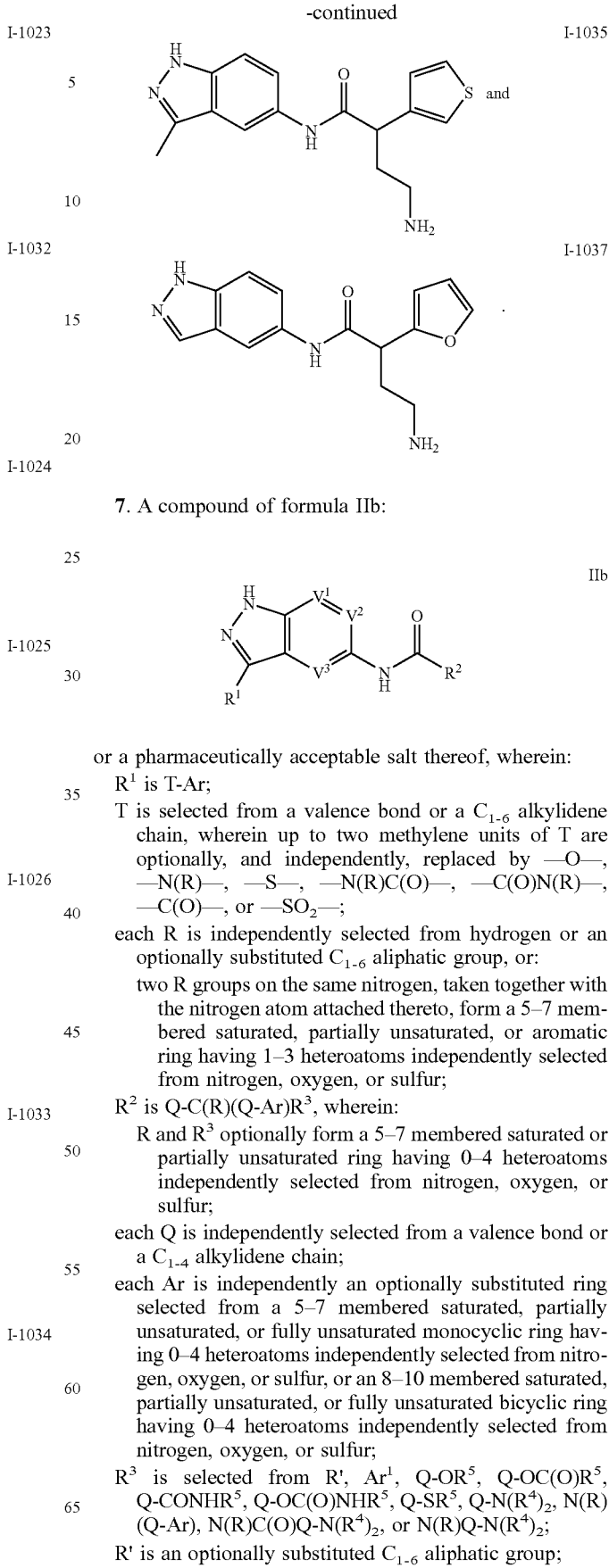

7. A compound of formula IIb:

or a pharmaceutically acceptable salt thereof, wherein:

$R^1$ is T-Ar;

T is selected from a valence bond or a $C_{1-6}$ alkylidene chain, wherein up to two methylene units of T are optionally, and independently, replaced by —O—, —N(R)—, —S—, —N(R)C(O)—, —C(O)N(R)—, —C(O)—, or —SO$_2$—;

each R is independently selected from hydrogen or an optionally substituted $C_{1-6}$ aliphatic group, or:

two R groups on the same nitrogen, taken together with the nitrogen atom attached thereto, form a 5–7 membered saturated, partially unsaturated, or aromatic ring having 1–3 heteroatoms independently selected from nitrogen, oxygen, or sulfur;

$R^2$ is Q-C(R)(Q-Ar)$R^3$, wherein:

R and $R^3$ optionally form a 5–7 membered saturated or partially unsaturated ring having 0–4 heteroatoms independently selected from nitrogen, oxygen, or sulfur;

each Q is independently selected from a valence bond or a $C_{1-4}$ alkylidene chain;

each Ar is independently an optionally substituted ring selected from a 5–7 membered saturated, partially unsaturated, or fully unsaturated monocyclic ring having 0–4 heteroatoms independently selected from nitrogen, oxygen, or sulfur, or an 8–10 membered saturated, partially unsaturated, or fully unsaturated bicyclic ring having 0–4 heteroatoms independently selected from nitrogen, oxygen, or sulfur;

$R^3$ is selected from R', $Ar^1$, Q-O$R^5$, Q-OC(O)$R^5$, Q-CONH$R^5$, Q-OC(O)NH$R^5$, Q-S$R^5$, Q-N$(R^4)_2$, N(R)(Q-Ar), N(R)C(O)Q-N$(R^4)_2$, or N(R)Q-N$(R^4)_2$;

R' is an optionally substituted $C_{1-6}$ aliphatic group;

each $R^4$ is independently selected from R, $COR^5$, $CO_2R^5$, $CON(R^5)_2$, $SO_2R^5$, $SO_2N(R^5)_2$, or $Ar^1$;

each $R^5$ is independently selected from R or Ar;

$V^1$, $V^2$ and $V^3$ are each independently $C(R^6)$;

each $R^6$ is independently selected from R, $Ar^1$, halogen, CN, $NO_2$, OR, SR, $N(R^4)_2$, N(R)COR, $N(R)CON(R^4)_2$, N(R)C(O)OR, $CON(R^4)_2$, $OC(O)N(R^4)_2$, $CO_2R$, OC(O)R, $N(R)SO_2R$, $N(R)SO_2N(R^4)_2$, $SO_2R$, or $SO_2N(R^4)_2$; and each $Ar^1$ is independently selected from an optionally substituted 5–7 membered saturated, partially unsaturated, or fully unsaturated monocyclic ring having 0–4 heteroatoms independently selected from nitrogen, oxygen, or sulfur;

provided that when $V^1$, $V^2$, and $V^3$ are each CH, T is a valence bond, and $R^2$ is $Q-C(R)(Q-Ar)R^3$, wherein Ar is an optionally substituted phenyl ring, then $R^3$ is other than $Q-OR^5$ or $C(O)NH_2$.

8. The compound according to claim 7, wherein:
$R^1$ is T-Ar, wherein:
T is selected from —NHC(O)—, —NH—, —NHCH$_2$—, NHSO$_2$—, —CH$_2$NH—, —C≡—, —CH$_2$— or —CH$_2$CH$_2$—; and
Ar is an optionally substituted 5–6 membered aryl ring having 0–4 heteroatoms independently selected from nitrogen, oxygen, or sulfur, or an optionally substituted 9–10 membered aryl ring having 0–4 heteroatoms independently selected from nitrogen, oxygen, or sulfur; and
$R^2$ is $Q-C(R)(Q-Ar)R^3$, wherein:
$R^3$ is R', $Q-OR^5$, $Q-N(R^4)_2$, $Ar^1$, $N(R)C(O)Q-N(R^4)_2$, or $N(R)Q-N(R^4)_2$;
each Q is independently selected from a valence bond, —CH$_2$—, or —CH$_2$CH$_2$—; and
Ar is an optionally substituted 5–6 membered saturated, partially unsaturated, or fully unsaturated monocyclic ring having 0–4 heteroatoms independently selected from nitrogen, oxygen, or sulfur, or an optionally substituted 9–10 membered saturated, partially unsaturated, or fully unsaturated bicyclic ring having 0–4 heteroatoms independently selected from nitrogen, oxygen, or sulfur.

9. The compound according to claim 8, wherein:
$R^3$ is $CH_2OH$, OH, $NH_2$, $CH_2NH_2$, $CH_2NHMe$, $CH_2N(Me)_2$, $CH_2CH_2NH_2$, $CH_2CH_2NHMe$, $CH_2CH_2N(Me)_2$, $CH_2CH_2NH_2$, $NHCO_2$t-butyl, phenyl, cyclopentyl, methyl, ethyl, isopropyl, cyclopropyl, $NH(CH_2)_3NH_2$, $NH(CH_2)_2NH_2$, $CH_2C(Me)_2NH_2$, $CH_2C(Me)_2CHMe$, $NH(CH_2)_2NHEt$, $NHCH_2$pyridyl, $NHSO_2$phenyl, $NHC(O)CH_2C(O)$Ot-butyl, $NHC(O)CH_2NH_3$, and $NHCH_2$-imidazol-4-yl.

10. The compound according to claim 7, wherein:
T is a valence bond; and
$R^2$ is $Q-C(R)(Q-Ar)R^3$, wherein:
R and $R^3$ optionally form a 5–7 membered saturated or partially unsaturated ring having 0–4 heteroatoms independently selected from nitrogen, oxygen, or sulfur;
$R^3$ is $Q-N(R^4)_2$, $Ar^1$, $N(R)C(O)Q-N(R^4)_2$, or $N(R)Q-N(R^4)_2$; and
Ar is an optionally substituted 5–6 membered saturated, partially unsaturated, or fully unsaturated monocyclic ring having 0–4 heteroatoms independently selected from nitrogen, oxygen, or sulfur, or an optionally substituted 9–10 membered saturated, partially unsaturated, or fully unsaturated bicyclic ring having 0–4 heteroatoms independently selected from nitrogen, oxygen, or sulfur.

11. The compound according to claim 10, wherein:
$R^3$ is $CH_2NHMe$, $CH_2N(Me)_2$, $CH_2CH_2NH_2$, $CH_2CH_2NHMe$, $CH_2CH_2N(Me)_2$, $CH_2C(Me)_2NH_2$, $CH_2C(Me)_2CHMe$, $NHCO_2$(t butyl), phenyl, NH$(CH_2)_3NH_2$, $NH(CH_2)_2NH_2$, $NH(CH_2)_2NHEt$, $NHCH_2$pyridyl, $NHSO_2$phenyl, $NHC(O)CH_2C(O)$Ot-butyl, $NHC(O)CH_2NH_3$, and $NHCH_2$-imidazol-4-yl.

12. The compound according to claim 7, wherein said compound is selected from the group consisting of:

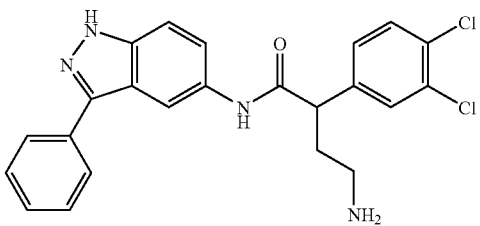

I-119

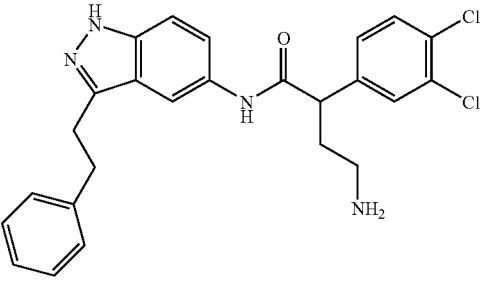

I-123

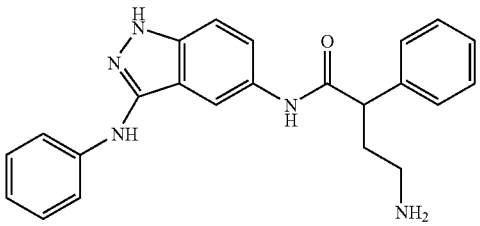

I-127

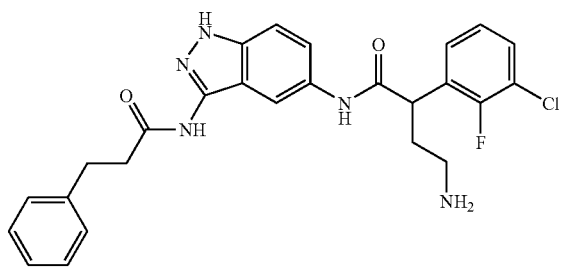

I-128

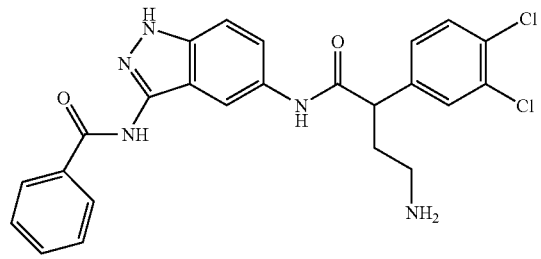

I-141

-continued

-continued
I-170
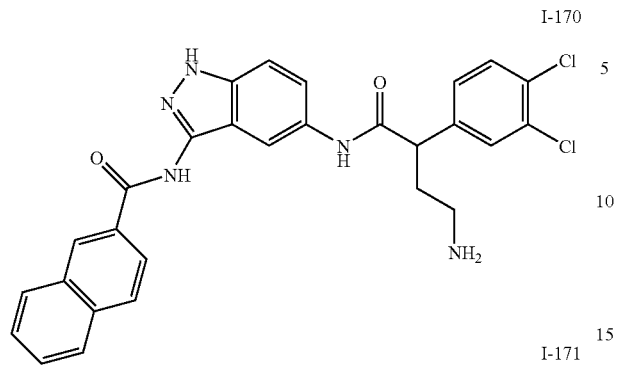
I-171
I-172
I-173
I-174
I-175
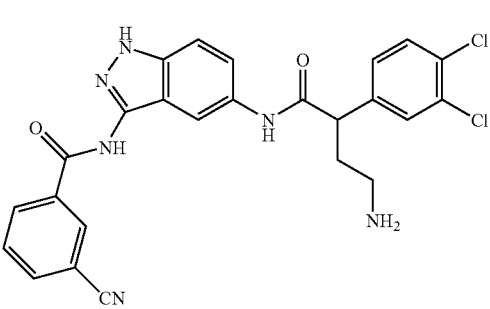
I-176
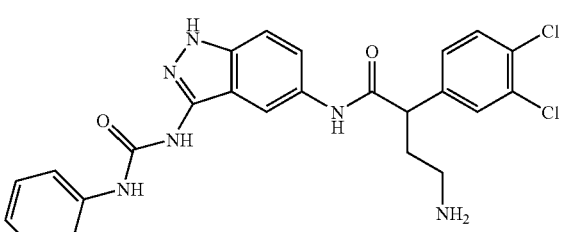
I-177
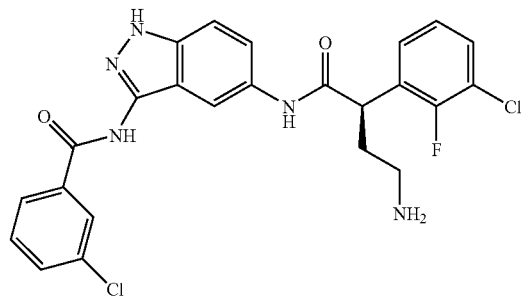
I-178
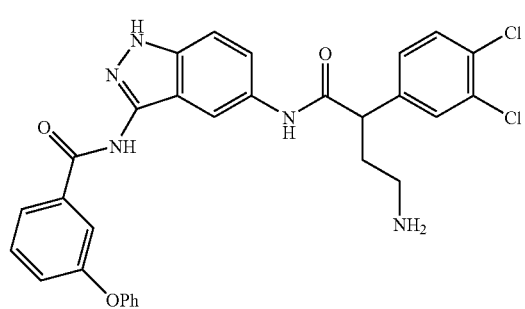
I-179
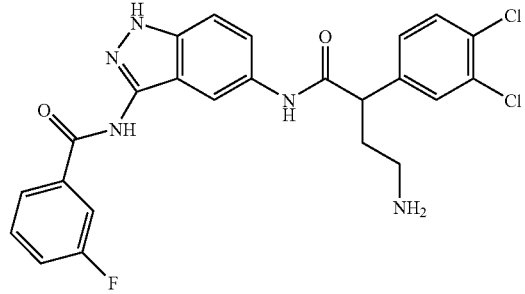

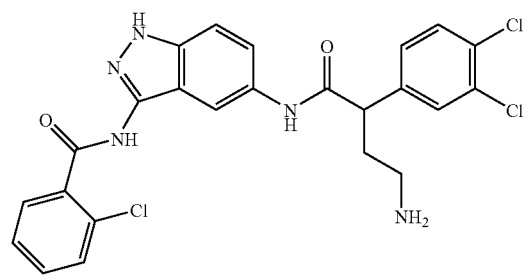
I-180
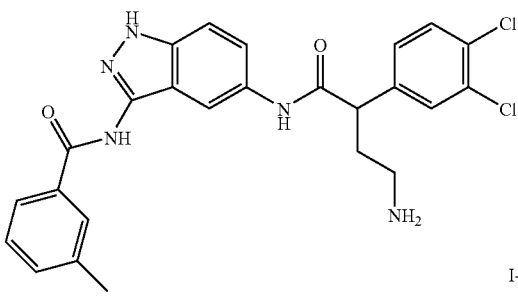
I-185
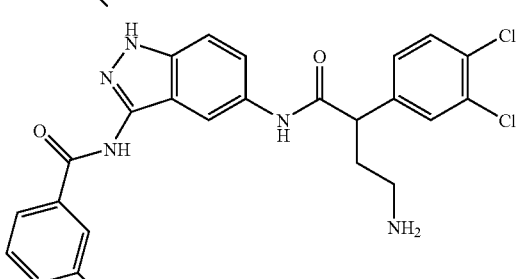
I-186
I-181
I-187
I-182
I-188
I-183
I-189
I-184
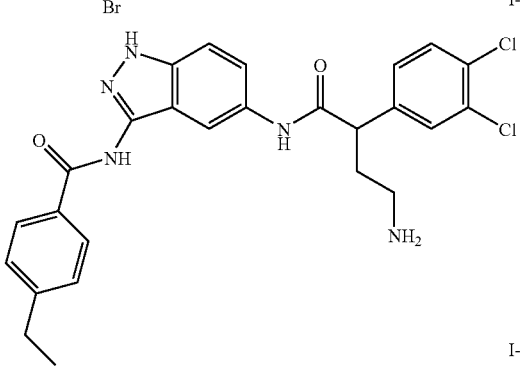
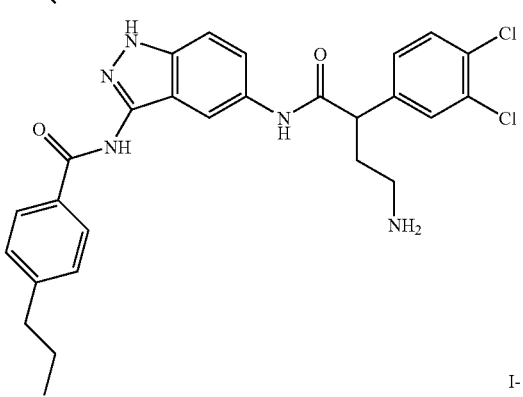
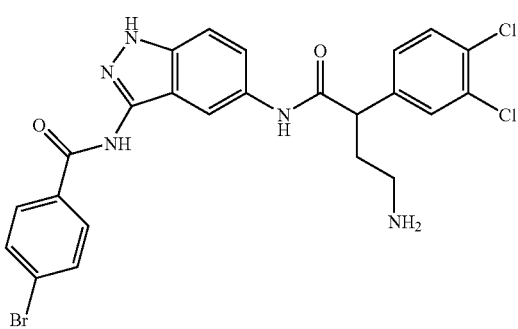

-continued
I-190
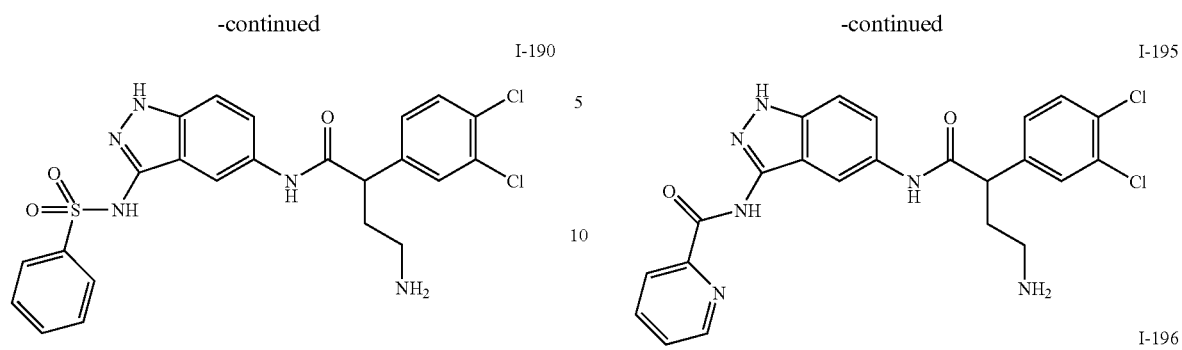
I-191
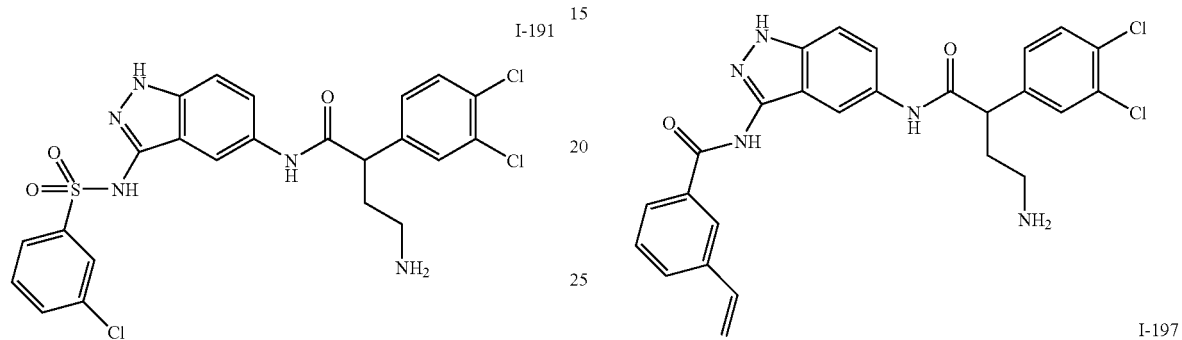
I-192
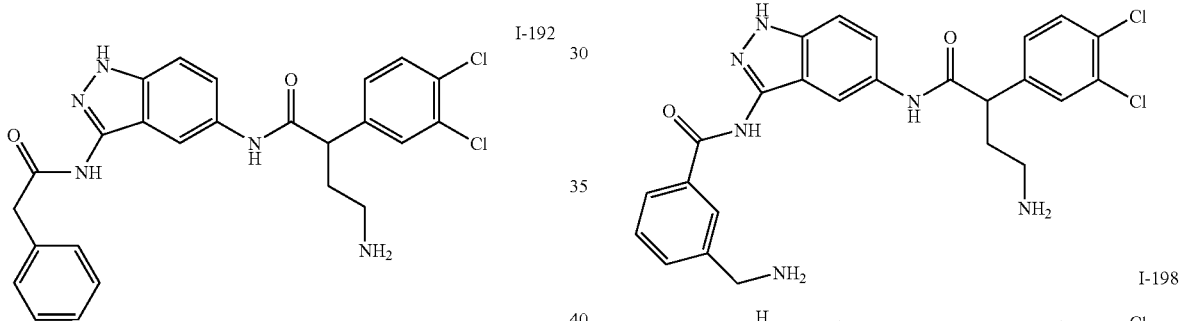
I-193
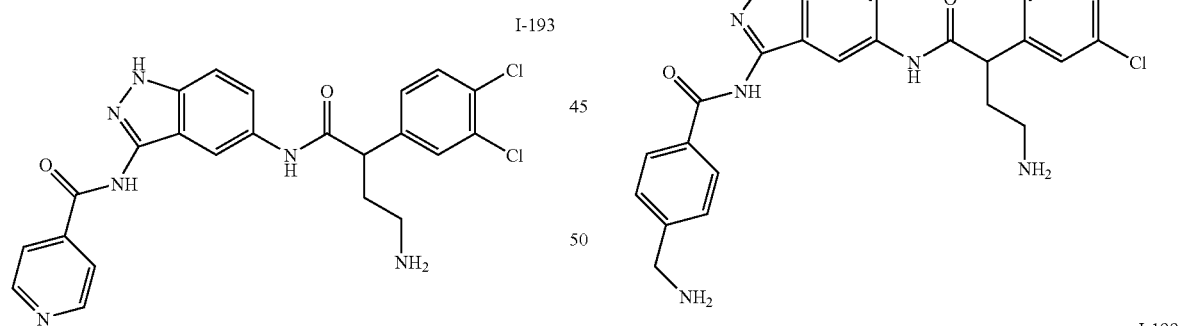
I-194
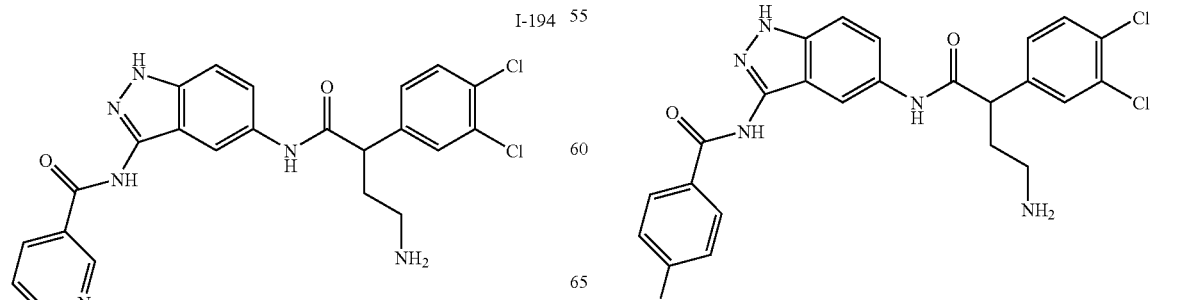
-continued
I-195
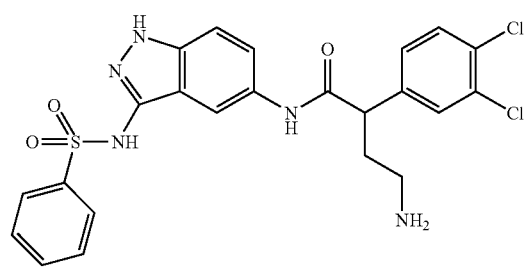
I-196
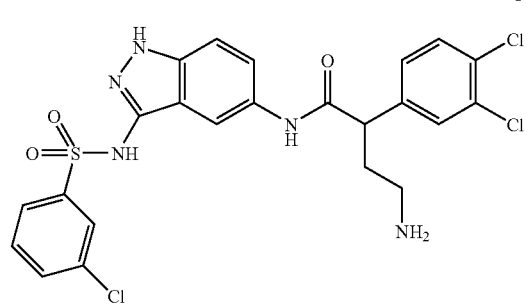
I-197
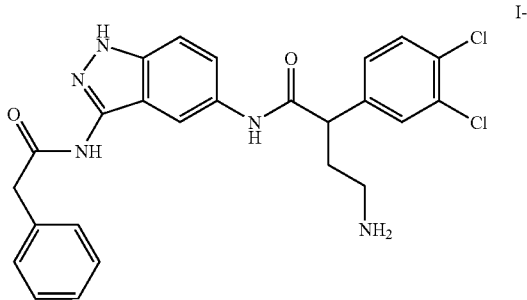
I-198
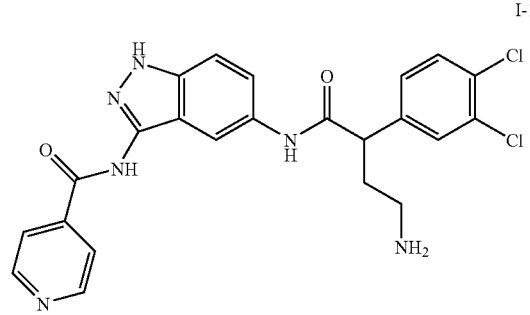
I-199
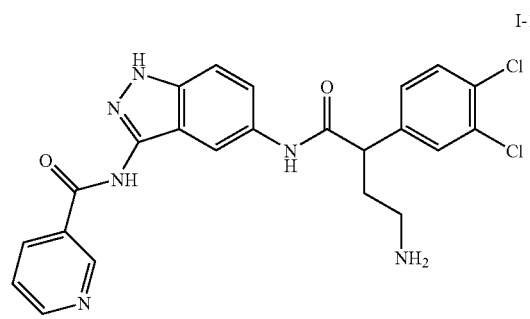

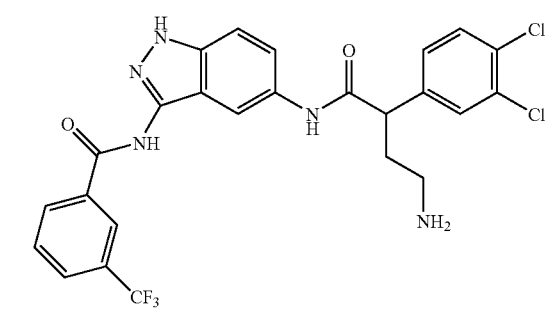

-continued
I-210
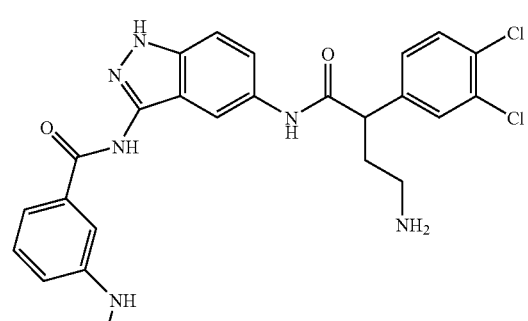
I-212
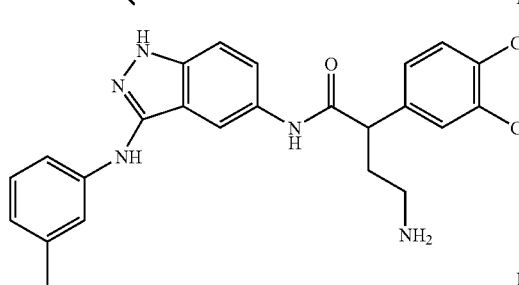
I-213
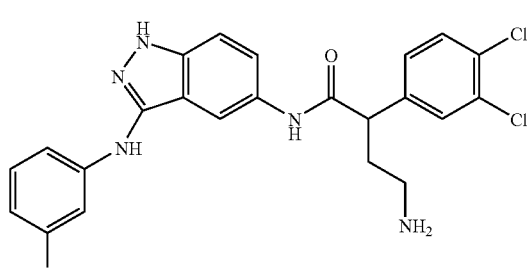
I-214
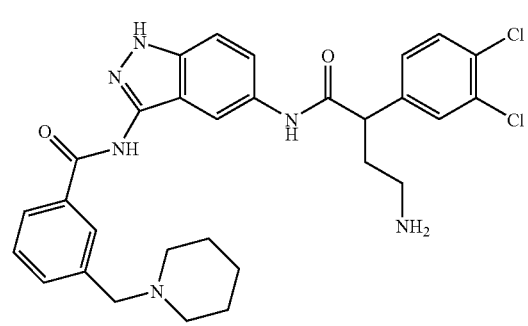
I-215
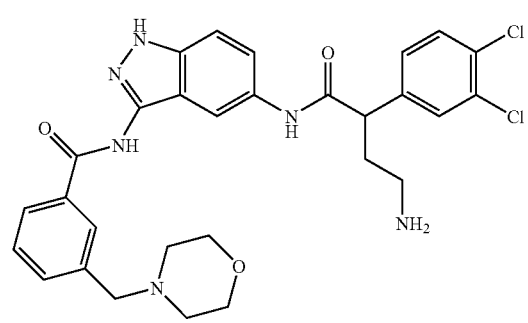
-continued
I-216
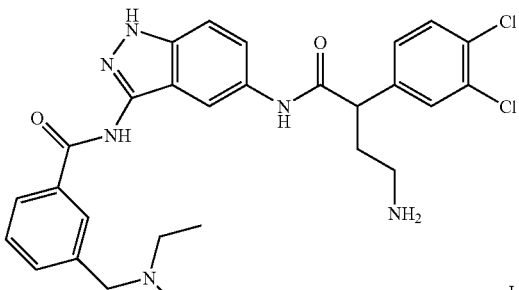
I-217
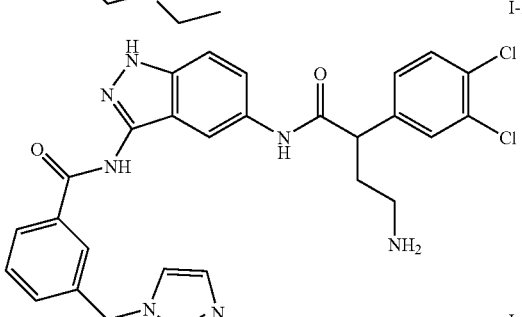
I-218
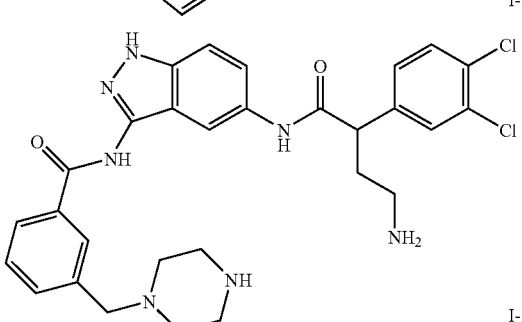
I-219
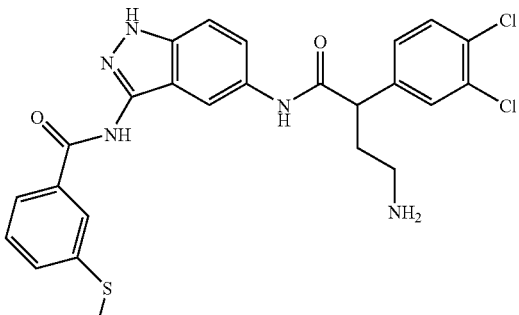
I-220
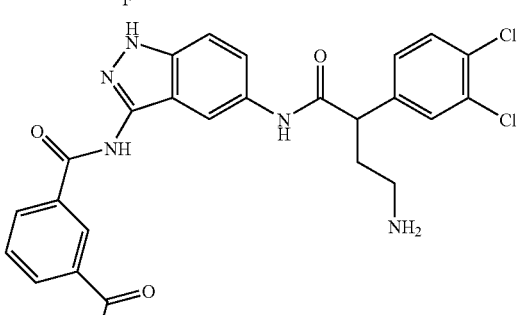

207
-continued
I-221
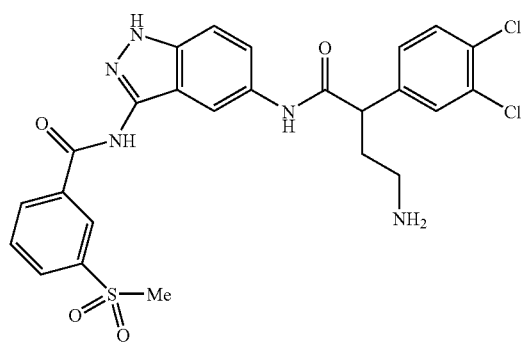
I-222
I-223
I-224
I-228
208
-continued
I-229
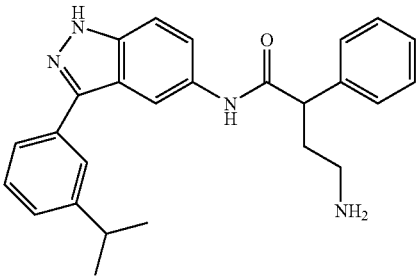
I-230
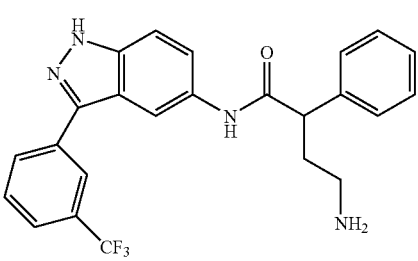
I-231
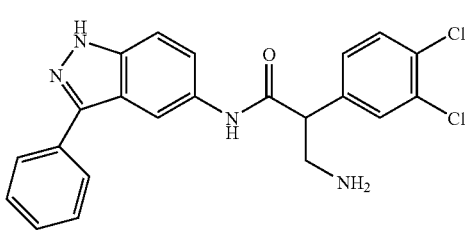
I-232
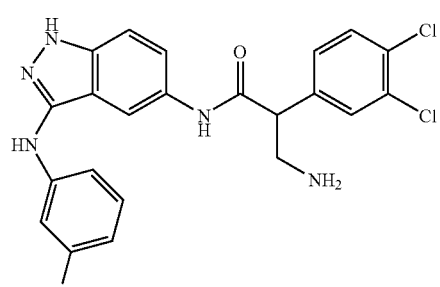
I-233
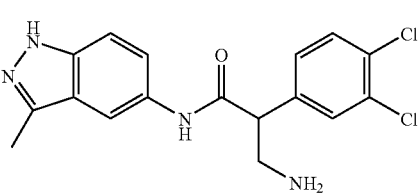
I-234
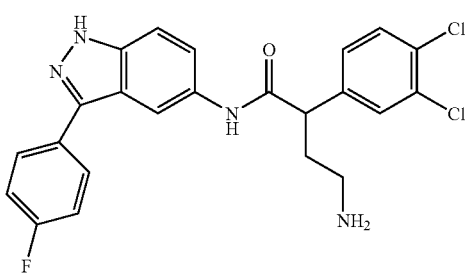

-continued
I-235
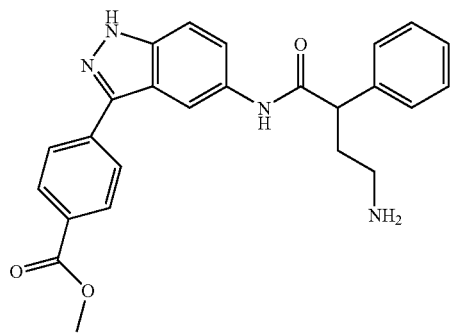
I-236
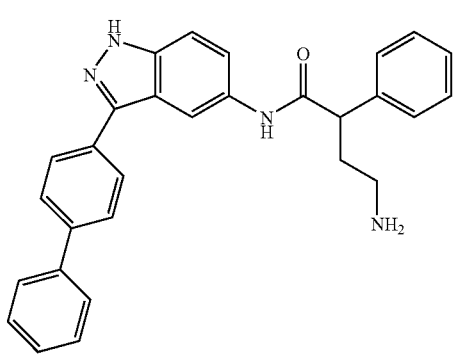
I-237
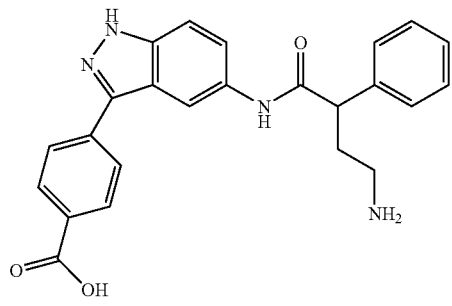
I-238
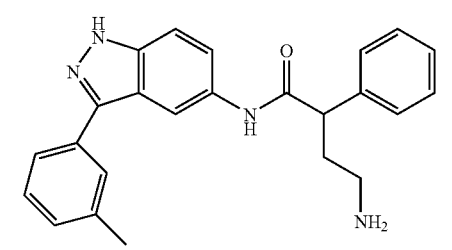
I-239
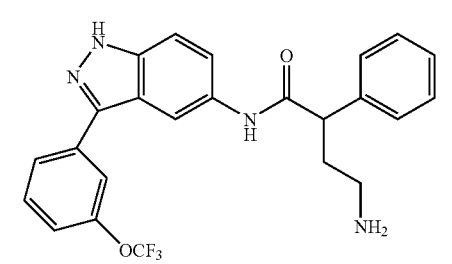
-continued
I-240
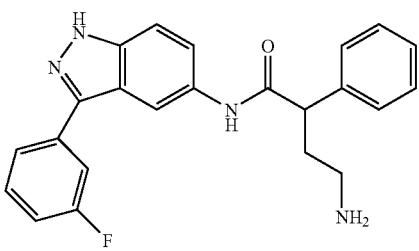
I-241
I-244
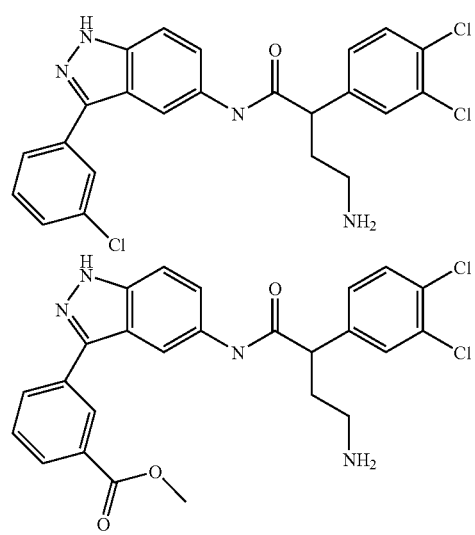
I-246
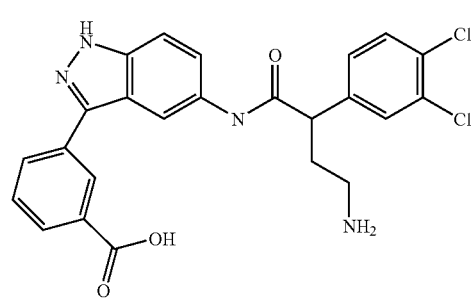
I-256
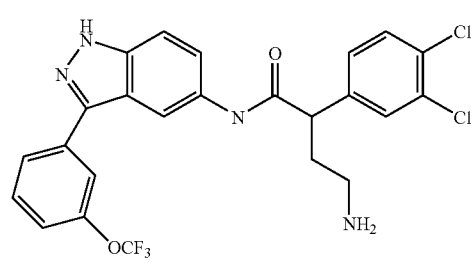
I-248
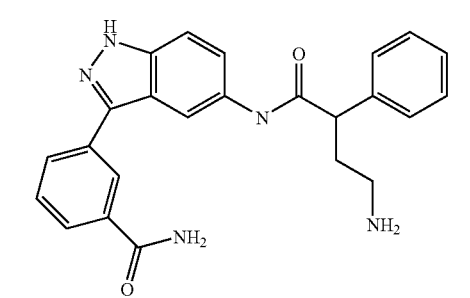

-continued
I-249
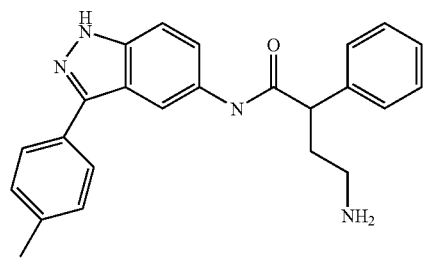
I-250
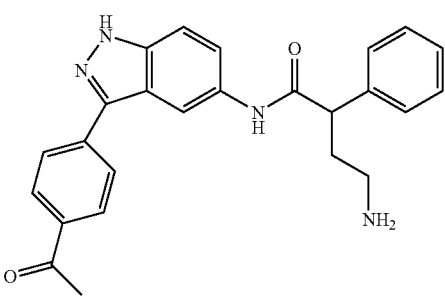
I-251
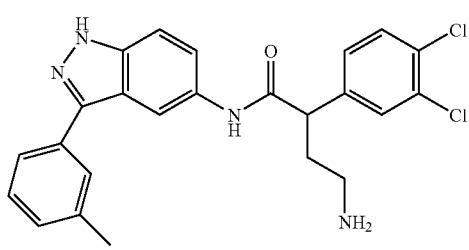
I-252
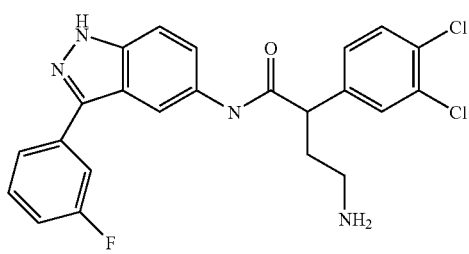
I-259
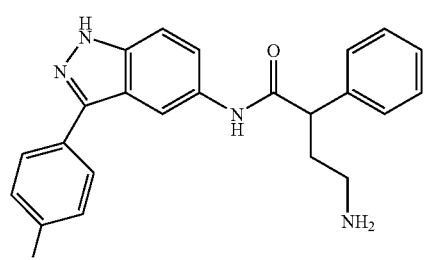
I-260
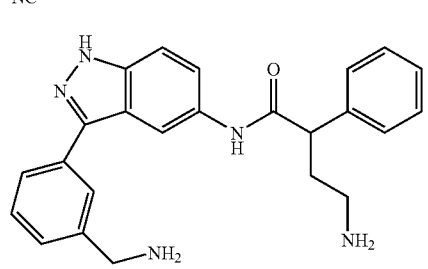
-continued
I-261
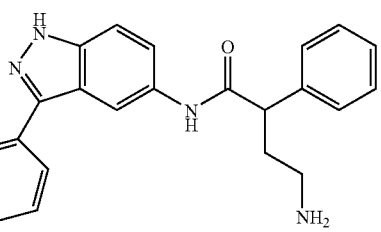
I-262
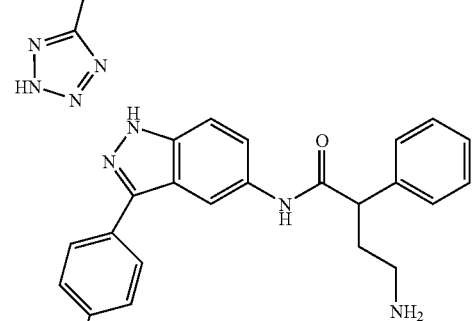
I-263
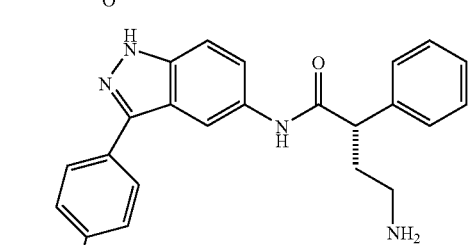
I-264
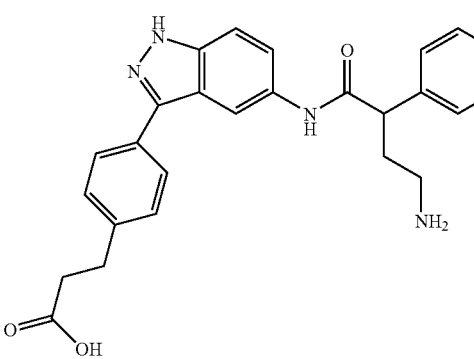
I-265
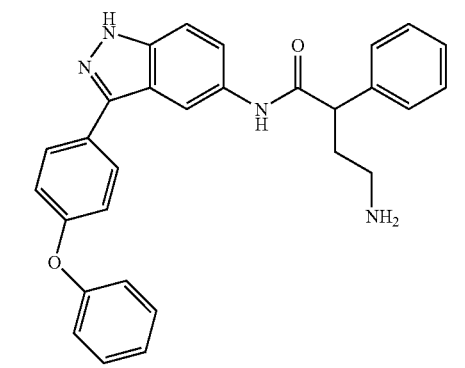

I-266 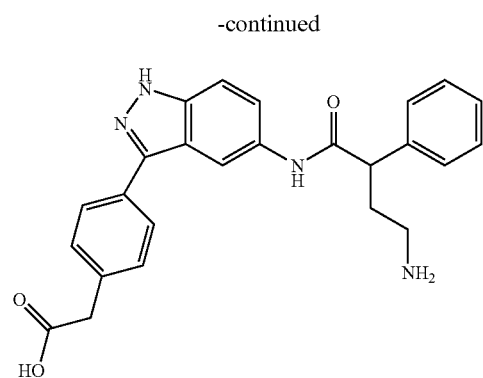
I-267 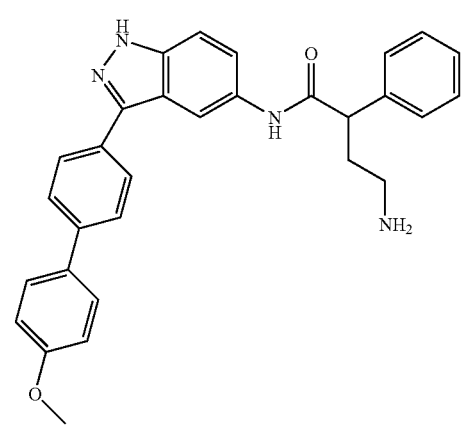
I-268 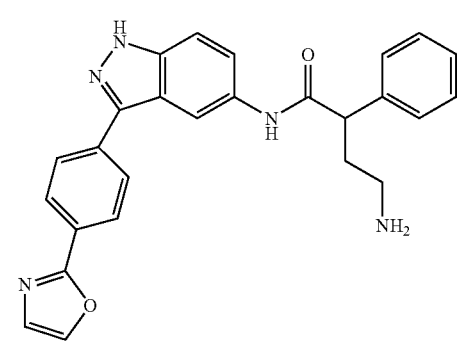
I-269 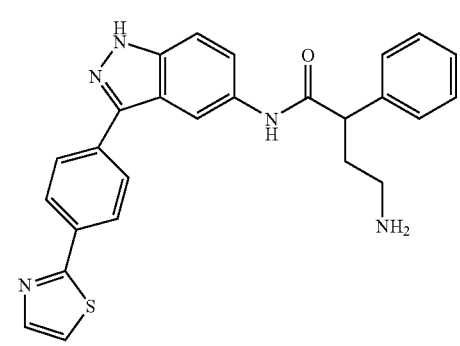
I-270 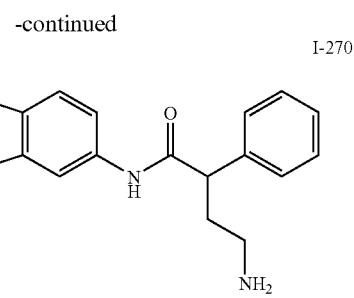
I-271
I-272
I-273
I-274

US 7,041,687 B2

215 216

-continued -continued

| | |
|---|---|
| I-287 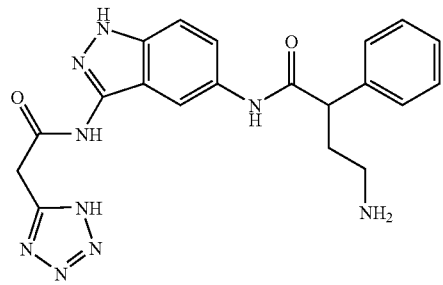 | I-1022 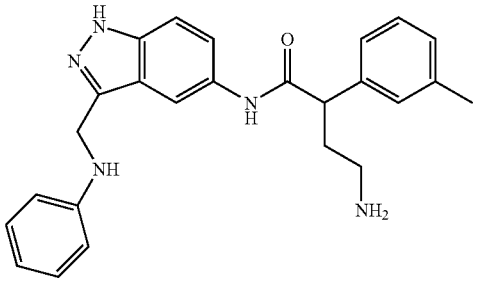 |
| I-288 | I-1027 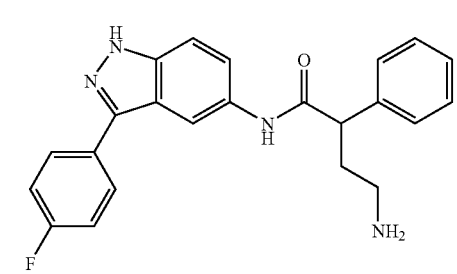 |
| I-289 | I-1028 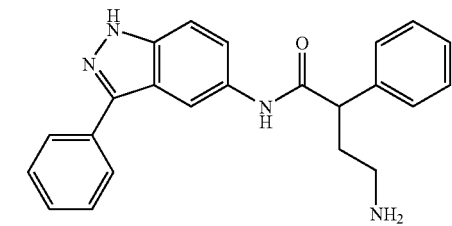 |
| I-1000 | I-1029 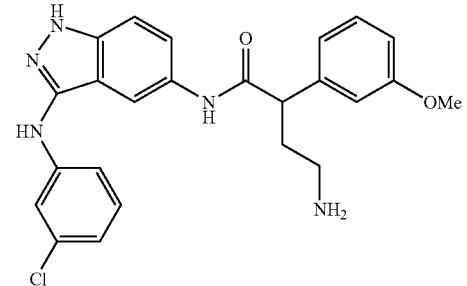 |
| I-1001 | I-1030 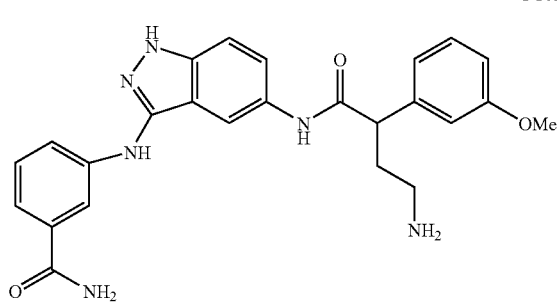 |

I-1031
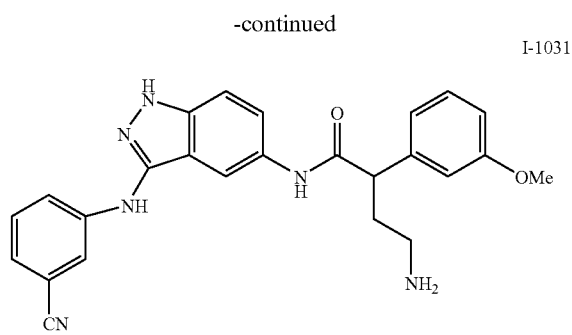
I-1036
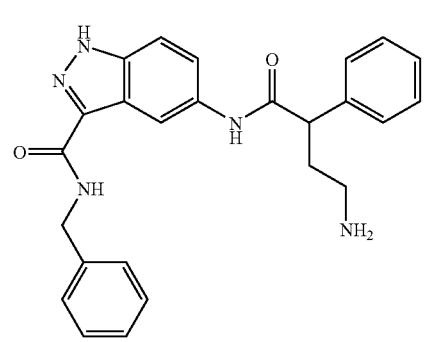
I-1038
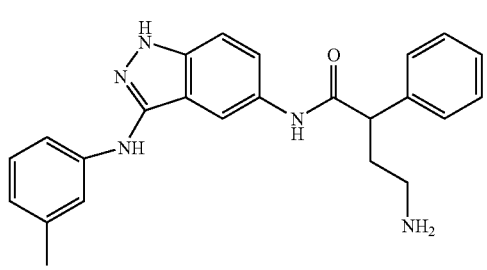
I-1039
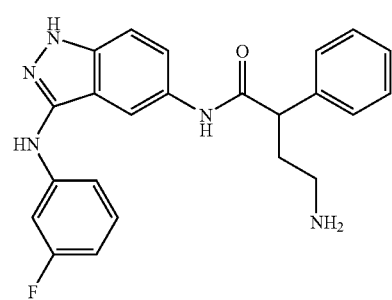
I-1040
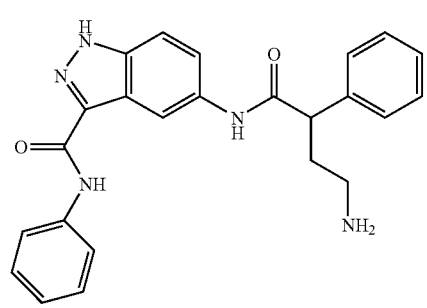
I-1041
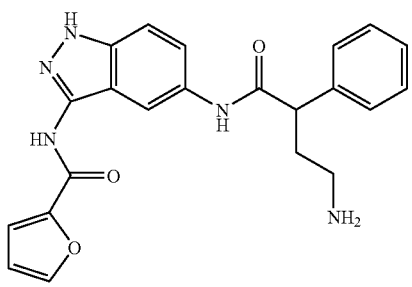
I-1042
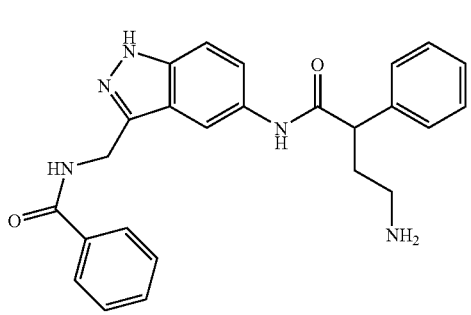
I-1043
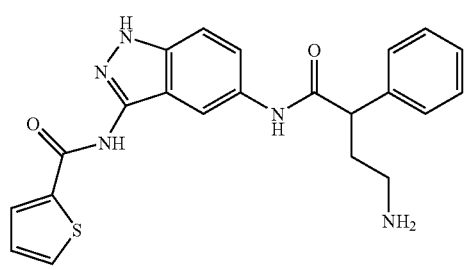
I-1044
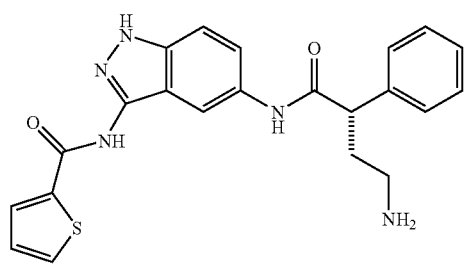
I-1045
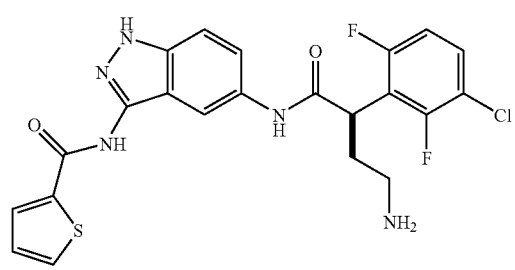

I-1046
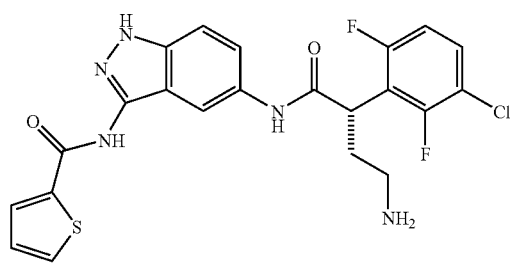
I-1047
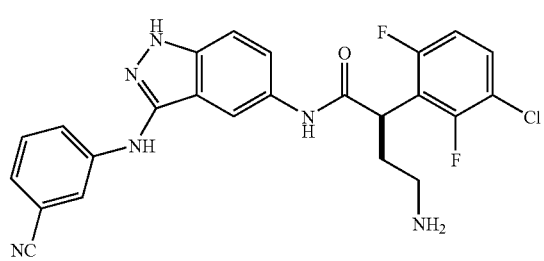
I-1048
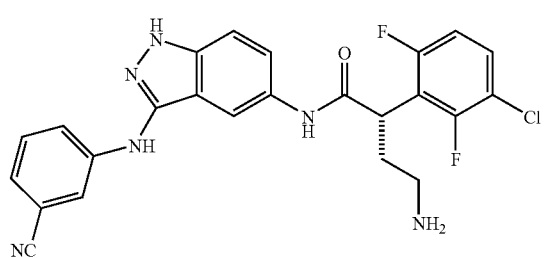
I-1049
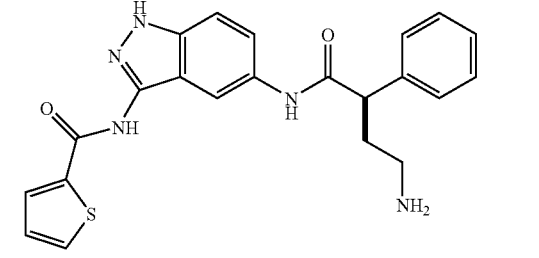
I-1050
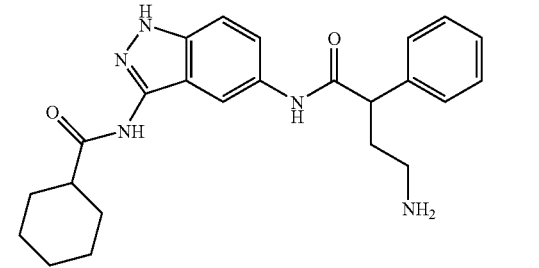
I-1051
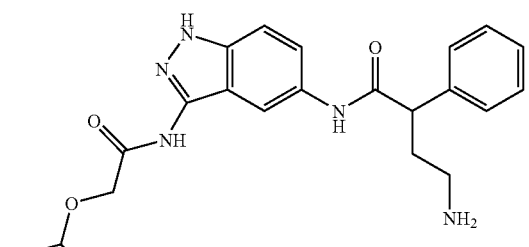
I-1052
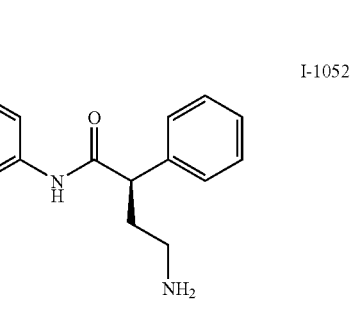
I-1053
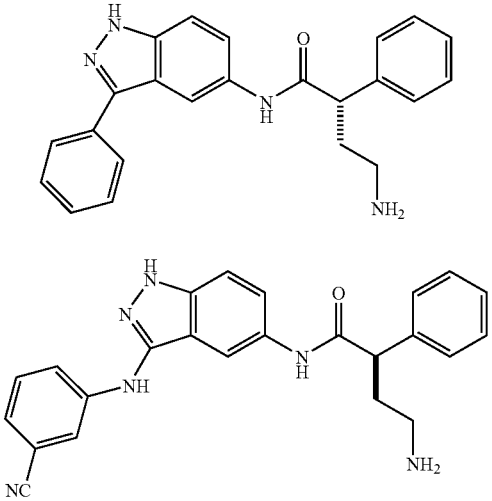
I-1054
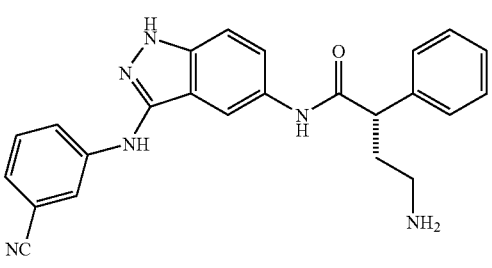
I-1055
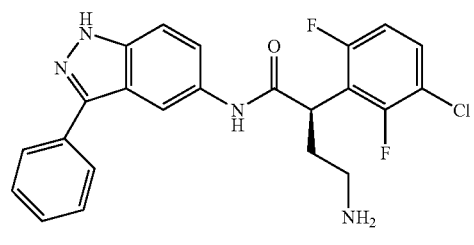
I-1056

-continued
I-1057
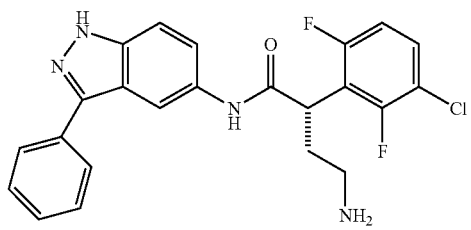
I-1058
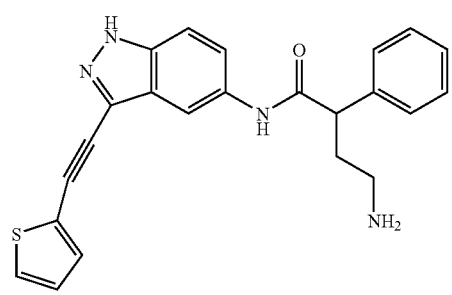
I-1059
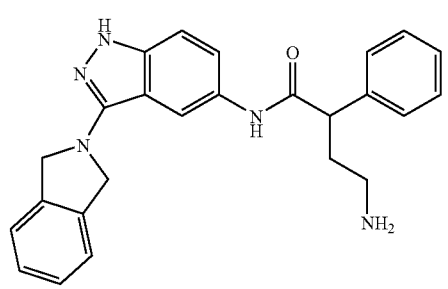
I-1060
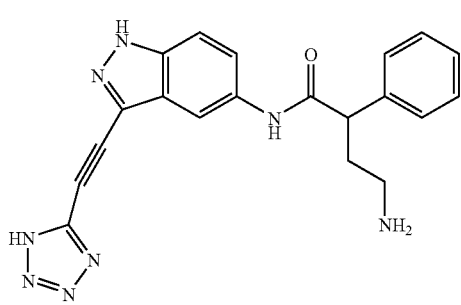
I-1061
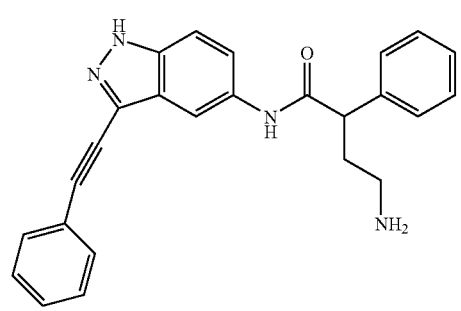
-continued
I-1062
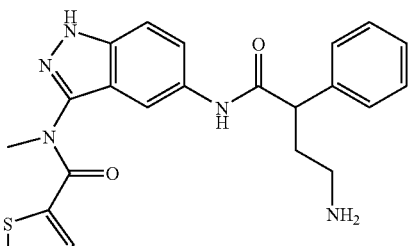
I-1063
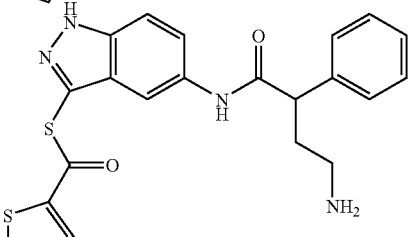
I-1064
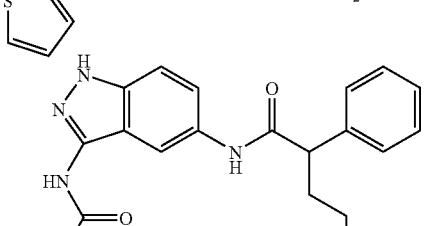
I-1065
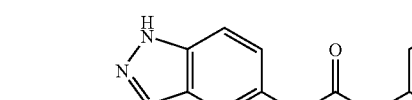
I-1066

13. The compound according to claim 7, wherein said compound has the formula V:

$$V$$

or a pharmaceutically acceptable salt thereof.

14. A composition comprising a compound according to either of claim 1 or 7, and a pharmaceutically acceptable carrier, adjuvant, or vehicle.

15. The composition according to claim 13, additionally comprising a therapeutic agent selected from an anti-proliferative agent, an anti-inflammatory agent, an immunomodulatory agent, a neurotrophic factor, an agent for treating cardiovascular disease, an agent for treating liver disease, an anti-viral agent, an agent for treating blood disorders, an agent for treating diabetes, or an agent for treating immunodeficiency disorders.

16. A method of inhibiting AKT, PKA, PDK1, p70S6K, or ROCK kinase activity comprising the step of contacting the kinase with a compound according to acyone of claims 1 through 13.

* * * * *